US007253146B2

(12) United States Patent
Obrecht et al.

(10) Patent No.: US 7,253,146 B2
(45) Date of Patent: Aug. 7, 2007

(54) TEMPLATE-FIXED PEPTIDOMIMETICS WITH ANTIMICROBIAL ACTIVITY

(75) Inventors: Daniel Obrecht, Basel (CH); John Anthony Robinson, Wermatswil (CH); Jan Wim Vrijbloed, Zürich (CH)

(73) Assignee: Polyphor Ltd, Allschwil (CH)

( * ) Notice: Subject to any disclaimer, the term of this patent is extended or adjusted under 35 U.S.C. 154(b) by 0 days.

(21) Appl. No.: 10/469,060

(22) PCT Filed: Feb. 18, 2002

(86) PCT No.: PCT/EP02/01711

§ 371 (c)(1),
(2), (4) Date: Feb. 5, 2004

(87) PCT Pub. No.: WO02/070547

PCT Pub. Date: Sep. 12, 2002

(65) Prior Publication Data

US 2004/0171066 A1    Sep. 2, 2004

(30) Foreign Application Priority Data

Feb. 23, 2001  (EP)  ............... PCT/EP01/02072

(51) Int. Cl.
| A61K 38/12 | (2006.01) |
| C07K 5/12 | (2006.01) |
| C07K 2/00 | (2006.01) |
| C07K 1/00 | (2006.01) |
| A61K 38/00 | (2006.01) |
| A61K 38/02 | (2006.01) |

(52) U.S. Cl. ............... 514/11; 514/2; 514/9; 530/300; 530/317; 530/321; 530/333

(58) Field of Classification Search .................... None
See application file for complete search history.

(56) References Cited

U.S. PATENT DOCUMENTS

| 4,698,327 | A | * | 10/1987 | Nagarajan et al. ............. 514/8 |
| 5,916,872 | A | | 6/1999 | Conway et al. |
| 6,878,804 | B1 | * | 4/2005 | Robinson et al. ........... 530/317 |

FOREIGN PATENT DOCUMENTS

WO    WO 01/16161    3/2001

OTHER PUBLICATIONS

J. Rudinger. In: Peptide Hormones, JA Parsons, Ed. (1976) 1-7.*
D.E. Smilek, et al. Proc. Natl. Acad. Sci. USA (1991) 88, pp. 9633-9637.*
W.S. Messer, "Vasopressin and Oxytocin", web document updated Apr. 3, 2000; <http://www.neurosci.pharm.utoledo.edu/MBC3320/vasopressin.htm>; 5 pages.*
S. Rudikoff, et al. Proc. Natl. Acad. Sci. USA (1982) 79, pp. 1979-7983.*
J. Späth, et al. Helv. Chim. Acta (1998) 81, pp. 1726-1738.*
L. Jiang, et al. Helv. Chim. Acta (2000) 83, pp. 3097-3112.*
J.C. J. Barna and D.H. Williams, "The structure and Mode of Action of Glycopeptide Antibiotics of the Vancomycin Group", Ann. Rev. Microbiol. 38, p. 339-357, 1984.
K.L. Piers and R.E.W. Hancock, "The Interaction of a Recombinant Cecropin/Melittin Hybrid Peptide with the Outer Memberane of *Pseudomonas aeruginosa*", Molecular Microbiology 194, 12, 951-958, see especially p. 954: Interaction of CEME with LPS.
K. Matsukaki, "Why and how are peptide-lipid interactions utilized for self Defense: Magainins and tachyplesins as archetypes", Biochimica et Biophysica Acta 1462 (1999), 1-10, particularly p. 3 et seq.
L. Zhang et al., "Interaction of Polyphemusin I and Structural Analogs with Bacterial Membranes, Lipopolysaccharide, and Lipid Monolayers", Biochemistry 2000, 39, 14504-14514.

(Continued)

*Primary Examiner*—Cecilia J. Tsang
*Assistant Examiner*—Andrew D. Kosar
(74) *Attorney, Agent, or Firm*—Hoffmann & Baron, LLP

(57) ABSTRACT

Template-fixed β-hairpin peptidomimetics of the general formulae (I) and (II) wherein Z, Z1 and Z2 are template-fixed chains of 8 to 16 α-amino acid residues which, depending on their positions in the chain (counted starting from the N-terminal amino acid) are Gly, or Pro, or of certain types which, as the remaining symbols in the above formulae, are defined in the description and the claims, and salts thereof, have the property to inhibit the growth of or to kill microorganisms and cancer cells. They can be used as disinfectants for foodstuffs, cosmetics, medicaments or other nutrient-containing materials or as medicaments to treat or prevent infections or diseases related to such infections and/or cancer. These β-hairpin peptidomimetics can be manufactured by a process which is based on a mixed solid- and solution phase synthetic strategy

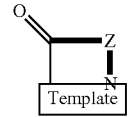

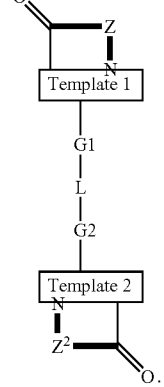

35 Claims, No Drawings

OTHER PUBLICATIONS

R. Gallo, K.M. Huttner, "Antimicrobial Peptides: An Emerging Concept in Cutaneous Biology", The Journal of Investigative Dermatology 111,739-743, 1998, see especially pp. 41 et seq.: Mechanism of action, see Fig. 1.

Y. Shai, "Mechanism of the binding, insertion and destabilization of phospholipids bilayer membranes by α-helical antimicrobial and cell non-selective membrane-lytic peptides", Biochim Biophys Acta 1999, 1462, 55-70.

A. Tossi et al., "Amphipatic, α-Helical Antimicrobial Peptides", Biopolymers 200, 55, 4-30.

M. Wu et al., "Mechanism of Interaction of Different Classes of Cationic Antimicrobial Peptides with Planar Bilayers and with the Cytoplasmic Membrane of *Esherichia coli*", Biochemisyry 1999, 38, 7235-7242.

Y. Shai, "Mode of Action of Membrane Active Antimicrobial Peptides", Biopolymers 66, 236-248, 2002.

S.C. Shankaramma, et al., "Macrocyclic Hairpin Memetics of the Cationic Antimicrobial Peptide Protegrin 1: A New Family of Broad-Spectrum Antibiotics", ChemBioChem 2002, 3, 1126-1133.

J.A. Robinson, et al. "Properties and structure-activity studies of cyclic β-hairpin peptidommetics based on the cationic antimicrobial peptide protegrin I", Bioorganic & Medicinal Chemistry 13 (2005) 2055-2064.

Favre et al.; Structural Mimicry of Canonical Conformations in Antibody Hypervariable Loops Using Cyclic Peptides Containing a Heterochiral Diproline Template; J. Am. Chem. Soc.; Mar. 31, 1999, vol. 121, No. 12, pp. 2679-2685.

Obrecht et al.; Novel Peptide Mimetic Building Blocks and Strategies for Efficient Lead Finding; Advances in Medicinal Chemistry, JAI Press, U.S.; Apr. 1999, pp. 1-68.

Robinson; The Design, Synthesis and Conformation of Some New beta-Hairpin Mimetics: Novel Reagents for Drug and Vaccine Discovery; Synlett, vol. 1999, No. 4, Apr. 2000, pp. 429-441.

Jiang et al.; Combinatorial Biomimetic Chemistry: Parallel Synthesis of a Small Library of beta-Haripin Mimetics Based on Loop III from Human Platelet-Derived Growth Factor B; Helvetica Chimica Acta; Vol. No. 83, No. 12, Dec. 2000; pp. 3097-3112.

McInnes; et al.; Development of the structural basis for antimicrobial and hemolytic activities of peptides based on gramicidin S and design of novel analogs using NMR spectroscopy; Journal of Biological Chemistry; Vol. No. 275 No. 19; May 12, 2000; pp. 14287-14294.

Hanessian et al.; Design and Synthesis of Conformationally Constrained Amino Acids as Versatile Scaffolds and Peptides Mimetics; Tetrahedron, Elsevier Science Publishers; Amsterdam, NL; vol. 53, No. 38, Sep. 22, 1997; pp. 12789-12854.

Belvisi et al.; Conformational analysis of azabicycloalkane amino acid scaffolds as reverse-turn inducer dipeptide mimics; Eur. J. Org. Chem.; 2000; vol. 14, pp. 2563-2569.

Pfeifer et al.; Synthesis and solution conformation of beta-hairpin mimetics utilizing a template derived from (2S, 3R, 4R)-diaminoproline; Helv. Chim. Acta; 2000; vol. 83(2); pp. 444-464.

Muller et al.; Are beta-turn mimetics of beta-turns? Angew. Chem. Int. Ed.; 2000; vol. 39(5); pp. 894-896.

Boatman et al.; Secondary Structure Peptide Mimetics: Design, Synthesis, and Evaluation of beta-Strand Mimetic Trombin Inhibitors; J. Med. Chem.; 1999; vol. 42(8), pp. 1367-1375.

Gennari et al.; Solid-phase synthesis of peptides containing reverse-turn mimetic bicyclic lactams; Eur. J. Or. Chem.; 1999; vol. (2); pp. 379-388.

Belvisi et al.; Conformational preferences of peptides containing reverse-turn mimetic bicyclic lactams, Inverse gamma-turns versus type-II beta-turns, Insights into beta-hairpin stability; Eur. J. Org. Chem.; 1999, vol. (2); pp. 389-400.

Pfeifer et al.; Stabilization of beta-hairpin conformations in a protein surface mimetic using a bicyclic template derived from (2S, 3R, 4R)-diaminoproline; Chem. Commun.; Cambridge; 1998. vol. 18, pp. 1977-1978.

Bisang et al.; Synthesis, Conformational Properties, and Immunogenicity of a Cyclic Template-Bound Peptide Mimetic Containing and NPNA Motif from a Circumsporozoite Protein of Plasmodium Falciparum; J. Am. Chem. Soc.; 1998; vol. 120 (30); pp. 7439-7449.

Li et al.; Conformationally Restricted TRH Analogs: The Compatability of a 6, 5-Bicyclic Lactam-Based Mimetic with Binding to TRH-R; J. Am. Chem. Soc.; 1996, vol. 118 (42); pp. 10106-10112.

* cited by examiner

TEMPLATE-FIXED PEPTIDOMIMETICS WITH ANTIMICROBIAL ACTIVITY

CROSS-REFERENCE TO RELATED APPLICATIONS

This application is the national stage filing under 35 U.S.C. §371 of PCT/EP02/01711, filed Feb. 18, 2002, which claims priority to PCT/EP01/02072, filed Feb. 23, 2001, both of which are incorporated by reference.

BACKGROUND OF THE INVENTION

1. Field of the Invention

The present invention provides template-fixed β-hairpin peptidomimetics incorporating template-fixed chains of 8 to 16 α-amino acid residues which, depending on their positions in the chains, are Gly or Pro, or of certain types, as defined hereinbelow. These template-fixed β-hairpin mimetics have broad spectrum antimicrobial and anticancer activity. In addition, the present invention provides an efficient synthetic process by which these compounds can, if desired, be made in parallel library-format. These β-hairpin peptidomimetics show improved efficacy, bioavailability, half-life and most importantly a significantly enhanced ratio between antibacterial and anticancer activity on the one hand, and hemolysis of red blood cells on the other.

2. Description of Relevant Art

The growing problem of microbial resistance to established antibiotics has stimulated intense interest in developing novel antimicrobial agents with new modes of action (H. Breithaupt, *Nat. Biotechnol.* 1999, 17, 1165–1169). One emerging class of antibiotics is based on naturally occurring cationic peptides (T. Ganz, R. L. Lehrer, *Mol. Medicine Today* 1999, 5, 292–297; R. M. Epand, H. J. Vogel, *Biochim. Biophys. Acta* 1999, 1462, 11–28). These include disulfide-bridged β-hairpin and β-sheet peptides (such as the protegrins [V. N. M.; O. V. Shamova, H. A. Korneva, R. I. Lehrer, *FEBS Lett.* 1993, 327, 231–236], tachyplesins [T. Nakamura, H. Furunaka, T. Miyata, F. Tokunaga, T. Muta, S. Iwanaga, M. Niwa, T. Takao, Y. Shimonishi, Y. *J. Biol. Chem.* 1988, 263, 16709–16713], and the defensins [R. I. Lehrer, A. K. Lichtenstein, T. Ganz, *Annu. Rev. Immunol.* 1993, 11, 105–128], amphipathic α-helical peptides (e.g. cecropins, dermaseptins, magainins, and mellitins [A. Tossi, L. Sandri, A. Giangaspero, *Biopolymers* 2000, 55, 4–30]), as well as other linear and loop-structured peptides. Although the mechanisms of action of antimicrobial cationic peptides are not yet fully understood, their primary site of interaction is the microbial cell membrane (H. W. Huang, *Biochemistry* 2000, 39, 8347–8352). Upon exposure to these agents, the cell membrane undergoes permeabilization, which is followed by rapid cell death. However, more complex mechanisms of action, for example, involving receptor-mediated signaling; cannot presently be ruled out (M. Wu, E. Maier, R. Benz, R. E. Hancock, *Biochemistry* 1999, 38, 7235–7242).

The antimicrobial activities of many of these cationic peptides usually correlate with their preferred secondary structures, observed either in aqueous solution or in membrane-like environments (N. Sitaram, R. Nagaraj, *Biochim. Biophys. Acta* 1999, 1462, 29–54). Structural studies by nuclear magnetic resonance (NMR) spectroscopy have shown that cationic peptides such as protegrin 1 (A. Aumelas, M. Mangoni, C. Roumestand, L. Chiche, E. Despaux, G. Grassy, B. Calas, A. Chavanieu, A. *Eur. J. Biochem.* 1996, 237, 575–583; R. L. Fahrner, T. Dieckmann, S. S. L. Harwig, R. I. Lehrer, D. Eisenberg, J. Feigon, *J. Chem. Biol.* 1996, 3, 543–550) and tachyplesin I (K. Kawano, T. Yoneya, T. Miyata, K. Yoshikawa, F. Tokunaga, Y. Terada, S. J. Iwanaga, S. *J. Biol. Chem.* 1990, 265, 15365–15367) adopt well defined β-hairpin conformations, due to the constraining effect of two disulfide bridges. In protegrin analogues lacking one or both of these disulfide bonds, the stability of the β-hairpin conformation is diminished, and the antimicrobial activity is reduced (J. Chen, T. J. Falla, H. J. Liu, M. A. Hurst, C. A. Fujii, D. A. Mosca, J. R. Embree D. J. Loury, P. A. Radel, C. C. Chang, L. Gu, J. C. Fiddes, *Biopolymers* 2000, 55, 88–98; S. L. Harwig, A. Waring, H. J. Yang, Y. Cho, L. Tan, R. I. Lehrer, R. J. *Eur. J. Biochem.* 1996, 240, 352–357; M. E. Mangoni, A. Aumelas, P. Charnet, C. Roumestand, L. Chiche, E. Despaux, G. Grassy, B. Calas, A. Chavanieu, *FEBS Lett.* 1996, 383, 93–98; H. Tamamura, T. Murakami, S. Noriuchi, K. Sugihara, A. Otaka, W. Takada, T. Ibuka, M. Waki, N. Tamamoto, N. Fujii, *Chem. Pharm. Bull.* 1995, 43, 853–858). Similar observations have been made in analogues of tachyplesin I (H. Tamamura, R. Ikoma, M. Niwa, S. Funakoshi, T. Murakami, N. Fujii, *Chem. Pharm. Bull.* 1993, 41, 978–980) and in hairpin-loop mimetics of rabbit defensin NP-2 (S. Thennarasu, R. Nagaraj, *Biochem. Biophys. Res. Comm.* 1999, 254, 281–283). These results show that the β-hairpin structure plays an important role in the antimicrobial activity and stability of these protegrin-like peptides. In the case of the cationic peptides preferring α-helical structures, the amphililic structure of the helix appears to play a key role in determining antimicrobial activity (A. Tossi, L. Sandri, A. Giangaspero, A. *Biopolymers* 2000, 55, 430). Gramicidin S is a backbone-cyclic peptide with a well defined β-hairpin structure (S. E. Hull, R. Karlsson, P. Main, M. M. Woolfson, E. J. Dodson, *Nature* 1978, 275, 206–275) that displays potent antimicrobial activity against gram-positive and gram-negative bacteria (L. H. Kondejewski, S. W. Farmer, D. S. Wishart, R. E. Hancock, R. S. Hodges, *Int. J. Peptide Prot. Res.* 1996, 47, 460–466). The high hemolytic activity of gramicidin S has, however, hindered its widespread use as an antibiotic. Recent structural studies by NMR have indicated that the high hemolytic activity apparently correlates with the highly amphipathic nature of this cyclic β-hairpin-like molecule, but that it is possible to dissociate antimicrobial and hemolytic activities by modulating the conformation and amphiphilicity (L. H. Kondejewski, M. Jelokhani-Niarali, S. W. Farmer, B. Lix, M. Kay, B. D. Sykes, R. E. Hancock, R. S. Hodges, *J. Biol. Chem.* 1999, 274, 13181–13192; C. McInnes L. H. Kondejewski, R. S. Hodges, B. D. Sykes, *J. Biol. Chem.* 2000, 275, 14287–14294).

A new cyclic antimicrobial peptide RTD-1 was reported recently from primate leukocytes (Y.-Q. Tang, J. Yuan, G. Ösapay, K. Ösapay, D. Tran, C. J. Miller, A. J. Oellette, M. E. Selsted, *Science* 1999, 286, 498–502. This peptide contains three disulfide bridges, which act to constrain the cyclic peptide backbone into a hairpin geometry. Cleavage of the three disulfide bonds leads to a significant loss of antimicrobial activity. Analogues of protegrins (J. P. Tam, C. Wu, J.-L. Yang, *Eur. J. Biochem.* 2000, 267, 3289–3300) and tachyplesins (J.-P. Tam, Y.-A. Lu, I.-L. Yang, *Biochemistry* 2000, 39, 7159–7169; N. Sitaram, R. Nagaraij, *Biochem. Biophys. Res. Comm.* 2000, 267, 783–790) containing a cyclic peptide backbone, as well as multiple disulfide bridges to enforce a amphiphilic hairpin structure, have also been reported. In these cases, removal of all the cystine constraints does not always lead to a large loss of antimicrobial activity, but does modulate the membranolytic selectivity (J. P. Tam, C. Wu, J.-L. Yang, *Eur. J. Biochem*. 2000, 267, 3289–3300).

A key issue in the design of new cationic antimicrobial peptides is selectivity. The naturally occurring protegrins and tachyplesins exert a significant hemolytic activity against human red blood cells. This is also the case for protegrin analogues such as IB367 (J. Chen, T. J. Falla, H. J. Liu, M. A. Hurst, C. A. Fujii, D. A. Mosca, J. R. Embree, D. J. Loury, P. A. Radel, C. C. Chang, L. Gu, J. C. Fiddes, *Biopolymers* 2000, 55, 88–98; C. Chang, L. Gu, J. Chen, U.S. Pat. No. 5,916,872, 1999). This high hemolytic activity essentially obviates its use in vivo, and represents a serious disadvantage in clinical applications. Also, the antibiotic activity of analogues often decreases significantly with increasing salt concentration, such that under in vivo conditions (ca. 100–150 mM NaCl) the antimicrobial activity may be severely reduced. Before intravenous use can be considered, the general toxicity, protein-binding activity in blood serum, as well as protease stability become serious issues which must be adequately addressed.

Protegrin 1 exhibits potent and similar activity against gram-positive and gram-negative bacteria as well as fungi in both low- and high-salt assays. This broad antimicrobial activity combined with a rapid mode of action, and their ability to kill bacteria resistant to other classes of antibiotics, make them attractive targets for development of clinically useful antibiotics. The activity against gram-positive bacteria is typically higher than against gram-negative bacteria. However, protegrin 1 also exhibits a high hemolytic activity against human red blood cells, and hence a low selectivity towards microbial cells. Oriented CD experiments (W. T. Heller, A. J. Waring, R. I. Lehrer, H. W. Huang, *Biochemistry* 1998, 37, 17331–17338) indicate that protegrin 1 may exist in two different states as it interacts with membranes, and these states are strongly influenced by lipid composition. Studies of cyclic protegrin analogues (J.-P. Tam, C. Wu, J.-L. Yang, *Eur. J. Biochem*. 2000, 267, 3289–3300) have revealed, that an increase in the conformational rigidity, resulting from backbone cyclization and multiple disulfide bridges, may confer membranolytic selectivity that dissociates antimicrobial activity from hemolytic activity, at least in the series of compounds studied. Protegrin 1 is an 18 residues linear peptide, with an amidated carboxyl terminus and two disulfide bridges. Tachyplesin I contains 17 residues, also has an amidated carboxyl terminus and contains two disulfide bridges. Recently described backbone-cyclic protegrin and tachyplesin analogues typically contain 18 residues and up to three disulfide bridges (J. P. Tam, C. Wu, J.-L. Yang, *Eur. J. Biochem*. 2000, 267, 3289–3300; J. P. Tam, Y.-A. Lu, J.-L. Yang, *Biochemistry* 2000, 39, 7159–7169; N. Sitaram, R. Nagaraij, *Biochem. Biophys. Res. Comm*. 2000, 267, 783–790).

Cathelicidin, a 37-residue linear helical-type cationic peptide, and analogues are currently under investigation as inhaled therapeutic agents for cystic fibrosis (CF) lung disease (L. Saiman, S. Tabibi, T. D. Starner, P. San Gabriel, P. L. Winokur, H. P. Jia, P. B. McGray, Jr., B. F. Tack, *Antimicrob. Agents and Chemother*. 2001, 45, 2838–2844; R. E. W. Hancock, R. Lehrer, *Trends Biotechnol*. 1998, 16, 82–88). Over 80% of CF patients become chronically infected with *pseudomonas aeruginosa* (C. A. Demko, P. J. Biard, P. B. Davies, *J. Clin. Epidemiol*. 1995, 48, 1041–1049; E. M. Kerem, R. Gold, H. Levinson, *J. Pediatr*. 1990, 116, 714–719).

In addition, there is evidence from the literature that some cationic peptides exibit interesting anticancer activity. Cerecropin B, a 35-residue α-helical cationic peptide isolated from the hemolymph of the giant silk moth, and shorter analogues derived from Cerecropin B have been investigated as potential anticancer compounds (A. J. Moore, D. A. Devine, M. C. Bibby, *Peptide Research* 1994, 7, 265–269).

SUMMARY OF THE INVENTION

In the compounds described below, a new strategy is introduced to stabilize β-hairpin conformations in backbone-cyclic cationic peptide mimetic exhibiting antimicrobial and anticancer activity. This involves transplanting the cationic and hydrophobic hairpin sequence onto a template, whose function is to restrain the peptide loop backbone into a hairpin geometry. The rigidity of the hairpin may be further influenced by introducing a disulfide bridge. The template moiety may also act as an attachment point for other organic groups, that may modulate the antimicrobial and/or membranolytic targeting selectivity of the molecule, and be useful for producing dimeric species, where the templates in each monomer unit are linked through a short spacer or linker. Template-bound hairpin mimetic peptides have been described in the literature (D, Obrecht, M. Altorfer, J. A. Robinson, *Adv. Med. Chem*. 1999, 4, 1–68; J. A. Robinson, *Syn. Lett*. 2000, 4, 429–441), but such molecules have not previously been evaluated for development of antimicrobial peptides. However, the ability to generate β-hairpin peptidomimetics using combinatorial and parallel synthesis methods has now been established (L. Jiang, K. Moehle, B. Dhanapal, D. Obrecht, J. A. Robinson, *Helv. Chim. Acta*. 2000, 83, 3097–3112).

These methods allow the synthesis and screening of large hairpin mimetic libraries, which in turn considerably facilitates structure-activity studies, and hence the discovery of new molecules with potent antimicrobial and anticancer activity and low hemolytic activity to human red blood cells. Furthermore, the present strategy allows to synthesize β-hairpin peptidomimetics with novel selectivities towards different types of pathogens, e.g. towards various multi-rug resistant *pseudomonas* strains. β-Hairpin peptidomimetics obtained by the approach described here can be used amongst other applications, e.g. as broad spectrum antibiotics, as therapeutics for cystic fibrosis lung disease and anticancer agents.

The β-hairpin peptidomimetics of the present invention are compounds of the general formulae

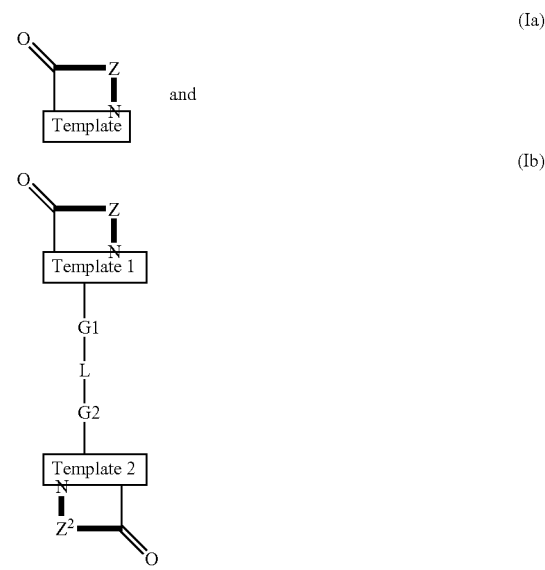

wherein
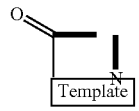
is a group of one of the formulae
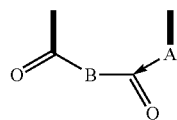
(a1)
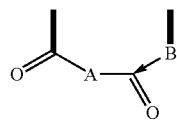
(a2)
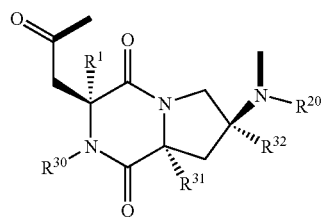
(b1)
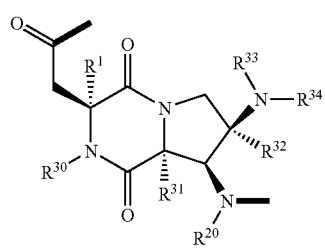
(b2)
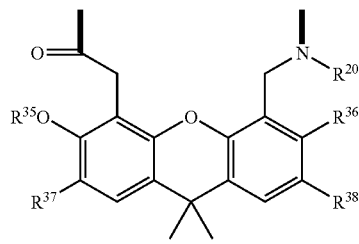
(c1)
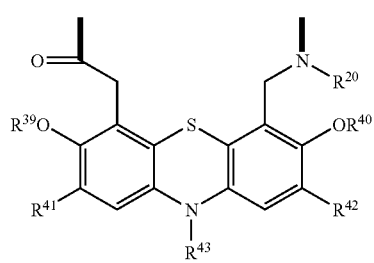
(c2)
-continued
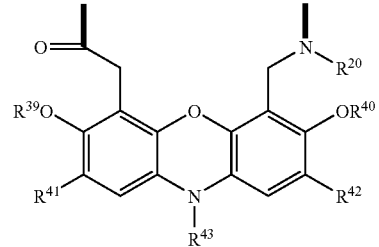
(c3)
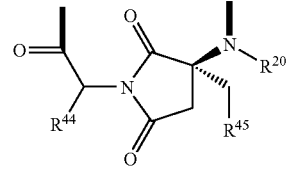
(d)
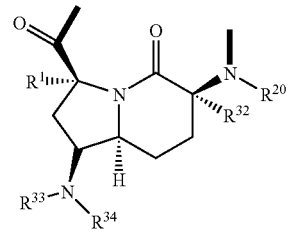
(e1)
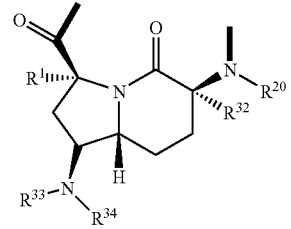
(e2)
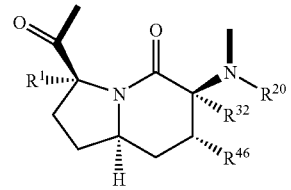
(e3)
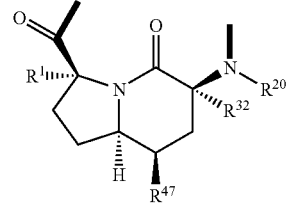
(e4)
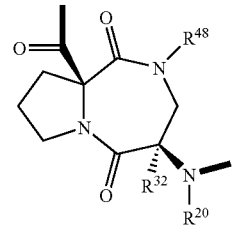
(f)

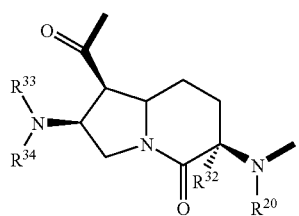
(g)
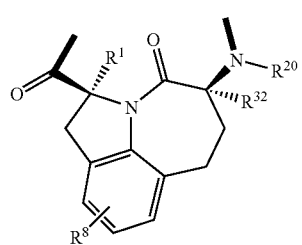
(h)
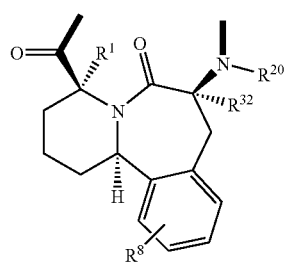
(i1)
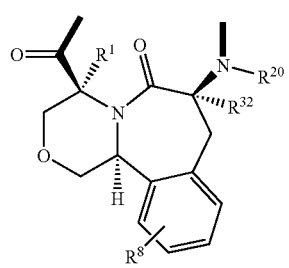
(i2)
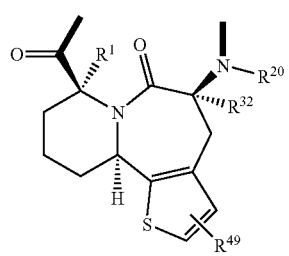
(i3)
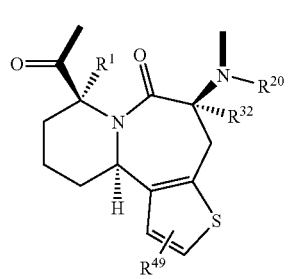
(i4)
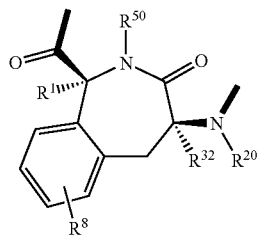
(j)
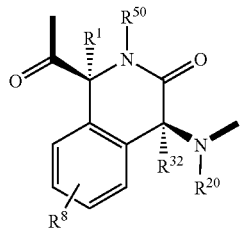
(k)
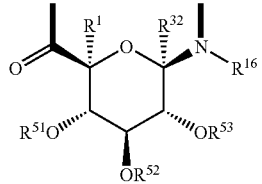
(l)
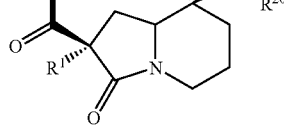
(m)
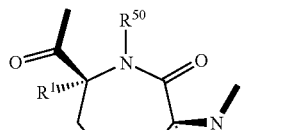
(n)
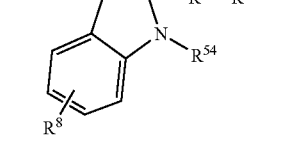
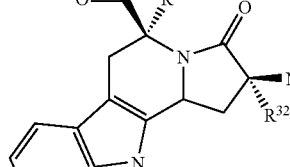
(o)
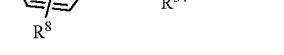
and -continued
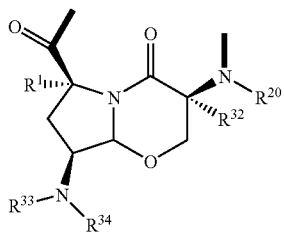
(p)
wherein
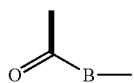
is the residue of an L-α-amino acid with B being a residue of formula —NR$^{20}$CH(R$^{71}$)— or the enantiomer of one of the groups A1 to A69 as defined hereinafter;
is a group of one of the formulae
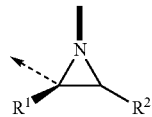
A1
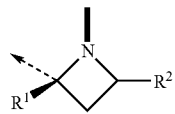
A2
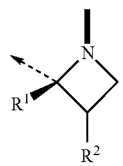
A3
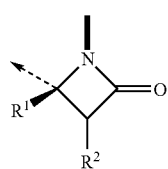
A4
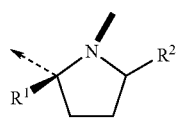
A5
-continued
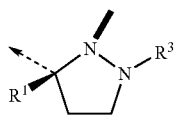
A6
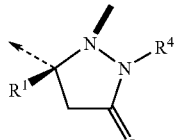
A7
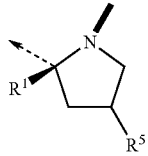
A8
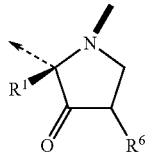
A9
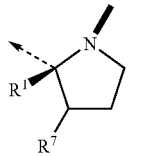
A10
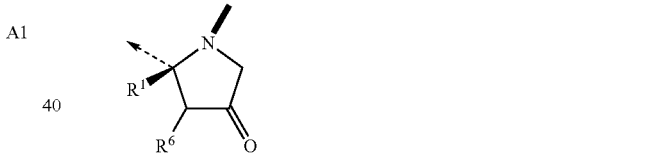
A11
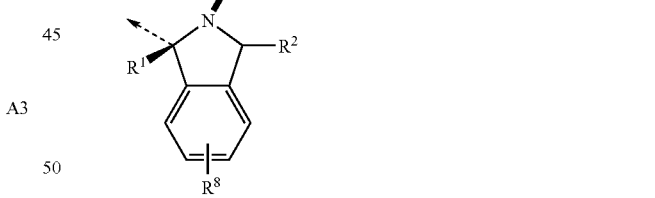
A12
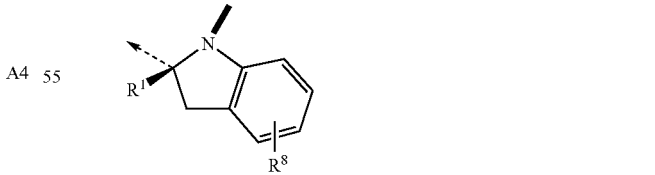
A13
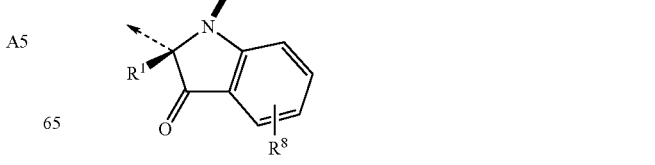
A14

-continued
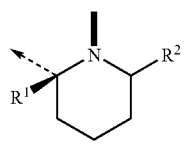
A15
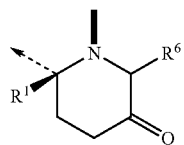
A16
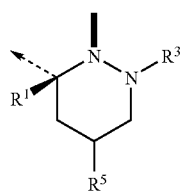
A17
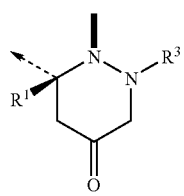
A18
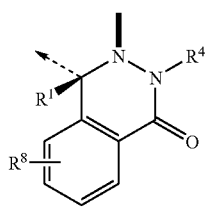
A19
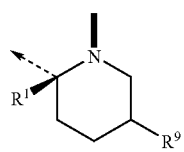
A20
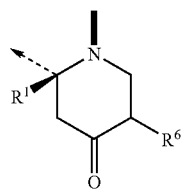
A21
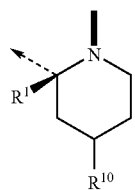
A22
-continued
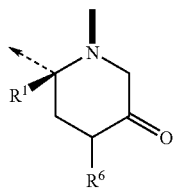
A23
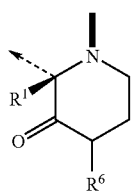
A24
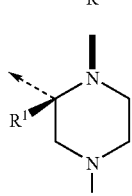
A25
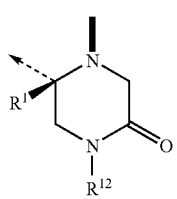
A26
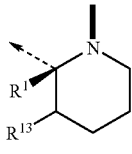
A27
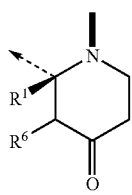
A28
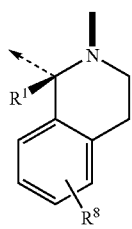
A29
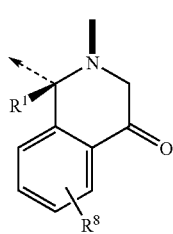
A30

-continued
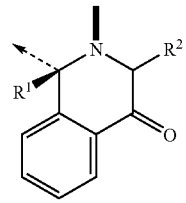 A31
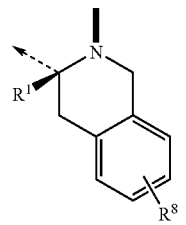 A32
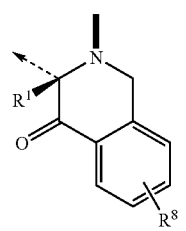 A33
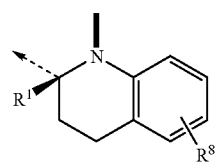 A34
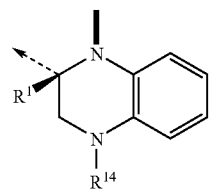 A35
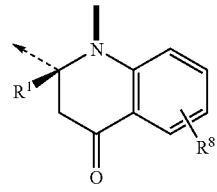 A36
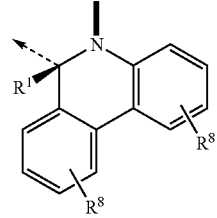 A37
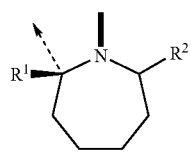 A38
-continued
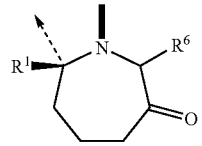 A39
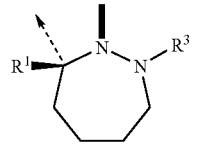 A40
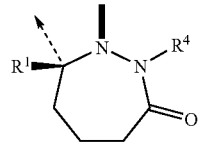 A41
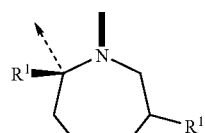 A42
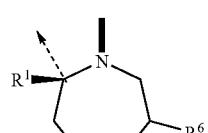 A43
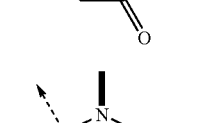 A44
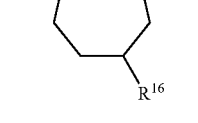 A45
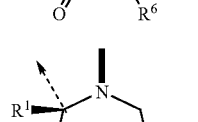 A46
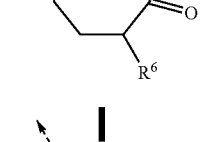 A47

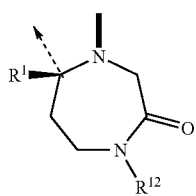 A48
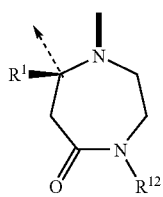 A49
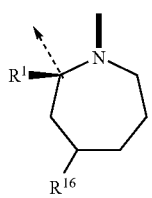 A50
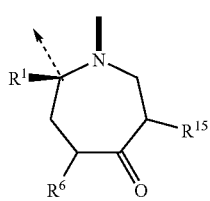 A51
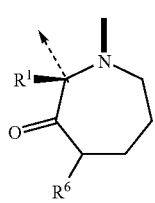 A52
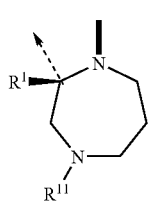 A53
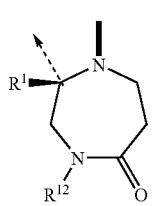 A54
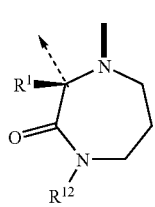 A55
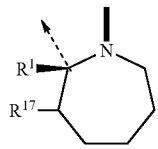 A56
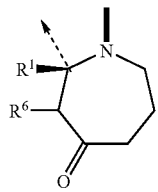 A57
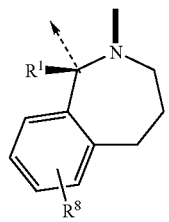 A58
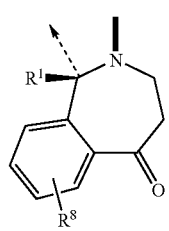 A59
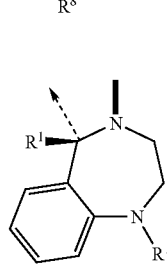 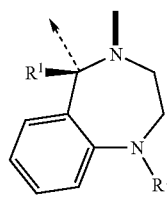 A60
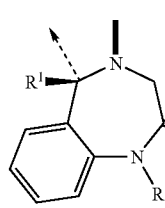 A61
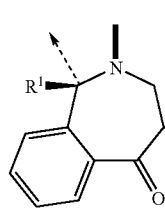 A62

-continued
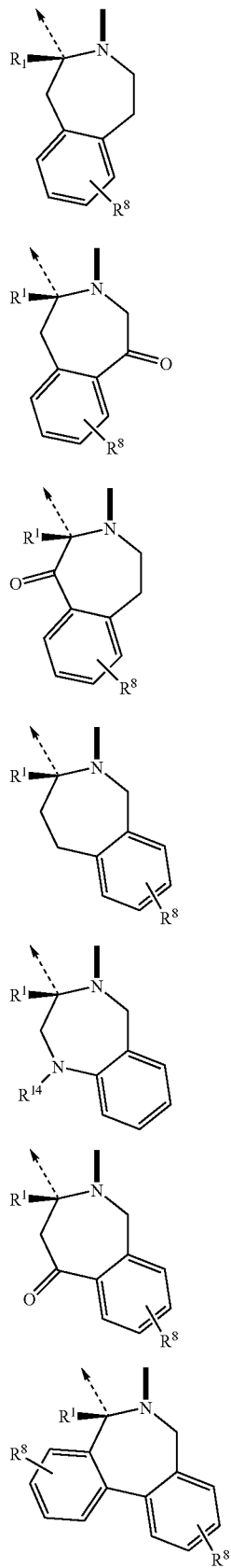
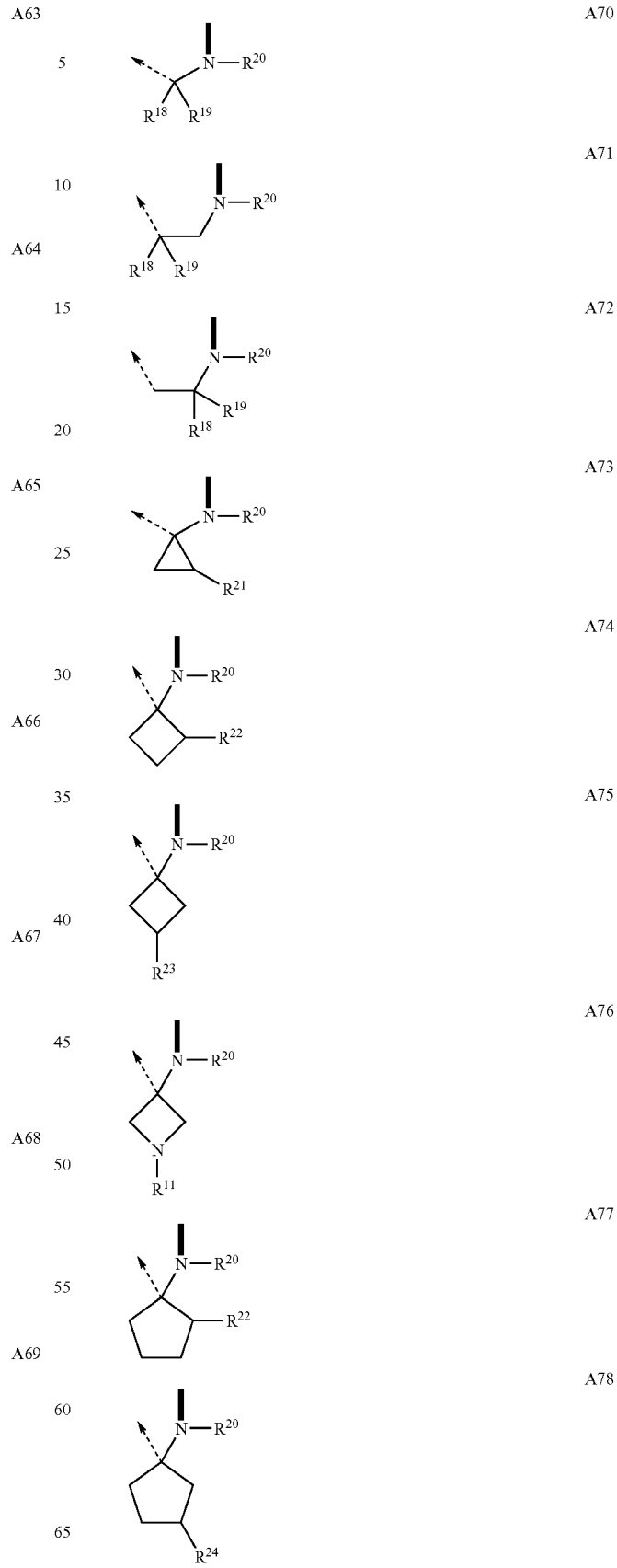

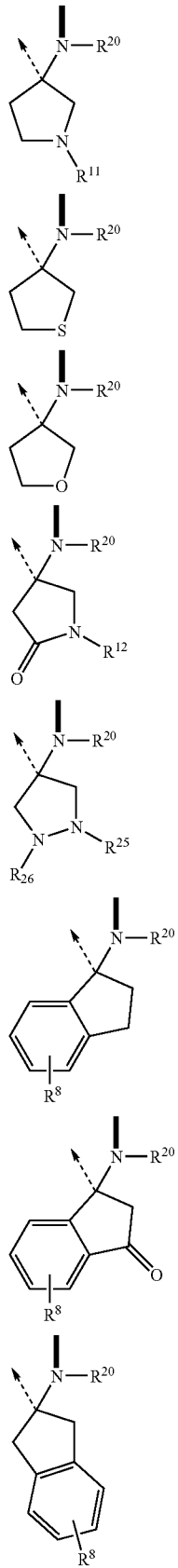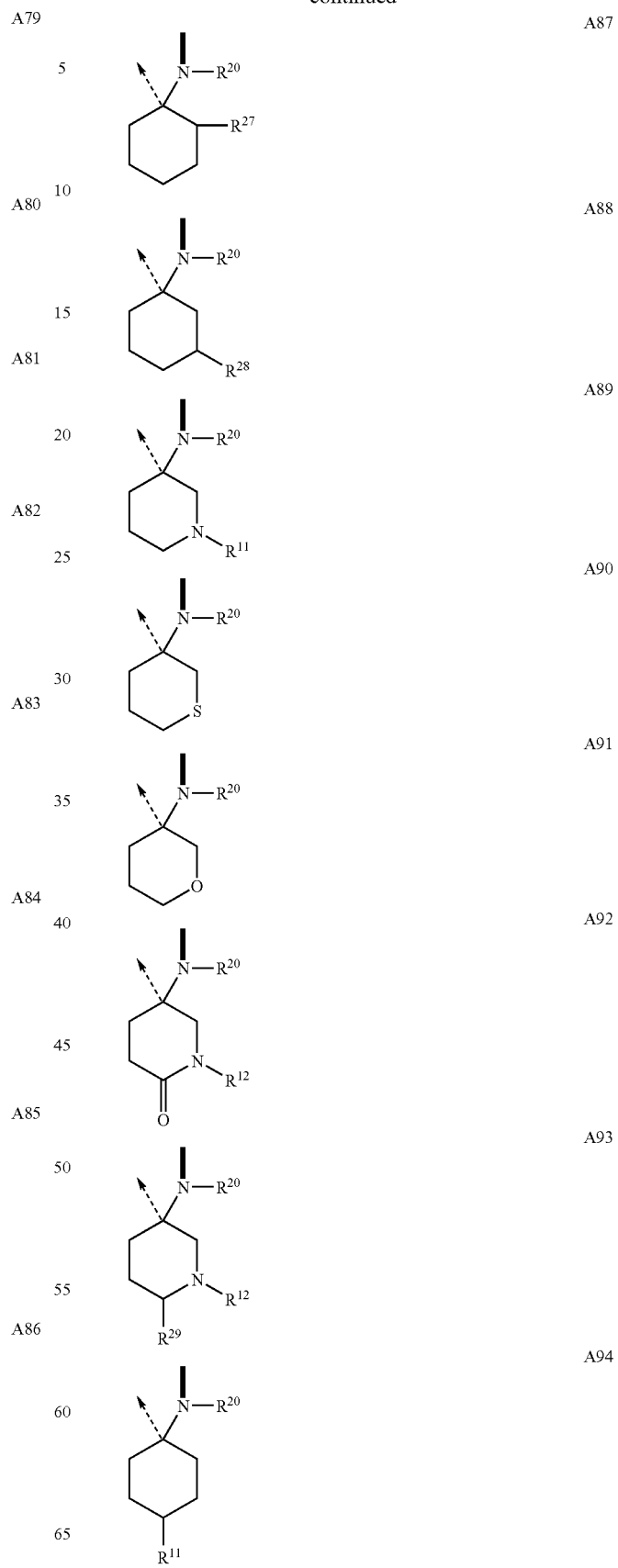

-continued

A95 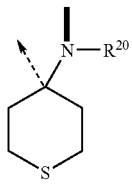

A96 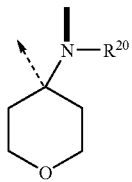

A97 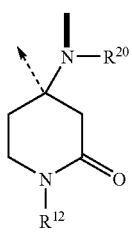

A98 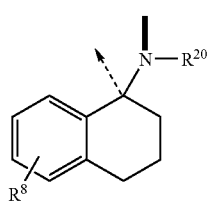

A99 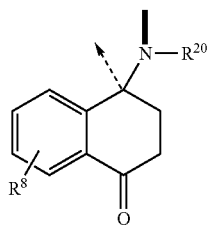

A100 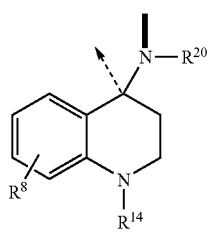

A101 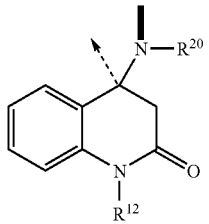

-continued

A102 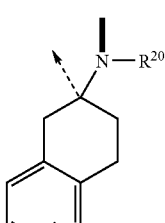

A103 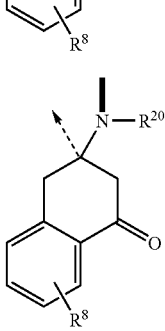

and

A104 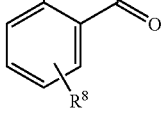

$R^1$ is H; lower alkyl; or aryl-lower allyl;

$R^2$ is H; allyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^3$ is H; allyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^4$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_p(CHR^{61})_sCOOR^{57}$; —$(CH_2)_p(CHR^{61})_sCONR^{58}R^{59}$; —$(CH_2)_p(CHR^{61})_sPO(OR^{60})_2$; —$(CH_2)_p(CHR^{61})_sSO_2R^{62}$; or —$(CH_2)_o(CHR^{61})_sC_6H_4R^8$;

$R^5$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^6$ is H; alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$;

—(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^7$ is alkyl; alkenyl; —(CH$_2$)$_q$(CHR$^{61}$)$_s$OR$^{55}$; —(CH$_2$)$_q$(CHR$^{61}$)$_s$NR$^{33}$R$^{34}$; —(CH$_2$)$_q$(CHR$^{61}$)$_s$OCONR$^{33}$R$^{75}$; —(CH$_2$)$_q$(CHR$^{61}$)$_s$NR$^{20}$CONR$^{33}$R$^{82}$; —(CH$_2$)$_q$(CHR$^{61}$)$_s$COOR$^{57}$; —(CH$_2$)$_r$(CHR$^{61}$)$_s$CONR$^{58}$R$^{59}$; —(CH$_2$)$_r$(CHR$^{61}$)$_s$PO(OR$^{60}$)$_2$; —(CH$_2$)$_r$(CHR$^{61}$)$_s$SO$_2$R$^{62}$; or —(CH$_2$)$_r$(CHR$^{61}$)$_s$C$_6$H$_4$R$^8$;

R$^8$ is H; Cl; F; CF$_3$; NO$_2$; lower alkyl; lower alkenyl; aryl; aryl-lower alkyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$COR$^{64}$;

R$^9$ is alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{10}$ is alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{11}$ is H; alkyl; alkenyl; —(CH$_2$)$_m$(CHR$^{61}$)$_s$OR$^{55}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{69}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_5$H$_4$R$^8$;

R$^{12}$ is H; alkyl; alkenyl; —(CH$_2$)$_m$(CHR$^{61}$)$_s$OR$^{55}$; —(CH$_2$)$_m$(CHR$^{61}$)$_s$SR$^{56}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_r$(CHR$^{61}$)$_s$COOR$^{57}$; —(CH$_2$)$_r$(CHR$^{61}$)$_s$CONR$^{58}$R$^{59}$; —(CH$_2$)$_r$(CHR$^{61}$)$_s$PO(OR$^{60}$)$_2$; —(CH$_2$)$_r$(CHR$^{61}$)$_s$SO$_2$R$^{62}$; or —(CH$_2$)$_r$(CHR$^{61}$)$_s$C$_6$H$_4$R$^8$;

R$^{13}$ is alkyl; alkenyl; —(CH$_2$)$_q$(CHR$^{61}$)$_s$OR$^{55}$; —(CH$_2$)$_q$(CHR$^{61}$)$_s$SR$^{56}$; —(CH$_2$)$_q$(CHR$^{61}$)$_s$NR$^{33}$R$^{34}$; —(CH$_2$)$_q$(CHR$^{61}$)$_s$OCONR$^{33}$R$^{75}$; —(CH$_2$)$_q$(CHR$^{61}$)$_s$NR$^{20}$CONR$^{33}$R$^{82}$; —(CH$_2$)$_q$(CHR$^{61}$)$_s$COOR$^{57}$; —(CH$_2$)$_q$(CHR$^{61}$)$_s$CONR$^{58}$R$^{59}$; —(CH$_2$)$_q$(CHR$^{61}$)$_s$PO(OR$^{60}$)$_2$; —(CH$_2$)$_q$(CHR$^{61}$)$_s$SO$_2$R$^{62}$; or —(CH$_2$)$_q$(CHR$^{61}$)$_s$C$_6$H$_4$R$^8$;

R$^{14}$ is H; alkyl; alkenyl; —(CH$_2$)$_m$(CHR$^{61}$)$_s$OR$^{55}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_q$(CHR$^{61}$)$_s$COOR$^{57}$; —(CH$_2$)$_q$(CHR$^{61}$)$_s$CONR$^{58}$R$^{59}$; —(CH$_2$)$_q$(CHR$^{61}$)$_s$PO(OR$^{60}$)$_2$; —(CH$_2$)$_q$(CHR$^{61}$)$_s$SOR$^{62}$; or —(CH$_2$)$_q$(CHR$^{61}$)$_s$C$_6$H$_4$R$^8$;

R$^{15}$ is alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_q$(CHR$^{61}$)$_s$SO$_2$R$^{62}$; or —(CH$_2$)$_o$(CHR$^{61}$)$_s$C$_6$H$_4$R$^8$;

R$^{16}$ is —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{17}$ is alkyl; alkenyl; —(CH$_2$)$_q$(CHR$^{61}$)$_s$OR$^{55}$; —(CH$_2$)$_q$(CHR$^{61}$)$_s$SR$^{56}$; —(CH$_2$)$_q$(CHR$^{61}$)$_s$NR$^{33}$R$^{34}$; —(CH$_2$)$_q$(CHR$^{61}$)$_s$OCONR$^{33}$R$^{75}$; —(CH$_2$)$_q$(CHR$^{61}$)$_s$NR$^{20}$CONR$^{33}$R$^{82}$; —(CH$_2$)$_q$(CHR$^{61}$)$_s$COOR$^{57}$; —(CH$_2$)$_q$(CHR$^{61}$)$_s$CONR$^{58}$R$^{59}$; —(CH$_2$)$_q$(CHR$^{61}$)$_s$PO(OR$^{60}$)$_2$; —(CH$_2$)$_q$(CHR$^{61}$)$_s$SO$_2$R$^{62}$; or —(CH$_2$)$_q$(CHR$^{61}$)$_s$C$_6$H$_4$R$^8$;

R$^{18}$ is alkyl; alkenyl; —(CH$_2$)$_p$(CHR$^{61}$)$_s$OR$^{55}$; —(CH$_2$)$_p$(CHR$^{61}$)$_s$SR$^{56}$; —(CH$_2$)$_p$(CHR$^{61}$)$_s$NR$^{33}$R$^{34}$; —(CH$_2$)$_p$(CHR$^{61}$)$_s$OCONR$^{33}$R$^{75}$; —(CH$_2$)$_p$(CHR$^{61}$)$_s$NR$^{20}$CONR$^{33}$R$^{82}$; —(CH$_2$)$_p$(CHR$^{61}$)$_s$COOR$^{57}$; —(CH$_2$)$_p$(CHR$^{61}$)$_s$CONR$^{58}$R$^{59}$; —(CH$_2$)$_p$(CHR$^{61}$)$_s$PO(OR$^{60}$)$_2$; —(CH$_2$)$_p$(CHR$^{61}$)$_s$SO$_2$R$^{62}$; or —(CH$_2$)$_o$(CHR$^{61}$)$_s$C$_6$H$_4$R$^8$;

R$^{19}$ is lower alkyl; —(CH$_2$)$_p$(CHR$^{61}$)$_s$OR$^{55}$; —(CH$_2$)$_p$(CHR$^{61}$)$_s$SR$^{56}$; —(CH$_2$)$_p$(CHR$^{61}$)$_s$NR$^{33}$R$^{34}$; —(CH$_2$)$_p$(CHR$^{61}$)$_s$OCONR$^{33}$R$^{75}$; —(CH$_2$)$_p$(CHR$^{61}$)$_s$NR$^{20}$CONR$^{33}$R$^{82}$; —(CH$_2$)$_p$(CHR$^{61}$)$_s$COOR$^{57}$; —(CH$_2$)$_p$(CHR$^{61}$)$_s$CONR$^{58}$R$^{59}$; —(CH$_2$)$_p$(CHR$^{61}$)$_s$PO(OR$^{60}$)$_2$; —(CH$_2$)$_p$(CHR$^{61}$)$_s$SO$_2$R$^{62}$; or —(CH$_2$)$_o$(CHR$^{61}$)$_s$C$_6$H$_4$R$^8$; or R$^{18}$ and R$^{19}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;

R$^{20}$ is H; alkyl; alkenyl; or aryl-lower alkyl;

R$^{21}$ is H; alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{22}$ is H; alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{23}$ is alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{24}$ is alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$))$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{25}$ is H; alkyl; alkenyl; —(CH$_2$)$_m$(CHR$^{61}$)$_s$OR$^{55}$; —(CH$_2$)$_m$(CHR$^{61}$)$_s$SR$^{56}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{26}$ is H; alkyl; alkenyl; —(CH$_2$)$_m$(CHR$^{61}$)$_s$OR$^{55}$; —(CH$_2$)$_m$(CHR$^{61}$)$_s$SR$^{56}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_o$(CHR$^{61}$)$_s$COOR$^{57}$;

—(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$; or

R$^{25}$ and R$^{26}$ taken together can form: —(CH$_2$)$_{2-6}$—; —(CH$_2$)$_r$O(CH$_2$)$_r$—; —(CH$_2$)$_r$S(CH$_2$)$_r$—; or —(CH$_2$)$_r$R$^{57}$(CH$_2$)$_r$—;

R$^{27}$ is H; alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{28}$ is alkyl; alkenyl; —(CH$_2$)$_o$(CHR$^{61}$)$_s$—OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{29}$ is alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$ SO$_2$R$^{62}$; or —(CH$_2$)$_o$(CHR$^{61}$)$_s$C$_6$H$_4$R$^8$;

R$^{30}$ is H; alkyl; alkenyl; or aryl-lower alkyl;

R$^{31}$ is H; alkyl; alkenyl; —(CH$_2$)$_p$(CHR$^{61}$)$_s$OR$^{55}$; —(CH$_2$)$_p$(CHR$^{61}$)$_s$NR$^{33}$R$^{34}$; —(CH$_2$)$_p$(CHR$^{61}$)$_s$OCONR$^{33}$R$^{75}$; —(CH$_2$)$_p$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{32}$ is H; lower alkyl; or aryl-lower alkyl;

R$^{33}$ is H; alkyl, alkenyl; —(CH$_2$)$_m$(CHR$^{61}$)$_s$OR$^{55}$; —(CH$_2$)$_m$(CHR$^{61}$)$_s$NR$^{34}$R$^{63}$; —(CH$_2$)$_m$(CHR$^{61}$)$_s$OCONR$^{75}$R$^{82}$; —(CH$_2$)$_m$(CHR$^{61}$)$_s$NR$^{20}$CONR$^{78}$R$^{82}$; —(CH$_2$)$_o$(CHR$^{61}$)$_s$COR$^{64}$; —(CH$_2$)$_o$(CHR$^{61}$)$_s$CONR$^{58}$R$^{59}$, —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{34}$ is H; lower alkyl; aryl, or aryl-lower alkyl;

R$^{33}$ and R$^{34}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;

R$^{35}$ is H; alkyl; alkenyl; —(CH$_2$)$_m$(CHR$^{61}$)$_s$OR$^{55}$; —(CH$_2$)$_m$(CHR$^{61}$)$_s$NR$^{33}$R$^{34}$; —(CH$_2$)$_m$(CHR$^{61}$)$_s$CONR$^{33}$R$^{75}$; —(CH$_2$)$_m$(CHR$^{61}$)$_s$NR$^{20}$CONR$^{33}$R$^{82}$; —(CH$_2$)$_p$(CHR$^{61}$)$_s$COOR$^{57}$; —(CH$_2$)$_p$(CHR$^{61}$)$_s$CONR$^{58}$R$^{59}$; —(CH$_2$)$_p$(CHR$^{61}$)$_s$PO(OR$^{60}$)$_2$; —(CH$_2$)$_p$(CHR$^{61}$)$_s$SO$_2$R$^{62}$; or —(CH$_2$)$_p$(CHR$^{61}$)$_s$C$_6$H$_4$R$^8$;

R$^{36}$ is H, alkyl; alkenyl; —(CH$_2$)$_p$(CHR$^{61}$)$_s$OR$^{55}$; —(CH$_2$)$_p$(CHR$^{61}$)$_s$NR$^{33}$R$^{34}$; —(CH$_2$)$_p$(CHR$^{61}$)$_s$OCONR$^{33}$R$^{75}$; —(CH$_2$)$_p$(CHR$^{61}$)$_s$NR$^{20}$CONR$^{33}$R$^{82}$; —(CH$_2$)$_p$(CHR$^{61}$)$_s$COOR$^{57}$; —(CH$_2$)$_p$(CHR$^{61}$)$_s$CONR$^{58}$R$^{59}$; —(CH$_2$)$_p$(CHR$^{61}$)$_s$PO(OR$^{60}$)$_2$; —(CH$_2$)$_p$(CHR$^{61}$)$_s$SO$_2$R$^{62}$; or —(CH$_2$)$_o$(CHR$^{61}$)$_s$C$_6$H$_4$R$^8$;

R$^{37}$ is H; F; Br, Cl; NO$_2$; CF$_3$; lower alkyl; —(CH$_2$)$_p$(CHR$^{61}$)$_s$OR$^{55}$; —(CH$_2$)$_p$(CH$_{61}$)$_s$NR$^{33}$R$^{34}$; —(CH$_2$)$_p$(CHR$^{61}$)$_s$OCONR$^{33}$R$^{75}$; —(CH$_2$)$_p$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{38}$ is H; F; Br, Cl; NO$_2$; CF$_3$; alkyl; alkenyl; —(CH$_2$)$_p$(CHR$^{61}$)$_s$OR$^{55}$; —(CH$_2$)$_p$(CHR$^{61}$)$_s$NR$^{33}$R$^{34}$; —(CH$_2$)$_p$(CHR$^{61}$)$_s$OCONR$^{33}$R$^{75}$; —(CH$_2$)$_p$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{39}$ is H; alkyl; alkenyl; or aryl-lower alkyl;

R$^{40}$ is H; alkyl; alkenyl; or aryl-lower alkyl;

R$^{41}$ is H; F; Br, Cl; NO$_2$; CF$_3$; alkyl; alkenyl; —(CH$_2$)$_p$(CHR$^{61}$)$_s$OR$^{55}$; —(CH$_2$)$_p$(CHR$^{61}$)$_s$NR$^{33}$R$^{34}$; —(CH$_2$)$_p$(CHR$^{61}$)$_s$OCONR$^{33}$R$^{75}$; —(CH$_2$)$_p$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{42}$ is H; F; Br, Cl; NO$_2$; CF$_3$; alkyl; alkenyl; —(CH$_2$)$_p$(CHR$^{61}$)$_s$OR$^{55}$; —(CH$_2$)$_p$(CHR$^{61}$)$_s$NR$^{33}$R$^{34}$; —(CH$_2$)$_p$(CHR$^{61}$)$_s$OCONR$^{33}$R$^{75}$; —(CH$_2$)$_p$(CHR$^{61}$)$_s$NR$^{20}$CONR$^{35}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{43}$ is H; alkyl; alkenyl; —(CH$_2$)$_m$(CHR$^{61}$)$_s$OR$^{55}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{44}$ is alkyl; alkenyl; —(CH$_2$)$_r$(CHR$^{61}$)$_s$OR$^{55}$; —(CH$_2$)$_r$(CHR$^{61}$)$_s$SR$^{56}$; —(CH$_2$)$_r$(CHR$^{61}$)$_s$NR$^{33}$R$^{34}$; —(CH$_2$)$_r$(CHR$^{61}$)$_s$OCONR$^{33}$R$^{75}$; —(CH$_2$)$_r$(CHR$^{61}$)$_s$NR$^{20}$CONR$^{33}$R$^{82}$; —(CH$_2$)$_r$(CHR$^{61}$)$_s$COOR$^{57}$; —(CH$_2$)$_r$(CHR$^{61}$)$_s$CONR$^{58}$R$^{59}$; —(CH$_2$)$_r$(CHR$^{61}$)$_s$PO(OR$^{60}$)$_2$; —(CH$_2$)$_r$(CHR$^{61}$)$_s$SO$_2$R$^{62}$; or —(CH$_2$)$_r$(CHR$^{61}$)$_s$C$_6$H$_4$R$^8$;

R$^{45}$ is H; alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$^2$)$_s$(CHR$^{61}$)$_s$CONR$^{58}$R$^{59}$; —(CH$_2$)$_s$(CHR$^{61}$)$_s$PO(OR$^{60}$)$_2$; —(CH$_2$)$_s$(CHR$^{61}$)$_s$SO$_2$R$^{62}$; or —(CH$_2$)$_o$(CHR$^{61}$)$_s$C$_6$H$_4$R$^8$;

R$^{46}$ is H; alkyl; alkenyl; or —(CH$_2$)$_o$(CHR$^{61}$)$_p$C$_6$H$_4$R$^8$;

R$^{47}$ is H; alkyl; alkenyl; or —(CH$_2$)$_o$(CHR$^{61}$)$_s$OR$^{55}$;

R$^{48}$ is H; lower alkyl; lower alkenyl; or aryl-lower alkyl;

R$^{49}$ is H; alkyl; alkenyl; —(CHR$^{61}$)$_s$COOR$^{57}$; (CHR$^{61}$)$_s$CONR$^{58}$R$^{59}$; (CHR$^{61}$)$_s$PO(OR$^{60}$)$_2$; —(CHR$^{61}$)$_s$SOR$^{62}$; or —(CHR$^{61}$)$_s$C$_6$H$_4$R$^8$;

R$^{50}$ is H; lower alkyl; or aryl-lower allyl;

R$^{57}$ is H; alkyl; alkenyl; —(CH$_2$)$_m$(CHR$^{61}$)$_s$OR$^{55}$; —(CH$_2$)$_m$(CHR$^{61}$)$_s$SR$^{56}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_p$PO(OR$^{60}$)$_2$; —(CH$_2$)$_p$(CHR$^{61}$)$_s$SO$_2$R$^{62}$; or —(CH$_2$)$_p$(CHR$^{61}$)$_s$C$_6$H$_4$R$^8$;

R$^{52}$ is H; alkyl; alkenyl; —(CH$_2$)$_m$(CHR$^{61}$)$_s$OR$^{55}$; —(CH$_2$)$_m$(CHR$^{61}$)$_s$SR$^{56}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_p$PO(OR$^{60}$)$_2$; —(CH$_2$)$_p$(CHR$^{61}$)$_s$SO$_2$R$^{62}$; or —(CH$_2$)$_p$(CHR$^{61}$)$_s$C$_6$H$_4$R$^8$;

R$^{53}$ is H; alkyl; alkenyl; —(CH$_2$)$_m$(CHR$^{61}$)$_s$OR$^{55}$; —(CH$_2$)$_m$(CHR$^{61}$)$_s$SR$^{56}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_o$(CHR$^{61}$)$_s$COOR$^{57}$;

—(CH$_2$)$_o$(CHR$^{61}$)$_s$CONR$^{58}$R$^{59}$; —(CH$_2$)$_o$(CHR$^{61}$)$_p$PO(OR$^{60}$)$_2$; —(CH$_2$)$_p$(CHR$^{61}$)$_s$SO$_2$R$^{62}$; or —(CH$_2$)$_p$(CHR$^{61}$)$_s$C$_6$H$_4$R$^8$;

R$^{54}$ is H; alkyl; alkenyl; —(CH$_2$)$_m$(CHR$^{61}$)$_s$OR$^{55}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_o$(CHR$^{61}$)COOR$^{57}$; —(CH$_2$)$_o$(CHR$^{61}$)$_s$CONR$^{58}$R$^{59}$; or —(CH$_2$)$_o$(CHR$^{61}$)$_s$C$_6$H$_4$R$^8$;

R$^{55}$ is H; lower alkyl; lower alkenyl; aryl-lower alkyl; —(CH$_2$)$_m$(CHR$^{61}$)$_s$OR$^{57}$; —(CH$_2$)$_m$(CHR$^{61}$)$_s$NR$^{34}$R$^{63}$; —(CH$_2$)$_m$(CHR$^{61}$)$_s$OCONR$^{75}$R$^{82}$; —(CH$_2$)$_m$(CHR$^{61}$)$_s$NR$^{20}$CONR$^{78}$R$^{82}$; —(CH$_2$)$_o$(CHR$^{61}$)$_s$—COR$^{64}$; —(CH$_2$)$_o$(CHR$^{61}$)COOR$^{57}$; or —(CH$_2$)$_o$(CHR$^{61}$)$_s$CONR$^{58}$R$^{59}$;

R$^{56}$ is H; lower alkyl; lower alkenyl; aryl-lower allyl; —(CH$_2$)$_m$(CHR$^{61}$)$_s$OR$^{57}$; —(CH$_2$)$_m$(CHR$^{61}$)$_s$NR$^{34}$R$^{63}$; —(CH$_2$)$_m$(CHR$^{61}$)$_s$OCONR$^{75}$R$^{82}$; —(CH$_2$)$_m$(CHR$^{61}$)$_s$NR$^{20}$CONR$^{78}$R$^{82}$; —(CH$_2$)$_o$(CHR$^{61}$)$_s$—COR$^{64}$; or —(CH$_2$)$_o$(CHR$^{61}$)$_s$CONR$^{58}$R$^{59}$;

R$^{57}$ is H; lower alkyl; lower alkenyl; aryl lower alkyl; or heteroaryl lower alkyl;

R$^{58}$ is H; lower alkyl; lower alkenyl; aryl; heteroaryl; aryl-lower alkyl; or heteroaryl-lower alkyl;

R$^{59}$ is H; lower alkyl; lower alkenyl; aryl; heteroaryl; aryl-lower alkyl; or heteroaryl-lower alkyl; or R$^{58}$ and R$^{59}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;

R$^{60}$ is H; lower alkyl; lower alkenyl; aryl; or aryl-lower alkyl;

R$^{61}$ is alkyl; alkenyl; aryl; heteroaryl; aryl-lower alkyl; heteroaryl-lower alkyl; —(CH$_2$)$_m$OR$^{55}$; —(CH$_2$)$_m$NR$^{33}$R$^{34}$; —(CH$_2$)$_m$OCONR$^{75}$R$^{82}$; —(CH$_2$)$_m$NR$^{20}$CONR$^{78}$R$^{82}$; —(CH$_2$)$_o$COOR$^{37}$; —(CH$_2$)$_o$R$^{58}$R$^{59}$; or —(CH$_2$)$_o$PO(COR$^{60}$)$_2$;

R$^{62}$ is lower alkyl; lower alkenyl; aryl, heteroaryl; or aryl-lower alkyl;

R$^{63}$ is H; lower alkyl; lower alkenyl; aryl; heteroaryl; aryl-lower alkyl; heteroaryl-lower alkyl; —COR$^{64}$; —COOR$^{57}$; —CONR$^{58}$R$^{59}$; —SO$_2$R$^{62}$; or —PO(OR$^{60}$)$_2$;

R$^{34}$ and R$^{63}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;

R$^{64}$ is H; lower alkyl; lower alkenyl; aryl; heteroaryl; aryl-lower alkyl; heteroaryl-lower alkyl; —(CH$_2$)$_p$(CHR$^{61}$)$_s$OR$^{65}$; —(CH$_2$)$_p$(CHR$^{61}$)$_s$SR$^{66}$; or —(CH$_2$)$_p$(CHR$^{61}$)$_s$NR$^{34}$R$^{63}$; —(CH$_2$)$_p$(CHR$^{61}$)$_s$OCONR$^{75}$R$^{82}$; —(CH$_2$)$_p$(CHR$^{61}$)$_s$NR$^{20}$CONR$^{78}$R$^{82}$;

R$^{65}$ is H; lower alkyl; lower alkenyl; aryl, aryl-lower alkyl; heteroaryl-lower alkyl; —COR$^{57}$; —COOR$^{57}$; or —CONR$^{58}$R$^{59}$;

R$^{65}$ is H; lower alkyl; lower alkenyl; aryl; aryl-lower alkyl; heteroaryl-lower alkyl; or —CONR$^{58}$R$^{59}$;

m is 2–4; o is 0–4; p is 1–4; q is 0–2; r is 1 or 2; s is 0 or 1;

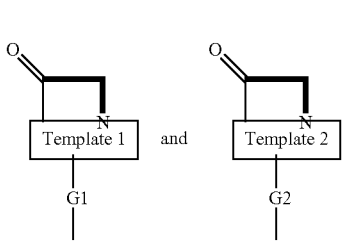

independently have any of the significances defined above for

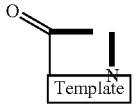

except (a1) or (a2) with B being —NR$^{20}$CH(R$^{71}$)— and with A being A80, A81, A90, A91, A95 or A96, and except (f) and (m), but wherein R$^2$ is —(CH$_2$)$_m$(CHR$^{61}$)$_s$O—; —(CH$_2$)$_m$(CHR$^{61}$)$_s$S—; —(CH$_2$)$_m$(CHR$^{61}$)$_s$NR$^{34}$—; or —(CH$_2$)$_o$(CHR$^{61}$)$_s$CO—;

R$^3$ is —(CH$_2$)$_m$(CHR$^{61}$)$_s$O—; —(CH$_2$)$_m$(CHR$^{61}$)$_s$S—; —(CH$_2$)$_m$(CHR$^{61}$)$_s$NR$^{34}$—; or —(CH$_2$)$_o$(CHR$^{61}$)$_s$CO—;

R$^4$ is —(CH$_2$)$_m$(CHR$^{61}$)$_s$O—; —(CH$_2$)$_m$(CHR$^{61}$)$_s$S—; —(CH$_2$)$_m$(CHR$^{61}$)$_s$NR$^3$—; or —(CH$_2$)$_p$(CHR$^{61}$)$_s$CO—;

R$^5$ is —(CH$_2$)$_o$(CHR$^{61}$)$_s$O—; —(CH$_2$)$_o$(CHR$^{61}$)$_s$S—; —(CH$_2$)$_o$(CHR$^{61}$)$_s$NR$^{34}$—; or —(CH$_2$)$_o$(CHR$^{61}$)$_s$CO—;

R$^6$ is —(CH$_2$)$_o$(CHR$^{61}$)$_s$O—; —(CH$_2$)$_o$(CHR$^{61}$)$_s$S—; —(CH$_2$)$_o$(CHR$^{61}$)$_s$NR$^{34}$—; or —(CH$_2$)$_o$(CHR$^{61}$)$_s$CO—;

R$^7$ is —(CH$_2$)$_q$(CHR$^{61}$)$_s$O—; —(CH$_2$)$_q$(CHR$^{61}$)$_s$NR$^{34}$; or —(CH$_2$)$_r$(CHR$^{61}$)$_s$CO—;

R$^8$ is —(CH$_2$)$_o$(CHR$^{61}$)$_s$O—; —(CH$_2$)$_o$(CHR$^{61}$)$_s$S—; —(CH$_2$)$_o$(CHR$^{61}$)$_s$NR$^{34}$—; or —(CH$_2$)$_o$(CHR$^{61}$)$_s$CO—;

R$^9$ is —(CH$_2$)$_o$(CHR$^{61}$)$_s$O—; —(CH$_2$)$_o$(CHR$^{61}$)$_s$S—; —(CH$_2$)$_o$(CHR$^{61}$)$_s$NR$^{34}$—; or —(CH$_2$)$_o$(CHR$^{61}$)$_s$CO—;

R$^{10}$ is —(CH$_2$)$_o$(CHR$^{61}$)$_s$O—; —(CH$_2$)$_o$(CHR$^{61}$)$_s$S—; —(CH$_2$)$_o$(CHR$^{61}$)$_s$NR$^{34}$—; or —(CH$_2$)$_o$(CHR$^{61}$)$_s$CO—;

R$^{11}$ is —(CH$_2$)$_m$(CHR$^{61}$)$_s$O—; —(CH$_2$)$_m$(CHR$^{61}$)$_s$NR$^{34}$—; or —(CH$_2$)$_o$(CHR$^{61}$)$_s$CO—;

R$^{12}$ is —(CH$_2$)$_m$(CHR$^{61}$)$_s$O—, —(CH$_2$)$_m$(CHR$^{61}$)$_s$NR$^{34}$—; or —(CH$_2$)$_r$(CHR$^{61}$)$_s$CO—;

R$^{13}$ is —(CH$_2$)$_q$(CHR$^{61}$)$_s$O—; —(CH$_2$)$_q$(CHR$^{61}$)$_s$S—; —(CH$_2$)$_q$(CHR$^{61}$)$_s$NR$^{34}$—; or —(CH$_2$)$_q$(CHR$^{61}$)$_s$CO—;

R$^{14}$ is —(CH$_2$)$_m$(CHR$^{61}$)$_s$O—; —(CH$_2$)$_m$(CHR$^{61}$)$_s$NR$^{34}$—; or —(CH$_2$)$_q$(CHR$^{61}$)$_s$CO—;

R$^{15}$ is —(CH$_2$)$_o$(CHR$^{61}$)$_s$O—; —(CH$_2$)$_o$(CHR$^{61}$)$_s$S—; —(CH$_2$)$_o$(CHR$^{61}$)$_s$NR$^{34}$—; or —(CH$_2$)$_o$(CHR$^{61}$)$_s$CO—;

R$^{16}$ is —(CH$_2$)$_o$(CHR$^{61}$)$_s$O—; —(CH$_2$)$_o$(CHR$^{61}$)$_s$S—; —(CH$_2$)$_o$(CHR$^{61}$)$_s$NR$^{34}$—; or —(CH$_2$)$_o$(CHR$^{61}$)$_s$CO—;

R$^{17}$ is —(CH$_2$)$_q$(CHR$^{61}$)$_s$O—; —(CH$_2$)$_q$(CHR$^{61}$)$_s$S—; —(CH$_2$)$_q$(CHR$^{61}$)$_s$NR$^{34}$—; or —(CH$_2$)$_q$(CHR$^{61}$)$_s$CO—;

R$^{18}$ is —(CH$_2$)$_p$(CHR$^{61}$)$_s$O—; —(CH$_2$)$_p$(CHR$^{61}$)$_s$S—; —(CH$_2$)$_p$(CHR$^{61}$)$_s$NR$^{34}$—; or —(CH$_2$)$_p$(CHR$^{61}$)$_s$CO—;

R$^{19}$ is —(CH$_2$)$_p$(CHR$^{61}$)$_s$O—; —(CH$_2$)$_p$(CHR$^{61}$)$_s$S—; —(CH$_2$)$_p$(CHR$^{61}$)$_s$NR$^{34}$—; or —(CH$_2$)$_p$(CHR$^{61}$)$_s$CO—;

R$^{21}$ is —(CH$_2$)$_o$(CHR$^{61}$)$_s$O—; —(CH$_2$)$_o$(CHR$^{61}$)$_s$S—; —(CH$_2$)$_o$(CHR$^{61}$)$_s$NR$^{34}$—; or —(CH$_2$)$_o$(CHR$^{61}$)$_s$CO—;

R$^{22}$ is —(CH$_2$)$_o$(CHR$^{61}$)$_s$O—; —(CH$_2$)$_o$(CHR$^{61}$)$_s$S—; —(CH$_2$)$_o$(CHR$^{61}$)$_s$NR$^{34}$—; or —(CH$_2$)$_o$(CHR$^{61}$)$_s$CO—;

R$^{23}$ is —(CH$_2$)$_o$(CHR$^{61}$)$_s$O; —(CH$_2$)$_o$(CHR$^{61}$)$_s$S—; —(CH$_2$)$_o$(CHR$^{61}$)$_s$NR$^{34}$—; or —(CH$_2$)$_o$(CHR$^{61}$)$_s$CO—;

R$^{24}$ is —(CH$_2$)$_o$(CHR$^{61}$)$_s$O; —(CH$_2$)$_o$(CHR$^{61}$)$_s$S—; —(CH$_2$)$_o$(CHR$^{61}$)$_s$NR$^{34}$—; or —(CH$_2$)$_o$(CHR$^{61}$)$_s$CO—;

R$^{25}$ is —(CH$_2$)$_m$(CHR$^{61}$)$_s$O—; —(CH$_2$)$_m$(CHR$^{61}$)$_s$S—; —(CH$_2$)$_m$(CHR$^{61}$)$_s$NR$^{34}$—; or —(CH$_2$)$_o$(CHR$^{61}$)$_s$CO—;

R$^{26}$ is —(CH$_2$)$_m$(CHR$^{61}$)$_s$O—; —(CH$_2$)$_m$(CHR$^{61}$)$_s$S—; —(CH$_2$)$_m$(CHR$^{61}$)$_s$NR$^{34}$—; or —(CH$_2$)$_o$(CHR$^{61}$)$_s$CO—;

R$^{27}$ is —(CH$_2$)$_o$(CHR$^{61}$)$_s$O—; —(CH$_2$)$_o$(CHR$^{61}$)$_s$S—; —(CH$_2$)$_o$(CHR$^{61}$)$_s$NR$^{34}$—; or —(CH$_2$)$_o$(CHR$^{61}$)$_s$CO—;

R$^{28}$ is —(CH$_2$)$_m$(CHR$^{61}$)$_s$O—; —(CH$_2$)$_m$(CHR$^{61}$)$_s$NR$^{34}$; or —(CH$_2$)$_o$(CHR$^{61}$)$_s$CO—;

$R^{29}$ is —$(CH_2)_o(CHR^{61})_sO$—; —$(CH_2)_o(CHR^{61})_sS$—; —$(CH_2)_o(CHR^{61})_sR^{34}$—; or —$(CH_2)_o(CHR^{61})_sCO$—;

$R^{31}$ is —$(CH_2)_p(CHR^{61})_sO$—; —$(CH_2)_p(CHR^{61})_sS$—; —$(CH_2)_p(CHR^{61})_sNR^{34}$—; or —$(CH_2)_o(CHR^{61})_sCO$—;

$R^{33}$ is —$(CH_2)_m(CHR^{61})_sO$—; —$(CH_2)_m(CH_2)_sNR^{34}$—; or —$(CH_2)_o(CHR^{61})_sCO$—;

$R^{37}$ is —$(CH_2)_p(CHR^{61})_sO$—; —$(CH_2)_p(CHR^{61})_sS$—; —$(CH_2)_p(CHR^{61})_sNR^{34}$—; or —$(CH_2)_o(CHR^{61})_sCO$—;

$R^{38}$ is —$(CH_2)_p(CHR^{61})_sO$—; —$(CH_2)_p(CHR^{61})_sS$—; —$(CH_2)_p(CHR^{61})_sNR^{34}$—; or —$(CH_2)_o(CHR^{61})_sCO$—;

$R^{41}$ is —$(CH_2)_p(CHR^{61})_sO$—; —$(CH_2)_p(CHR^{61})_sS$—; —$(CH_2)_p(CHR^{61})_sNR^{34}$—; or —$(CH_2)_o(CHR^{61})_sCO$—;

$R^{42}$ is —$(CH_2)_p(CHR^{61})_sO$—; —$(CH_2)_p(CHR^{61})_sS$—; —$(CH_2)_p(CHR^{61})_sNR^{34}$—; or —$(CH_2)_o(CHR^{61})_sCO$—;

$R^{43}$ is —$(CH_2)_m(CHR^{61})_sO$; —$(CH_2)_m(CHR^{61})_sNR^{34}$—; or —$(CH_2)_o(CHR^{61})_sCO$—;

$R^{45}$ is —$(CH_2)_o(CHR^{61})_sO$—; —$(CH_2)_o(CHR^{61})_sS$—; —$(CH_2)_o(CHR^{61})_sNR^{34}$—; or —$(CH_2)_s(CHR^{61})_sCO$—;

$R^{47}$ is —$(CH_2)_o(CHR^{61})_sO$—;

$R^{49}$ is —$(CHR^{61})_sO$—; —$(CHR^{61})_sS$—; —$(CHR^{61})_sNR^{34}$—; or —$(CHR^{61})_sCO$—;

$R^{51}$ is —$(CH_2)_m(CHR^{61})_sO$—; —$(CH_2)_m(CHR^{61})_sS$—; —$(CH_2)_m(CHR^{61})_sNR^{34}$—; or —$(CH_2)_o(CHR^{61})_sCO$—;

$R^{52}$ is —$(CH_2)_m(CHR^{61})_sO$—; —$(CH_2)_m(CHR^{61})_sS$—; —$(CH_2)_m(CHR^{61})_sNR^{34}$—; or —$(CH_2)_o(CHR^{61})_sCO$—;

$R^{53}$ is —$(CH_2)_m(CHR^{61})_sO$—; —$(CH_2)_m(CHR^{61})_sS$—; —$(CH_2)_m(CHR^{61})_sNR^{34}$—; or —$(CH_2)_o(CHR^{61})_sCO$—;

$R^{54}$ is —$(CH_2)_m(CHR^{61})_sO$—; —$(CH_2)_m(CHR^{61})_sNR^{34}$—; or —$(CH_2)_o(CHR^{61})_sCO$—;

$R^{55}$ is —$(CH_2)_m(CHR^{61})_sO$—; —$(CH_2)_m(CHR^{61})_sNR^{34}$—; or —$(CH_2)_o(CHR^{61})_sCO$—;

$R^{56}$ is —$(CH_2)_m(CHR^{61})_sO$—; —$(CH_2)_m(CHR^{61})_sNR^{34}$—; or —$(CH_2)_o(CHR^{61})_sCO$—;

$R^{64}$ is —$(CH_2)_p(CHR^{61})_sO$—; —$(CH_2)_p(CHR^{61})_sS$—; or —$(CH_2)_p(CHR^{61})_sNR^{34}$—;

m, o, p, q, r and s being as defined above;

with the proviso that if more than one of the substituents $R^2$ to $R^{19}$, $R^{21}$ to $R^{19}$, $R^{31}$, $R^{33}$, $R^{37}$, $R^{38}$, $R^{41}$ to $R^{43}$, $R^{45}$, $R^{47}$, $R^{49}$, $R^{51}$ to $R^{56}$ and $R^{64}$ is present, only one of these has one of the significances just mentioned whilst the other(s) has/have any of the significance(s) mentioned earlier;

L is a direct bond or one of the linkers

L1: —$(CH_2)_pCHR^{61}[X(CH_2)_pCHR^{61}]_o$—;
L2: —$CO(CH_2)_pCHR^{61}[X(CH_2)_pCHR^{61}]_oCO$—;
L3: —$CONR^{34}(CH_2)_pCHR^{61}[X(CH_2)_pCHR^{61}]_oNR^{34}CO$—;
L4: —$O(CH_2)_pCHR^{61}[X(CH_2)pCHR^{61}]_oO$—;
L5: —$S(CH_2)_pCHR^{61}[X(CH_2)pCHR^{61}]_oS$—;
L6: —$NR^{34}(CH_2)_pCHR^{61}[X(CH_2)pCHR^{61}]_oNR^{34}$—;
L7: —$(CH_2)_oCHR^{61}Y(CH_2)_oCHR^{61}$—;
L8: —$CO(CH_2)_oCHR^{61}Y(CH_2)_oCHR^{61}CO$—;
L9: —$CONR^{34}(CH_2)_oCHR^{61}Y(CH_2)_oCHR^{61}NR^{34}CO$—;
L10: —$O(CH_2)_oCHR^{61}Y(CH_2)_oCHR^{61}O$—;
L11: —$S(CH_2)_oCHR^{61}Y(CH_2)_oCHR^{61}S$—;
L12: —$NR^{34}(CH_2)_oCHR^{61}Y(CH_2)_oCHR^{61}NR^{34}$—;
L13: —$CO(CH_2)_pCHR^{61}[X(CH_2)pCHM^{61}]_oNR^{34}$—;
L14: —$CO(CH_2)_oCHR^{61}Y(CH_2)_oCHR^{61}NR^{34}$—;
L15 —$NR^{34}(CH_2)_pCHR^{61}[X(CH_2)pCHR^{61}]_oCO$—; and
L16 —$NR^{34}(CH_2)_oCHR^{61}Y(CH_2)_oCHR^{61}CO$—;

m, o, p, q, r and s being as defined above; X being O; S; $NR^{34}$; —$NR^{32}CONR^{34}$—; or —OCOO—; and Y being —$C^6R^{67}R^{68}R^{69}R^{70}$—;

$R^{67}$ being H; Cl; Br; F; $NO_2$; —$NR^{34}COR^{57}$; lower alkyl; or lower alkenyl;

$R^{68}$ being H; Cl; Br; F; $NO_2$; —$NR^{34}COR^{57}$; lower alkyl; or lower alkenyl;

$R^{69}$ being H; Cl; Br; F; $NO_2$; —$NR^{34}COR^{57}$; lower alkyl; or lower alkenyl; and $R^{70}$ being H; Cl; Br; F; $NO_2$; —$NR^{34}COR^{57}$; lower alkyl; or lower alkenyl;

with the proviso that at least two of $R^{67}$, $R^{68}$, $R^{69}$ and $R^{70}$ are H; and with the further proviso that —$(CH_2)_m(CHR^{61})_sO$— can be combined with linker L1, L2, L3, L7, L8 or L9;

—$(CH_2)_o(CHR^{61})_sO$— can be combined with linker L1, L2, L3, L7, L8 or L9;

—$(CH_2)_p(CHR^{61})_sO$— can be combined with linker L1, L2, L3, L7, L8 or L9;

—$(CH_2)_q(CHR^{61})_sO$— can be combined with linker L1, L2, L3, L7, L8 or L9;

—$(CHR^{61})_sO$— can be combined with linker L1, L2, L3, L7, L8 or L9;

—$(CH_2)_m(CHR^{61})_sS$— can be combined with linker L1, L2, L3, L7, L8 or L9; or can form a disulfide bond with —$(CH_2)_m(CHR^{61})_sS$—; —$(CH_2)_o(CHR^{61})_sS$—; —$(CH_2)_p(CHR^{61})_sS$—; —$(CHR^2)_q(CHR^{61})_sS$—; or —$(CHR^{61})_sS$—;

—$(CH_2)_o(CHR^{61})_sS$— can be combined with linker L1, L2, L3, L7, L8 or L9; or can form a disulfide bond with —$(CH_2)_m(CHR^{61})_sS$—; —$(CH_2)_o(CHR^{61})_sS$—; —$(CH_2)_p(CHR^{61})_sS$—; —$(CH_2)_q(CHR^{61})_sS$—; or —$(CHR^{61})_sS$—;

—$(CH_2)_p(CHR^{61})_sS$— can be combined with linker L1, L2, L3, L7, L8 or L9; or can form a disulfide bond with —$(CH_2)_m(CHR^{61})_sS$—; —$(CH_2)_o(CHR^{61})_sS$—; —$(CH_2)_p(CHR^{61})_sS$—; —$(CH_2)_q(CHR^{61})_sS$—; or —$(CHR^{61})_sS$—;

—$(CH_2)_q(CHR^{61})_sS$— can be combined with linker L1, L2, L3, L7, L8 or L9; or can form a disulfide bond with —$(CH_2)_m(CHR^{61})_sS$—; —$(CH_2)_o(CHR^{61})_sS$—; —$(CH_2)_p(CHR^{61})_sS$—; —$(CH_2)_q(CHR^{61})_sS$—; or —$(CHR^{61})_sS$—;

—$(CHR^{61})_sS$— can be combined with linker L1, L2, L3, L7, L8 or L9; or form a disulfide bond with —$(CH_2)_m(CHR^{61})_sS$—; —$(CH_2)_o(CHR^{61})_sS$—; —$(CH_2)_p(CHR^{61})_sS$—; —$(CH_2)_q(CHR^{61})_sS$—; or —$(CHR^{61})_sS$—;

—$(CH_2)_m(CHR^{61})_sNR^{34}$— can be combined with linker L1, L2, L3, L7, L8 or L9;

—$(CH_2)_o(CHR^{61})_sNR^{34}$— can be combined with linker L1, L2, L3, L7, L8 or L9;

—$(CH_2)_p(CHR^{61})_sNR^{34}$— can be combined with linker L1, L2, L3, L7, L8 or L9;

—$(CH_2)_q(CHR^{61})_sNR^{34}$— can be combined with linker L1, L2, L3, L7, L8 or L9;

—$(CHR^{61})_sNR^{34}$— can be combined with linker L1, L2, L3, L7, L8 or L9;

—$(CH_2)_o(CHR^{61})_sCO$— can be combined with linker L4, L5, L6, L1, L11 or L12;

—$(CH_2)_p(CHR^{61})_sCO$— can be combined with linker L4, L5, L6, L1, L11 or L12;

—$(CH_2)_q(CHR^{61})_sCO$— can be combined with linker L4, L5, L6, L10, L11 or L12;

—$(CH_2)_r(CHR^{61})_sCO$— can be combined with linker L4, L5, L6, L10, L11 or L12;

—$(CHR^{61})_sCO$— can be combined with linker L4, L5, L6, L10, L11 or L12;

—$(CH_2)_m(CHR^{61})_sO$— can be combined with linker L13 or L14 and the resulting combination with —$(CH_2)_m(CHR^{61})_sCO$—; —$(CH_2)_o(CHR^{61})_pCO$—; —$(CH_2)_q(CHR^{61})_sCO$—; or —$(CHR^{61})_sCO$—;

—(CH$_2$)$_o$(CHR$^{61}$)$_s$O— can be combined with linker L13 or L14 and the resulting combination with —(CH$_2$)$_o$(CHR$^{61}$)$_s$CO—; —(CH$_2$)$_o$(CHR$^{61}$)$_p$CO—; —(CH$_2$)$_q$(CHR$^{61}$)$_s$CO—; or —(CHR$^{61}$)$_s$CO—;

—(CH$_2$)$_p$(CHR$^{61}$)$_s$CO— can be combined with linker L13 or L14 and the resulting combination with —(CH$_2$)$_o$(CHR$^{61}$)$_s$CO—; —(CH$_2$)$_o$(CHR$^{61}$)$_p$CO—; —(CH$_2$)$_q$(CHR$^{61}$)$_s$CO—; or —(CHR$^{61}$)$_s$CO—;

—(CH$_2$)$_q$(CHR$^{61}$)$_s$O— can be combined with linker L13 or L14 and the resulting combination with —(CH$_2$)$_o$(CHR$^{61}$)$_s$CO—; —(CH$_2$)$_o$(CHR$^{61}$)$_p$CO—; —(CH$_2$)$_q$(CHR$^{61}$)$_s$CO—; or —(CHR$^{61}$)$_s$CO—;

—(CHR$^{61}$)$_s$O— can be combined with linker L13 or L14 and the resulting combination with —(CH$_2$)$_o$(CHR$^{61}$)$_s$CO—; —(CH$_2$)$_o$(CHR$^{61}$)$_p$CO—; —(CH$_2$)$_q$(CHR$^{61}$)$_s$CO—; or —(CHR$^{61}$)$_s$CO—;

—(CH$_2$)$_m$(CHR$^{61}$)$_s$S— can be combined with linker L13 or L14 and the resulting combination with —(CH$_2$)$_o$(CHR$^{61}$)$_s$CO—; —(CH$_2$)$_o$(CHR$^{61}$)$_p$CO—; —(CH$_2$)$_q$(CHR$^{61}$)$_s$CO—; or —(CHR$^{61}$)$_s$CO—;

—(CH$_2$)$_o$(CHR$^{61}$)$_s$S— can be combined with linker L13 or L14 and the resulting combination with —(CH$_2$)$_o$(CHR$^{61}$)$_s$CO—; —(CH$_2$)$_o$(CHR$^{61}$)$_p$CO—; —(CH$_2$)$_q$(CHR$^{61}$)$_s$CO—; or —(CHR$^{61}$)$_s$CO—;

—(CH$_2$)$_p$(CHR$^{61}$)$_s$S— can be combined with linker L13 or L14 and the resulting combination with —(CH$_2$)$_o$(CHR$^{61}$)$_s$CO—; —(CH$_2$)$_o$(CHR$^{61}$)$_p$CO—; —(CH$_2$)$_q$(CHR$^{61}$)$_s$CO—; or —(CHR$^{61}$)$_s$CO—;

—(CH$_2$)$_q$(CHR$^{61}$)$_s$S— can be combined with linker L13 or L14 and the resulting combination with —(CH$_2$)$_o$(CHR$^{61}$)$_s$CO—; —(CH$_2$)$_o$(CHR$^{61}$)$_p$CO—; —(CH$_2$)$_q$(CHR$^{61}$)$_s$CO—; or —(CHR$^{61}$)$_s$CO—;

—(CHR$^{61}$)$_s$S— can be combined with linker L13 or L14 and the resulting combination with —(CH$_2$)$_o$(CHR$^{61}$)$_s$CO—; —(CH$_2$)$_o$(CHR$^{61}$)$_p$CO—; —(CH$_2$)$_q$(CHR$^{61}$)$_s$CO—; or —(CHR$^{61}$)$_s$CO—;

—(CH$_2$)$_m$(CHR$^{61}$)$_s$NR$^{34}$— can be combined with linker L13 or L14 and the resulting combination with —(CH$_2$)$_o$(CHR$^{61}$)$_s$CO—, —(CH$_2$)$_o$(CHR$^{61}$)$_p$CO—; —(CH$_2$)$_q$(CHR$^{61}$)$_s$CO—; or —(CHR$^{61}$)$_s$CO—;

—(CH$_2$)$_o$(CHR$^{61}$)$_s$NR$^{34}$— can be combined with linker L13 or L14 and the resulting combination with —(CH$_2$)$_o$(CHR$^{61}$)$_s$CO—; —(CH$_2$)$_o$(CHR$^{61}$)$_p$CO—; —(CH$_2$)$_q$(CHR$^{61}$)$_s$CO—; or —(CHR$^{61}$)$_s$CO—;

—(CH$_2$)$_p$(CHR$^{61}$)$_s$NR$^{34}$— can be combined with linker L13 or L14 and the resulting combination with —(CH$_2$)$_o$(CHR$^{61}$)$_s$CO—; —(CH$_2$)$_o$(CHR$^{61}$)$_p$CO—; —(CH$_2$)$_q$(CHR$^{61}$)$_s$CO—; or —(CHR$^{61}$)$_s$CO—;

—(CH$_2$)$_q$(CHR$^{61}$)$_s$NR$^{34}$— can be combined with linker L13 or L14 and the resulting combination with —(CH$_2$)$_o$(CHR$^{61}$)$_s$CO—; —(CH$_2$)$_o$(CHR$^{61}$)$_p$CO—; —(CH$_2$)$_q$(CHR$^{61}$)$_s$CO—; or —(CHR$^{61}$)$_s$CO—;

—(CHR$^{61}$)$_s$NR$^{34}$— can be combined with linker L13 or L14 and the resulting combination with —(CH$_2$)$_o$(CHR$^{61}$)$_s$CO—; —(CH$_2$)$_o$(CHR$^{61}$)$_p$CO—; —(CH$_2$)$_q$(CHR$^{61}$)$_s$CO—; or —(CHR$^{61}$)$_s$CO—;

—(CH$_2$)$_o$(CHR$^{61}$)$_s$CO— can be combined with linker L15 or L16 and the resulting combination with —(CH$_2$)$_m$(CHR$^{61}$)$_s$X—, —(CH$_2$)$_o$(CHR$^{61}$)$_s$X—, —(CH$_2$)$_p$(CHR$^{61}$)$_s$X—, —(CH$_2$)$_q$(CHR$^{61}$)$_s$X—; or —(CHR$^{61}$)$_s$X—;

—(CH$_2$)$_p$(CHR$^{61}$)$_s$CO— can be combined with linker L15 or L16 and the resulting combination with —(CH$_2$)$_m$(CHR$^{61}$)$_s$X—, —(CH$_2$)$_o$(CHR$^{61}$)$_s$X—, —(CH$_2$)$_p$(CHR$^{61}$)$_s$X—, —(CH$_2$)$_q$(CHR$^{61}$)$_s$X—; or —(CHR$^{61}$)$_s$X—;

—(CH$_2$)$_q$(CHR$^{61}$)$_s$CO— can be combined with linker L15 or L16 and the resulting combination with —(CH$_2$)$_m$(CHR$^{61}$)$_s$X—, —(CH$_2$)$_o$(CHR$^{61}$)$_s$X—, —(CH$_2$)$_p$(CHR$^{61}$)$_s$X—, —(CH$_2$)$_q$(CHR$^{61}$)$_s$X—; or —(CHR$^{61}$)$_s$X—;

—(CH$_2$)$_r$(CHR$^{61}$)$_s$CO— can be combined with linker L15 or L16 and the resulting combination with —(CH$_2$)$_m$(CHR$^{61}$)$_s$X—, —(CH$_2$)$_o$(CHR$^{61}$)$_s$X—, —(CH$_2$)$_p$(CHR$^{61}$)$_s$X—, —(CH$_2$)$_q$(CHR$^{61}$)$_s$X—; or —(CHR$^{61}$)$_s$X—;

—(CHR$^{61}$)$_s$CO— can be combined with linker L15 or L16 and the resulting combination with —(CH$_2$)$_m$(CHR$^{61}$)$_s$X—; —(CH$_2$)$_o$(CHR$^{61}$)$_s$X—; —(CH$_2$)$_p$(CHR$^{61}$)$_s$X—; —(CH$_2$)$_q$(CHR$^{61}$)$_s$X—; or —(CHR$^{61}$)$_s$X—;

Z, Z$^1$ and Z$^2$ independently are chains of n α-amino acid residues, n being an integer from 8 to 16, the positions of said amino acid residues in said chains being counted starting from the N-terminal amino acid, whereby these amino acid residues are, depending on their position in the chains, Gly, or Pro, or of formula -A-CO—, or of formula —B—CO—, or of one of the types

C: —NR$^{20}$CH(R$^{72}$)CO—;

D: —NR$^{20}$CH(R$^{73}$)CO—;

E: —NR$^{20}$CH(R$^{74}$)CO—;

F: —NR$^{20}$CH(R$^{84}$)CO—; and

H: —NR$^{20}$—(CH(CO—)—(CH$_2$)$_{4-7}$—(CH(CO—)—NR$^{20}$—; —NR$^{20}$—CH(CO—)—(CH$_2$)$_p$SS(CH$_2$)$_p$—(CH(CO—)—NR$^{20}$—; —NR$^{20}$—CH(CO—)—(CH$_2$)$_p$NR$^{20}$CO(CH$_2$)$_p$—CH(CO—)—NR$^{20}$—; and —NR$^{20}$—(CH(CO—)—(—(CH$_2$)$_p$NR$^{20}$CONR$^{20}$(CH$_2$)$_p$—(CH(CO—)—NR$^{20}$—;

R$^{71}$ is H; lower alkyl; lower alkenyl; —(CH$_2$)$_p$(CHR$^{61}$)$_s$OR$^{75}$; —(CH$_2$)$_p$(CHR$^{61}$)$_s$SR$^{75}$; —(CH$_2$)$_p$(CHR$^{61}$)$_s$NR$^{33}$R$^{34}$; —(CH$_2$)$_p$(CHR$^{61}$)$_s$OCONR$^{33}$R$^{75}$; —(CH$_2$)$_p$(CHR$^{61}$)$_s$NR$^{20}$CONR$^{33}$R$^{82}$; —(CH$_2$)$_o$(CHR$^{61}$)$_s$COOR$^{75}$; —(CH$_2$)$_p$CONR$^{58}$R$^{59}$; —(CH$_2$)$_p$PO(OR$^{62}$)$_2$; —(CH$_2$)$_p$SO$_2$R$^{62}$; or —(CH$_2$)$_o$—C$_6$R$^{67}$R$^{68}$R$^{69}$R$^{70}$R$^{76}$;

R$^{72}$ is H; lower alkyl; lower alkenyl; —(CH$_2$)$_p$(CHR$^{61}$)$_s$OR$^{85}$; or —(CH$_2$)$_p$(CHR$^{61}$)$_s$SR$^{85}$;

R$^{73}$ is —(CH$_2$)$_r$R$^{77}$; —(CH$_2$)$_r$O(CH$_2$)$_o$R$^{77}$; —(CH$_2$)$_r$S(CH$_2$)$_o$R$^{77}$; or —(CH$_2$)$_r$NR$^{20}$(CH$_2$)$_o$R$^{77}$;

R$^{74}$ is —(CH$_2$)$_p$NR$^{78}$R$^{79}$; —(CH$_2$)$_p$NR$^{77}$R$^{80}$; —(CH$_2$)$_p$C(=NR$^{80}$)NR$^{78}$R$^{79}$; —(CH$_2$)$_p$C(=NOR$^{50}$)NR$^{78}$R$^{79}$; —(CH$_2$)$_p$C(=NNR$^{78}$R$^{79}$)NR$^{78}$R$^{79}$; —(CH$_2$)$_p$NR$^{80}$C(=NR$^{80}$)NR$^{78}$R$^{79}$; —(CH$_2$)$_p$N=C(NR$^{78}$R$^{80}$)NR$^{79}$R$^{80}$; —(CH$_2$)$_p$C$_6$H$_4$NR$^{78}$R$^{79}$; —(CH$_2$)$_p$C$_6$H$_4$NR$^{77}$R$^{80}$; —(CH$_2$)$_p$C$_6$H$_4$C(=NR$^{80}$)NR$^{78}$R$^{79}$; —(CH$_2$)$_p$C$_6$H$_4$C(=NOR$^{50}$)NR$^{78}$R$^{79}$; —(CH$_2$)$_p$C$_6$H$_4$C(=NNR$^{78}$R$^{79}$)NR$^{78}$R$^{79}$; —(CH$_2$)$_p$C$_6$H$_4$NR$^{80}$C(=NR$^{80}$)NR$^{78}$R$^{79}$; —(CH$_2$)$_p$C$_6$H$_4$N=C(NR$^{78}$R$^{80}$)NR$^{79}$R$^{80}$; —(CH$_2$)$_r$O(CH$_2$)$_m$NR$^{78}$R$^{79}$; —(CH$_2$)$_r$O(CH$_2$)$_m$NR$^{77}$R$^{80}$; —(CH$_2$)$_r$O(CH$_2$)$_p$C(=NR$^{80}$)NR$^{78}$R$^{79}$; —(CH$_2$)$_r$O(CH$_2$)$_p$C(=NOR$^{50}$)NR$^{78}$R$^{79}$; —(CH$_2$)$_r$O(CH$_2$)$_p$C(=NNR$^{78}$R$^{79}$)NR$^{78}$R$^{79}$; —(CH$_2$)$_r$O(CH$_2$)$_m$NR$^{80}$C(=NR$^{80}$)NR$^{78}$R$^{79}$; —(CH$_2$)$_r$O(CH$_2$)$_m$N=C(NR$^{78}$R$^{80}$)NR$^{79}$R$^{80}$; —(CH$_2$)$_r$O(CH$_2$)$_p$C$_6$H$_4$CNR$^{78}$R$^{79}$; —(CH$_2$)$_r$O(CH$_2$)$_p$C$_6$H$_4$C(=NR$^{80}$)NR$^{78}$R$^{79}$; —(CH$_2$)$_r$O(CH$_2$)$_p$C$_6$H$_4$C(=NOR$^{50}$)NR$_{78}$R$^{79}$; —(CH$_2$)$_r$O(CH$_2$)$_p$C$_6$H$_4$C(=NNR$^{78}$R$^{79}$)NR$^{78}$R$^{79}$; —(CH$_2$)$_r$O(CH$_2$)$_p$C$_6$H$_4$NR$^{80}$C(=NR$^{80}$)NR$^{78}$R$^{79}$; —(CH$_2$)$_r$S(CH$_2$)$_m$NR$^{78}$R$^{79}$; —(CH$_2$)$_r$S(CH$_2$)$_m$NR$^{77}$R$^{80}$; —(CH$_2$)$_r$S(CH$_2$)$_p$C(=NR$^{80}$)NR$^{78}$R$^{79}$; —(CH$_2$)$_r$S(CH$_2$)$_p$C(=NOR$^{50}$)NR$^{78}$R$^{79}$; —(CH$_2$)$_r$S(CH$_2$)$_p$C(=NNR$^{78}$R$^{79}$)NR$^{78}$R$^{79}$; —(CH$_2$)$_r$S(CH$_2$)$_m$NR$^{80}$C(=NR$^{80}$)NR$^{78}$R$^{79}$; —(CH$_2$)$_r$S(CH$_2$)$_m$N=C(NR$^{78}$R$^{80}$)NR$^{79}$R$^{80}$; —(CH$_2$)$_r$S(CH$_2$)$_p$C$_6$H$_4$CNR$^{78}$R$^{79}$; —(CH$_2$)$_r$S(CH$_2$)$_p$C$_6$H$_4$C(=NR$^{80}$)NR$^{78}$R$^{79}$; —(CH$_2$)$_r$S(CH$_2$)$_p$C$_6$H$_4$C(=NOR$^{50}$)NR$^{78}$R$^{79}$; —(CH$_2$)$_r$S(CH$_2$)$_p$

C₆H₄C(=NNR⁷⁸R⁷⁹)NR⁷⁸R⁷⁹; —(CH₂)ᵣS(CH₂)ₚ
C₆H₄NR⁸⁰C(=NR⁸⁰)NR⁷⁸R⁷⁹; —(CH₂)ₚNR⁸⁰COR⁶⁴;
—(CH₂)ₚNR⁸⁰COR⁷⁷; —(CH₂)ₚNR⁸⁰CONR⁷⁸R⁷⁹; or
—(CH₂)ₚC₆H₄NR⁸⁰CONR⁷⁸R⁷⁹;

R⁷⁵ is lower alkyl; lower alkenyl; or aryl-lower allyl;

R³³ and R⁷⁵ taken together can form: —(CH₂)₂₋₆—; —(CH₂)₂O(CH₂)₂—; —(CH₂)₂S(CH₂)₂—; or —(CH₂)₂NR⁵⁷(CH₂)₂—;

R⁷⁵ and R⁸² taken together can form —(CH₂)₂₋₆—; —(CH₂)₂ O(CH₂)₂—; —(CH₂)₂S(CH₂)₂—; or —(CH₂)₂NR⁵⁷(CH₂)₂—;

R⁷⁶ is H; lower alkyl; lower alkenyl; aryl-lower alkyl; —(CH₂)ₒOR⁷²; —(CH₂)ₒSR⁷²; —(CH₂)ₒNR³³R³⁴; —(CH₂)ₒOCONR³³R⁷⁵; —(CH₂)ₙNR²⁰CONR³³R⁸²; —(CH₂)ₒCOOR⁷⁵; —(CH₂)ₒCONR⁵⁸R⁵⁹; —(CH₂)ₒPO(OR⁶⁰)₂; —(CH₂)ₚSO₂R⁶²; or —(CH₂)ₒCOR⁶⁴;

R⁷⁷ is —C₆R⁶⁷R⁶⁸R⁶⁹R⁷⁰R⁷⁶; or a heteroaryl group of one of the formulae

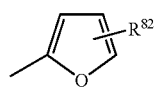
H1

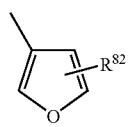
H2

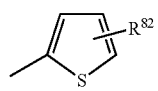
H3

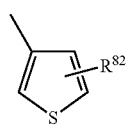
H4

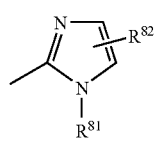
H5

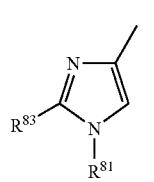
H6

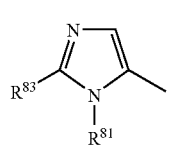
H7

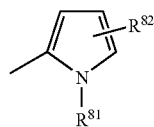
H8

-continued

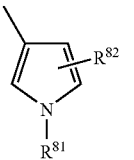
H9

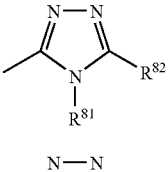
H10

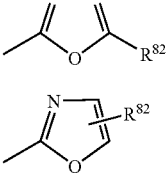
H11

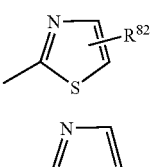
H12

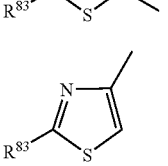
H13

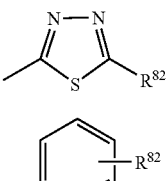
H14

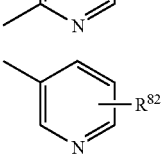
H15

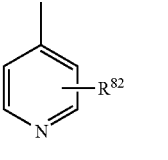
H16

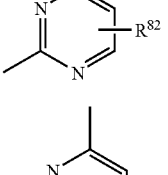
H17

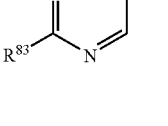
H18

H19

H20

H21

-continued
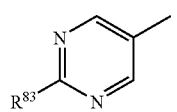 H22
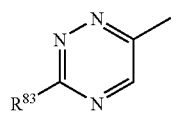 H23
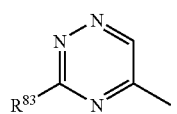 H24
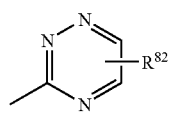 H25
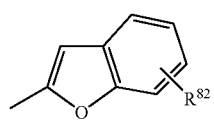 H26
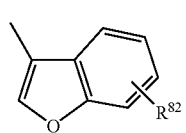 H27
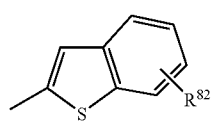 H28
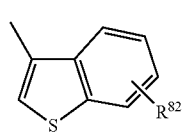 H29
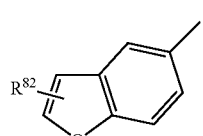 H30
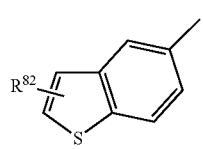 H31
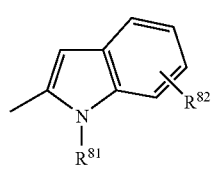 H32
-continued
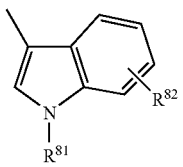 H33
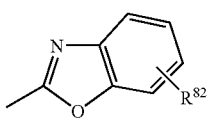 H34
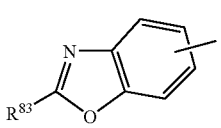 H35
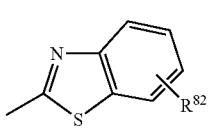 H36
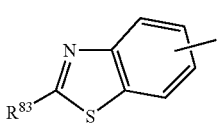 H37
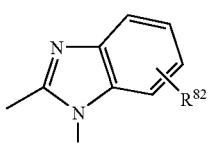 H38
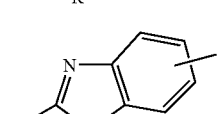 H39
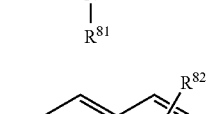 H40
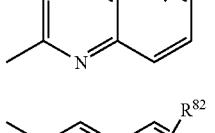 H41
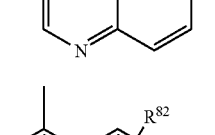 H42
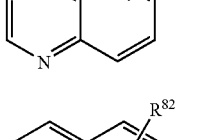 H43
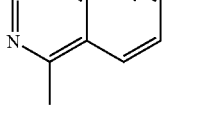

-continued

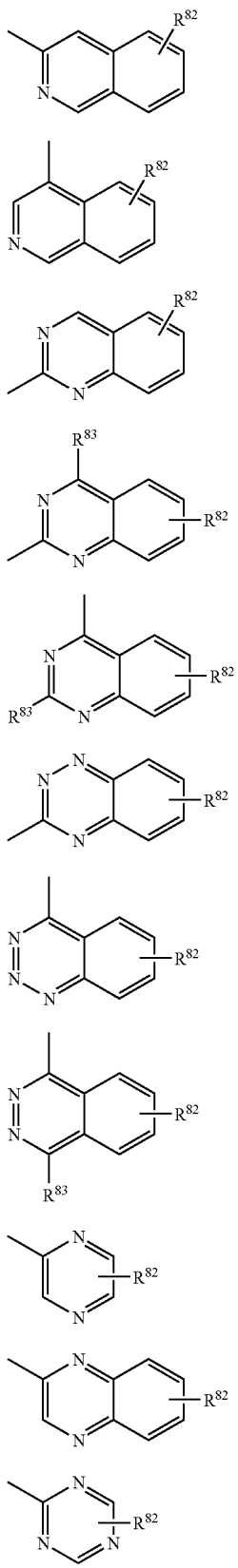

$R^{78}$ is H; lower alkyl; aryl; or aryl-lower alkyl;
$R^{78}$ and $R^{82}$ taken together can form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$;
$R^{79}$ is H; lower alkyl; aryl; or aryl-lower alkyl; or
$R^{78}$ and $R^{79}$, taken together, can be $-(CH_2)_{2-7}-$; $-(CH_2)_2O(CH_2)_2-$; or $-(CH_2)_2NR^{57}(CH_2)_2-$;
$R^{80}$ is H; or lower alkyl;
$R^{81}$ is H; lower alkyl; or aryl-lower alkyl;
$R^{82}$ is H; lower alkyl; aryl; heteroaryl; or aryl-lower alkyl;
$R^{33}$ and $R^{82}$ taken together can form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$;
$R^{83}$ is H; lower allyl; aryl; or $-NR^{78}R^{79}$;
$R^{84}$ is $-(CH_2)_m(CHR^{61})_sOH$; $-(CH_2)_pCONR^{78}R^{79}$; $-(CH_2)_pNR^{80}CONR^{78}R^{79}$; $-(CH_2)_pC_6H_4CONR^{78}R^{79}$; or $-(CH_2)_pC_6H_4NR^{80}CONR^{78}R^{79}$;
$R^{85}$ is lower alkyl; or lower alkenyl;
with the proviso that in said chain(s) of n α-amino acid residues Z, $Z^1$ and $Z^2$
if n is 8, the amino acid residues in positions 1 to 8 are:
P1: of type C or of type D or of type E or of type F, or the residue is Pro;
P2: of type E or of type D or of type F;
P3: of type E or of type C, or the residue is Pro;
P4: of type E or of formula -A-CO—;
P5: of type E or of formula —B—CO—, or the residue is Gly;
P6: of type D, or the residue is Pro;
P7: of type or of type C or of type D; and
P8: of type C or of type D or of type E or of type F, or the residue is Pro; or
P2 and P7, taken together, can form a group of type H; and at P4 and P5 also D-isomers being possible;
if n is 9, the amino acid residues in positions 1 to 9 are:
P1: of type C or of type D or of type E or of type F, or the residue is Pro;
P2: of type E or of type D or of type F;
P3: of type C or of type D or of type E, or the residue is Pro;
P4: of type E or of type D, or the residue is Pro;
P5: of type E, or the residue is Gly or Pro;
P6: of type D or of type E, or the residue is Gly or Pro;
P7: of type E or of type D or of type C, or the residue is Pro;
P8: of type E or of type D; and
P9: of type C or of type D or of type E or of type F, or the residue is Pro; or
P2 and P8, taken together, can form a group of type H; and at P4, P5 and P6 also D-isomers being possible;
if n is 10, the amino acid residues in positions 1 to 10 are:
P1: of type C or of type D or of type E or of type F, or the residue is Pro;
P2: of type E or of type D, or the residue is Pro;
P3: of type C or of type E;
P4: of type E or of type D or of type F, or the residue is Pro;
P5: of type E or of type F or of formula -A-CO—, or the residue is Gly;
P6: of type E or of formula —B—CO—, or the residue is Gly;
P7: of type D or of type E, or the residue is Gly or Pro;
P8: of type D or of type E;
P9: of type E or of type D or of type C, or the residue is Pro; and
P10: of type C or of type D or of type E or of type F; or P3 and P8, taken together, can form a group of type H; and at P5 and P6 also D-isomers being possible;

if n is 11, the amino acid residues in positions 1 to 11 are:
P1: of type C or of type D or of type E or of type F, or the residue is Pro;
P2: of type E or of type C or of type D;
P3: of type D or of type E, or the residue is Pro;
P4: of type E or of type C or of type F;
P5: of type E or of type F, or the residue is Gly or Pro;
P6: of type E or of type F, or the residue is Gly or Pro;
P7: of type E or of type F, or the residue is Gly or Pro;
P8: of type D or of type E or of type F;
P9: of type D or of type E, or the residue is Pro;
P10: of type E or of type C or of type D; and
P11: of type C or of type D or of type E or of type F, or the residue is Pro; or
P4 and P8 and/or P2 and P10, taken together, can form a group of type H; and at P5, P6 and P7 also D-isomers being possible;

if n is 12, the amino acid residues in positions 1 to 12 are:
P1: of type C or of type D or of type E or of type F, or the residue is Pro;
P2: of type E or of type D;
P3: of type C or of type D, or the residue is Pro;
P4: of type E or of type F or of type D;
P5: of type E or of type D or of type C, or the residue is Gly or Pro;
P6: of type E or of type F or of formula -A-CO—, or the residue is Gly;
P7: of type E or of type F or of formula —B—CO—;
P8: of type D or of type C, or the residue is Pro;
P9: of type E or of type D or of type F;
P10: of type D or of type C, or the residue is Pro;
P11: of type E or of type D; and
P12: of type C or of type D or of type E or of type F, or the residue is Pro; or
P4 and P9 and/or P2 and P11, taken together, can form a group of type H; and
at P6 and P7 also D-isomers being possible;

if n is 13, the amino acid residues in positions 1 to 13 are:
P1: of type C or of type D or of type E or of type F, or the residue is Pro;
P2: of type E or of type F or of type D;
P3: of type C or of type D or of type E, or the residue is Pro;
P4: of type E of type C or of type F;
P5: of type E or of type D, or the residue is Gly or Pro;
P6: of type B or of type F, or the residue is Gly or Pro;
P7: of type E or of type F, or the residue is Pro;
P8: of type D or of type E or of type F, or the residue is Pro;
P9: of type D or of type E, or the residue is Pro;
P10: of type E or of type C or of type F;
P11: of type C or of type E, or the residue is Pro;
P12: of type E or of type D or of type C; and
P13: of type C or of type D or of type E or of type F, or the residue is Pro; or P4 and P10 and/or P2 and P12, taken together, can form a group of type H; and at P6, P7 and P8 also D-isomers being possible;

if n is 14, the amino acid residues in positions 1 to 14 are:
P1: of type C or of type D or of type E or of type F, or the residue is Pro;
P2: of type E or of type C or of type D, or the residue is Pro;
P3: of type C or of type D or of type E;
P4: of type D or of type C or of type E, or the residue is Pro;
P5: of type E or of type D;
P6: of type E or of type F, or the residue is Gly or Pro;
P7: of type E or of type F or of formula -A-CO—, or the residue is Gly;
P8: of type E or of type F or of formula —B—CO—, or the residue is Gly;
P9: of type D or of type E, or the residue is Pro;
P10: of type C or of type D or of type E;
P11: of type E or of type D or of type F, or the residue is Pro;
P12: of type D or of type E;
P13: of type E or of type C or of type D, or the residue is Pro; and
P14: of type C or of type D or of type E or of type F, or the residue is Pro; or
P5 and P10 and/or P3 and P12, taken together, can form a group of type H; and at P7 and P8 also D-isomers being possible;

if n is 15, the amino acid residues in positions 1 to 15 are:
P1: of type C or of type D or of type E or of type F, or the residue is Pro;
P2: of type E or of type F or of type D;
P3: of type C or of type D or of type E, or the residue is Pro;
P4: of type E or of type D or of type F;
P5: of type C or of type D or of type E, or the residue is Pro;
P6: of type E or of type D or of type F;
P7: of type C or of type E, or the residue is Pro;
P8: of type E or of type F, or the residue is Gly or Pro;
P9: of type E or of type F, or the residue is Gly or Pro;
P10: of type E or of type D;
P11: of type C or of type D or of type E, or the residue is Pro;
P12: of type E or of type C or of type F;
P13: of type D or of type E, or the residue is Pro;
P14: of type E or of type C or of type D; and
P15: of type C or of type D or of type E or of type F, or the residue is Pro; or
P6 and P10 and/or P4 and P12 and/or P2 and P14, taken together, can form a group of type H; and at P7, P8 and P9 also D-isomers being possible; and if n is 16, the amino acid residues in positions 1 to 16 are:
P1: of type D, or of type E or of type C or of type F, or the residue is Pro;
P2: of type E or of type F or of type D;
P3: of type C or of type D or of type E, or the residue is Pro;
P4: of type E or of type D or of type F;
P5: of type D or of type C or of type E, or the residue is Pro;
P6: of type E or of type D;
P7: of type E or of type F, or the residue is Gly or Pro;
P8: of type E or of type F or of formula -A-CO—, or the residue is Gly;
P9: of type E or of formula —B—CO—, or the residue is Gly;
P10: of type D or of type E, or the residue is Pro;
P11: of type E or of type C or of type D;
P12: of type D or of type C or of type E, or the residue is Pro;
P13; of type E or of type C or of type F;
P14: of type C or of type D or of type E, or the residue is Pro;
P15: of type E or of type C or of type D; and
P16: of type C or of type D or of type E or of type F, or the residue is Pro; or P6 and P11 and/or P4 and P13 and/or P2 and P15, taken together, can form a group of type H; and at P8 and P9 also D-isomers being possible;

and pharmaceutically acceptable salts thereof.

In accordance with the present invention these β-hairpin peptidomimetics can be prepared by a process which comprises (a) coupling an appropriately functionalized solid support with an appropriately N-protected derivative of that amino acid which in the desired end-product is in position $n/2$, $n/2+1$ or $n/2-1$ if n is an even number and, respectively, in position $n/2+\frac{1}{2}$ or $n/2-\frac{1}{2}$ if n is an odd number, any functional group which may be present in said N-protected amino acid derivative being likewise appropriately protected;

(b) removing the N-protecting group from the product thus obtained;

(c) coupling the product thus obtained with an appropriately N-protected derivative of that amino acid which in the desired end-product is one position nearer the N-terminal amino acid residue, any functional group which may be present in said N-protected amino acid derivative being likewise appropriately protected;

(d) removing the N-protecting group from the product thus obtained;

(e) repeating, if necessary, steps (c) and (d) until the N-terminal amino acid residue has been introduced;

(f) coupling the product thus obtained to a compound of the general formula

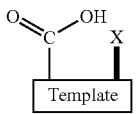

II wherein

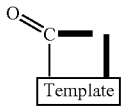

is as defined above and X is an N-protecting group or, if

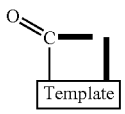

is to be group (a1) or (a2), above, alternatively (fa) coupling the product obtained in step (d) or (e) with an appropriately N-protected derivative of an amino acid of the general formula

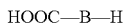  III or

  IV wherein B and A are as defined above, any functional group which may be present in said N-protected amino acid derivative being likewise appropriately protected;

(fb) removing the N-protecting group from the product thus obtained; and (fc) coupling the product thus obtained with an appropriately N-protected derivative of an amino acid of the above general formula IV and, respectively, III, any functional group which may be present in said N-protected amino acid derivative being likewise appropriately protected;

(g) removing the N-protecting group from the product obtained in step (f) or (fc);

(h) coupling the product thus obtained to an appropriately N-protected derivative of that amino acid which in the desired end-product is in position n, any functional group which may be present in said N-protected amino acid derivative being likewise appropriately protected;

(i) removing the N-protecting group from the product thus obtained;

(j) coupling the product thus obtained to an appropriately N-protected derivative of that amino acid which in the desired end-product is one position farther away from position n, any functional group which may be present in said N-protected amino acid derivative being likewise appropriately protected;

(k) removing the N-protecting group from the product thus obtained;

(l) repeating, if necessary, steps (j) and (k) until all amino acid residues have been introduced;

(m) if desired, selectively deprotecting one or several protected functional group(s) present in the molecule and appropriately substituting the reactive group(s) thus liberated;

(o) detaching the product thus obtained from the solid support;

(p) cyclizing the product cleaved from the solid support;

(q) if, desired (qa) forming one or several interstrand linkage(s) between side-chains of appropriate amino acid residues at opposite positions of the β-stand region; and/or (qb) connecting two building blocks of the type of formula Ia via a bridge -G1-L-G2-;

(r) removing any protecting groups present on functional groups of any members of the chain of amino acid residues and, if desired, any protecting group(s) which may in addition be present in the molecule; and (s) if desired, converting the product thus obtained into a pharmaceutically acceptable salt or converting a pharmaceutically acceptable, or unacceptable, salt thus obtained into the corresponding free compound of formula I or into a different, pharmaceutically acceptable, salt.

The peptidomimetics of the present invention can also be enantiomers of the compounds of formulae Ia and Ib. These enantiomers can be prepared by a modification of the above process in which enantiomers of all chiral starting materials are used.

DETAILED DESCRIPTION OF THE INVENTION

As used in this description, the term "alkyl", taken alone or in combinations, designates saturated, straight-chain or branched hydrocarbon radicals having up to 24, preferably up to 12, carbon atoms. Similarly, the term "alkenyl" designates straight chain or branched hydrocarbon radicals having up to 24, preferably up to 12, carbon atoms and containing at least one or, depending on the chain length, up to four olefinic double bonds. The term "lower" designates radicals and compounds having up to 6 carbon atoms. Thus, for example, the term "lower alkyl" designates saturated, straight-chain or branched hydrocarbon radicals having up to 6 carbon atoms, such as methyl, ethyl, n-propyl, isopropyl, n-butyl, sec.-butyl, isobutyl, tert.-butyl and the like. The term "aryl" designates aromatic carbocyclic hydrocarbon radicals containing one or two six-membered rings, such as phenyl or naphthyl, which may be substituted by up to three substituents such as Br, Cl, F, $CF_3$, $NO_2$, lower alkyl or lower alkenyl. The term "heteroaryl" designates aromatic heterocyclic radicals containing one or two five- and/or six-membered rings, at least one of them containing up to three heteroatoms selected from the group consisting of O, S and N and said ring(s) being optionally substituted; representative examples of such optionally substituted heteroaryl radicals are indicated hereinabove in connection with the definition of $R^{77}$.

The structural element -A-CO— designates amino acid building blocks which in combination with the structural element —B—CO— form templates (a1) and (a2). Templates (a) through (p) constitute building blocks which have an N-terminus and a C-terminus oriented in space in such a way that the distance between those two groups may lie between 4.0–5.5 Å. A peptide chain Z, $Z^1$ or $Z^2$ is linked to the C-terminus and the N-terminus of the templates (a) through (p) via the corresponding N- and C-termini so that the template and the chain form a cyclic structure such as that depicted in formula Ia. In a case as here where the distance between the N- and C-termini of the template lies between 4.0–5.5 Å the template will induce the H-bond network necessary for the formation of a β-hairpin conformation in the peptide chain Z, $Z^1$ or $Z^2$. Thus template and peptide chain form a β-hairpin mimetic. The β-hairpin mimetics can also be coupled through groups G1 and G2 and a linker unit L to form the dimeric constructs of formula Ib.

The β-hairpin conformation is highly relevant for the antibiotic and anticancer activities of the β-hairpin mimetics of the present invention. The β-hairpin stabilizing conformational properties of the templates (a) through (p) play a key role not only for antibiotic and anticancer activity but also for the synthesis process defined hereinabove, as incorporation of the templates near the middle of the linear protected peptide precursors enhance significantly cyclization yields.

Building blocks A1–A69 belong to a class of amino acids wherein the N-terminus is a secondary amine forming part of a ring. Among the genetically encoded amino acids only proline falls into this class. The configuration of building block A1 through A69 is (D), and they are combined with a building block —B—CO— of (L)-configuration. Preferred combinations for templates (a1) are-$^D$A1-CO-$^L$B-CO— to $^D$A69-CO-$^L$B-CO—. Thus, for example, $^D$Pro-$^L$Pro constitutes the prototype of templates (a1). Less preferred, but possible are combinations where templates (a2) are -$^L$A1-CO-$^D$B-CO— to $^L$A69-CO-$^D$BCO—. Thus, for example, $^L$Pro-$^D$Pro constitutes a less preferred prototype of template (a2).

It will be appreciated that building blocks -A1-CO— to -A69-CO— in which A has (D)-configuration, are carrying a group $R^1$ at the α-position to the N-terminus. The preferred values for $R^1$ are H and lower alkyl with the most preferred values for $R^1$ being H and methyl. It will be recognized by those skilled in the art, that A1–A69 are shown in (D)-configuration which, for $R^1$ being H and methyl, corresponds to the (R)-configuration. Depending on the priority of other values for $R^1$ according to the Cahn, Ingold and Prelog-rules, this configuration may also have to be expressed as (S).

In addition to $R^1$ building blocks -$A^1$-CO— to -A69-CO— can carry an additional substituent designated as $R^2$ to $R^{17}$. This additional substituent can be H, and if it is other than H, it is preferably a small to medium-sized aliphatic or aromatic group. Examples of preferred values for $R^2$ to $R^{17}$ are:

$R^2$: H; lower alkyl; lower alkenyl; $(CH_2)_m OR^{55}$ (where $R^{55}$: lower alkyl; or lower alkenyl); —$(CH_2)_m SR^{56}$ (where $R^{56}$: lower alkyl; or lower alkenyl); —$(CH_2)_m NR^{33}R^{34}$ (where $R^{33}$: lower alkyl; or lower alkenyl; $R^{34}$: H; or lower alkyl; $R^{33}$ and $R^{34}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$—; $R^{57}$: H; or lower alkyl); —$(CH_2)_m OCONR^{33}R^{75}$ (where $R^{33}$: H; or lower allyl; or lower alkenyl; $R^{75}$: lower alkyl; or $R^{33}$ and $R^{75}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$—; where $R^{57}$: H; or lower alkyl); —$(CH_2)_m NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$—; where $R^{57}$: H; or lower alkyl); —$(CH_2)_o N(R^{20})COR^{64}$ (where: $R^{20}$: H; or lower alkyl; $R^{64}$: lower alkyl; or lower alkenyl); —$(CH_2)_o COOR^{57}$ (where $R^{57}$: lower alkyl; or lower alkenyl); —$(CH_2)_o CONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$—; where $R^{57}$: H; or lower alkyl); —$(CH_2)_o PO(OR^{60})_2$ (where $R^{60}$: lower alkyl; or lower alkenyl); —$(CH_2)_o SO_2 R^{62}$ (where $R^{62}$: lower alkyl; or lower alkenyl); or —$(CH_2)_q C_6 H_4 R^8$ (where $R^8$: H; F; Cl; $CF_3$; lower alkyl; lower alkenyl; or lower alkoxy).

$R^3$: H; lower alkyl; lower alkenyl; —$(CH_2)_m OR^{55}$ (where $R^{55}$: lower alkyl; or lower alkenyl); —$(CH_2)_m SR^{56}$ (where $R^{56}$: lower alkyl; or lower alkenyl); —$(CH_2)_m NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$—; where $R^{57}$: H; or lower alkyl); —$(CH_2)_m OCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$—; where $R^{57}$: H; or lower alkyl); —$(CH_2)_m NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$—; where $R^{57}$: H; or lower alkyl); —$(CH^2)_o N(R^{20})COR^{64}$ (where: $R^{20}$: H; or lower alkyl; $R^{64}$: lower alkyl; or lower alkenyl); —$(CH_2)_o COOR^{57}$ (where $R^{57}$: lower alkyl; or lower alkenyl); —$(CH_2)_o CONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$—, where $R^{57}$: H; or lower alkyl); —$(CH_2)_o (OR^{60})_2$ (where $R^{60}$: lower alkyl; or lower alkenyl); —$(CH_2)_o SO_2 R^{62}$ (where $R^{62}$:

lower alkyl; or lower alkenyl); or $-(CH_2)_qC_6H_4R^8$ (where $R^8$: H; F; Cl; $CF_3$; lower alkyl; lower alkenyl; or lower alkoxy).

$R^4$: H; lower alkyl; lower alkenyl; $-(CH_2)_mOR^{55}$ (where $R^{55}$: lower alkyl; or lower alkenyl); $-(CH_2)_mS^{56}$ (where $R^{56}$: lower alkyl; or lower alkenyl); $-(CH_2)_mNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH^2)_mN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^5$: lower alkyl; lower alkenyl; $-(CH_2)_oOR^{55}$ (where $R^{55}$: lower alkyl; or lower alkenyl); $-(CH_2)_oSR^{56}$ (where $R^{56}$: lower alkyl; or lower alkenyl); $-(CH_2)_oNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; $R^{57}$: where H; or lower alkyl); $-(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH^2)_oN(R^{20})COR^{64}$ (where: $R^{20}$: H; or lower alkyl; $R^{64}$: alkyl; alkenyl; aryl; and aryl-lower alkyl; heteroaryl-lower alkyl); $-(CH_2)_oCOOR^{57}$ (where $R^{57}$: lower alkyl; or lower alkenyl); $-(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^6$: H; lower alkyl; lower alkenyl; $-(CH_2)_oOR^{55}$ (where $R^{55}$: lower alkyl; or lower alkenyl); $-(CH_2)_oSR^{56}$ (where $R^{56}$: lower alkyl; or lower alkenyl); $-(CH_2)_oNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH^2)_oN(R_{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^7$: lower alkyl; lower alkenyl; $-(CH_2)_qOR^{55}$ (where $R^{55}$: lower alkyl; or lower alkenyl); $-(CH_2)_qSR^{56}$ (where $R^{56}$: lower alkyl; or lower alkenyl); $-(CH_2)_qNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_qOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $(CH_2)_qNR_{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_qN(R^{20})COR^{64}$ (where: $R^{20}$: H; or lower alkyl; $R^{64}$: lower alkyl; or lower alkenyl); $-(CH_2)_rCOOR^{57}$ (where $R^{57}$: lower alkyl; or lower alkenyl); $-(CH_2)_qCONR^{58}R^{59}$ (where $R^{58}$: lower alkyl; or lower alkenyl; and $R^{59}$: H; or lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_rPO(OR^{60})_2$ (where $R^{60}$: lower alkyl; or lower alkenyl); $-(CH_2)_rSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^8$: H; F; Cl; $CF_3$; lower alkyl; lower alkenyl; $-(CH_2)_oOR^{55}$ (where $R^{55}$: lower alkyl; or lower alkenyl); $-(CH^2)_oSR^{56}$ (where $R^{56}$: lower alkyl; or lower alkenyl); $-(CH_2)_oNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2\text{-}6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: $-(CH_2)_{2\text{-}6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: $-(CH_2)_{2\text{-}6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^9$: lower alkyl; lower alkenyl; $-(CH_2)_oOR^{55}$ (where $R^{55}$: lower alkyl; or lower alkenyl); $-(CH_2)_oSR^5$, (where $R^{56}$: lower alkyl; or lower alkenyl); $-(CH_2)_oNR^{33}R^{34}$ (where $R^{33}$: lower alkyl; or lower alkenyl; $R^{34}$: H; or lower allyl; or $R^{33}$ and $R^{34}$ taken together form: $-(CH_2)_{2\text{-}6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2\text{-}6}-$; $-(CH_2)_2O(CH_2)_2-$, $-(CH_2)_2S(CH_2)_2-$; or $-(CH_2)_2NR^{57}(CH_2)_2-$; where $R^{57}$: H; or lower alkyl); $-(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: $-(CH_2)_{2\text{-}6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: $-(CH_2)_{2\text{-}6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^{10}$: lower alkyl; lower alkenyl; $-(CH_2)_oOR^{55}$ (where $R^{55}$: lower alkyl; or lower alkenyl); $-(CH_2)_oSR^{56}$ (where $R^{56}$: lower alkyl; or lower alkenyl); $-(CH_2)_oNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2\text{-}6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2\text{-}6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: $-(CH_2)_{2\text{-}6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl; or lower alkenyl; and $R^{59}$: H; lower alkyl; or $R^{58}$ and $R^{59}$ taken together form: $-(CH_2)_{2\text{-}6}-$; $-(CH_2)_2O(CH_2)_2-$; $-(CH_2)_2S(CH_2)_2-$, or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^{11}$: H; lower alkyl; lower alkenyl; $-(CH_2)_mOR^{55}$ (where $R^{55}$: lower alkyl; or lower alkenyl); $-(CH_2)_mSR^{56}$ (where $R^{56}$: lower alkyl; or lower alkenyl); $-(CH_2)_mNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2\text{-}6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2\text{-}6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: $-(CH_2)_{2\text{-}6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl; or lower alkenyl; and $R^{59}$: H; lower alkyl; or $R^{58}$ and $R^{59}$ taken together form: $-(CH_2)_{2\text{-}6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^{12}$: H; lower alkyl; lower alkenyl; $-(CH_2)_mOR^{55}$ (where $R^{55}$: lower alkyl; or lower alkenyl); $-(CH_2)_mSR^{56}$ (where $R^{56}$: lower alkyl; or lower alkenyl); $-(CH_2)_mNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2\text{-}6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2\text{-}6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: $-(CH_2)_{2\text{-}6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mN(R^{20})COR^{64}$ (where: $R^{20}$: H; or lower alkyl; $R^{64}$: lower alkyl; or lower alkenyl); $-(CH_2)_rCOOR^{57}$ (where $R^{57}$: lower alkyl; or lower alkenyl); $-(CH_2)_rCONR^{58}R^{59}$ (where $R^{58}$: lower alkyl; or lower alkenyl; and $R^{59}$: H; or lower alkyl; or $R^{58}$ and $R^{59}$ taken together form:

—$(CH_2)_{2-6}$—; —$(CH_2)_2O(CH_2)_2$—; or —$(CH_2)_2S(CH_2)_2$—; or —$(CH_2)_2NR^{57}(CH_2)_2$—; where $R^{57}$: H; or lower alkyl); —$(CH_2)_rPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{13}$: lower alkyl; lower alkenyl; —$(CH_2)_qOR^{55}$ (where $R^{55}$: lower alkyl; or lower alkenyl); —$(CH_2)_qSR^{56}$ (where $R^{56}$: lower alkyl; or lower alkenyl); —$(CH_2)_qNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qN(R^{20})COR^{64}$ (where: $R^{20}$: H; or lower alkyl; $R^{64}$: lower alkyl; or lower alkenyl); —$(CH_2)_rCOO^{57}$ (where $R^{57}$: lower alkyl; or lower alkenyl); —$(CH_2)_qCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_rPO(OR^{60})_2$ (where $R^{60}$: lower alkyl; or lower alkenyl); —$(CH_2)_rSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{14}$: H; lower alkyl; lower alkenyl; —$(CH_2)_mOR^{55}$ (where $R^{55}$: lower alkyl; or lower alkenyl); —$(CH_2)_mSR^{56}$ (where $R^{56}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); —$(CH_2)_qC^6H_4R^8$ (where $R^8$: H; F; Cl; $CF_3$; lower alkyl; lower alkenyl; or lower alkoxy).

$R^{15}$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); particularly favoured are $NR^{20}$CO lower alkyl ($R^{20}$=H; or lower alkyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{16}$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{17}$: lower alkyl; lower alkenyl; —$(CH_2)_qOR^{55}$ (where $R^{55}$: lower alkyl; or lower alkenyl); —$(CH_2)_qSR^{56}$ (where $R^{56}$: lower alkyl; or lower alkenyl); —$(CH_2)_qNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—;

—(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_q$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_q$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$^2$)$_q$N(R$^{20}$)COR$^{64}$ (where: R$^{20}$: H; or lower alkyl; R$^{64}$: lower alkyl; or lower alkenyl); —(CH$_2$)$_r$COOR$^{57}$ (where R$^{57}$: lower alkyl; or lower alkenyl); —(CH$_2$)$_q$CONR$^{58}$R$^{59}$ (where R$^{58}$: lower alkyl; or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_r$PO(OR$^{60}$)$_2$ (where R$^{60}$: lower alkyl; or lower alkenyl); —(CH$_2$)$_r$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

Among the building blocks A1 to A69 the following are preferred: A5 with R$^2$ being H, A8, A22, A25, A38 with R$^2$ being H, A42, A47, and A50. Most preferred are building blocks of type A8':

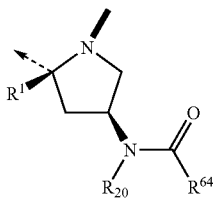

A8' wherein R$^{20}$ is H or lower alkyl; and R$^{64}$ is alkyl; alkenyl; aryl; aryl-lower alkyl; or heteroaryl-lower alkyl; especially those wherein R$^{64}$ is n-hexyl (A8'-1); n-heptyl (A8'-2); 4-(phenyl)benzyl (A8'-3); diphenylmethyl (A8'-4); 3-amino-propyl (A8'-5); 5-amino-pentyl (A8'-6); methyl (A8'-7); ethyl (A8'-8); isopropyl (A8'-9); isobutyl (A8'-10); n-propyl (A8'-11); cyclohexyl (A8'-12); cyclohexylmethyl (A8'-13); n-butyl (A8'-14); phenyl (A8'-15); benzyl (A8'-16); (3-in-dolyl)methyl (A8'-17); 2-(3-indolyl)ethyl (A8'-18); (4-phe-nyl)phenyl (A8'-19); and n-nonyl (A8'-20).

Building block A70 belongs to the class of open-chained α-substituted α-amino acids, building blocks A71 and A72 to the corresponding β-amino acid analogues and building blocks A73–A104 to the cyclic analogues of A70. Such amino acid derivatives have been shown to constrain small peptides in well defined reverse turn or U-shaped conformations (C. M. Venkatachalam, *Biopolymers*, 1968, 6, 1425–1434; W. Kabsch, C Sander, *Biopolymers* 1983, 22, 2577). Such building blocks or templates are ideally suited for the stabilization of β-hairpin conformations in peptide loops (D. Obrecht, M. Altorfer, J. A. Robinson, "Novel Peptide Mimetic Building Blocks and Strategies for Efficient Lead Finding", *Adv. Med Chem*. 1999, Vol. 4, 1–68; P. Balaram, "Non-standard amino acids in peptide design and protein engineering", *Curr. Opin. Struct. Biol.* 1992, 2, 845–851; M. Crisma, G. Valle, C. Toniolo, S. Prasad, R. B. Rao, P. Balaram, "β-turn conformations in crystal structures of model peptides containing α,α-disubstituted amino acids", *Biopolymers* 1995, 35, 1–9; V. J. Hruby, F. Al-Obeidi, W. Kazmierski, *Biochem. J.* 1990, 268, 249–262).

It has been shown that both enantiomers of building blocks -A70-CO— to A104-CO— in combination with a building block —B—CO— of L-configuration can efficiently stabilize and induce β-hairpin conformations (D. Obrecht, M. Altorfer, J. A. Robinson, "Novel Peptide Mimetic Building Blocks and Strategies for Efficient Lead Finding", *Adv. Med Chem* 1999, Vol. 4, 1–68; D. Obrecht, C. Spiegler, P. Schorholm, K. Müller, H. Heimgartner, F. Stierli, *Helv. Chin. Acta* 1992, 75, 1666–1696; D. Obrecht, U. Bohdal, J. Daly, C. Lehmann, P. Schönholzer, K. Müller, *Tetrahedron* 1995, 51, 10883–10900; D. Obrecht, C. Lehmann, C. Ruffieux, P. Schönholzer, K. Müller, *Helv. Chim. Acta* 1995, 78, 1567–1587; D. Obrecht, U. Bohdal, C. Broger, D. Bur, C. Lehmann, R. Ruffieux, P. Schönholzer, C. Spiegler, *Helv. Chim. Acta* 1995, 78, 563–580; D. Obrecht, H. Karajiannis, C. Lehmann, P. Schönholzer, C. Spiegler, *Helv. Chim. Acta* 1995, 78, 703–714).

Thus, for the purposes of the present invention templates (a1) can also consist of -A70-CO— to A104-CO— where building block A70 to A104 is of either (D)- or (L)-configuration, in combination with a building block —B—CO— of (L)-configuration.

Preferred values for R$^{20}$ in A70 to A104 are H or lower alkyl with methyl being most preferred. Preferred values for R$^{18}$, R$^{19}$ and R$^{21}$–R$^{29}$ in building blocks A70 to A104 are the following:

R$^{18}$: lower alkyl.

R$^{19}$: lower alkyl; lower alkenyl; —(CH$_2$)$_p$OR$^{55}$ (where R$^{55}$: lower alkyl; or lower alkenyl); —(CH$_2$)$_p$SR$^{56}$ (where R$^{56}$: lower alkyl; or lower alkenyl); —(CH$_2$)$_p$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(C H$_2$)$_2$—; or —(CH$_2$)$_2$NR$^{57}$(CH$_2$)$_2$—; where R$^{57}$: H; or lower alkyl); —(CH$_2$)$_p$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(C H$_2$)$_2$—; —(CH$_2$)$_2$S(CH$_2$)$_2$—; or —(CH$_2$)$_2$NR$^{57}$(C H$_2$)$_2$—; where R$^{57}$: H; or lower alkyl); —(CH$^2$)$_p$N(R$^{20}$)COR$^{64}$ (where: R$^{20}$: H; or lower alkyl; R$^{64}$: lower alkyl; or lower alkenyl); —(CH$_2$)$_p$COOR$^{57}$ (where R$^{57}$: lower alkyl; or lower alkenyl); —(CH$_2$)$_p$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(C H$_2$)$_2$—; or —(CH$_2$)$_2$NR$^{57}$(CH$_2$)$_2$—; where R$^{57}$: H; or lower alkyl); —(CH$_2$)$_o$O(OR$^{60}$)$_2$ (where R$^{60}$: lower alkyl; or lower alkenyl); —(CH$_2$)$_p$SO$_2$R$^{62}$ (where R$^{62}$: lower alkyl; or lower alkenyl); or —(CH$_2$)$_o$C$_6$H$_4$R$^8$ (where R$^8$: H; F; Cl; CF$_3$; lower alkyl; lower alkenyl; or lower alkoxy).

R$^{21}$: H; lower alkyl; lower alkenyl; —(CH$_2$)$_o$OR$^{55}$ (where R$^{55}$: lower alkyl; or lower alkenyl); —(CH$_2$)$_o$SR$^{56}$ (where R$^{56}$: lower alkyl; or lower alkenyl); —(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;

where $R^{57}$: H; or lower alkyl); —(CH$_2$)$_o$OCONR$^{33}$R$^{75}$ (where $R^{33}$: H; or lower alkyl; or lower alkenyl; $R^{75}$: lower alkyl; or $R^{33}$ and $R^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where $R^{57}$: H; or lower alkyl); —(CH$_2$)$_o$NR$^{20}$CONR$^{33}$R$^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where $R^{57}$: H; or lower alkyl); —(CH$^2$)$_o$N(R$^{20}$)COR$^{64}$ (where: $R^{20}$: H; or lower alkyl; $R^{64}$: lower alkyl; or lower alkenyl); —(CH$_2$)$_o$COOR$^{57}$ (where $R^{57}$: lower alkyl; or lower alkenyl); —(CH$_2$)$_o$CONR$^{58}$R$^{59}$ (where $R^{58}$: lower alkyl, or lower alkenyl; and $R^{59}$: H; lower alkyl; or $R^{58}$ and $R^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where $R^{57}$: H; or lower alkyl); —(CH$_2$)$_o$PO(OR$^{60}$)$_2$ (where $R^{60}$: lower alkyl; or lower alkenyl); —(CH$_2$)$_o$SO$_2$R$^{62}$ (where $R^{62}$: lower alkyl; or lower alkenyl); or (CH$_2$)$_q$C$_6$H$_4$R$^8$ (where $R^8$: H; F; Cl; CF$_3$; lower alkyl; lower alkenyl; or lower alkoxy).

$R^{22}$: lower alkyl; lower alkenyl; —(CH$_2$)$_o$OR$^{55}$ (where $R^{55}$: lower alkyl; or lower alkenyl); —(CH$_2$)$_o$SR$^{56}$ (where $R^{56}$: lower alkyl; or lower alkenyl); —(CH$_2$)$_o$R$^{33}$R$^{34}$ (where $R^{33}$: lower alkyl; or lower alkenyl; $R^{34}$: H; or lower alkyl; or $R^{33}$ and $R^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where $R^{57}$: H; or lower alkyl); —(CH$_2$)$_o$OCONR$^{33}$R$^{75}$ (where $R^{33}$: H; or lower alkyl; or lower alkenyl; $R^{75}$: lower alkyl; or $R^{33}$ and $R^{75}$ taken together form: —(CH$_2$)$_{2-6}$—; —(CH$_2$)$_2$O(CH$_2$)$_2$—; —(CH$_2$)$_2$S(CH$_2$)—; or —(CH$_2$)$_2$NR$^{57}$(CH$_2$)$_2$—; where $R^{57}$: H; or lower alkyl); —(CH$_2$)$_o$NR$^{20}$CONR$^{33}$R$^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where $R^{57}$: H; or lower alkyl); —(CH$_2$)$_o$N(R$^{20}$)COR$^{64}$ (where: $R^{20}$: H; or lower alkyl; $R^{64}$: lower alkyl; or lower alkenyl); —(CH$_2$)$_o$COOR$^{57}$ (where $R^{57}$: lower alkyl; or lower alkenyl); —(CH$_2$)$_o$CONR$^{58}$R$^{59}$ (where $R^{58}$: lower alkyl, or lower alkenyl; and $R^{59}$: H; lower alkyl; or $R^{58}$ and $R^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where $R^{57}$: H; or lower alkyl); —(CH$_2$)$_o$PO(OR$^{60}$)$_2$ (where $R^{60}$: lower alkyl; or lower alkenyl); —(CH$_2$)$_o$SO$_2$R$^{62}$ (where $R^{62}$: lower alkyl; or lower alkenyl); or —(CH$_2$)$_q$C$_6$H$_4$R$^8$ (where $R^8$: H; F; Cl; CF; lower alkyl; lower alkenyl; or lower alkoxy).

$R^{23}$: H; lower alkyl; lower alkenyl; —(CH$_2$)$_o$OR$^{55}$ (where $R^{55}$: lower alkyl; or lower alkenyl); —(CH$_2$)$_o$SR$^{56}$ (where $R^{56}$: lower alkyl; or lower alkenyl); —(CH$_2$)$_o$NR$^{33}$R$^{34}$ (where $R^{33}$: lower alkyl; or lower alkenyl; $R^{34}$: H; or lower alkyl; or $R^{33}$ and $R^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where $R^{57}$: H; or lower alkyl); —(CH$_2$)$_o$OCONR$^{33}$R$^{75}$ (where $R^{33}$: H; or lower alkyl; or lower alkenyl; $R^{75}$: lower alkyl; or $R^{33}$ and $R^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where $R^{57}$: H; or lower alkyl); —(CH$_2$)$_o$NR$^{20}$CONR$^{33}$R$^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where $R^{57}$: H; or lower alkyl); —(CH$_2$)$_o$N(R$^{20}$)COR$^{64}$ (where: $R^{20}$: H; or lower alkyl; $R^{64}$: lower alkyl; or lower alkenyl); particularly favoured are NR$^{20}$CO lower alkyl ($R^{20}$=H; or lower alkyl); —(CH$_2$)$_o$COOR$^{57}$ (where $R^{57}$: lower alkyl; or lower alkenyl); —(CH$_2$)$_o$CONR$^{58}$R$^{59}$ (where $R^{58}$: lower alkyl, or lower alkenyl; and $R^{59}$: H; lower alkyl; or $R^{58}$ and $R^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where $R^{57}$: H; or lower alkyl); —(CH$_2$)$_o$PO(OR$^{60}$)$_2$ (where $R^{60}$: lower alkyl; or lower alkenyl); —(CH$_2$)$_o$SO$_2$R$^{62}$ (where $R^{62}$: lower alkyl; or lower alkenyl); or —(CH$_2$)$_q$C$_6$H$_4$R$^8$ (where $R^8$: H; F; Cl; CF$_3$, lower alkyl; lower alkenyl; or lower alkoxy);

$R^{24}$: lower alkyl; lower alkenyl; —(CH$_2$)$_o$OR$^{55}$ (where $R^{55}$: lower alkyl; or lower alkenyl); —(CH$_2$)$_o$SR$^{56}$ (where $R^{56}$: lower alkyl; or lower alkenyl); —(CH$_2$)$_o$NR$^{33}$R$^{34}$ (where $R^{33}$: lower alkyl; or lower alkenyl; $R^{34}$: H; or lower alkyl; or $R^{33}$ and $R^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where $R^{57}$: H; or lower alkyl); —(CH$_2$)$_o$OCONR$^{33}$R$^{75}$ (where $R^{33}$: H; or lower alkyl; or lower alkenyl; $R^{75}$: lower alkyl; or $R^{33}$ and $R^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where $R^{57}$: H; or lower alkyl); —(CH$_2$)$_o$NR$^{20}$CONR$^{33}$R$^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where $R^{57}$: H; or lower alkyl); —(CH$_2$)$_o$N(R$^{20}$)COR$^{64}$ (where: $R^{20}$: H; or lower alkyl; $R^{64}$: lower alkyl; or lower alkenyl); particularly favoured are NR$^{20}$CO lower alkyl ($R^{20}$=H ; or lower alkyl); —(CH$_2$)$_o$COOR$^{57}$ (where $R^{57}$: lower alkyl; or lower alkenyl); —(CH$_2$)$_o$CONR$^{58}$R$^{59}$ (where $R^{58}$: lower alkyl, or lower alkenyl; and $R^{59}$: H; lower alkyl; or $R^{58}$ and $R^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where $R^{57}$: H; or lower alkyl); —(CH$_2$)$_o$PO(OR$^{60}$)$_2$ (where $R^{60}$: lower alkyl; or lower alkenyl); —(CH$_2$)$_o$SO$_2$R$^{62}$ (where $R^{62}$: lower alkyl; or lower alkenyl); or —(CH$_2$)$_q$C$_6$H$_4$R$^8$ (where $R^8$: H; F; Cl; CF$_3$; lower alkyl; lower alkenyl; or lower alkoxy);

$R^{25}$: H; lower alkyl; lower alkenyl; —(CH$_2$)$_m$OR$^{55}$ (where $R^{55}$: lower alkyl; or lower alkenyl); —(CH$_2$)$_m$NR$^{33}$R$^{34}$ (where $R^{33}$: lower alkyl; or lower alkenyl; $R^{34}$: H; or lower alkyl; or $R^{33}$ and $R^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where $R^{57}$: H; or lower alkyl); —(CH$_2$)$_m$OCONR$^{33}$R$^{75}$ (where $R^{33}$: H; or lower alkyl; or lower alkenyl; $R^{75}$: lower alkyl; or $R^{33}$ and $R^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where $R^{57}$: H; or lower alkyl); —(CH$_2$)$_m$NR$^{20}$CONR$^{33}$R$^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where $R^{57}$: H; or lower alkyl); —(CH$_2$)$_m$N(R$^{20}$)COR$^{64}$ (where: $R^{20}$: H; or lower alkyl; $R^{64}$: lower alkyl; or lower alkenyl); —(CH$_2$)$_o$COOR$^{57}$ (where $R^{57}$: lower alkyl; or lower alkenyl); —(CH$_2$)$_o$CONR$^{58}$R$^{59}$ (where $R^{58}$: lower alkyl; or lower alkenyl; and $R^{59}$: H; lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^{26}$: H; lower alkyl; lower alkenyl; $-(CH_2)_mOR^{55}$ (where $R^{55}$: lower alkyl; or lower alkenyl); $-(CH_2)_mNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH^2)_mN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl; or lower alkenyl; and $R^{59}$: H; lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

Alternatively. $R^{25}$ and $R^{26}$ taken together can be $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl).

$R^{27}$: H; lower alkyl; lower alkenyl; $-(CH_2)_oOR^{55}$ (where $R^{55}$: lower alkyl; or lower alkenyl); $-(CH_2)_oSR^{56}$ (where $R^{56}$: lower alkyl; or lower alkenyl); $-(CH_2)_oNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH^2)_oN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl, or lower alkenyl; and $R^{59}$: H; lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^{28}$: lower alkyl; lower alkenyl; $-(CH_2)_oOR^{55}$ (where $R^{55}$: lower alkyl; or lower alkenyl); $-(CH_2)_oSR^{56}$ (where $R^{56}$: lower alkyl; or lower alkenyl); $-(CH_2)_oNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH^2)_oN(R^{20})COR^{64}$ (where $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl, or lower alkenyl; and $R^{59}$: H; lower alkyl; or $R^{58}$ and $R^{59}$ taken together form $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^{29}$: lower alkyl; lower alkenyl; $-(CH_2)_oOR^{55}$ (where $R^{55}$: lower alkyl; or lower alkenyl); $-(CH_2)_oSR^{56}$ (where $R^{56}$: lower alkyl; or lower alkenyl); $-(CH_2)_oNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oN(R^{20})_oCOR^{64}$ (where: $R^{20}$: H; or lower alkyl; $R^{64}$: lower alkyl; or lower alkenyl); particularly favored are $NR^{20}CO$ lower-alkyl ($R^{20}$=H; or lower alkyl); $-(CH_2)_oCOOR^{57}$ (where $R^{57}$: lower alkyl; or lower alkenyl); $-(CH_2)_oCONR^{58}R^{59}$ (where $R^{58}$: lower alkyl, or lower alkenyl; and $R^{59}$: H; lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH^2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

For templates (b) to (p), such as (b1) and (c1), the preferred values for the various symbols are the following:

$R^8$: H; F; Cl; $CF_3$; lower alkyl; lower alkenyl; $-(CH_2)_oOR^{55}$ (where $R^{55}$: lower alkyl; or lower alkenyl); $-(CH_2)_sR^{56}$ (where $R^{56}$: lower alkyl; or lower alkenyl); $-(CH_2)_oNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_2-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^{20}$: H; or lower alkyl.

$R^{30}$: H, methyl.

$R^{31}$: H; lower alkyl; lower alkenyl; $-(CH_2)_pOR^{55}$ (where $R^{55}$: lower alkyl; or lower alkenyl); $-(CH_2)_pNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_pOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_pNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_pN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $(-(CH_2)_oCONR^{58}R^{59}$ (where $R^{58}$: lower alkyl, or lower alkenyl; and $R^{59}$: H; lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_rC_6H_4R^8$ (where $R^8$: H; F; Cl; $CF_3$; lower alkyl; lower alkenyl; or lower alkoxy); most preferred is $-CH_2CONR^{58}R^{59}$ ($R^{58}$: H; or lower alkyl; $R^{59}$: lower alkyl; or lower alkenyl).

$R^{32}$: H, methyl.

$R^{33}$: lower alkyl; lower alkenyl; $-(CH_2)_mOR^{55}$ (where $R^{55}$: lower alkyl; or lower alkenyl); $-(CH_2)_mNR^{34}R^{63}$ (where $R^{34}$: lower alkyl; or lower alkenyl; $R^{63}$: H; or lower alkyl; or $R^{34}$ and $R^{63}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $(CH_2)_mOCONR^{75}R^{82}$ (where $R^{75}$: lower alkyl; or lower alkenyl; $R^{82}$: H; or lower alkyl; or $R^{75}$ and $R^{82}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH^2)_mNR^{20}CONR^{78}R^{82}$ (where $R^{20}$: H; or lower lower alkyl; $R^{78}$: H; or lower alkyl; or lower alkenyl; $R^{82}$: H; or lower alkyl; or $R^{78}$ and $R^{82}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl; or lower alkenyl; and $R^{59}$: H; lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl).

$R^{34}$: H; or lower alkyl.

$R^{35}$: H; lower alkyl; lower alkenyl; $-(CH_2)_mOR^{55}$ (where $R^{55}$: lower alkyl; or lower alkenyl); $-(CH_2)_mNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH^2)_mN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl; or lower alkenyl; and $R^{59}$: H; lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl).

$R^{36}$: lower alkyl; lower alkenyl; or aryl-lower alkyl.

$R^{37}$: H; lower alkyl; lower alkenyl; $-(CH_2)_pOR^{55}$ (where $R^{55}$: lower alkyl; or lower alkenyl); $-(CH_2)_pNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_pOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH^2)_pNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); —(CH$_2$)$_p$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{38}$: H; lower alkyl; lower alkenyl; —(CH$_2$)$_p$OR$^{55}$ (where R$^{55}$: lower alkyl; or lower alkenyl); —(CH$_2$)$_p$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$NR$^{20}$CONR$^{33}$R$^{82}$ (where R$^{20}$: H; or lower alkyl or lower alkenyl; R$^{33}$: H; or lower alkyl; or lower alkenyl; R$^{82}$: H; or lower alkyl; or R$^{33}$ and R$^{82}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{82}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{39}$: H; lower alkyl; lower alkenyl; —(CH$_2$)$_m$OR$^{55}$ (where R$^{55}$: lower alkyl; or lower alkenyl); —(CH$_2$)$_m$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; lower alkyl; or R$^{58}$ and R$^{59}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl).

R$^{40}$: lower alkyl; lower alkenyl; or aryl-lower alkyl.

R$^{41}$: H; lower alkyl; lower alkenyl; —(CH$_2$)$_p$OR$^{55}$ (where R$^{55}$: lower alkyl; or lower alkenyl); —(CH$_2$)$_p$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2\text{-}6}$—; —(CH$_2$)$_2$O(CH$_2$)$_2$—, —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$NR$^{20}$CONR$^{33}$R$^{82}$ (where R$^{20}$: H; or lower alkyl or lower alkenyl; R$^{33}$: H; or lower alkyl; or lower alkenyl; R$^{82}$: H; or lower alkyl; or R$^{33}$ and R$^{82}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl or lower alkenyl; and R$^{59}$: H; lower alkyl; or R$^{58}$ and R$^{59}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$C$_4$R$^8$ (where R$^{81}$: H; F; Cl; CF$_3$; lower alkyl; lower alkenyl; or lower alkoxy).

R$^{42}$: H; lower alkyl; lower alkenyl; —(CH$_2$)$_p$OR$^{55}$ (where R$^{55}$: lower alkyl; or lower alkenyl); —(CH$_2$)$_p$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$NR$^{20}$CONR$^{33}$R$^{82}$ (where R$^{20}$: H; or lower alkyl; or lower alkenyl; R$^{33}$: H; or lower alkyl; or lower alkenyl; R$^{82}$: H; or lower alkyl; or R$^{33}$ and R$^{82}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl or lower alkenyl; and R$^{59}$: H; lower alkyl; or R$^{58}$ and R$^{59}$ taken together form —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$^2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{43}$: H; lower alkyl; lower alkenyl; —(CH$_2$)$_m$OR$^{55}$ (where R$^{55}$: lower alkyl; or lower alkenyl); —(CH$_2$)$_m$SR$^{56}$ (where R$^{56}$: lower alkyl; or lower alkenyl); —(CH$^2$)$_m$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$R$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2\text{-}6}$—; —(CH$_2$)$_2$O(CH$_2$)$_2$—; —(CH$_2$)$_2$S(CH$_2$)—; or —(CH$_2$)$_2$NR$^{57}$(CH$_2$)$_2$—; where R$^{57}$: H; or lower alkyl); —(CH$_2$)$_m$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; lower alkyl; or R$^{58}$ and R$^{59}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{44}$: lower alkyl; lower alkenyl; —(CH$_2$)$_p$OR$^{55}$ (where R$^{55}$: lower alkyl; or lower alkenyl); —(CH$_2$)$_p$SR$^{56}$ (where R$^{56}$: lower alkyl; or lower alkenyl); —(CH$_2$)$_p$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$OCONR$^{33}$R$^{75}$ (where R$^{33}$: H; or lower alkyl; or lower alkenyl; R$^{75}$: lower alkyl; or R$^{33}$ and R$^{78}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—, —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$N(R$^{20}$)COR$^{64}$ (where: R$^{20}$: H; or lower alkyl; R$^{64}$: lower alkyl; or lower alkenyl); —(CH$_2$)$_p$COOR$^{57}$ (where R$^{57}$: lower alkyl; or lower alkenyl); —(CH$_2$)$_p$CONR$^{58}$R$^{59}$ (where R$^{58}$: lower alkyl; or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); or —(CH$_2$)$_o$C$_6$H$_4$R$^8$ (where R$^8$: H; F; Cl; CF$_3$; lower alkyl; lower alkenyl; or lower alkoxy).

R$^{45}$: H; lower alkyl; lower alkenyl; —(CH$_2$)$_o$OR$^{55}$ (where R$^{55}$: lower alkyl; or lower alkenyl); —(CH$_2$)$_o$SR$^{56}$ (where R$^{56}$: lower alkyl; or lower alkenyl); —(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_s$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—, —(CH$_2$)$_2$S(CH$_2$)$_2$—; or —(CH$_2$)$_2$NR$^{57}$(CH$_2$)$_2$—; where R$^{57}$: H; or lower alkyl); —(CH$^2$)$_o$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); or —(CH$_2$)$_s$C$_6$H$_4$R$^8$ (where R$^8$: H; F; Cl; CF$_3$; lower alkyl; lower alkenyl; or lower alkoxy).

R$^{46}$: H; lower alkyl; lower alkenyl; —(CH$_2$)$_s$OR$^{55}$ (where R$^{55}$: lower alkyl; or lower alkenyl); —(CH$_2$)$_s$SR$^{56}$ (where R$^{56}$: lower alkyl; or lower alkenyl); —(CH$_2$)$_s$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_s$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_s$NR$^{20}$CONR$^{33}$R$^{82}$ (where R$^{20}$: H; or lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_s$N(R$^{20}$)$_o$COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—, or —(CH$_2$)$_2$NR$^{57}$(CH$_2$)—; where R$^{57}$: H; or lower alkyl); or —(CH$_2$)$_s$C$_6$H$_4$R$^3$ (where R$^8$: H; F; Cl; CF$_3$; lower alkyl; lower alkenyl; or lower alkoxy).

R$^{47}$: H; or OR$^{55}$ (where R$^{55}$: lower alkyl; or lower alkenyl).

R$^{48}$: H; or lower alkyl.

R$^{49}$: H; lower alkyl; —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); or (CH$_2$)$_o$C$_6$H$_4$R$^8$ (where R$^8$: H; F; Cl; CF$_3$; lower alkyl; lower alkenyl; or lower alkoxy).

R$^{50}$: H; methyl.

R$^{51}$: H; lower alkyl; lower alkenyl; —(CH$_2$)$_m$OR$^{55}$ (where R$^{55}$: lower alkyl; or lower alkenyl); —(CH$_2$)$_m$NR$^{33}$R$^{34}$ (where R$^{33}$: lower alkyl; or lower alkenyl; R$^3$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); (CH$_2$)$_m$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$^2$)$_m$N(R$^{20}$)COR$^{64}$ (where: R$^{20}$: H; or lower alkyl; R$^{64}$: lower alkyl; or lower alkenyl); —(CH$_2$)$_p$COOR$^{57}$ (where R$^{57}$: lower alkyl; or lower alkenyl); —(CH$_2$)$_p$CONR$^{58}$R$^{59}$ (where R$^{58}$: lower alkyl; or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); or —(CH$_2$)$_r$C$_6$H$_4$R$^8$ (where R$^{85}$: H; F; Cl; CF$_3$; lower alkyl; lower alkenyl; or lower alkoxy).

R$^{52}$: H; lower alkyl; lower alkenyl; —(CH$_2$)$_m$OR$^{55}$ (where R$^{55}$: lower alkyl; or lower alkenyl); —(CH$_2$)$_m$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$NR$^{20}$CONR$^{33}$R$^{82}$ (where R$^{20}$:

H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; $R^{57}$: H; or lower alkyl); —$(CH^2)_mN(R^{20})COR^{64}$ (where: $R^{20}$: H; or lower alkyl; $R^{64}$: lower alkyl; or lower alkenyl); —$(CH_2)_pCOOR^{57}$ (where $R^{57}$: lower alkyl; or lower alkenyl); —$(CH_2)_pCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_rC_6H_4R^8$ (where $R^8$: H; F; Cl; $CF_3$; lower alkyl; lower alkenyl; or lower alkoxy).

$R^{53}$: H; lower alkyl; lower alkenyl; —$(CH_2)_mOR^{55}$ (where $R^{55}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH^2)_mN(R^{20})COR^{64}$ (where: $R^{20}$: H; or lower alkyl; $R^{64}$: lower alkyl; or lower alkenyl); —$(CH_2)_pCOOR^{57}$ (where $R^{57}$: lower alkyl; or lower alkenyl); —$(CH_2)_pCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_rC_6H_4R^8$ (where $R^8$: H; F; Cl; $CF_3$; lower alkyl; lower alkenyl; or lower alkoxy).

$R^{54}$: lower alkyl; lower alkenyl; or aryl-lower alkyl.

Among the building blocks A70 to A104 the following are preferred: A74 with $R^{22}$ being H, A75, A76, A77 with $R^{22}$ being H, A78 and A79.

The building block —B—CO— within template (a1) and (a2) designates an L-amino acid residue. Preferred values for B are: —$NR^{20}CH(R^{71})$— and enantiomers of groups A5 with $R^2$ being H, A8, A22, A25, A38 with $R^2$ being H, A42, A47, and A50. Most preferred are

| | |
|---|---|
| Ala | L-Alanine |
| Arg | L-Arginine |
| Asn | L-Asparagine |
| Cys | L-Cysteine |
| Gln | L-Glutamine |
| Gly | Glycine |
| His | L-Histidine |
| Ile | L-Isoleucine |
| Leu | L-Leucine |
| Lys | L-Lysine |
| Met | L-Methionine |
| Phe | L-Phenylalanine |
| Pro | L-Proline |
| Ser | L-Serine |
| Thr | L-Threonine |
| Trp | L-Tryptophan |
| Tyr | L-Tyrosine |

-continued

| | |
|---|---|
| Val | L-Valine |
| Cit | L-Citrulline |
| Orn | L-Ornithine |
| tBuA | L-t-Butylalanine |
| Sar | Sarcosine |
| t-BuG | L-tert.-Butylglycine |
| 4AmPhe | L-para-Aminophenylalanine |
| 3AmPhe | L-meta-Aminophenylalanine |
| 2AmPhe | L-ortho-Aminophenylalanine |
| Phe(mC(NH$_2$)=NH) | L-meta-Amidinophenylalanine |
| Phe(pC(NH$_2$)=NH) | L-para-Amidinophenylalanine |
| Phe(mNHC (NH$_2$)=NH) | L-meta-Guanidinophenylalanine |
| Phe(pNHC (NH$_2$)=NH) | L-para-Guanidinophenylalanine |
| Phg | L-Phenylglycine |
| Cha | L-Cyclohexylalanine |
| C$_4$al | L-3-Cyclobutylalanine |
| C$_5$al | L-3-Cyclopentylalanine |
| Nle | L-Norleucine |
| 2-Nal | L-2-Naphthylalanine |
| 1-Nal | L-1-Naphthylalanine |
| 4Cl-Phe | L-4-Chlorophenylalanine |
| 3Cl-Phe | L-3-Chlorophenylalanine |
| 2Cl-Phe | L-2-Chlorophenylalanine |
| 3,4Cl$_2$-Phe | L-3,4-Dichlorophenylalanine |
| 4F-Phe | L-4-Fluorophenylalanine |
| 3F-Phe | L-3-Fluorophenylalanine |
| 2F-Phe | L-2-Fluorophenylalanine |
| Tic | L-1,2,3,4-Tetrahydroisoquinoline-3-carboxylic acid |
| Thi | L-β-2-Thienylalanine |
| Tza | L-2-Thiazolylalanine |
| Mso | L-Methionine sulfoxide |
| AcLys | L-N-Acetyllysine |
| Dpr | L-2,3-Diaminopropionic acid |
| A$_2$Bu | L-2,4-Diaminobutyric acid |
| Dbu | (S)-2,3-Diaminobutyric acid |
| Abu | γ-Aminobutyric acid (GABA) |
| Aha | ε-Aminohexanoic acid |
| Aib | α-Aminoisobutyric acid |
| Y(Bzl) | L-O-Benzyltyrosine |
| Bip | L-Biphenylalanine |
| S(Bzl) | L-O-Benzylserine |
| T(Bzl) | L-O-Benzylthreonine |
| hCha | L-Homo-cyclohexylalanine |
| hCys | L-Homo-cysteine |
| hSer | L-Homo-serine |
| hArg | L-Homo-arginine |
| hPhe | L-Homo-phenylalanine |
| Bpa | L-4-Benzoylphenylalanine |
| Pip | L-Pipecolic acid |
| OctG | L-Octylglycine |
| MePhe | L-N-Methylphenylalanine |
| MeNle | L-N-Methylnorleucine |
| MeAla | L-N-Methylalanine |
| MeIle | L-N-Methylisoleucine |
| MeVal | L-N-Methvaline |
| MeLeu | L-N-Methylleucine |

In addition, the most preferred values for B also include groups of type A8″ of (L)-configuration:

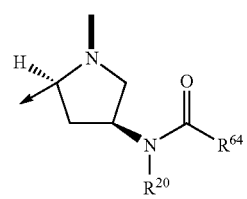

A8″ wherein $R^{20}$ is H or lower alkyl and $R^{64}$ is alkyl; alkenyl; aryl; aryl-lower alkyl; or heteroaryl-lower alkyl; especially those wherein $R^{64}$ is n-hexyl (A8″-21); n-heptyl (A8″-22);

4-(phenyl)benzyl (A8"-23); diphenylmethyl (A8"-24); 3-amino-propyl (A8"-25); 5-amino-pentyl (A8"-26); methyl (A8"-27); ethyl (A8"-28); isopropyl (A8"-29); isobutyl (A8"-30); n-propyl (A8"-31); cyclohexyl (A8"-32); cyclohexyhnethyl (A8"-33); n-butyl (A8"-34); phenyl (A8"-35); benzyl (A8"-36), (3-indolyl)methyl (A8"-37); 2-(3-indolyl) ethyl (A8"-38); (4-phenyl)phenyl (A8"-39); and n-nonyl (A8"-40).

The peptidic chains Z, $Z^1$ and $Z^2$ of the β-hairpin mimetics described herein are generally defined in terms of amino acid residues belonging to one of the following groups:

Group C —$NR^{20}CH(R^{72})CO$—; "hydrophobic: small to medium-sized"

Group D —$NR^{20}CH(R^{73})CO$—; "hydrophobic: large aromatic or heteroaromatic"

Group E —$NR^{20}CH(R^{74})CO$—; "polar-cationic", "acylamino" and "urea-derived"

Group F —$NR^{20}CH(R^{84})CO$—; "polar-non-charged"

Group H —$NR^{20}$—$CH(CO$—$)$—$(CH_2)_{4-7}$—CH(CO—)—$NR^{20}$—; —$NR^{20}$—$CH(CO$—$)$—$(CH_2)_p SS(CH_2)_p$—$CH(CO$—$)$—$NR^{20}$—; —$NR^{20}$—CH(CO—)—(—$(CH_2)_p NR^{20}CO(CH_2)_p$ —$CH(CO$—$)$—$NR^{20}$—; and —$NR^{20}$—$CH(CO$—$)$—(—$(CH_2)_p$ $CONR^{20}(CH_2)_p$—$CH(CO$—$)$—$NR^{20}$—; "interstrand linkage"

Furthermore, the amino acid residues in chains Z, $Z^1$ and $Z^2$ can also be of formula -A-CO— or of formula —B—CO— wherein A and B are as defined above. Finally, Gly can also be an amino acid residue in chains Z, $Z^1$ and $Z^2$, and Pro can be an amino acid residue in chains Z, $Z^1$ and $Z^2$, too, with the exception of positions where interstrand linkages (E) are possible.

Group C comprises amino acid residues with small to medium-sized hydrophobic side chain groups according to the general definition for substituent $R^{72}$. A hydrophobic residue refers to an amino acid side chain that is uncharged at physiological pH and that is repelled by aqueous solution. Furthermore these side chains generally do not contain hydrogen bond donor groups, such as (but not limited to) primary and secondary amides, primary and secondary amines and the corresponding protonated salts thereof, thiols, alcohols, phosphonates, phosphates, ureas or thioureas. However, they may contain hydrogen bond acceptor groups such as ethers, thioethers, esters, tertiary amides, alkyl- or aryl phosphonates and phosphates or tertiary amines. Genetically encoded small-to-medium-sized amino acids include alanine, isoleucine, leucine, methionine and valine.

Group D comprises amino acid residues with aromatic and heteroaromatic side chain groups according to the general definition for substituent $R^{73}$. An aromatic amino acid residue refers to a hydrophobic amino acid having a side chain containing at least one ring having a conjugated π-electron system (aromatic group). In addition they may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tertiary amides, alkyl—or aryl phosphonates—and phosphates or tertiary amines. Genetically encoded aromatic amino acids include phenylalanine and tyrosine.

A heteroaromatic amino acid residue refers to a hydrophobic amino acid having a side chain containing at least one ring having a conjugated π-system incorporating at least one heteroatom such as (but not limited to) O, S and N according to the general definition for substituent $R^{77}$. In addition such residues may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tetriary amides, alkyl—or aryl phosphonates and phosphates or tertiary amines. Genetically encoded heteroaromatic amino acids include tryptophan and histidine.

Group E comprises amino acids containing side chains with polar-cationic, acylamino- and urea-derived residues according to the general definition for substituen $R^{74}$. Polar-cationic refers to a basic side chain which is protonated at physiological pH. Genetically encoded polar-cationic amino acids include arginine, lysine and histidine. Citrulline is an example for an urea derived amino acid residue.

Group F comprises amino acids containing side chains with polar-non-charged residues according to the general definition for substituent $R^{84}$. A polar-non-charged residue refers to a hydrophilic side chain that is uncharged at physiological pH, but that is not repelled by aqueous solutions. Such side chains typically contain hydrogen bond donor groups such as (but not limited to) primary and secondary amides, primary and secondary amines, thiols, alcohols, phosphonates, phosphates, ureas or thioureas. These groups can form hydrogen bond networks with water molecules. In addition they may also contain hydrogen bond acceptor groups such as (but not limited to) ethers, thioethers, esters, tetriary amides, alkyl- or aryl phosphonates and phosphates or tertiary amines. Genetically encoded polar-non-charged amino acids include asparagine, cysteine, glutamine, serine and threonine.

Group H comprises side chains of preferably (L)-amino acids at opposite positions of the β-strand region that can form an interstrand linkage. The most widely known linkage is the disulfide bridge formed by cysteines and homocysteines positioned at opposite positions of the β-strand. Various methods are known to form disulfide linkages including those described by: J. P. Tam et al. *Synthesis* 1979, 955–957; Stewart et al., *Solid Phase Peptide Synthesis*, 2d Ed., Pierce Chemical Company, III., 1984; Ahmed et al. J. Biol. Chem. 1975, 250, 8477–8482; and Pennington et al., *Peptides*, pages 164–166, Giralt and Andreu, Eds., ESCOM Leiden, The Netherlands, 1990. Most advantageously, for the scope of the present invention, disulfide linkages can be prepared as described hereinafter in the pertinent Examples (procedure 3), using acetamidomethyl (Acm)—protective groups for cysteine. A well established interstrand linkage consists in linking ornithines and lysines, respectively, with glutamic and aspartic acid residues located at opposite β-strand positions by means of an amide bond formation. Preferred protective groups for the side chain amino-groups of ornithine and lysine are alkyloxycarbonyl (Alloc) and alkylesters for aspartic and glutamic acid as described hereinafter in the pertinent Examples (procedure 4). Finally, interstrand linkages can also be established by linking the amino groups of lysine and omithine located at opposite β-strand positions with reagents such as N,N-arbonylimidazole to form cyclic ureas.

As mentioned earlier, positions for interstrand linkages are the following:

If n=8: Positions P2 and n taken together,
if n=9: Positions P2 and P8 taken together,
if n=10:Positions P3 and P8 taken together,
if n=11:Positions P4 and P8; and/or P2 and P10 taken together;

if n=12: Positions P4 and P9; and/or P2 and P11 taken together, if n=13: Positions P4 and P10; and/or Positions P2 and P12 taken together;

if n=14: Positions P5 and P10; and/or P3 and P12 taken together; and if n=15: Positions P6 and P10; and/or P4 and P12; and/or n and P14.

if n=16: Positions P6 and P11; and/or P4 and P13; and/or P2 and P15 taken together.

Such interstrand linkages are known to stabilize the β-hairpin conformations and thus constitute an important structural element for the design of β-hairpin mimetics.

Most preferred amino acid residues chains Z, $Z^1$ and $Z^2$ are those derived from natural α-amino acids. Hereinafter follows a list of amino acids which, or the residues of which, are suitable for the purposes of the present invention, the abbreviations corresponding to generally adopted usual practice:

| three letter code | | one letter code |
|---|---|---|
| Ala | L-Alanine | A |
| Arg | L-Arginine | R |
| Asn | L-Asparagine | N |
| Asp | L-Aspartic acid | D |
| Cys | L-Cysteine | C |
| Glu | L-Glutamic acid | E |
| Gln | L-Glutamine | Q |
| Gly | Glycine | G |
| His | L-Histidine | H |
| Ile | L-Isoleucine | I |
| Leu | L-Leucine | L |
| Lys | L-Lysine | K |
| Met | L-Methionine | M |
| Phe | L-Phenylalanine | F |
| Pro | L-Proline | P |
| $^D$Pro | D-Proline | $^D$P |
| Ser | L-Serine | S |
| Thr | L-Threonine | T |
| Trp | L-Tryptophan | W |
| Tyr | L-Tyrosine | Y |
| Val | L-Valine | V |

Other α-amino acids which, or the residues of which, are suitable for the purposes of the present invention include:

| | |
|---|---|
| Cit | L-Citrulline |
| Orn | L-Ornithine |
| tBuA | L-t-Butylalanine |
| Sar | Sarcosine |
| Pen | L-Penicillamine |
| t-BuG | L-tert-Butylglycine |
| 4AmPhe | L-para-Aminophenylalanine |
| 3AmPhe | L-meta-Aminophenylalanine |
| 2AmPhe | L-ortho-Aminophenylalanine |
| Phe(mC($NH_2$)=NH) | L-meta-Amidinophenylalanine |
| Phe(pC($NH_2$)=NH) | L-para-Amidinophenylalanine |
| Phe(mNHC($NH_2$)=NH) | L-meta-Guanidinophenylalanine |
| Phe(pNHC($NH_2$)=NH) | L-para-Guanidinophenylalanine |
| Phg | L-Phenylglycine |
| Cha | L-Cyclohexylalanine |
| $C_4$al | L-3-Cyclobutylalanine |
| $C_5$al | L-3-Cyclopentylalanine |
| Nle | L-Norleucine |
| 2-Nal | L-2-Naphthylalanine |
| 1-Nal | L-1-Naphthylalanine |
| 4Cl-Phe | L-4-Chlorophenylalanine |
| 3Cl-Phe | L-3-Chlorophenylalanine |
| 2Cl-Phe | L-2-Chlorophenylalanine |
| 3,4$Cl_2$-Phe | L-3,4-Dichlorophenylalanine |

-continued

| | |
|---|---|
| 4F-Phe | L-4-Fluorophenylalanine |
| 3F-Phe | L-3-Fluorophenylalanine |
| 2F-Phe | L-2-Fluorophenylalanine |
| Tic | 1,2,3,4-Tetrahydroisoquinoline-3-carboxylic acid |
| Thi | L-β-2-Thienylalanine |
| Tza | L-2-Thiazolylalanine |
| Mso | L-Methionine sulfoxide |
| AcLys | N-Acetyllysine |
| Dpr | 2,3-Diaminopropionic acid |
| $A_2$Bu | 2,4-Diaminobutyric acid |
| Dbu | (S)-2,3-Diaminobutyric acid |
| Abu | γ-Aminobutyric acid (GABA) |
| Aha | ε-Aminohexanoic acid |
| Aib | α-Aminoisobutyric acid |
| Y(Bzl) | L-O-Benzyltyrosine |
| Bip | L-(4-phenyl)phenylalanine |
| S(Bzl) | L-O-Benzylserine |
| T(Bzl) | L-O-Benzylthreonine |
| hCha | L-Homo-cyclohexylalanine |
| hCys | L-Homo-cysteine |
| hSer | L-Homo-serine |
| hArg | L-Homo-arginine |
| hPhe | L-Homo-phenylalanine |
| Bpa | L-4-Benzoylphenylalanine |
| 4-AmPyrr1 | (2S,4S)-4-Amino-pyrrolidine-L-carboxylic acid |
| 4-AmPyrr2 | (2S,4R)-4-Amino-pyrrolidine-L-carboxylic acid |
| 4-PhePyrr1 | (2S,5R)-4-Phenyl-pyrrolidine-L-carboxylic acid |
| 4-PhePyrr2 | (2S,5S)-4-Phenyl-pyrrolidine-L-carboxylic acid |
| 5-PhePyrr1 | (2S,5R)-5-Phenyl-pyrrolidine-L-carboxylic acid |
| 5-PhePyrr2 | (2S,5S)-5-Phenyl-pyrrolidine-L-carboxylic acid |
| Pro(4-OH)1 | (4S)-L-Hydroxyproline |
| Pro(4-OH)2 | (4R)-L-Hydroxyproline |
| Pip | L-Pipecolic acid |
| $^D$Pip | D-Pipecolic acid |
| OctG | L-Octylglycine |
| MePhe | L-N-Methylphenylalanine |
| MeNle | L-N-Methylnorleucine |
| MeAla | L-N-Methylalanine |
| MeIle | L-N-Methylisoleucine |
| MeVal | L-N-Methylvaline |
| MeLeu | L-N-Methylleucine |

Particularly preferred residues for group C are:

| | |
|---|---|
| Ala | L-Alanine |
| Ile | L-Isoleucine |
| Leu | L-Leucine |
| Met | L-Methionine |
| Val | L-Valine |
| tBuA | L-t-Butylalanine |
| t-BuG | L-tert-Butylglycine |
| Cha | L-Cyclohexylalanine |
| $C_4$al | L-3-Cyclobutylalanine |
| $C_5$al | L-3-Cyclopentylalanine |
| Nle | L-Norleucine |
| hCha | L-Homo-cyclohexylalanine |
| OctG | L-Octylglycine |
| MePhe | L-N-Methylphenylalanine |
| MeNle | L-N-Methylnorleucine |
| MeAla | L-N-Methylalanine |
| MeIle | L-N-Methylisoleucine |
| MeVal | L-N-Methylvaline |
| MeLeu | L-N-Methylleucine |

Particularlily preferred residues for group D are:

| | |
|---|---|
| His | L-Histidine |
| Phe | L-Phenylalanine |
| Trp | L-Tryptophan |
| Tyr | L-Tyrosine |
| Phg | L-Phenylglycine |

-continued

| | |
|---|---|
| 2-Nal | L-2-Naphthylalanine |
| 1-Nal | L-1-Naphthylalanine |
| 4Cl-Phe | L-4-Chlorophenylalanine |
| 3Cl-Phe | L-3-Chlorophenylalanine |
| 2Cl-Phe | L-2-Chlorophenylalanine |
| 3,4Cl$_2$-Phe | L-3,4-Dichlorophenylalanine |
| 4F-Phe | L-4-Fluorophenylalanine |
| 3F-Phe | L-3-Fluorophenylalanine |
| 2F-Phe | L-2-Fluorophenylalanine |
| Thi | L-β-2-Thienylalanine |
| Tza | L-2-Thiazolylalanine |
| Y(Bzl) | L-O-Benzyltyrosine |
| Bip | L-Biphenylalanine |
| S(Bzl) | L-O-Benzylserine |
| T(Bzl) | L-O-Benzylthreonine |
| hPhe | L-Homo-phenylalanine |
| Bpa | L-4-Benzoylphenylalanine |

Particularly preferred residues for group E are

| | |
|---|---|
| Arg | L-Arginine |
| Lys | L-Lysine |
| Orn | L-Ornithine |
| Dpr | L-2,3-Diaminopropionic acid |
| A$_2$Bu | L-2,4-Diaminobutyric acid |
| Dbu | (S)-2,3-Diaminobutyric acid |
| Phe(pNH$_2$) | L-para-Aminophenylalanine |
| Phe(mNH$_2$) | L-meta-Aminophenylalanine |
| Phe(oNH$_2$) | L-ortho-Aminophenylalanine |
| hArg | L-Homo-arginine |
| Phe(mC(NH$_2$)=NH) | L-meta-Amidinophenylalanine |
| Phe(pC(NH$_2$)=NH) | L-para-Amidinophenylalanine |
| Phe(mNHC(NH$_2$)=NH) | L-meta-Guanidinophenylalanine |
| Phe(pNHC(NH$_2$)=NH) | L-para-Guanidinophenylalanine |
| Cit | L-Citrulline |

Particularly preferred residues for group F are

| | |
|---|---|
| Asn | L-Asparagine |
| Cys | L-Cysteine |
| Glu | L-Glutamine |
| Ser | L-Serine |
| Thr | L-Threonine |
| Cit | L-Citrulline |
| Pen | L-Penicillamine |
| AcLys | L-N$^\epsilon$-Acetyllysine |
| hCys | L-Homo-cysteine |
| hSer | L-Homo-serine |

In the dimeric structures Ib the preferred substituents forming groups G1 and G2 are the following, with the proviso that $R^{33}$ is lower alkyl; or lower alkenyl; $R^{34}$ is H; or lower alkyl; and $R^{61}$ is H:

$R^2$: —(CH$_2$)$_m$O—; —(CH$_2$)$_m$NR$^{33}$R$^{34}$—; —(CH$_2$)$_o$CO—

$R^5$: —(CH$_2$)$_o$O—; —(CH$_2$)$_o$NR$^{33}$R$^{34}$—; —(CH$_2$)$_o$CO—

$R^6$: —(CH$_2$)$_o$O—; —(CH$_2$)$_o$NR$^{33}$R$^{34}$—; —(CH$_2$)$_o$CO—

$R^8$: —(CH$_2$)$_o$O—; —(CH$_2$)$_o$NR$^{33}$R$^{34}$—; —(CH$_2$)$_o$CO—

$R^9$: —(CH$_2$)$_p$O—; —(CH$_2$)$_p$NR$^{33}$R$^{34}$—; —(CH$_2$)$_p$CO—

$R^{10}$: —(CH$_2$)$_o$O—; —(CH$_2$)$_o$NR$^{33}$R$^{34}$—; —(CH$_2$)$_o$CO—

$R^{11}$: —(CH$_2$)$_m$O—; —(CH$_2$)$_m$NR$^{33}$R$^{34}$—; —(CH$_2$)$_o$CO—

$R^{14}$: —(CH$_2$)$_m$O—; —(CH$_2$)$_m$NR$^{33}$R$^{34}$—; —(CH$_2$)$_o$CO—

$R^{15}$: —(CH$_2$)$_m$O—; —(CH$_2$)$_m$NR$^{33}$R$^{34}$—; —(CH$_2$)$_o$CO—

$R^{16}$: —(CH$_2$)$_m$O—; —(CH$_2$)$_m$NR$^{33}$R$^{34}$—; —(CH$_2$)$_o$CO—

$R^{18}$: —(CH$_2$)$_p$O—; —(CH$_2$)$_p$NR$^{33}$R$^{34}$—; —(CH$_2$)$_p$CO—

$R^{19}$: —(CH$_2$)$_p$O—; —(CH$_2$)$_p$NR$^{33}$R$^{34}$—; —(CH$_2$)$_p$CO—

$R^{21}$: —(CH$_2$)$_o$O—; —(CH$_2$)$_o$NR$^{33}$R$^{34}$—; —(CH$_2$)$_o$CO—

$R^{23}$: —(CH$_2$)$_o$O—; —(CH$_2$)$_o$NR$^{33}$R$^{34}$—; —(CH$_2$)$_o$CO—

$R^{24}$: —(CH$_2$)$_o$O—, —(CH$_2$)$_o$NR$^{33}$R$^{34}$—; —(CH$_2$)$_o$CO—

$R^{25}$: —(CH$_2$)$_m$O—; —(CH$_2$)$_m$NR$^{33}$R$^{34}$—; —(CH$_2$)$_o$CO—

$R^{26}$: —(CH$_2$)$_m$O—; —(CH$_2$)$_m$NR$^{33}$R$^{34}$—; —(CH$_2$)$_o$CO—

$R^{28}$: —(CH$_2$)$_o$O—; —(CH$_2$)$_o$NR$^{33}$R$^{34}$—; —(CH$_2$)$_o$CO—

$R^{29}$: —(CH$_2$)$_o$O—; —(CH$_2$)$_o$NR$^{33}$R$^{34}$—; —(CH$_2$)$_o$CO—

$R^{31}$: —(CH$_2$)$_p$O—; —(CH$_2$)$_p$NR$^{33}$R$^{34}$—; —(CH$_2$)$_p$CO—

$R^{37}$: —(CH$_2$)$_p$O—; —(CH$_2$)$_p$NR$^{33}$R$^{34}$—; —(CH$_2$)$_o$CO—

$R^{38}$: —(CH$_2$)$_p$O—; —(CH$_2$)$_p$NR$^{33}$R$^{34}$—; —(CH$_2$)$_o$CO—

$R^{41}$: —(CH$_2$)$_p$O—; —(CH$_2$)$_p$NR$^{33}$R$^{34}$—; —(CH$_2$)$_o$CO—

$R^{42}$: —(CH$_2$)$_p$O—; —(CH$_2$)$_p$NR$^{33}$R$^{34}$—; —(CH$_2$)$_o$CO—

$R^{45}$: —(CH$_2$)$_o$O—; —(CH$_2$)$_o$NR$^{33}$R$^{34}$—; —(CH$_2$)$_s$CO—

$R^{47}$: —(CH$_2$)$_o$O—

$R^{49}$: —(CH$_2$)$_s$O—; —(CH$_2$)$_s$CO—

$R^{51}$: —(CH$_2$)$_m$O—; —(CH$_2$)$_m$NR$^{33}$R$^{34}$—; —(CH$_2$)$_o$CO—

$R^{52}$: —(CH$_2$)$_m$O—; —(CH$_2$)$_m$NR$^{33}$R$^{34}$—; —(CH$_2$)$_o$CO—

$R^{53}$: —(CH$_2$)$_m$O—; —(CH$_2$)$_m$NR$^{33}$R$^{34}$—; —(CH$_2$)$_o$CO— and with the further provisos that the preferred linker molecules L are as defined below, that $R^{34}$ is H; or lower alkyl; X is O; S; NR$^{34}$; —NR$^{34}$CONR$^{34}$; or —OCOO—; and Y is C$_6$R$^{67}$R$^{68}$R$^{69}$R$^{70}$;

L1: —(CH$_2$)$_p$[X(CH$_2$)$_p$]$_o$—
L2: —CO(CH$_2$)$_p$[X(CHR$^2$)$_p$]$_o$CO—
L3: —CONR$^{34}$(CH$_2$)$_p$[X(CH$_2$)$_p$]$_o$NR$^{34}$CO—
L4: —O(CH$_2$)$_p$[X(CH$_2$)$_p$]$_o$O—
L6: —NR$^{34}$(CH$_2$)$_p$[X(CH$_2$)$_p$]$_o$NR$^{34}$—
L7: —(CH$_2$)$_o$Y(CH$_2$)$_o$—
L8: —CO(CH$_2$)$_o$Y(CH$_2$)$_o$CO—
L9: —CONR$^{34}$(CH$_2$)$_o$Y(CH$_2$)$_o$NR$^{34}$CO—
L10: —O(CH$_2$)$_o$Y(CH$_2$)$_o$O—
L11: —S(CH$_2$)$_o$Y(CH$_2$)$_o$S—
L12: —NR$^{34}$(CH$_2$)$_o$Y(CH$_2$)$_o$NR$^{34}$—
L13: —CO(CH$_2$)$_p$[X(CH$_2$)$_p$]$_o$NR$^{34}$—
L14: —CO(CH$_2$)$_o$Y(CH$_2$)$_o$NR$^{34}$—
L15 —NR$^{34}$(CH$_2$)$_p$[X(CH$_2$)$_p$]$_o$CO—
L16 —NR$^{34}$(CH$_2$)$_o$Y(CH$_2$)$_o$CO— with the proviso that

—(CH$_2$)$_m$O— can be combined with linker L1, L2, L3, L7, L8 or L9;

—(CH$_2$)$_o$O— can be combined with linker L1, L2, L3, L7, L8 or L9;

—(CH$_2$)$_p$O— can be combined with linker L1, L2, L3, L7, L8 or L9;

—(CH$_2$)$_s$O— can be combined with linker L1, L2, L3, L7, L8 or L9;
—(CH$_2$)$_m$NR$^{34}$— can be combined with liker L, L2, L3, L7, L8 or L9;
—(CH$_2$)$_o$NR$^{34}$— can be combined with linker L1, L2, L3, L7, L8 or L9;
—(CH$_2$)$_p$NR$^{34}$— can be combined with linker L1, L2, L3, L7, L8 or L9;
—(CH$_2$)$_o$CO— can be combined with linker L4, L5, L6, L10, L11 or L12;
—(CH$_2$)$_p$CO— can be combined with linker L4, L5, L6, L10, L11 or L12;
—(CH$_2$)$_s$CO— can be combined with linker L4, L5, L6, L10, L11 or L12;
—(CH$_2$)$_m$O— can be combined with linker L13 or L14 and the resulting combination with —(CH$_2$)$_o$CO—; —(CH$_2$)$_p$CO—; or —(CH$_2$)$_s$CO—;
—(CH$_2$)$_o$O— can be combined with linker L13 or L14 and the resulting combination with —(CH$_2$)$_o$CO—; —(CH$_2$)$_p$CO—; or —(CH$_2$)$_s$CO—;
(CH$_2$)$_p$O— can be combined with linker L13 or L14 and the resulting combination with —(CH$_2$)$_o$CO—; —(CH$_2$)$_p$CO—; or —(CH$_2$)$_s$CO—;
—(CH$_2$)$_s$O— can be combined with linker L13 or L14 and the resulting combination with —(CH$_2$)$_o$CO—; —(CH$_2$)$_p$CO—; or —(CH$_2$)$_s$CO—;
—(CH$_2$)$_m$NR$^{34}$— can be combined with linker L13 or L14 and the resulting combination with —(CH$_2$)$_o$CO—; —(CH$_2$)$_p$CO—; or —(CH$_2$)$_s$CO—;
—(CH$_2$)$_o$NR$^{34}$— can be combined with linker L13 or L14 and the resulting combination with —(CH$_2$)$_o$CO—; —(CH$_2$)$_p$CO—; or —(CH$_2$)$_s$CO—;
—(CH$_2$)$_p$NR$^{34}$— can be combined with linker L13 or L14 and the resulting combination with —(CH$_2$)$_o$CO—; —(CH$_2$)$_p$CO—; or —(CH$_2$)$_s$CO—;
—(CH$_2$)$_o$CO— can be combined with linker L15 or L16 and the resulting combination with —(CH$_2$)$_m$X—; —(CH$_2$)$_o$X—; —(CH$_2$)$_p$X—; or —(CH$_2$)$_q$—;
—(CH$_2$)$_p$CO— can be combined with linker L15 or L16 and the resulting combination with —(CH$_2$)$_m$X—; —(CH$_2$)$_o$X—; —(CH$_2$)$_p$X—; or —(CH$_2$)$_q$X—;
—(CH$_2$)$_s$CO— can be combined with linker L15 or L16 and the resulting combination with —(CH$_2$)$_m$X—; —(CH$_2$)$_o$X—; —(CH$_2$)$_p$X—; or —(CH$_2$)$_q$X—.

Generally, the peptidic chain Z, Z$^1$ or Z$^2$ within the β-hairpin mimetics of the invention comprises 8–16 amino acid residues (n=8–16). The positions P$^1$ to P$^n$ of each amino acid residue in the chain Z, Z$^1$ or Z$^2$ are unequivocally defined as follows: P$^1$ represents the first amino acid in the chain Z, Z$^1$ or Z$^2$ that is coupled with its N-terminus to the C-terminus of the templates (b)–(p) or of group —B—CO— in template (a1), or of group -A-CO— in template a2, and P$^n$ represents the last amino acid in the chain Z, Z$^1$ or Z$^2$ that is coupled with its C-terminus to the N-terminus of the templates (b)–(p) or of group -A-CO— in template (a1) or of group —B—CO— in template (a2). Each of the positions P$^1$ to P$^n$ will preferably contain an amino acid residue belonging to one or two of above types C to F, as follows:

If n is 8, the amino acid residues in position 1–8 are preferably:
P1: of type C or of type D; or of type E;
P2: of type E; or of type D;
P3: of type E;
P4: of type E or of formula -A1–A69-CO—;
P5: of type E or of formula —B—CO—;
P6: of type D;
P7: of type E; or of type D and
P8: of type C or of type D; or of type E;
at P4 and P5 also D-isomers being possible;

if n is 9, the amino acid residues in position 1–9 are preferably:
P1: of type C or of type D; or of type E;
P2: of type E; or of type D;
P3: of type C;
P4: of type E, or the residue is Pro;
P5: of type E, or the residue is Pro;
P6: of type D or of type E, or the residue is Pro;
P7: of type E or of type D;
P8: of type E; or of type D and
P9: of type C or of type D; or of type E;
at P4, P5 and P6 also D isomers being possible;

if n is 10, the amino acid residues in position 1–10 are preferably:
P1: of type C or of type D; or of type E;
P2: of type E; or of type D;
P3: of type C;
P4: of type E or of type D;
P5: of type E or of formula -A1–A69CO—;
P6: of type E or of formula —B—CO—;
P7: of type D or of type E;
P8: of type D;
P9: of type E; or of type D and
P10: of type C or of type D; or of type E;
at P5 and P6 also D-isomers being possible;

if n is 11, the amino acid residues in position 1–11 are preferably:
P1: of type C or of type D; or of type E;
P2: of type E; or of type D;
P3: of type D;
P4: of type E or of type C;
P5: of type E, or the residue is Pro;
P6: of type E, or the residue is Pro;
P7: of type E, or the residue is Pro;
P8: of type D or of type E;
P9: of type D;
P10: of type E; or of type D and
P11: of type C or of type D; or of type E;
at P5, P6 and P7 also D-isomers being possible;

if n is 12, the amino acid residues in position 1–12 are preferably:
P1: of type C or of type E; or of type D; or of type F;
P2: of type E; or of type D;
P3: of type C or of type D;
P4: of type E;
P5: of type E; or of type C;
P6: of type E or of type F or of formula -A1–A69-CO—;
P7: of type E or of formula —B—CO—;
P8: of type D;
P9: of type E or of ype D;
P10: of type D;
P11: of type E; or of type D and
P12: of type C or of type E; or of type D; or of type F;
at P6 and P7 also D-isomers being possible;

if n is 13, the amino acid residues in position 1–13 are preferably:
P1: of type C or of type D; or of type E;
P2: of type E; or of type D;
P3: of type C or of type D;
P4: of type E or of type C;
P5: of type E or of type D;
P6: of type E or of type F, or the residue is Pro;
P7: of type E, or the residue is Pro;

P8: of type D, or the residue is Pro;
P9: of type D;
P10: of type E or of type C;
P11: of type C or of type D;
P12: of type E; or of type D and
P13: of type C or of type D; or of type E;
at P6, P7 and P8 also D-isomers being possible;
if n is 14, the amino acid residues in position 1–14 are preferably:
P1: of type C or of type D; or of type E;
P2: of type E; or of type D;
P3: of type C or of type D;
P4: of type D;
P5: of type E;
P6: of type E;
P7: of type E or of type F or of formula -A1–A69-CO—;
P8: of type E or of formula —B—CO—;
P9: of type D;
P10: of type C;
P11: of type E or of type D;
P12: of type D or of type C;
P13: of type E; or of type D and
P14: of type C or of type D; or of type E;
at P7 and P8 also D-isomers being possible;
if n is 15, the amino acid residues in position 1–15 are preferably:
P1: of type C and of type D; or of type E;
P2: of type E; or of type D;
P3: of type C and of type D;
P4: of type E or of type C;
P5: of type C;
P6: of type E or of type D;
P7: of type C, or the residue is Pro;
P8: of type E or of type F, or the residue is Pro;
P9: of type E or of type F, or the residue is Pro;
P10: of type E;
P11: of type C;
P12: of type E or of type C;
P13: of type D or of type C;
P14: of type E; or of type D and
P15: of type C and of type D; or of type E;
at P7, P8 and P9 also D-isomers being possible; and
if n is 16, the amino acid residues in position 1–16 are preferably:
P1: of type D; or of type E;
P2: of type E; or of type D;
P3: of type C or of type D;
P4: of type E or of type D;
P5: of type D;
P6: of type E;
P7: of type E or of type F;
P8: of type E or of type F or of formula -A1–A69-CO—;
P9: of type E or of formula —B—CO—;
P10: of type D;
P11: of type E;
P12: of type D;
P13: of type E or of type C;
P14: of type C or of type D;
P15: of type E; or of type D and
P16: of type C or of type D; or of type E;
at P8 and P9 also D-isomers being possible.
If n is 12, the amino acid residues in position 1–12 are most preferably:
P1: Leu; Arg; Lys; Tyr; Trp; Val; Gln; or 4-AmPhe;
P2: Arg; Trp; or Gln;
P3: Leu; Val; Ile; or Phe;
P4: Lys; Arg; Gln; or Orn;
P5: Lys; or Arg,
P6: Arg; Y(Bzl); or $^D$Y(Bzl);
P7: Arg;
P8: Trp; Bip; 1-Nal; Y(Bzl); or Val;
P9: Lys; Arg; Orn; Tyr, Trp; or Gln;
P10: Tyr; T(Bzl); or Y(Bzl);
P11: Arg; or Tyr; and
P12: Val; Arg; 1-Nal; or 4-AmPhe.

Particularly preferred β-peptidomimetics of the invention include those described in Examples 106, 137, 161, 197, 206, 222, 230, 250, 256, 267, 277, 281, 283, 284, 285, 286, 289, 294, 295, 296, 297, and 298.

The process of the invention can advantageously be carried out as parallel array synthesis to yield libraries of template-fixed β-hairpin peptidomimetics of the above general formula I. Such parallel synthesis allows one to obtain arrays of numerous (normally 24 to 192, typically 96) compounds of general formula I in high yields and defined purities, minimizing the formation of dimeric and polymeric by-products. The proper choice of the functionalized solid-support (i.e. solid support plus linker molecule), templates and site of cyclization play thereby key roles.

The functionalized solid support is conveniently derived from polystyrene crosslinked with, preferably 1–5%, divinylbenzene; polystyrene coated with polyethyleneglycol spacers (Tentagel$^R$); and polyacrylamide resins (see also Obrecht, D.; Villalgordo, J.-M, "Solid-Supported Combinatorial and Parallel Synthesis of Small-Molecular-Weight Compound Libraries", *Tetrahedron Organic Chemistry Series*, Vol. 17, Pergamon, Elsevier Science, 1998).

The solid support is functionalized by means of a linker, i.e. a bifunctional spacer molecule which contains on one end an anchoring group for attachment to the solid support and on the other end a selectively cleavable functional group used for the subsequent chemical transformations and cleavage procedures. For the purposes of the present invention the linker must be designed to eventually release the carboxyl group under mild acidic conditions which do not affect protecting groups present on any functional group in the side-chains of the various amino acids. Linkers which are suitable for the purposes of the present invention form acid-labile esters with the carboxyl group of the amino acids, usually acid-labile benzyl, benzhydryl and trityl esters; examples of linker structures of this kind include 2-methoxy-4-hydroxymethylphenoxy (Sasrin$^R$ linker), 4-(2,4-dimethoxyphenyl-hydroxymethyl)-phenoxy (Rink linker), 4-(4-hydroxymethyl-3-methoxyphenoxy)butyric acid (HMPB linker), trityl and 2-chlorotrityl.

Preferably, the support is derived from polystyrene crosslinked with, most preferably 1–5%, divinylbenzene and functionalized by means of the 2-chlorotrityl linker.

When carried out as a parallel array synthesis the process of the invention can be advantageously carried out as described hereinbelow but it will be immediately apparent to those skilled in the art how this procedure will have to be modified in case it is desired to synthesize one single compound of the above formula Ia or Ib.

A number of reaction vessels (normally 24 to 192, typically 96) equal to the total number of compounds to be synthesized by the parallel method are loaded with 25 to 1000 mg, preferably 100 mg, of the appropriate functionalized solid support, preferably 1 to 3% cross linked polystyrene or tentagel resin.

The solvent to be used must be capable of swelling the resin and includes, but is not limited to, dichloromethane (DCM), dimethylformamide (DMF), N-methylpyrrolidone (NMP), dioxane, toluene, tetrahydrofuran (THF), ethanol (EtOH), trifluoroethanol (TFE), isopropylalcohol and the like. Solvent mixtures containing as at least one component a polar solvent (e.g. 20% TFE/DCM, 35% THF/NMP) are beneficial for ensuring high reactivity and solvation of the resin-bound peptide chains (Fields, G. B., Fields, C. G., *J. Am. Chem. Soc.* 1991, 113, 4202–4207).

With the development of various linkers that release the C-terminal carboxylic acid group under mild acidic conditions, not affecting acid-labile groups protecting functional groups in the side chain(s), considerable progresses have been made in the synthesis of protected peptide fragments. The 2-methoxy-4-hydroxybenzylalcohol-derived linker (Sasrin$^R$ linker, Mergler et al., *Tetrahedron Lett.* 1988, 29 4005–4008) is cleavable with diluted trifluoroacetic acid (0.5–1% TFA in DCM) and is stable to Fmoc deprotection conditions during the peptide synthesis, Boc/tBu-based additional protecting groups being compatible with this protection scheme. Other linkers which are suitable for the process of the invention include the super acid labile 4-(2, 4-dimethoxyphenyl-hydroxymethyl)-phenoxy linker (Rink linker, Rink, H. *Tetrahedron Lett.* 1987, 28, 3787–3790), where the removal of the peptide requires 10% acetic acid in DCM or 0.2% trifluoroacetic acid in DCM; the 4-(4-hydroxymethyl-3-methoxyphenoxy)butyric acid-derived linker (HMPB-linker, Florsheimer & Riniker, *Peptides* 1991, 1990 131) which is also cleaved with 1% TFA/DCM in order to yield a peptide fragment containing all acid labile side-chain protective groups; and, in addition, the 2-chlorotritylchloride linker (Barlos et al., *Tetrahedron Lett.* 1989, 30, 3943–3946), which allows the peptide detachment using a mixture of glacial acetic acid/trifluoroethanol/DCM (1:2: 7) for 30 min.

Suitable protecting groups for amino acids and, respectively, for their residues are, for example, for the amino group (as is present e. g. also in the side-chain of lysine)

| | |
|---|---|
| Cbz | benzyloxycarbonyl |
| Boc | tert.-butyloxycarbonyl |
| Fmoc | 9-fluorenylmethoxycarbonyl |
| Alloc | allyloxycarbonyl |
| Teoc | trimethylsilylethoxycarbonyl |
| Tcc | trichloroethoxycarbonyl |
| Nps | o-nitrophenylsulfonyl; |
| Trt | triphenymethyl or trityl | for the carboxyl group (as is present e. g. also in the side-chain of aspartic and glutamic acid) by conversion into esters with the alcohol components

| | |
|---|---|
| tBu | tert.-butyl |
| Bn | benzyl |
| Me | methyl |
| Ph | phenyl |
| Pac | Phenacyl |
| | Allyl |
| Tse | trimethylsilylethyl |
| Tce | trichloroethyl; | for the guanidino group (as is present e. g. in the side-chain of arginine)

| | |
|---|---|
| Pmc | 2,2,5,7,8-pentamethylchroman-6-sulfonyl |
| Ts | tosyl (i.e. p-toluenesulfonyl) |
| Cbz | benzyloxycarbonyl |
| Pbf | pentamethyldihydrobenzofuran-5-sulfonyl | for the hydroxy group (as is present e. g. in the side-chain of threonine and serine)

| | |
|---|---|
| tBu | tert.-butyl |
| Bn | benzyl |
| Trt | trityl | and for the mercapto group (as is present e. g. in the side-chain of cysteine)

| | |
|---|---|
| Acm | acetamidomethyl |
| tBu | tert.-butyl |
| Bn | benzyl |
| Trt | trityl |
| Mtr | 4-methoxytrityl. |

The 9-fluorenylmethoxycarbonyl-(Fmoc)-protected amino acid derivatives are preferably used as the building blocks for the construction of the template-fixed β-hairpin loop mimetics of formulae Ia and Ib. For the deprotection, i.e. cleaving off of the Fmoc group, 20% piperidine in DMF or 2% DBU/2% piperidine in DMF can be used.

The quantity of the reactant, i.e. of the amino acid derivative, is usually 1 to 20 equivalents based on the milliequivalents per gram (meq/g) loading of the functionalized solid support (typically 0.1 to 2.85 meq/g for polystyrene resins) originally weighed into the reaction tube. Additional equivalents of reactants can be used if required to drive the reaction to completion in a reasonable time. The reaction tubes, in combination with the holder block and the manifold, are reinserted into the reservoir block and the apparatus is fastened together. Gas flow through the manifold is initiated to provide a controlled environment, for example, nitrogen, argon, air and the like. The gas flow may also be heated or chilled prior to flow through the manifold. Heating or cooling of the reaction wells is achieved by heating the reaction block or cooling externally with isopropanol/dry ice and the like to bring about the desired synthetic reactions. Agitation is achieved by shaking or magnetic stirring (within the reaction tube). The preferred workstations (without, however, being limited thereto) are Labsource's Combi-chem station and MultiSyn Tech's-Syro synthesizer.

Amide bond formation requires the activation of the α-carboxyl group for the acylation step. When this activation is being carried out by means of the commonly used carbodiimides such as dicyclohexylcarbodiimide (DCC, Sheehan & Hess, *J. Am. Chem. Soc.* 1955, 77, 1067–1068) or diisopropylcarbodiimide (DIC, Sarantakis et al *Biochem Biophys. Res. Commun.* 1976, 73, 336–342), the resulting dicyclohexylurea is insoluble and, respectively, diisopropylurea is soluble in the solvents generally used. In a variation of the carbodiimide method 1-hydroxybenzotriazole (HOBt, König & Geiger, *Chem. Ber* 1970, 103, 788–798) is included as an additive to the coupling mixture. HOBt prevents dehydration, suppresses racemization of the activated amino acids and acts as a catalyst to improve the sluggish coupling reactions. Certain phosphonium reagents have been used as direct coupling reagents, such as benzotriazol-1-yl-oxy-tris-(dimethylamino)-phosphonium hexafluorophosphate (BOP) (Castro et al., *Tetrahedron Lett.* 1975, 14, 1219–1222; *Synthesis*, 1976, 751–752), or benzotriazol-1-yl-oxy-tris-pyrrolidino-phosphonium hexaflurophoshate (Py-BOP, Coste et al., *Tetrahedron Lett.* 1990, 31, 205–208), or 2-(1H-benzotriazol-1-yl-)1,1,3,3-tetramethyluronium terafluoroborate (TBTU), or hexafluorophosphate (HBTU, Knorr et al., *Tetrahedron Lett.* 1989, 30, 1927–1930); these phosphonium reagents are also suitable for in situ formation of HOBt esters with the protected amino acid derivatives. More recently diphenoxyphosphoryl azide (DPPA) or O-(7-aza-benzotriazol-1-yl)-N,N,N',N'-tetramethyluronium tetrafluoroborate (TATU) or O-(7-aza-benzotriazol-1-yl)-N,N,N',N'-tetramethyluronium hexafluorophosphate (HATU)/7-aza-1-hydroxy benzotriazole (HOAt, Carpino et al., *Tetrahedron Lett.* 1994, 35, 2279–2281) have also been used as coupling reagents.

Due to the fact that near-quantitative coupling reactions are essential it is desirable to have experimental evidence for completion of the reactions. The ninhydrin test raiser et al., *Anal. Biochemistry* 1970, 34, 595), where a positive colorimetric response to an aliquot of resin-bound peptide indicates qualitatively the presence of the primary amine, can easily and quickly be performed after each coupling step. Fmoc chemistry allows the spectrophotometric detection of the Fmoc chromophore when it is released with the base (Meienhofer et al., *Int. J. Peptide Protein Res.* 1979, 13, 35–42).

The resin-bound intermediate within each reaction tube is washed free of excess of retained reagents, of solvents, and of by-products by repetitive exposure to pure solvent(s) by one of the two following methods:

1) The reaction wells are filled with solvent (preferably 5 ml), the reaction tubes, in combination with the holder block and manifold, are immersed and agitated for 5 to 300 minutes, preferably 15 minutes, and drained by gravity followed by gas pressure applied through the manifold inlet (while closing the outlet) to expel the solvent;
2) The manifold is removed from the holder block, aliquots of solvent (preferably 5 ml) are dispensed through the top of the reaction tubes and drained by gravity through a filter into a receiving vessel such as a test tube or vial.

Both of the above washing procedures are repeated up to about 50 times (preferably about 10 times), monitoring the efficiency of reagent, solvent, and byproduct removal by methods such as TLC, GC, or inspection of the washings.

The above described procedure of reacting the resin-bound compound with reagents within the reaction wells followed by removal of excess reagents, by-products, and solvents is repeated with each successive transformation until the final Tesin-bound fully protected linear peptide has been obtained.

Before this fully protected linear peptide is detached from the solid support, it is possible, if desired, to selectively deprotect one or several protected functional group(s) present in the molecule and to appropriately substitute the reactive group(s) thus liberated. To this effect, the functional group(s) in question must initially be protected by a protecting group which can be selectively removed without affecting the remaining protecting groups present. Alloc (alkyloxycarbonyl) is an example for such a protecting group for amino which can be selectively removed, e.g. by means of Pd° and phenylsilane in $CH_2Cl_2$, without affecting the remaining protecting groups, such as Fmoc, present in the molecule. The reactive group thus liberated can then be treated with an agent suitable for introducing the desired substituent. Thus, for example, an amino group can be acylated by means of an acylating agent corresponding to the acyl substituent to be introduced.

Detachment of the fully protected linear peptide from the solid support is achieved by immersion of the reaction tubes, in combination with the holder block and manifold, in reaction wells containing a solution of the cleavage reagent (preferably 3 to 5 ml). Gas flow, temperature control, agitation, and reaction monitoring are implemented as described above and as desired to effect the detachment reaction. The reaction tubes, in combination with the holder block and manifold, are disassembled from the reservoir block and raised above the solution level but below the upper lip of the reaction wells, and gas pressure is applied through the manifold inlet (while closing the outlet) to efficiently expel the final product solution into the reservoir wells. The resin remaining in the reaction tubes is then washed 2 to 5 times as above with 3 to 5 ml of an appropriate solvent to extract (wash out) as much of the detached product as possible. The product solutions thus obtained are combined, taking care to avoid cross-mixing. The individual solutions/extracts are then manipulated as needed to isolate the final compounds. Typical manipulations include, but are not limited to, evaporation, concentration, liquid/liquid extraction, acidification, basification, neutralization or additional reactions in solution.

The solutions containing fully protected linear peptide derivatives which have been cleaved off from the solid support and neutralized with a base, are evaporated. Cyclization is then effected in solution using solvents such as DCM, DMF, dioxane, ThF and the like. Various coupling reagents which were mentioned earlier can be used for the cyclization. The duration of the cyclization is about 6–48 hours, preferably about 24 hours. The progress of the reaction is followed, e.g. by RP-HPLC (Reverse Phase High Performance Liquid Chromatography). Then the solvent is removed by evaporation, the fully protected cyclic peptide derivative is dissolved in a solvent which is not miscible with water, such as DCM, and the solution is extracted with water or a mixture of water-miscible solvents, in order to remove any excess of the coupling reagent.

Before removing the protecting groups from the fully protected cyclic peptide, it is possible, if desired, to form an interstrand linkage between side-chains of appropriate amino acid residues at opposite positions of the β-strand region; and/or to connect two building blocks of the type of formula Ia via a bridge -G1-L-G2- to give a dimeric structure of the type of formula Ib.

Interstrand linkages and their formation have been discussed above, in connection with the explanations made regarding groups of the type H which can, for example, be disulfide bridges formed by cysteines and homocysteines at opposite positions of the β-strand, or glutamic and aspartic acid residues linking ornithines and, respectively, lysines located at opposite β-strand positions by amide bond formation. The formation of such interstrand linkages can be effected by methods well known in the art.

Interstrand linkages and their formation have been discussed above, in connection with the explanations made regarding groups of the type H which can, for example, be disulfide bridges formed by cysteines and homocysteines at opposite positions of the β-strand, or glutamic and aspartic acid residues linking ornithines and, respectively, lysines located at opposite β-strand positions by amide bond formation. The formation of such interstrand linkages can be effected by methods well known in the art.

For building up a bridge -G1-L-G2- to give a dimeric structure, methods well known in the art can be used, too. Thus, for example, a fully side-chain protected β-hairpin peptidomimetic carrying a group G1 or G2 containing an appropriately protected alcohol group (e.g. as tert.-butyl-diphenylsilyl protected), thiol group (e.g. as acetamidomethyl protected) or amino group ($NR^{34}$; e.g. as alkyloxycarbonyl protected) can selectively be deprotected employing methods well known by the skilled in the art and reacted with suitably activated linker (L) precursors; e.g:

for L1 the corresponding building block is $Br(Cl,I)(CH_2)_p CHR^{61}[X(CH_2)_p CHR^{61}]_o OH$: the resulting alcohol can be transformed into the corresponding bromide (chloride or iodide) by methods well known to those skilled in the art (e.g. $P(Ph)_3$, $CBr_4$) and combined with a second β-hairpin mimetic carrying a group G1 or G2 containing an alcohol, thiol or amine group. The dimeric fully side-chain protected molecule can be fully deprotected and purified by preparative HPLC chromatography as described in procedure 1, hereinbelow.

for L2 the corresponding building block is $ClOC(CH_2)_p CHR^{61}[X(CH_2)_p CHR^{61}]_o COOAllyl$: the resulting ester can be transformed into the corresponding acid by methods well known in the art and combined with a second β-hairpin mimetic carrying a group G1 or G2 containing an alcohol, thiol or amine group. The dimeric fully side-chain protected molecule can be fully deprotected and purified by preparative HPLC chromatography as described in procedure 1, hereinbelow.

For L3 the corresponding building block is $O{=}C{=}N(CH_2)_p CHR^{61}[X(CH_2)_p CHR^{61}]_o NR^{34}Alloc$: the resulting Alloc-protected amine can be deprotected and transformed into the corresponding isocyanate by methods familiar to those skilled in the art (e.g. triphosgene) and combined with a second β-hairpin mimetic carrying a group G1 or G2 containing an alcohol, thiol or amine group. The dimeric fully side-chain protected molecule can be fully deprotected and purified by preparative HPLC chromatography as described in procedure 1, hereinbelow.

For L7 the corresponding building block is $Br(Cl,I)(CH_2)_o CHR^{61}Y(CH_2)_o CHR^{61}OH$: the resulting alcohol can be transformed into the corresponding bromide (chloride or iodide) by methods well known in the art (e.g. $P(Ph)_3$, $CBr_4$) and combined with a second β-hairpin mimetic carrying a group G1 or G2 containing an alcohol, thiol or amine group. The dimeric fully side-chain protected molecule can be deprotected and purified by preparative HPLC chromatography as described in procedure 1, hereinbelow.

For L8 the corresponding building block is $ClOC(CH_2)_o CHR^{61}Y(CH_2)_o CHR^{61}COOAllyl$: the resulting ester can be transformed into the corresponding acid by methods well known to those skilled in the art and combined with a second β-hairpin mimetic carrying a group G1 or G2 containing an alcohol, thiol or amine group. The dimeric fully side-chain protected molecule can be deprotected and purified by preparative HPLC chromatography as described in procedure 1, hereinbelow.

For L9 the corresponding building block is $O{=}C{=}N(CH_2)_o CHR^{61}Y(CH_2)_o CHR^{61}NR^{34}Alloc$: the resulting Alloc-protected amine can be deprotected and transformed into the corresponding isocyanate by methods well known in the art (e.g. triphosgene) and combined with a second β-hairpin mimetic carrying a group G1 or G2 containing an alcohol, thiol or amine group. The dimeric fully side-chain protected molecule can be deprotected and purified by preparative HPLC chromatography as described in procedure 1, hereinbelow.

For L13 the corresponding building block is $ClOC(CH_2)_p CHR^{61}[X(CH_2)_p CHR^{61}]_o NR^{34}Alloc$: the resulting Alloc-protected amine can be deprotected by methods readily available to those skilled in the art and combined with a second β-hairpin mimetic carrying a group G1 or G2 containing a carboxylic acid group. The dimeric fully side-chain protected molecule can be deprotected and purified by preparative HPLC chromatography as described in procedure 1, hereinbelow.

For L14 the corresponding building block is $ClOC(CH_2)_o CHR^{61}Y(CH_2)_o CHR^{61}N^{34}Alloc$: the resulting Alloc-protected amine can be deprotected by conventional methods and combined with a second β-hairpin mimetic carrying a group G1 or G2 containing a carboxylic acid group. The dimeric fully side-chain protected molecule can be deprotected and purified by preparative HPLC chromatography as described in procedure 1, hereinbelow.

Alternatively, a fully side-chain protected β-hairpin peptidomimetic carrying a group G1 or G2 containing an appropriately protected thiol group (e.g. as acetamidomethyl protected) can selectively be deprotected employing methods well known to those skilled in the art and reacted with a second β-hairpin peptidomimetic carrying a group G1 or G2 containing a thiol group forming a disulfide bond by oxidation (air or iodine). The dimeric molecule can subsequently be fully deprotected and purified by preparative HPLC chromatography as described in procedure 1, hereinbelow.

Finally, a fully side-chain protected β-hairpin peptidomimetic carrying a group G1 or G2 containing an appropriately protected carboxylic acid group (e.g. alkyl ester), can selectively be deprotected employing methods well known in the art and reacted with a suitably activated linker (L) precursor; e.g:

For L4 the corresponding building block is $HO(CH_2)_p CHR^{61}[X(CH_2)_p CHR^{61}]_o OAlloc$: the resulting Alloc-protected alcohol can be deprotected by methods well known to those skilled in the art and combined with a second β-hairpin mimetic carrying a group G1 or G2 containing a carboxylic acid group. The dimeric fully side-chain protected molecule can be deprotected and purified by preparative HPLC chromatography as described in procedure 1, hereinbelow.

For L5 the corresponding building block is $HS(CH_2)_p CHR^{61}[X(CH_2)_p CHR^{61}]_o SAlloc$: the resulting Alloc-protected thiol can be deprotected by methods well known in the art and combined with a second β-hairpin mimetic carrying a group G1 or G2 containing a carboxylic acid group. The dimeric fully side-chain protected molecule can be deprotected and purified by preparative HPLC chromatography as described in procedure 1, hereinbelow.

For L6 the corresponding building block is $HNR^{34}(CH_2)_p CHR^{61}[X(CH_2)_p CHR^{61}]_o NR^{34}Alloc$: the resulting Alloc-protected amine can be deprotected by methods familiar to those skilled in the art and combined with a second β-hairpin mimetic carrying a group G1 or G2 containing a carboxylic acid group. The dimeric fully side-chain protected molecule can be deprotected and purified by preparative HPLC chromatography as described in procedure 1, hereinbelow.

For L10 the corresponding building block is HO(CH$_2$)$_o$CHR$^{61}$Y(CH$_2$)$_o$CHR$^{61}$OAlloc: the resulting Alloc-protected alcohol can be deprotected by methods well known to those skilled in the art and combined with a second β-hairpin mimetic carrying a group G1 or G2 containing a carboxylic acid group. The dimeric fully side-chain protected molecule can be deprotected and purified by preparative HPLC chromatography as described in procedure 1, hereinbelow.

For L11 the corresponding building block is HS(CH$_2$)$_o$CHR$^{61}$Y(CH$_2$)$_o$CHR$^{61}$SAlloc: the resulting Alloc-protected thiol can be deprotected by methods well known in the art and combined with a second β-hairpin mimetic carrying a group G1 or G2 containing a carboxylic acid group. The dimeric fully side-chain protected molecule can be deprotected and purified by preparative HPLC chromatography as described in procedure 1, hereinbelow.

For L12 the corresponding building block is HNR$^{34}$(CH$_2$)$_o$CHR$^{61}$Y(CH$_2$)$_o$CHR$^{61}$NR$^{34}$Alloc: the resulting Alloc-protected amine can be deprotected by methods well known to those skilled in the art and combined with a second β-hairpin mimetic carrying a group G1 or G2 containing a carboxylic acid group. The dimeric fully side-chain protected molecule can be deprotected and purified by preparative HPLC chromatography as described in procedure 1, hereinbelow.

For L15 the corresponding building block is HNR$^{34}$(CH$_2$)$_p$CHR$^{61}$[X(CH$_2$)$_p$CHR$^{61}$]$_o$COOAllyl: the resulting Allylester can be deprotected by conventional methods and combined with a second β-hairpin mimetic carrying a group G1 or G2 containing an alcohol group, a thiol group or an amino (NR$^{34}$) group. The dimeric fully side-chain protected molecule can be deprotected and purified by preparative HPLC chromatography as described in procedure 1, hereinbelow.

For L16 the corresponding building block is HNR$^{34}$(CH$_2$)$_o$CHR$^{61}$Y(CH$_2$)$_o$CHR$^{61}$COOAllyl: the resulting Allylester can be deprotected by methods well known to those skilled in the art and combined with a second β-hairpin mimetic carrying a group G1 or G2 containing an alcohol group, a thiol group or an amino (NR$^{34}$) group. The dimeric fully side-chain protected molecule can be deprotected and purified by preparative HPLC chromatography as described in procedure 1, hereinbelow.

Finally, the fully protected peptide derivative of type Ia or Ib is treated with 95% TFA, 2.5% H$_2$O, 2.5% TIS or another combination of scavengers for effecting the cleavage of protecting groups. The cleavage reaction time is commonly 30 minutes to 12 hours, preferably about 2 hours. Thereafter most of the TFA is evaporated and the product is precipitated with ether/hexane (1:1) or other solvents which are suitable therefor. After careful removal of the solvent, the cyclic peptide derivative obtained as end-product can be isolated. Depending on its purity, this peptide derivative can be used directly for biological assays, or it has to be further purified, for example by preparative HPLC.

As mentioned earlier, it is thereafter possible, if desired, to convert a fully deprotected product thus obtained into a pharmaceutically acceptable salt or to convert a pharmaceutically acceptable, or unacceptable, salt thus obtained into the corresponding free compound of formula Ia and Ib or into a different, pharmaceutically acceptable, salt. Any of these operations can be carried out by methods well known in the art.

The starting materials used in the process of the invention, pre-starting materials therefor, and the preparation of these starting and pre-starting materials will now be discussed in detail.

Building blocks of type A can be synthesized according to the literature methods described below. The corresponding amino acids have been described either as unprotected or as Boc- or Fmoc-protected racemates, (D) or (L)-isomers. It will be appreciated that unprotected amino acid building blocks can be easily transformed into the corresponding Fmoc-protected amino acid building blocks required for the present invention by standard protecting group manipulations. Reviews describing general methods for the synthesis of α-amino acids include: R. Duthaler, *Tetrahedron (Report)* 1994, 349, 1540–1650; R. M. Williams, "Synthesis of optically active α-amino acids", *Tetrahedron Organic Chemistry Series*, Vol. 7, J. E. Baldwin, P. D. Magnus (Eds.), Pergamon Press., Oxford 1989. An especially useful method for the synthesis of optically active α-amino acids relevant for this invention includes kinetic resolution using hydrolytic enzymes (M. A. Verhovskaya, I. A. Yamskov, *Russian Chem. Rev.* 1991, 60, 1163–1179; R. M. Williams, "Synthesis of optically active α-amino acids", *Tetrahedron Organic Chemistry Series*, Vol. 7, J. E. Baldwin, P. D. Magnus (Eds.), Pergamon Press., Oxford 1989, Chapter 7, p. 257–279). Hydrolytic enzymes involve hydrolysis of amides and nitriles by aminopeptidases or nitrilases, cleavage of N-acyl groups by acylases, and ester hydrolysis by lipases or proteases. It is well documented that certain enzymes will lead specifically to pure (L)-enantiomers whereas others yield the corresponding (D)-enantiomers (e.g.: R. Duthaler, *Tetrahedron Report* 1994, 349, 1540–1650; R. M. Williams, "Synthesis of optically active α-amino acids", *Tetrahedron Organic Chemistry Series*, Vol. 7, J. E. Baldwin, P. D. Magnus (Eds.), Pergamon Press., Oxford 1989).

A1: See D. Ben-Ishai, *Tetrahedron* 1977, 33, 881–883; K. Sato, A. P. Kozikowski, *Tetrahedron Lett.* 1989, 30, 4073–4076; J. E. Baldwin, C. N. Farthing, A. T. Russell, C. J. Schofield, A. C. Spirey, *Tetrahedron Lett.* 1996, 37, 3761–3767; J. E. Baldwin, R. M. Adlington, N. G. Robinson, *J. Chem. Soc. Chem. Commun.* 1987, 153–157; P. Wipf, Y. Uto, *Tetrahedron Lett.* 1999, 40, 5165–5170; J. E. Baldwin, R. M. Adlington, A. O'Neil, A. C. Spirey, J. B. Sweeney, *J. Chem. Soc. Chem. Commun.* 1989, 1852–1854 (for R$^1$=H, R$^2$=H); T. Hiyama, *Bull. Chem. Soc. Jpn.* 1974, 47, 2909–2910; T. Wakamiya, K. Shimbo, T. Shiba, K. Nakajima, M. Neya, K. Okawa, *Bull. Chem. Soc. Jpn.* 1982, 55, 3878–3881; I. Shima, N. Shimazaki, K. Imai, K. Hemmi, M. Hashimoto, *Chem. Pharm. Bull.* 1990, 38, 564–566; H. Han, J. Yoon, K. D. Janda, *J. Org. Chem.* 1998, 63, 2045–2048 (R$^1$=H, R$^2$=Me); J. Legters, G. H. Willems, L. Thijs, B. Zwannenburg, *Recl. Trav. Chim. Pays-Bas* 1992, 111, 59–68 (R$^1$=H, R$^2$=hexyl); J. Legters, L. Thijs, B. Zwannenburg, *Recl. Trav. Chim. Pays-Bas* 1992, 111, 16–21; G. A. Molander, P. J. Stengel, *J. Org. Chem.* 1995, 21, 6660–6661 (R$^1$=H, R$^2$=Ph); I. Funaki, L. Thijs, B. Zwannenburg, *Tetrahedron* 1996, 52, 9909–9924 (R$^1$=H, R$^2$=Bn); A. S. Pepito, D. C. Dittmer, *J. Org. Chem.* 1997, 62, 7920–7925; (R$^1$=H, R$^2$=CH$_2$OH); M. Egli, A. S. Dreiding, *Helv. Chim. Acta* 1986, 69, 1442–1460 (R$^2$=CH(OH)CH$_2$OH); M. Carducci, S. Fioravanti, M. A. Loreto, L. Pellacani, P. A. Tardella, *Tetrahedron Lett.* 1996, 37, 3777–3778; F. J. Lakner, L. P. Hager, *Tetrahedron: Asymmetry* 1997, 21, 3547–3550 (R$^1$=Me, R$^2$=H, Me); G. A.

Molander, P. J. Stengel, *Tetrahedron* 1997, 26, 8887–8912; M. A. Loreto, F. Pompei, P. A. Tardella, D. Tofani, *Tetrahedron* 1997, 53, 15853–15858 ($R^1$=Me, $R^2$=$CH_2SiMe_3$); H. Shao, J. K. Rueter, M. Goodman, *J. Org. Chem.* 1998, 63, 5240–5244 ($R^1$=Me, $R^2$=Me).

A2: See A. Rao, M. K. Gurjär, V. Vivarr, *Tetrahedron: Asymmetry* 1992, 3, 859–862; R. L. Johnson, G. Rayakumar, K.-L. Yu, R. K. Misra, *J. Med. Chem.* 1986, 29, 2104–2107 ($R^1$=H, $R^2$=H); J. E. Baldwin, R. M. Adlington, R. H. Jones, C. J. Schofield, C. Zarcostas, *J. Chem. Soc. Chem. Commun.* 1985, 196–196; J. E. Baldwin, R. M. Adlington, R. H. Jones, C. J. Schofield, C. Zarcostas, *Tetrahedron* 1986, 42, 4879–4888 ($R^1$=H, $R^2$=$CH_2OH$, $CH_2CHO$, $CH_2CH_2COOH$, $CH_2CH_2OH$); A. P. Kozikowski, W. Tueckmantel, I. J. Reynolds, J. T. Wroblewski, *J. Med. Chem.* 1990, 33, 1561–1571; A. P. Kozikowski, W. Tueclanantel, Y. Liao, H. Manev, S. Ikonomovic J. T. Wroblenski, *J. Med. Chem.* 1993, 36, 2706–2708 ($R^1$=H, $R^2$=$CH_2OH$, $CHCONH_2$, $CONHCH_2COOH$, COOtBu); D. Seebach, T. Vettiger, H.-M. Müller, D. Plattner, W. Petter, *Liebigs Ann. Chem.* 1990, 687–695 ($R^1$=ArylCH(OH), $R^2$=H); D. Seebach, E. Dziadulewicz, L. Behrendt, S. Cantoreggi, R. Fitzi, *Liebigs Ann. Chem.* 1989, 1215–1232 ($R^1$=Me, Et, $R^2$=H).

A3: See A. P. Kozikowski, Y. Liao, W. Tueckmantel, S. Wang, S. Pshsenichkin, *Bioorg. Med. Chem. Lett.* 1996, 6, 2559–2564 ($R^1$=H; $R^2$=CHCHO, $CH_2OH$, $CH_2CH_2OH$, $CH_2COOH$, COOH); Isono, *J. Am. Chem. Soc*, 1969, 91, 7490 ($R^1$=H; $R^2$=Et); P. J. Blythin, M. J. Green, M. J. Mary, H. Shue, *J. Org. Chem.* 1994, 59, 6098–6100; S. Hanessian, N. Bernstein, R.-Y. Yang, R. Maquire, *Bioorg. Chem. Lett.* 1994, 9, 1437–1442 ($R^1$=H; $R^2$=Ph).

A4: See G. Emmer, *Tetrahedron* 1992, 48, 7165–7172; M. P. Meyer, P. L. Feldman, H. Rapoport, *J. Org. Chem.* 1985, 50, 5223–5230 ($R^1$=H; $R^2$=H); A. J. Bose, M. S. Manhas, J. E. Vincent, I. F. Fernandez, *J. Org. Chem.* 1982, 47, 4075–4081 ($R^1$=H; $R^2$=$NHCOCH_2OPh$); D. L. Boger, J. B. Meyers, *J. Org. Chem.* 1991, 56, 5385–5390 ($R^1$=H; $R^2$=$NHCOCH_2Ph$); K.-D. Kampe, *Tetrahedron Lett.* 1969, 117–120 ($R^1$=$CH_2OH$; $R^2$=Ph); M. D. Andrews, M. G. Maloney, K. L. Owen, *J. Chem. Soc. Perkin Trans.* 1, 1996, 227–228 ($R^1$=$CH_2OH$; $R^2$=H).

A5: See C. Bisang, C. Weber, J. Inglis, C. A. Schiffer, W. F. van Gunsteren, J. A. Robinson, *J. Am. Chem. Soc.* 1995, 117, 7904 ($R^1$=$CH_3$; $R^2$=H); S. Takano, M. Morija, Y. Iwabuki, K. Ogasawara, *Tetrahedron Lett.* 1989, 30, 3805–3806 ($R^1$=H; $R^2$=COOH); M. D. Bachi, R. Breiman, H. Meshulam, *J. Org. Chem.* 1983, 48, 1439–1444 ($R^1$=H; $R^2$=CH(Et)COOH); D. S. Kemp, T. P. Curran, *Tetrahedron Lett.* 1988, 29, 4931–4934; D. S. Kemp, T. P. Curran, W. M. Davies, *J. Org. Chem.* 1991, 56, 6672–6682 ($R^1$=H; $R^2$=$CH_2OH$); F. Manfre, J.-M. Kern, J.-F. Biellmann, *J. Org. Chem.* 1992, 57, 2060–2065 ($R^1$=H; $R^2$=H, $CH$=$CH_2$, CCH); B. W. Bycroft, S. R. Chabra, *J. Chem. Soc. Chem. Commun.* 1989, 423–425 ($R^1$=H; $R^2$=$CH_2COOtBu$; Y. Xu, J. Choi, M. I. Calaza, S. Turner, H. Rapoport, *J. Org. Chem.* 1999, 64, 4069–4078 ($R^1$=H; $R^2$=3-pyridyl); E. M. Khalil, W. J. Ojala, A. Pradham, V. D. Nair, W. B. Gleason, *J. Med. Chem.* 1999, 42, 628–637; E. M. Khalil, N. L. Subasinghe, R. L. Johnson, *Tetrahedron Lett.* 1996, 37, 3441–3444 ($R^1$=alkyl; $R^2$=H); A. DeNicola, J.-L. Luche, *Tetrahedron Lett.* 1992, 33, 6461–6464; S. Thaisrivongs, D. T. Pals, J. A. Lawson, S. Turner, D. W. Harris, *J. Med. Chem.* 1987, 30, 536–541; E. M. Khalil, L. Subasinghe, R. L. Johnson, *Tetrahedron Lett.* 1996, 37, 3441–3444; A. Lewis, J. Wilkie, T. J. Rutherford, D. Gani, *J. Chem. Soc. Perkin Trans.* 1, 1998, 3777–3794 ($R^1$=Me; $R^2$=H); A. Lewis, J. Wilkie, T. J. Rutherford, D. Gani, *J. Chem. Soc. Perkin Trans.* 1, 1998, 3777–3794 ($R^1$=$CH_2COOMe$; $R^2$=H); N. L. Subasinghe, E. M. Khalil, R. L. Johnson, *Tetrahedron Lett.* 1997, 38, 1317–1320 ($R^1$=$CH_2CHO$; $R^2$=H); D. J. Witter, S. J. Famiglietti, J. C. Gambier, A. L. Castelhano, *Bioorg. Med. Chem. Lett.* 1998, 8, 3137–3142; E. H. Khalil, W. H. Ojada, A. Pradham, V. D. Nair, W. B. Gleason, *J. Med. Chem.* 1999, 42, 628–637 ($R^1$=$CH_2CH_2CHO$; $R^2$=H).

A6: See DeNardo, *Farmaco Ed. Sci.* 1977, 32, 522–529 ($R^1$=H; $R^3$=H); P. J. T. Floris, N. Terhuis, H. Hiemstra, N. W. Speckamp, *Tetrahedron*, 1993, 49, 8605–8628; S. Kanemasa, N. Tomoshige, O. Tsuge, *Bull. Chem. Soc. Jpn.* 1989, 62, 3944–3949 ($R^1$=H; $R^3$=H); Sucrow, *Chem. Ber.* 1979, 112, 1719.

A7: See Fichter, *J. Prakt. Chem.* 1906, 74, 310 ($R^1$=Me; $R^4$=Ph).

A8: See L. Lapantsanis, G. Milias, K. Froussios, M. Kolovos, *Synthesis* 1983, 641–673; H. Nedev, H. Naharisoa, *Tetrahedron Lett.* 1993, 34, 4201–4204; D. Y. Jackson, C. Quan, D. R. Artis, T. Rawson, B. Blackburn, *J. Med. Chem.* 1997, 40, 3359–3368; D. Konopinska, H. Bartosz-Bechowski, G. Rosinski, W. Sobotka, *Bull. Pol. Acad. Sci. Chem.* 1993, 41, 27–40; J. Hondrelis, G. Lonergan, S. Voliotis, J. Matsukas, *Tetrahedron* 1990, 46, 565–576; T. Nakamura, H. Matsuyama, H. Kanigata, M. Iyoda, *J. Org. Chem.* 1992, 57, 3783–3789; C. E. O'Connell, K. Ackermanr, C. A. Rowell, A. Garcia, M. D. Lewis, C. E. Schwartz, *Bioorg. Med. Chem. Lett.* 1999, 9, 2095–2100; G. Lowe, T. Vilaivan, *J. Chem. Soc. Perkin Trans.* 1997, 547–554; B. Bellier, I. McCourt-Tranchepain, B. Ducos, S. Danascimenta, H. Mundal, *J. Med. Chem.* 1997, 40, 3947–3956; M. Peterson, R. Vince *J. Med. Chem.* 1991, 34, 2787–2797; E. M. Smith, G. F. Swiss, B. R. Neustadt, E. H. Gold, J. A. Sommer, *J. Med. Chem.* 1988, 31, 875–885; E. Rubini, C. Gilon, Z. Selinger, M. Chorev, *Tetrahedron* 1986, 42, 6039–6045 ($R^1$=H; $R^5$=OH); C. R. Noe, M. Knollmueller, H. Voellenkle, M. Noe-Letschnig, A. Weigand, J. Mülh, *Pharmazie*, 1996, 51, 800–804 ($R^1$=$CH_3$; $R^5$=OH); J. Kitchin, R. C. Berthel, N. Cammack, S. Dolan, D. N. Evans, *J. Med. Chem.* 1994, 37, 3703–3716; D. Y. Jackson, C. Quan, D. R. Artis, T. Rawson, B. Blackburn, *J. Med. Chem.* 1997, 40, 3359–3368 ($R^1$=H; $R^5$=OBn); J. E. Baldwin, A. R. Field, C. C. Lawrence, K. D. Merritt, C. J. Schofield, *Tetrahedron Lett.* 1993, 34, 7489–7492; K. Hashimoto, Y. Shima, H. Shirahama, *Heterocycles* 1996, 42, 489–492 ($R^1$=H; $R^5$=OTs); T. R. Webb, C. Eigenbrot, *J. Org. Chem.* 1991, 56, 3009–3016; D. C. Cafferty, C. A. Slate, B. M. Nakhle, H. D. Graham, T. L. Anstell, *Tetrahedron* 1995, 51, 9859–9872 ($R^1$=H; $R^5$=$NH_2$); T. R. Webb, C. Eigenbrot, *J. Org. Chem.* 1991, 56, 3009–3016 ($R^1$=H; $R^5$=$CH_2NH_2$); J. K. Thottathil, J. L. Moniot, *Tetrahedron Lett.* 1986, 27, 151–154 ($R^1$=H; $R^5$=Ph); K. Plucinska, T. Kataoka, M. Yodo, W. Cody, *J. Med. Chem.* 1993, 36, 1902–1913 ($R^1$=H; $R^5$=SBn); J. Krapcho, C. Turk, D. W. Cushman, J. R. Powell, *J. Med. Chem.* 1988, 31, 1148–1160 ($R^1$=H; $R^5$=SPh); A. J. Verbiscar, B. Witkop, *J. Org. Chem.* 1970, 35, 1924–1927 ($R^1$=H; $R^5$=$SCH_2$(4-OMe)$C_6H_4$); S. I. Klein, J. M. Denner, B. F. Molino, C. Gardner, R. D'Alisa, *Bioorg. Med. Chem. Lett.* 1996, 6, 2225–2230 ($R^1$=H; $R^5$=$O(CH_2)_3Ph$); R. Zhang, F. Brownewell, J. S. Madalengoita, *Tetrahedron Lett.* 1999, 40, 2707–2710 ($R^1$=H; $R^5$=$CH_2COOBn$).

A9: See Blake, *J. Am. Chem. Soc.* 1964, 86, 5293–5297; J. Cooper, R. T. Gallagher, D. T. Knight, *J. Chem. Soc. Chem. Perkin Trans.* 1, 1993, 1313–1318; D. W. Knight, A. W. Sibley, *J. Chem. Soc. Perkin Trans.* 1, 1997, 2179, 2188 ($R^1$=H; $R^6$=H); Blake, *J. Am. Chem. Soc.* 1964, 86, 5293–5297; Y. Yamada, T. Ishii, M. Kimura, K. Hosaka, *Tetrahedron Lett.* 1981, 1353–1354 ($R^1$=H; $R^6$=OH); Y. Umio, *Yakugahu Zasshi*, 1958, 78, 727 ($R^1$=H; $R^6$=iPr); Miyamoto, *Yahugaku Zasshi*, 1957, 77, 580–584; Tanaka, *Proc. Jpn. Acad.* 1957, 33, 47–50 ($R^1$=H; $R^6$=CH(CH$_3$) CH$_2$N(CH$_3$)$_2$); L. E. Overman, B. N. Rodgers, J. E. Tellew, W. C. Trenkle, *J. Am. Chem. Soc.* 1997, 119, 7159–7160 ($R^1$=H; $R^6$=alkyl); Ohki, *Chem. Pharm. Bull.* 1976, 24, 1362–1369 ($R^1$=CH$_3$; $R^6$=H).

A10: See J. Mulzer, A. Meier, J. Buschmann, P. Luger, *Synthesis* 1996, 123–132 ($R^1$=H; $R^7$=CH=CH$_2$); J. Cooper, P. T. Gallagher, D. W. Knight, *J. Chem. Soc. Chem. Commun.* 1988, 509–510; E. Götschi, C. Jenny, P. Reindl, F. Ricklin, *Helv. Chim. Acta* 1996, 79, 2219–2234 ($R^1$=H; $R^7$=OH); N. A. Sasald, R. Pauli, C. Fontaine, A. Chiaroni, C. Riche, P. Potier, *Tetrahedron Lett.* 1994, 35, 241–244 ($R^1$=H; $R^7$=COOH); R. Cotton, A. N. C. Johnstone, M. North, *Tetrahedron* 1995, 51, 8525–8544 ($R^1$=H; $R^7$=COOMe); J. S. Sabol, G. A. Flynn, D. Friedrich, E. W. Huber, *Tetrahedron Lett.* 1997, 38, 3687–3690 ($R^1$=H; $R^7$=CONH$_2$); P. P. Waid, G. A. Flynn, E. W. Huber, J. S. Sabol, *Tetrahedron Lett.* 1996, 37, 4091–4094 ($R^1$=H; $R^1$=(4-BnO)C$_6$H$_4$); N. A. Sasaki, R. Pauli, P. Potier, *Tetrahedron Lett.* 1994, 35, 237–240 ($R^1$=H; $R^7$=SO$_2$Ph); R. J. Heffner, J. Jiang, M. Jouillié, *J. Am. Chem. Soc.* 1992, 114, 10181–10189; U. Schmidt, H. Griesser, A. Lieberknecht, J. Häusler, *Angew. Chem.* 1981, 93, 272–273 ($R^1$=H; $R^7$=OAryl); H. Mosberg, A. L. Lomize, C. Wang, H. Kroona, D. L. Heyl, *J. Med. Chem.* 1994, 37, 4371–4383 ($R^1$=H; $R^7$=4-OHC$_6$H$_4$); S. A. Kolodziej, G. V. Nikiforovich, R. Sceean, M.-F. Lignon, J. Martinez, G. R. Marshall, *J. Med. Chem.* 1995, 38, 137–149 ($R^1$=H; $R^7$=SCH$_2$(4-Me)C$_6$H$_4$).

A11: See Kuhn, Osswald, *Chem. Ber.* 1956, 89, 1423–1434; Patchett, Witkop, *J. Am. Chem. Soc.* 1957, 79, 185–189; Benz, *Helv. Chim. Acta* 1974, 57, 2459–2475; P. Wessig, *Synlett*, 1999, 9, 1465–1467; E. M. Smit, G. F. Swiss, B. R. Neustadt, E. H. Gold, J. A. Sommer, *J. Med. Chem.* 1988, 31, 875–885; J. Krapcho, C. Turk, D. W. Cushman, J. R. Powell, J. M. DeForrest, *J. Med. Chem.* 1988, 31, 1148 ($R^1$=H; $R^6$=H); D. BenIshai, S. Hirsh, *Tetrahedron* 1988, 44, 5441–5450 ($R^1$=H; $R^6$=CH$_3$); M. W. Holladay, C. W. Lin, C. S. Garvey, D. G. Witte, *J. Med. Chem.* 1991, 34, 455–457 ($R^1$=H; $R^6$=alkyl); P. Barralough, P. Hudhomme, C. A. Spray, D. W. Young, *Tetrahedron* 1995, 51, 4195–4212 ($R^1$=H; $R^6$=Et); J. E. Baldwin, M. Rudolf, *Tetrahedron Lett.* 1994, 35, 6163–6166; J. E. Baldwin, S. J. Bamford, A. M. Fryer, M. Rudolf, M. E. Wood, *Tetrahedron* 1997, 53, 5233–5254 ($R^1$=H; $R^6$=CH$_2$COOtBu); P. Gill, W. D. Lubell, *J. Org. Chem.* 1995, 60, 2658–2659 ($R^1$=H; $R^6$=CH$_3$; Bn; alkyl; CH$_2$COOMe); M. J. Blanco, F. J. Sardina, *J. Org. Chem.* 1998, 63, 3411–3466 ($R^1$=H; $R^6$=OCH$_2$OMe).

A12: See Ahmed, Cheeseman, *Tetrahedron* 1977, 33, 2255–2257; J. S. New, J. P. Yevich, *J. Heterocycl. Chem.* 1984, 21, 1355–1360; R. Kikumoto, Y. Tamao, K. Ohkubo, T. Tezuka, S. Tonomura, *J. Med. Chem.* 1980, 23, 1293–1299; C. J. Blankley, J. S. Kaltenbronn, D. E. DeJohn, A. Werner, L. R. Bennett, *J. Med. Chem.* 1987, 30, 992–998; S. Klutcho, C. J. Blankley, R. W. Fleming, J. M. Hinkley, R. E. Werner, *J. Med. Chem.* 1986, 29, 1953–1961 ($R^1$=H; $R^8$=H); L. J. Beeley, C. J. M. Rockwell, *Tetrahedron Lett.* 1990, 31, 417–420 ($R^1$=COOEt; $R^8$=H).

A13: See G. Flouret, W. Brieher, T. Majewski, K. Mahan, *J. Med. Chem.* 1991, 43, 2089–2094; G. Galiendo, P. Grieco, E. Perissuti, V. Santagada, *Farmaco*, 1996, 51, 197–202; D. F. McComsey, M. J. Hawkins, P. Andrade-Gordon, M. F. Addo, B. E. Maryanoff, *Bioorg. Med. Chem. Lett.* 1999, 9, 1423–1428; G. B. Jones, S. B. Heaton, B. J. Chapman, M. Guzel, *Tetrahedron: Asymmetry* 1997, 8, 3625–3636; M. Asami, H. Watanabe, K. Honda, S. Inoue, *Tetrahedron: Asymmetry* 1998, 9, 4165–4174; K. Gross, Y. M. Yun, P. Beak, *J. Org. Chem.* 1997, 62, 7679–7689 ($R^1$=H; $R^6$=H; $R^8$=H); K. Gross, Y. M. Yun, P. Beak, *J. Org. Chem.* 1997, 62, 7679–7689 ($R^1$=H; $R^6$=H; $R^8$=6-Cl); Ch. Noe, M. Knollmueller, C. Schoedl, M. L. Berger, *Sci. Pharm.* 1996, 64, 577–590; E. Reiman, W. Erdle, H. Unger, *Pharmazie*, 1994, 54, 418–421 ($R^1$=H; $R^6$=CH$_2$COOH; $R^8$=H); V. Collot, M. Scbmitt, A. K. Marwah, B. Norerg, J.-J. Bourgignon, *Tetrahedron Lett.* 1997, 38, 8033–8036 ($R^1$=H; $R^6$=Ph; $R^8$=H); L. V. Dunkerton, H. Chen, B. P. McKillican, *Tetrahedron Lett.* 1988, 29, 2539–2542 ($R^1$=C(CH$_3$)$_2$CH=CH$_2$; $R^6$=H; $R^8$=H); E. J. Corey, *J. Am. Chem. Soc.* 1970, 92, 2476–2488; Neunhoeffer, Lehmann, *Chem. Ber.* 1961, 94, 2960–2963 ($R^1$=CH$_3$; $R^6$=H; $R^8$=H).

A14: Amino acids of type A14 can be made according to Scheme 1.

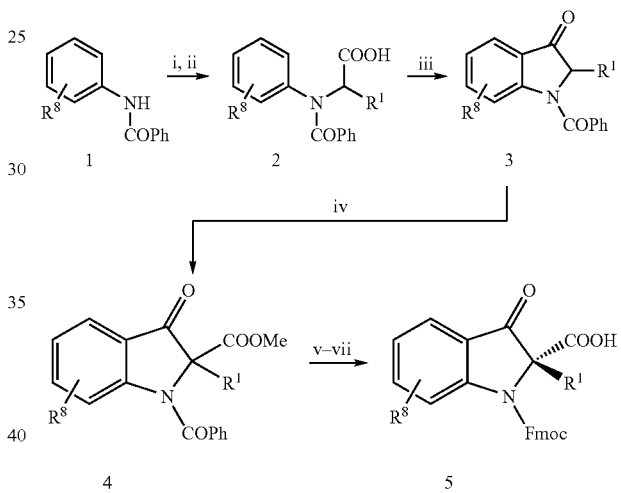

i: NaH, BrCH($R^1$)COOMe, DMF; ii: LiOHx1H$_2$O, MeOH, H$_2$O;
iii: polyphosporic acid(PPA); iv: NaH, ClCOOMe, THF; v: enzymatic resolution (e.g. lipase); vi: NaOH, MeOH, H$_2$O, heat; vii: FmocOSu, Na$_2$CO$_3$aq., dioxane A15: See D. S. Perlow, J. M. Erb, N. P. Gould, R. D. Tung, R. M. Freidinger, *J. Org. Chem.* 1992, 57, 4394–4400; D. Y. Jackson, C. Quan, D. R. Artis, T. Rawson, B. Blackburn, *J. Med. Chem.* 1997, 40, 3359–3368 ($R^1$=H; $R^2$=H); H. H. Wasserman, K. Rodrigues, K. Kucharozyl, *Tetrahedron Lett.* 1989, 30, 6077–6080 ($R^1$=H; $R^2$=COOH).

A16: See Beyerman, Boekee, *Recl. Trav. Chim. Pays-Bas*, 1959, 78, 648–653; M. E. Freed, A. R. Day, *J. Org. Chem.* 1960, 25, 2105–2107; D. R. Adams, P. D. Bailey, I. D. Collier, J. D. Heferman, S. Slokes, *J. Chem. Soc. Chem. Commun.* 1996, 349–350; J. E. Baldwin, R. M. Adlington, C. R. A. Godfrey, D. W. Collins, J. D. Vaughan, *J. Chem. Soc. Chem. Commun.* 1993, 1434–1435; Y. Matsuanura, Y. Takeshima, H. Ohita, *Bull. Chem. Soc. Jpn.* 1994, 67, 304–306 ($R^1$=H; $R^6$=H); C. Herdeis, W. Engel, *Arch. Pharm.* 1991, 324, 670 ($R^1$=COOMe; $R^6$=CH$_3$).

A17, A18: See C. R. Davies, J. S. Davies, *J. Chem. Soc. Perkin Trans* 1, 1976, 2390–2394; K. Bevan, *J. Chem. Soc. C*, 1971, 514–522; K. Umezawa, K. Nakazawa, Y. Ikeda, H. Naganawa, S. Kondo, *J. Org. Chem.* 1999, 64, 3034–3038 ($R^1$=$R^3$=H); P. D. Williams, M. G. Bock, R. D. Tung, V.

M. Garsky, D. S. Parlow, *J. Med. Chem*, 1992, 35, 3905–3918; K. Tamaki, K. Tanzawa, S. Kurihara, T. Oikawa, S. Monma, *Chem. Pharm. Bull*. 1995, 43, 1883–1893 ($R^1=R^5=H$; $R^3=COOBn$); K. J. Hale, J. Cai V. Delisser, S. Manaviazar, S. A. Peak *Tetrahedron* 1996, 52, 1047–1068; M. H. Chen, O. P. Goel, J.-W. Hyun, J. Magano, J. R. Rubin, *Bioorg. Med. Chem. Lett*. 1999, 9, 1587–1592 ($R^1=R^5=H$; $R^3=COOtBu$); R. Baenteli, I. Brun, P. Hall, R. Metternich, *Tetrahedron Lett*. 1999, 40, 2109–2112 ($R^1=R^5=H$; $R^3=COR$); K. J. Hale, N. Jogiya, S. Manaviazar, *Tetrahedron* 1998, 39, 7163–7166 ($R^1=H$; $R^3=COOBn$; $R^5=OBn$); T. Kamenecka, S. J. Danishewsky, *Angew. Chem. Int. Ed. Engl*. 1998, 37, 2995–2998 ($R^1=H$; $R^3=COO(CH_2)_2SiMe_3$; $R^5=OSiMe_2tBu$).

A19: See Beilstein, Registry Number 648833 ($R^1=R^4=R^8=H$). Compounds of this type can be prepared according to Scheme 2.

35, 490–501; H. Kessler, M. Kuehn, T. Löschner, *Liebigs Ann. Chem*. 1986, 1–20 ($R^1=R^6=H$); C. Herdeis, W. Engel, *Arch. Pharm*. 1992, 7, 419–424 ($R^1=R^6=Bn$); C. Herdeis, W. Engel, *Arch. Pharm*. 1992, 411–418 ($R^1=COOMe$; $R^6=H$); C. Herdeis, W. Engel, *Arch. Pharm*. 1992, 419–424 ($R^1=COOMe$; $R^6=Bn$).

A22: See P. D. Leeson, B. J. Williams, R. Baker, T. Ladduwahetty, K. W. Moore, M. Rowley, *J. Chem. Soc. Chem. Comm*. 1990, 1578–1580 ($R^1=H$; $R^{10}=NHOBn$).

A23: See Beyerman, Boekee, *Recl. Tray. Chim. Pays-Bas* 1959, 78, 648–653; D. R. Adams, P. D. Bailey, I. D. Collier, J. D. Heffernan, S. Stokes *J. Chem. Soc. Chem. Commun*. 1996, 349–350; J. E. Baldwin, R. M. Adlington, C. Godfrey, D. W. Collins, J. G. Vaughan, *J. Chem. Soc. Chem. Comm*. 1993, 1434–1435 ($R^1=R^6=H$); C. Herdeis, W. Engel, *Arch. Pharm*. 1993, 297–302 ($R^1=COOMe$; $R^6=H$).

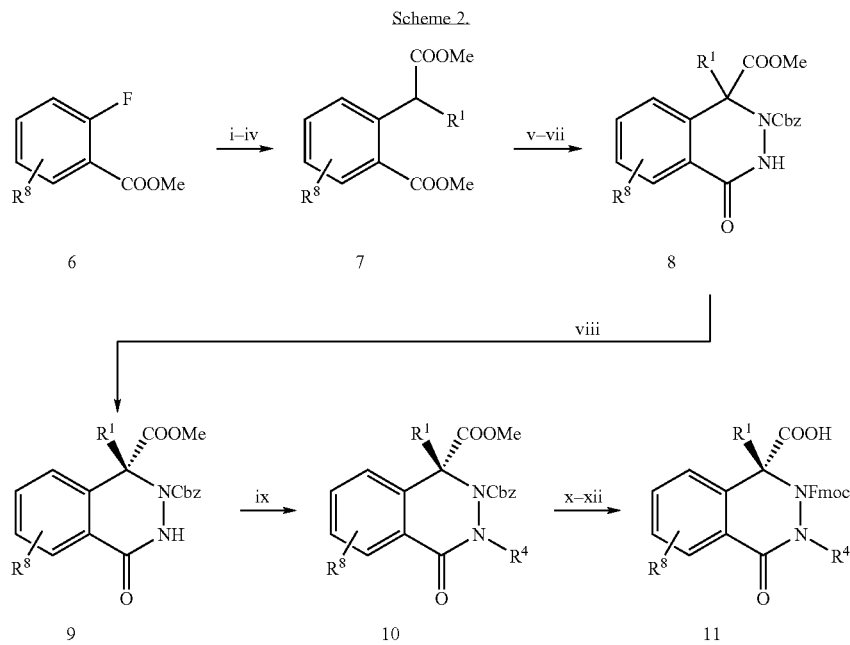

Scheme 2.

i: NaH, $CH_2(COOMe)_2$, DMSO; ii: NaH, $R^1-X$, DMSO; iii: NaOHaq., MeOH, 75°; iv: DBU, MeI, DMF; v: LDA, BocN=NBoc; vi: TFA, $CH_2Cl_2$; vii: CbzCl, $Na_2CO_3$aq., dioxane; viii: enzymatic resolution (e.g. lipase); then DBU, MeI, DMF; ix: NaH, $R^4-X$, THF; x: Pd/C, $H_2$, EtOH; xi: LiOHx$1H_2O$, MeOH, $H_2O$; xii: FmocOSu, $Na_2CO_3$aq., dioxane A20: See D. Hagiwara, H. Miyake, N. Igari, M. Karino, Y. Maeda, *J. Med. Chem*. 1994, 37, 2090–2099 ($R^1=H$; $R^9=OH$); Y. Arakawa, M. Yasuda, M. Ohnishi, S. Yoshifuji, *Chem. Pharm. Bull*. 1997, 45, 255–259 ($R^1=H$; $R^9=COOH$); P. J. Murray, I. D. Starkey, *Tetrahedron Lett*. 1996, 37, 1875–1878 ($R^1=H$; $R^9=(CH_2)_2NHCOCH_2Ph$); K. Clinch, A. Vasella, R. Schauer, *Tetrahedron Lett*. 1987, 28, 6425–6428 ($R^1=H$; $R^9=NHAc$).

A21: See A. Golubev, N. Sewald, K. Burger, *Tetrahedron Lett*. 1995, 36, 2037–2040; F. Machetti, F. M. Cordero, F. DeSario, A. Guarna, A. Brandi, *Tetrahedron Lett*. 1996, 37, 4205–4208; P. L. Ornstein, D. D. Schoepp, M. B. Arnold, J. D. Leander, D. Lodge, *J. Med. Chem*. 1991, 34, 90–97; $R^1=R^6=H$); P. D. Leeson, B. J. Williams, R. Baker, T. Ladduwahetty, K. W. Moore, M. Rowley, *J. Chem. Soc. Chem. Commun*. 1990, 1578–1580; D. I. C. Scopes, N. F. Hayes, D. E. Bays, D. Belton, J. Brain, *J. Med. Chem*. 1992, A24: See Plieninger, Leonhäuser, *Chem. Ber*. 1959, 92, 1579–1584; D. W. Knight, N. Lewis, A. C. Share, D. Haigh, *J. Chem. Soc. Perkin Trans*. 1 1998, 22, 3673–3684; J. Drummond, G. Johnson, D. G. Nickell, D. F. Ortwine, R. F. Bruns, B. Welbaum, *J. Med. Chem*. 1989, 32, 2116–2128; M. P. Moyer, P. L. Feldman, H. Rapoport, *J. Org. Chem*. 1985, 50, 5223–5230 ($R^1=R^6=H$); McElvain, Laughton, *J. Am. Chem. Soc*. 1951, 73, 448–451 ($R^1=H$; $R^6$—Ph); McElvain, Laughton, *J. Am. Chem. Soc*. 1951, 73, 448–451 ($R^1=Ph$; $R^6=H$);

A25: See L.-Y. Hu, T. R. Ryder, S. S. Nikam, E. Millerman, B. G. Szoke, M. F. Rafferty, *Bioorg. Med. Chem. Lett*. 1999, 9, 1121–1126; W. C. Lumma, R. D. Hartman, W. S. Saari, E. L. Engelhardt, V. J. Lotti, C. A. Stone, *J. Med. Chem*. 1981, 24, 93–101; N. Hosten, M. J. O. Antenuis, *Bull. Soc. Chim. Belg*. 1988, 97, 48–50; C. F. Bigge, S. J. Hays, P. M. Novak, J. T. Drummond, G. Johnson, T. P. Bobovski, *Tetrahedron Lett*. 1989, 30, 5193–5191; B. Aebischer, P.

Frey, H.-P. Haerter, P. L. Herrling, W. Müller, *Helv. Chim. Acta* 1989, 72, 1043–1051; W. J. Hoeckstra, B. E. Maryanoff, B. P. Damiano, P. Andrade-Gordon, J. H. Cohen, M. J. Constanzo, B. J. Haertlein, L. R. Hecker, B. L. Hulshizer, J. A. Kaufnan, P. Keane, *J. Med. Chem.* 1999, 42, 5254–5265 ($R^1$=H; $R^{11}$=H); B. D. Dorsey, R. B. Levin, S. L. McDaniel, J. P. Vacca, J. P. Guare, *J. Med. Chem.* 1994, 37, 3443–3451; M. Cheng, B. De, S. Pikul, N. G. Almstaed, M. G. Natchus, M. V. Anastasio, S. J. McPhail, C. J. Snider, Y. O. Taiwo, L. Chen, C. M. Dunaway, *J. Med. Chem.* 2000, 43, 369–380; R. Kuwano, Y. Ito, *J. Org. Chem.* 1999, 64, 1232–1237 ($R^1$=H; $R^{11}$=COOtBu); J. Kitchin, R. C. Bethell, N. Cammack, S. Dolan, D. N. Evans, *J. Med. Chem.* 1994, 37, 3707–3716 ($R^1$=H; $R^{11}$=COOPh); C. F. Bigge, S. J. Hays, P. M. Novak, J. T. Drummond, G. Johnson, T. P. Bobovski, *J. Med. Chem.* 1990, 33, 2916–2924 ($R^1$=H; $R^{11}$=COOtBu; $(CH_2)_3COOEt$; $(CH_2)_3PO(Me)OH$; $(CH_2PO(OH)_2$; $(CH_2)_2PO(OEt)_2$; $(CH_2)_2PO(OH)_2$).

Compounds of type A25 can also be prepared according to Scheme 3:

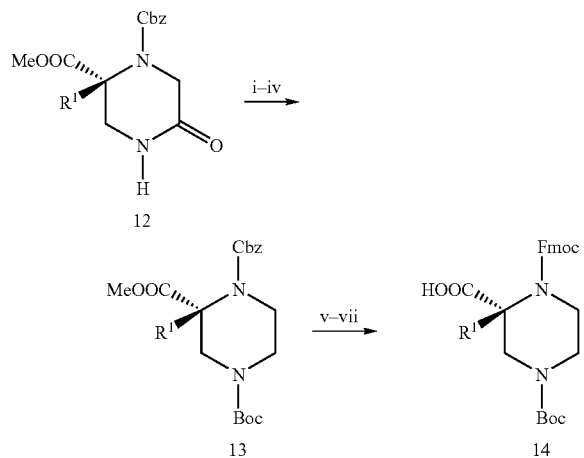

Scheme 3 i: Lawesson reagent, toluene, 80°; ii: DBU, MeI, DMF; iii: NaBH$_4$ or NaCNBH$_3$, MeOH; iv: Boc$_2$O, THF; v: LiOHx1H$_2$O, MeOH, H$_2$O; vi: Pd/C, H$_2$, EtOH; vii: FmocOSu, Na$_2$CO$_3$aq., dioxane A26: See Koegel, *J. Biol. Chem.* 1953, 201, 547 ($R^1$=$R^{12}$=H).

A27: See G. Makara, G. R. Marshall, *Tetrahedron Lett.* 1997, 38, 5069–5072; R. N. Patel, A. Banedee, R. L. Hanson, D. B. Brzozowski, L. W. Parker, L. J. Szarka, *Tetrahedron: Asymmetry* 1999, 10, 31–36 ($R^1$=H; $R^{13}$=OH, OtBu); J. E. Johanson, B. D. Christie, H. Rapoport, *J. Org. Chem.* 1981, 46, 4914–4920; N. Moss, J.-S. Duceppe, J.-M- Ferland, J. Gauthier, *J. Med. Chem.* 1996, 39, 2178–2187 ($R^1$=H; $R^{13}$=CONHMe); G. M. Makara, G. R. Marshall, *Tetrahedron Lett.* 1997, 38, 5069–5072 ($R^1$=H; $R^{13}$=SCH$_2$(4-MeO)C$_6$H$_4$).

A28: See A. Golubev, N. Sewald, K. Burger, *Tetrahedron Lett.* 1995, 36, 2037–2040; P. L. Ornstein, D. D. Schoepp, M. B. Amold, 3. D. Leander, D. Lodge, *J. Med. Chem.* 1991, 34, 90–97 ($R^1$=$R^6$=H); P. D. Leeson, B. J. Williams, R. Baker, T. Ladduwahetty, K. W. Moore, M. Rowley, *J. Chem. Soc. Chem. Commun.* 1990, 22, 1578–1580; C. Herdeis, W. Engel, *Arch. Pharm.* 1991, 324, 670 ($R^1$=H; $R^6$=Me); C. Herdeis, W. Engel, *Arch. Pharm.* 1991, 324, 670 ($R^1$=COOMe; $R^6$=H, Me).

A29: See Kawase, Masami, *Chem. Pharm. Bull.* 1997, 45, 1248–1253; I. G. C. Coutts, J. A. Hadfield, P. R. Huddleston, *J. Chem. Res. Miniprint*, 1987, 9, 2472–2500; I. G. C. Coutts, J. A. Hadfield, P. R. Huddleston, *J. Chem. Res. Miniprint*, 1987, 9, 2472–2500; V. J. Hrubi, W. L. Cody, A. M. Castrucci M. E. Hadley, *Collect. Czech. Chem. Commun.* 1988, 53, 2549–2573; R. T. Shuman, R. B. Rothenberger, C. S. Campbell, G. F. Smith, D. S. Gifford-Moore, P. D. Gesellchen, *J. Med. Chem.* 1993, 36, 314–319; M. Kawase, Y. Okada, H. Miyamae, *Heterocycles*, 1998, 48, 285–294 ($R^1$=$R^8$=H); Kawase, Masami, *Chem. Pharm. Bull.* 1997, 45, 1248–1253 ($R^1$=H; $R^8$=6,7-(MeO$_2$)); D. F. Ortwine, T. C. Malone, C. F. Bigge, J. T. Drummond, C. Humblet, *J. Med. Chem.* 1992, 35, 1345–1370 ($R^1$=H; $R^8$=7-H$_2$PO(OEt)$_2$); E. J. Corey, D. Y. Gin, *Tetrahedron Lett.* 1996, 37, 7163–7166 ($R^1$=CH$_2$SCOOtBu); P. Dostert, M. Varasi, A. DellaTorre, C. Monti, V. Rizzo, Eur. *J. Med. Chim. Ther.* 1992, 27, 57–59 ($R^1$=Me; $R^8$=6,7-(OH)$_2$); Z. Czarnocki, D. Suh, D. B. McLean, P. G. Hultin, W. A. Szarek, *Can. J. Chem.* 1992, 70, 1555–1561; B. Schönenberger, A. Brossi, *Helv. Chim. Acta* 1986, 69, 1486–1497 ($R^1$=Me; $R^8$=6-OH; 7-MeO); Hahn, Stiel, *Chem. Ber.* 1936, 69, 2627; M. Chrzanowska, B. Schönenberger, A. Brossi, J. L. Flippen-Anderson, *Helv. Chim. Acta* 1987, 70, 1721–1731; T. Hudlicky, *J. Org. Chem.* 1981, 46, 1738–1741 ($R^1$=Bn; $R^8$=6,7-(OH)$_2$); A. I. Meyers, M. A. Gonzalez, V. Struzka, A. Akahane, J. Guiles, J. S. Warmus, *Tetrahedron Lett.* 1991, 32, 5501–5504 ($R^1$=CH$_2$(3,4-methylenedioxy)C$_6$H$_3$; $R^8$=6,7-(OMe)$_2$).

A30 and A31 can be prepared according to Schemes 4 and 5.

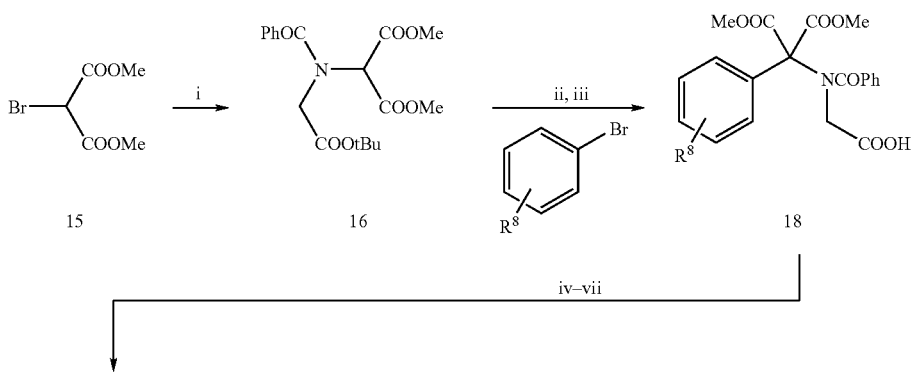

Scheme 4

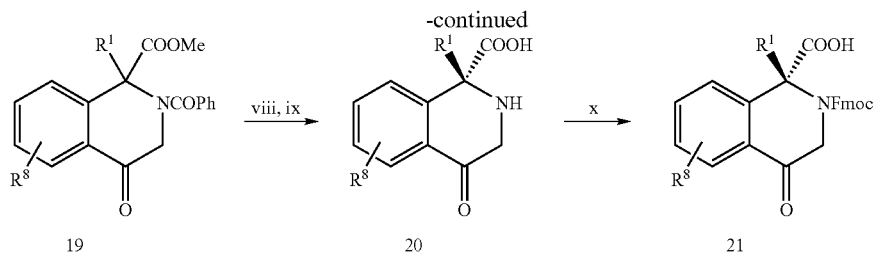

i: NaH, tert.-butyl N-benzoyl glycinate, DMF; ii: NaH, Pd(O), toluene; iii: TFA, CH$_2$Cl$_2$; iv: polyphosphoric acid; v: NaOHaq., MeOH, 75°; then HClaq; vi: DBU, MeI, DMF; vii: lithium hexamethyldisilazide, THF, chloro trimethylsilane, -78°; then R$^1$—X; viii: enzymatic resolution(e.g. lipase); then isolation as methylester: DBU, MeI, DMF; ix: NaOHaq., MeOH, heat; x: FmocOSu, Na$_2$CO$_3$aq., dioxane

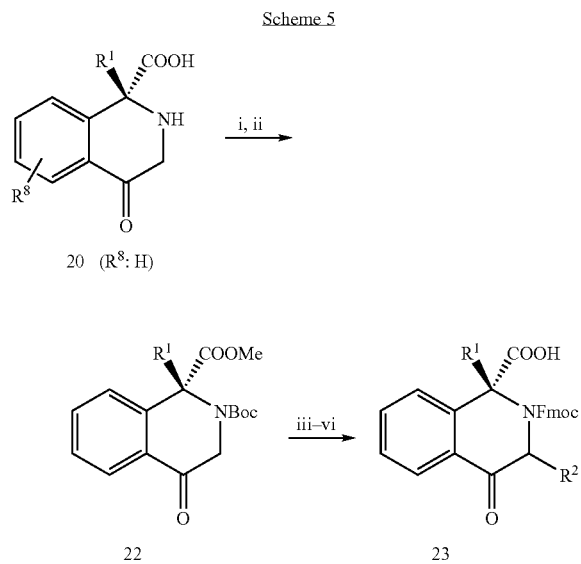

Scheme 5 i: Boc$_2$O, Na$_2$CO$_3$aq., dioxane; ii: DBU, MeI, DMF; iii: lithium hexamethyldisilazide, THF, chlorotrimethylsilane, -78°; then R$^2$—X;
iv: LiOHx$_1$H$_2$O, MeOH, H$_2$O; v: TFA, CH$_2$Cl$_2$; vi: FmocOSu, Na$_2$CO$_3$aq., dioxane A32 can be prepared according to P. W. Schiller, G. Weltrowska, T. M.-D. Nguyen, C. Lemieux, N. Nga, *J. Med. Chem.* 1991, 34, 3125–3132; V. S. Goodfellow, M. V. Marathe, K. G. Kuhlman, T. D. Fitzpatrick, D. Cuadrato, *J. Med. Chem.* 1996, 39, 1472–1484; G. Caliendo, F. Fiorino, P. Grieco, E. Perissutti, S. DeLuca, A. Guiliano, G. Santelli, D. Califano, B. Severino, V. Santagada, *Farmacao*, 1999, 54, 785–790; V. S. Goodfellow, M. V. Marathe, K. G. Kuhlman, T. D. Fitzpatrick, D. Cuadro, *J. Med. Chem.* 1996, 39, 1472–1484 (R$^1$=R$^8$=H); D. Tourwe, E. Mannekens, N. T. Trang, P. Verheyden, H. Jaspers, *J. Med. Chem.* 1998, 41, 5167–5176; A.-K. Szardenings, M. Gordeev, D. V. Patel, *Tetrahedron Lett.* 1996, 37, 3635–3638; W. Wiczk, K. Stachowiak, P. Skurski, L. Lankiewicz, A. Michniewicz, A. Roy, *J. Am. Chem. Soc.* 1996, 118, 8300–8307; K. Verschuren, G. Toth, D. Tourwe, M. Lebl., G. van Binst, V. Hrubi, *Synthesis* 1992, 458–460 (R$^1$=H; R$^8$=6-OH); P. L. Ornstein, M. B. Arnold, N. K. Augenstein, J. W. Paschal, *J. Org. Chem.* 1991, 56, 4388–4392 (R$^1$=H; R$^8$=6-MeO); D. Ma, Z. Ma, A. P. Kozikowski, S. Pshenichlin, J. T. Wroblenski, *Bioorg. Med. Lett.* 1998, 8, 2447–2450 (R$^1$=H; R$^8$=6-COOH); U. Schöllkopf, R. Hinrichs, R. Lonsky, *Angew. Chem.* 1987, 99, 137–138 (R$^1$=Me; R$^8$=H); B. O. Kammermeier, U. Lerch, C. Sommer, *Synthesis* 1992, 1157–1160 (R$^1$=COOMe; R$^8$=H); T. Gees, W. B. Schweizer, D. Seebach, *Helv. Chim. Acta* 1993, 76, 2640–2653 (R$^1$=Me; R$^8$=6,7-(MeO$_2$).

A33: See Hinton, Mann, *J. Chem. Soc.* 1959, 599–608.

A34: See G. P. Zecchini, M. P. Paradisi, *J. Heterocycl. Chem.* 1979, 16, 1589–1597; S. Cerrini, *J. Chem. Soc. Perkin Trans.* 1, 1979, 1013–1019; P. L. Ornstein, J. W. Paschal, P. D. Gesellchen, *J. Org. Chem.* 1990, 55, 738–741; G. M. Ksander, A. M. Yan, C. G. Diefenbacher, J. L. Stanton, *J. Med. Chem.* 1985, 28, 1606–1611; J. A. Robl, D. S. Karanewsky, M. M. Asaad, *Tetrahedron Lett.* 1995, 36, 1593–1596; S. Katayama, N. Ae, R. Nagata, *Tetrahedron: Asymmetry* 1998, 9, 4295–4300 (R$^1$=R$^8$=H); K. Hino, Y. Nagai, H. Uno, *Chem. Pharm. Bull.* 1988, 36, 2386–2400 (R$^1$=Me; R$^8$=H).

A35: See Beilstein Registry Numbers: 530775, 883013 (R$^1$=R$^8$=H).

A36: See R. W. Carling, P. D. Leeson, A. M. Moseley, R. Baker, A. C. Foster, *J. Med. Chem.* 1992, 35, 1942–1953; S. Kano, T. Ebata, S. Shibuya, *J. Chem. Soc. Perkin Trans.* 1, 1980, 2105–2111 (R$^1$=R$^8$=H); R. W. Carling, P. D. Leeson, A. M. Moseley, R. Baker, A. C. Foster, *J. Med. Chem.* 1992, 35, 1942–1953 (R$^1$=H; R$^8$=5-Cl; 7-Cl).

A37: See Nagarajan, *Indian J. Chem.* 1973, 11, 112 (R$^1$=CH$_2$COOMe; R$^8$=H).

A38: See R. Pauly, N. A. Sasaki, P. Potire, *Tetrahedron Lett.* 1994, 35, 237–240; J. Podlech, D. Seebach, *Liebigs Ann. Org. Bioorg. Chem.* 1995, 7, 1217–1228; K. C. Nicolaou, G.-Q. Shi, K. Namoto, F. Bernal, *J. Chem. Soc. Chem. Commun.* 1998, 1757–1758 (R$^1$=H; R$^2$=H).

A39: See Beilstein, Registry Number 782885.

A40; See F. P. J. C. Rutjes, N. M. Terhuis, H. Hiemstra, N. W. Speckamp, *Tetrahedron* 1993, 49, 8605–8628 (R$^1$=H; R$^3$=Bn); compounds of this type can be prepared according to Scheme 6.

Scheme 6

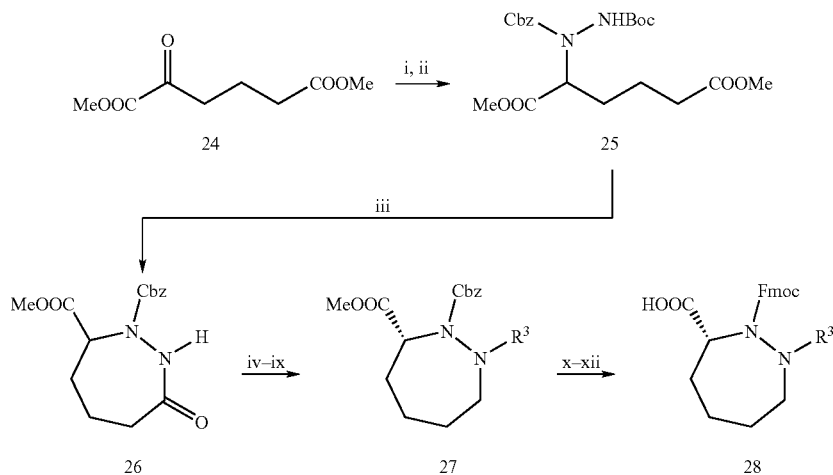

i: BocNHNH₂, NaCNBH₃, MeOH, AcOH; ii: CbzCl, Et₃N, CH₂Cl₂; iii: TFA, CH₂Cl₂; then pyridine, DMAP, heat; iv: resolution (e.g. lipase); v: DBU, MeI, DMF; vi: Lawesson reagent, toluene, 75°; vii: DBU, MeI, DMF; viii: NaBH₄ or NaCNBH₃, MeOH; ix: $R^3$ introduced by reductive amination, alkylation or acylation; x: LiOHx1H₂O, MeOH, H₂O; xi: Pd/C, H₂, EtOH; xii: FmocOSu, Na₂CO₃aq., dioxane A41: Compounds of this type can be prepared according to Scheme 7.

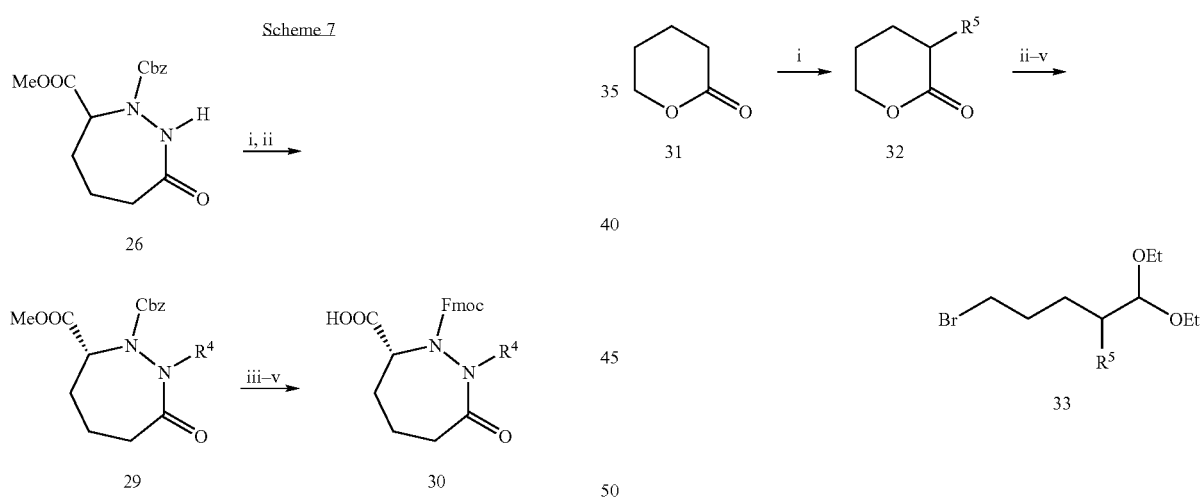

i: resolution (e.g. lipase); then isolation as methylester: DBU, MeI, DMF;
ii: NaH, $R^4$—X, THF; iii: LiOHx₁H₂O, MeOH, H₂O; iv: Pd/C, H₂, EtOH;
v: FmocOSu, Na₂CO₃aq., dioxane A42 to A46: Compounds of this type can be prepared according to Scheme, 8 to 12. Key intermediate 34 and α-amino acid synthesis involving this building block include: R. M. Williams, M.-N. Im, *Tetrahedron Lett.* 1988, 29, 6079–6082; R. M. Williams, M.-N. Im, *J. Am. Chem. Soc.* 1991, 113, 9276–9286; J. F. Dellaria, B. D. Santarsiero, *Tetrahedron Lett.* 1988, 29, 6079–6082; J. F. Dellaria, B. D. Santarsiero, *J. Org. Chem.* 1989, 54, 3916–3926; J. E. Baldwin, V. Lee, C. J. Schofield, *Synlett* 1992, 249–251; J. E. Baldwin, V. Lee, C. J. Schofield, *Heterocycles* 1992, 34, 903–906.

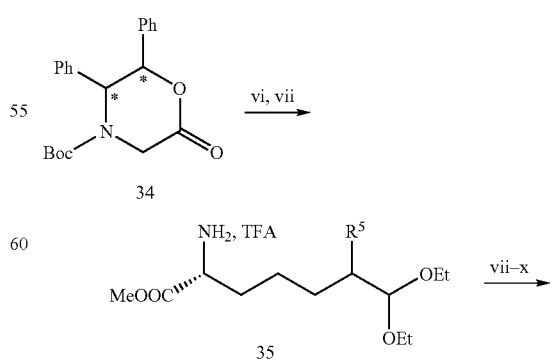

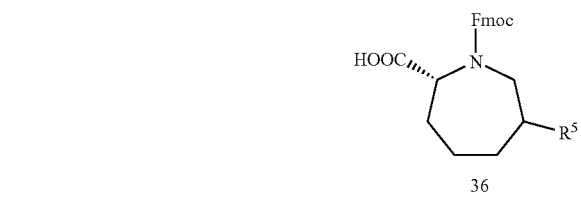

36 i: lithium hexamethyldisilazide, THF, chlorotrimethylsilane, -78°; then R⁵—X;
ii: HBr; iii: DBU, MeI, DMF; iv: DIBAL-H, THF; v: EtOH, pyridinium p-toluenesulfonate, mol. sieves 4A; vi: lithium hexamethyldisilazide, THF, -78°, 33; vii: Pd/C, H₂, EtOH; then DBU, MeI, DMF; then TFA, CH₂Cl₂;
viii: HClaq., THF; then Na(OAc)₃BH, AcOH, dichloroethane;
ix: LiOHx1H₂O, MeOH, H₂O; x: FmocOSu, Na₂CO₃aq., dioxane

Scheme 9

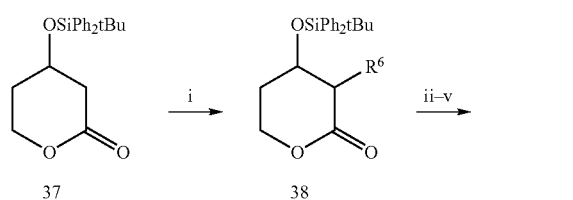

37    38

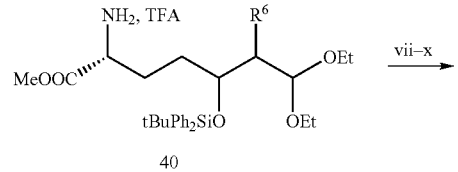

39

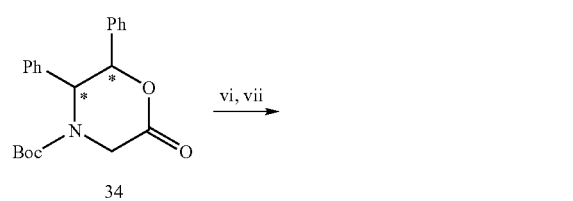

34

40

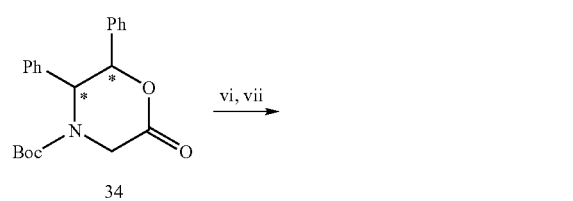

41 i: lithium hexamethyldisilazide, THF, chlorotrimethylsilane, -78°; then R⁶—X;
ii: HBr; iii: DBU, MeI, DMF; iv: DIBAL-H, THF; v: EtOH, pyridinium p-toluenesulfonate, mol. sieves 4A; vi: lithium hexamethyldisilazide, THF, -78°, 39; vii: Pd/C, H₂, EtOH; then DBU, MeI, DMF; then TFA, CH₂Cl₂;
viii: HClaq., THF; then Na(OAc)₃BH, AcOH, dichloroethane;
ix: Bu₄NFx10H₂O, THF; ix: pyridinium chlorochromate; x: LiOHx1H₂O, MeOH, H₂O;
xi: TFA, CH₂Cl₂; xii: FmocOSu, Na₂CO₃aq., dioxane

Scheme 10

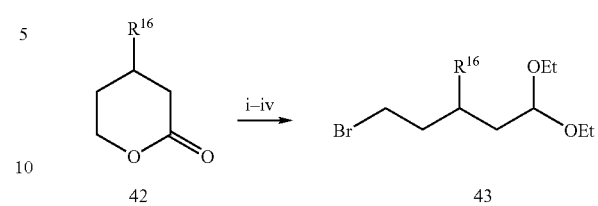

42    43

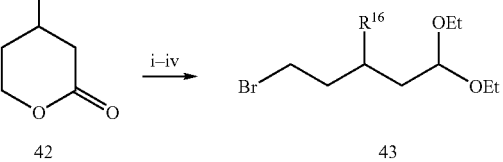

34

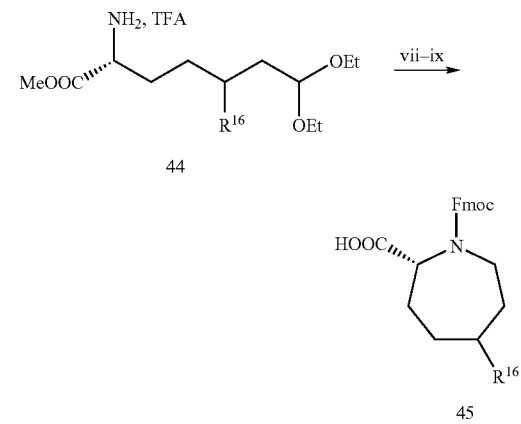

44

45 i: HBr; ii: DBU, MeI, DMF; iii: DIBAL-H, HF; iv: EtOH, pyridinium p-toluenesulfonate, mol. sieves 4A;
v: lithium hexamethyldisilazide, THF, -78°, 43; vi: Pd/C, H₂ EtOH; then DBU, MeI, DMF; then TFA, CH₂Cl₂; vii: HClaq., THF; then Na(OAc)₃BH, AcOH, dichloroethane; viii: LiOHx1H₂O, MeOH, H₂O; ix: FmocOSu, Na₂CO₃aq., dioxane

Scheme 11

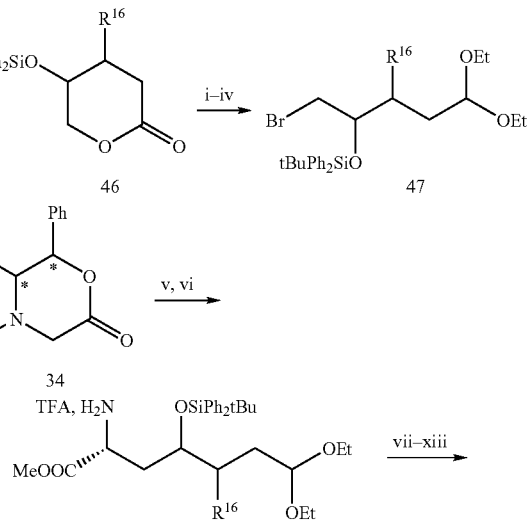

46    47

34

48

-continued

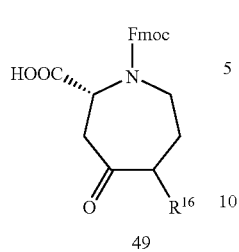

49 i: HBr; ii: DBU, MeI, DMF; iii: DIBAL-H, THF; iv: EtOH, pyridinium p-toluenesulfonate, mol. sieves 4A;
v: lithium hexamethyldisilazide, THF, -78°, 47; vi: Pd/C, H$_2$, EtOH; then DBU, MeI, DMF; then TFA, CH$_2$Cl$_2$; vii: HClaq., THF;
then Na(OAc)$_3$BH, AcOH, dichloroethane; viii: LiOHx1H$_2$O, MeOH, H$_2$O; xii: TFA, CH$_2$Cl$_2$; xiii: FmocOSu, Na$_2$CO$_3$aq., dioxane Scheme 12

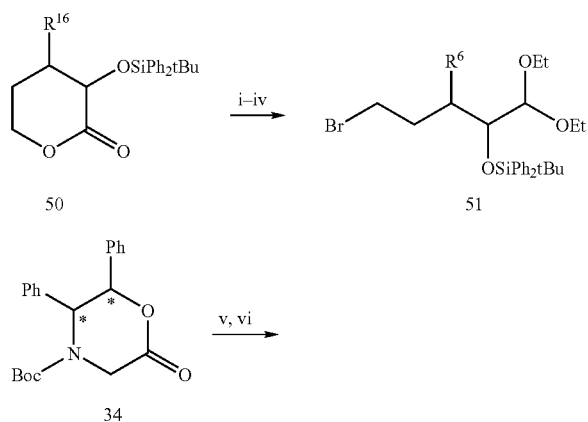

-continued

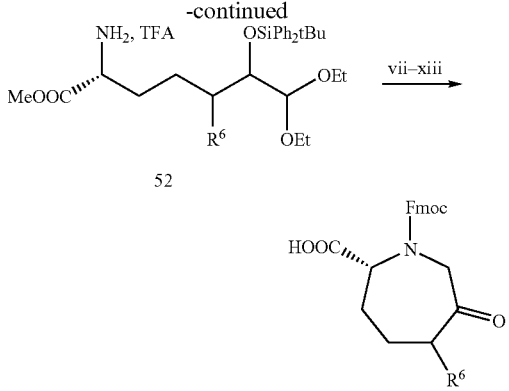

i: HBr; ii: DBU, MeI, DMF; iii: DIBAL-H, THF; iv: EtOH, pyridinium p-toluenesulfonate, mol. sieves 4A;
v: lithium hexamethyldisilazide, THF, -78°, 51; vi: Pd/C, H$_2$, EtOH; then DBU, MeI, DMF; then TFA, CH$_2$Cl$_2$; vii: HClaq., THF;
then Na(OAc)$_3$BH, AcOH, dichloroethane; viii: Boc$_2$O, Et$_3$N, CH$_2$Cl$_2$; ix: Bu$_4$NFx10H$_2$O, THF; x: pyridinium chlorochromate; xi: LiOHx1H$_2$O, MeOH, H$_2$O; xii: TFA. CH$_2$Cl$_2$; xiii: FmocOSu, Na$_2$CO$_3$aq., dioxane A47: See P. Barraclough, R. D. Farrant, D. Kettle, S. Smith, *J. Chem. Res. Miniprint* 1991, 11, 2876–2884 ($R^1=R^{11}=H$, Bn, —(CH$_2$)$_2$PO(OEt)$_2$).

A48: See A. Nouvet, M. Binard, F. Lamaty, J. Martinez, R. Lazaro, *Tetrahedron* 1999, 55, 4685–4698 ($R^1=R^{12}=H$).

A49: See M. Y. Kolleganov, I. G. Kolleganova, M. D. Mitrofanova, L. I. Martynenko, P. P. Nazarov, V. I. Spitsyn, *Bull. Acad. Sci. USSR Div. Chem. Sci (Engl. Trans.)* 1983, 32, 1293–1299; *Izv. Akad. Nauk SSSR Ser. Khim.* 1983, 6, 1293–1299; V. P. Vasilev, T. D. Orlova, S. F. Ledenkov, *J. Gen. Chem. USSR* (Engl. Trans. 1989, 59, 1629–1634; *Zh. Obshchi. Khim.* 1989, 59, 1828–1833 ($R^1=H$; $R^{12}=CH(COOH)CH_2COOH$). Compounds of type A49 can also be prepared according to Scheme 13.

Scheme 13

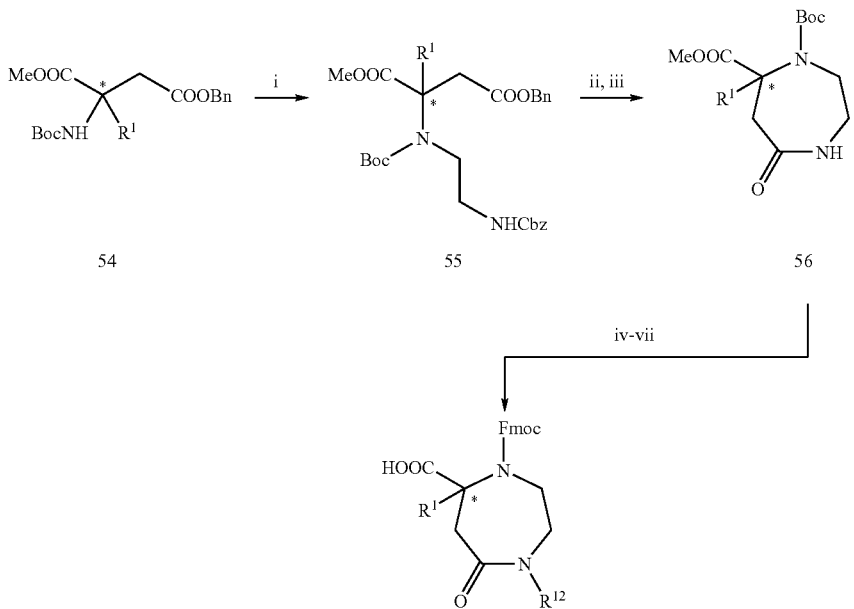

i: NaH, CbzNH(CH$_2$)$_2$Br, THF; ii: Pd/C, H$_2$, EtOH; iii: EDCl, CH$_2$Cl$_2$, diisopropylethylamin; iv: NaH, $R^{12}$—X, THF; v: LiOHx1H$_2$O, MeOH, H$_2$O; vi: TFA, CH$_2$Cl$_2$; vii: FmocOSu, Na$_2$CO$_3$aq., dioxane A50 and A51: Compounds of these types can be prepared according to Schemes 14 and 15.

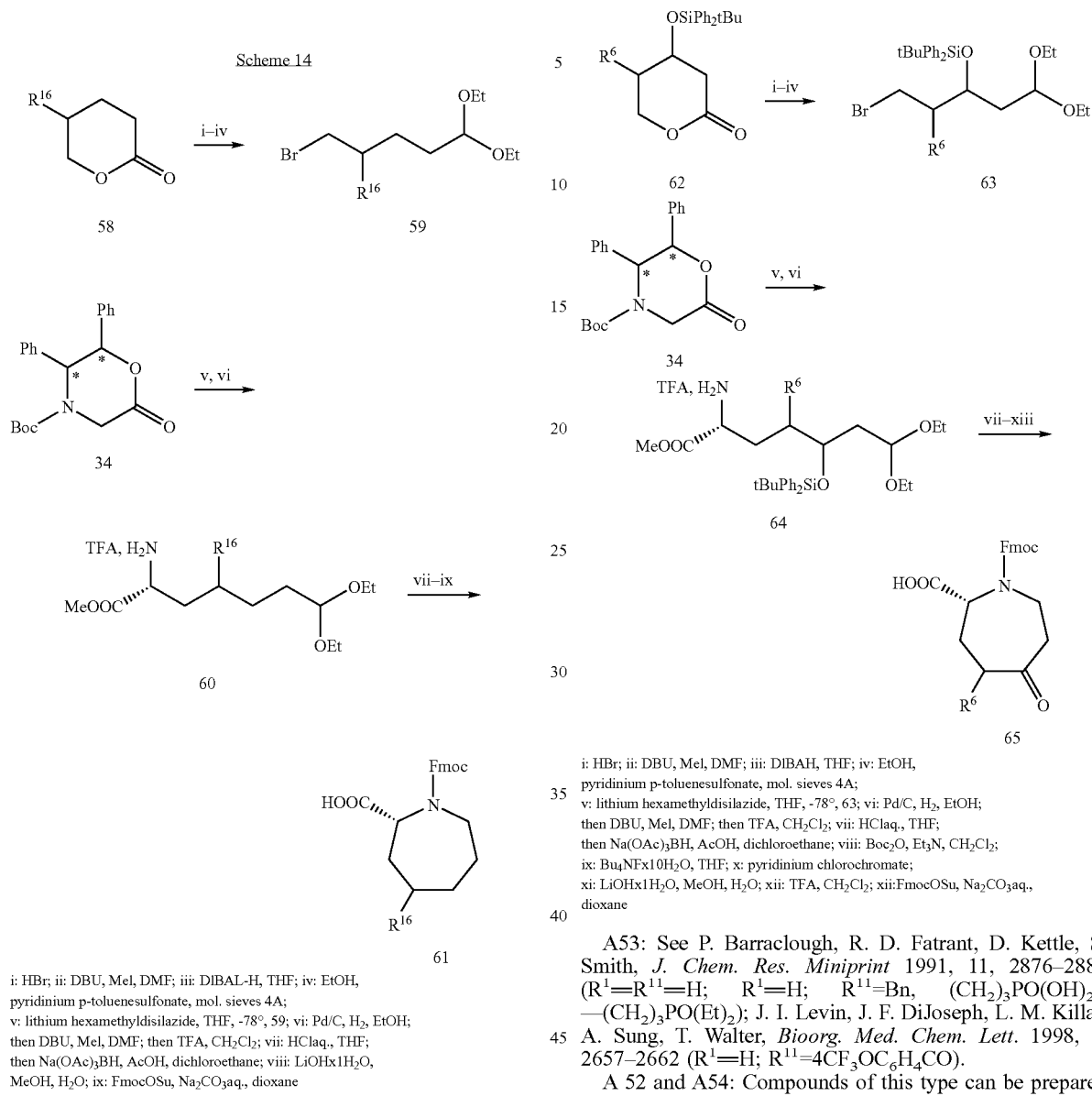

i: HBr; ii: DBU, MeI, DMF; iii: DIBAL-H, THF; iv: EtOH, pyridinium p-toluenesulfonate, mol. sieves 4A;
v: lithium hexamethyldisilazide, THF, -78°, 59; vi: Pd/C, H$_2$, EtOH; then DBU, MeI, DMF; then TFA, CH$_2$Cl$_2$; vii: HClaq., THF; then Na(OAc)$_3$BH, AcOH, dichloroethane; viii: LiOHx1H$_2$O, MeOH, H$_2$O; ix: FmocOSu, Na$_2$CO$_3$aq., dioxane i: HBr; ii: DBU, MeI, DMF; iii: DIBAH, THF; iv: EtOH, pyridinium p-toluenesulfonate, mol. sieves 4A;
v: lithium hexamethyldisilazide, THF, -78°, 63; vi: Pd/C, H$_2$, EtOH; then DBU, MeI, DMF; then TFA, CH$_2$Cl$_2$; vii: HClaq., THF; then Na(OAc)$_3$BH, AcOH, dichloroethane; viii: Boc$_2$O, Et$_3$N, CH$_2$Cl$_2$; ix: Bu$_4$NFx10H$_2$O, THF; x: pyridinium chlorochromate; xi: LiOHx1H$_2$O, MeOH, H$_2$O; xii: TFA, CH$_2$Cl$_2$; xiii:FmocOSu, Na$_2$CO$_3$aq., dioxane A53: See P. Barraclough, R. D. Fatrant, D. Kettle, S. Smith, *J. Chem. Res. Miniprint* 1991, 11, 2876–2884 ($R^1$=$R^{11}$=H; $R^1$=H; $R^{11}$=Bn, (CH$_2$)$_3$PO(OH)$_2$); —(CH$_2$)$_3$PO(Et)$_2$); J. I. Levin, J. F. DiJoseph, L. M. Killar, A. Sung, T. Walter, *Bioorg. Med. Chem. Lett.* 1998, 8, 2657–2662 ($R^1$=H; $R^{11}$=4CF$_3$OC$_6$H$_4$CO).

A 52 and A54: Compounds of this type can be prepared according to Schemes 16 and 17.

Scheme 16

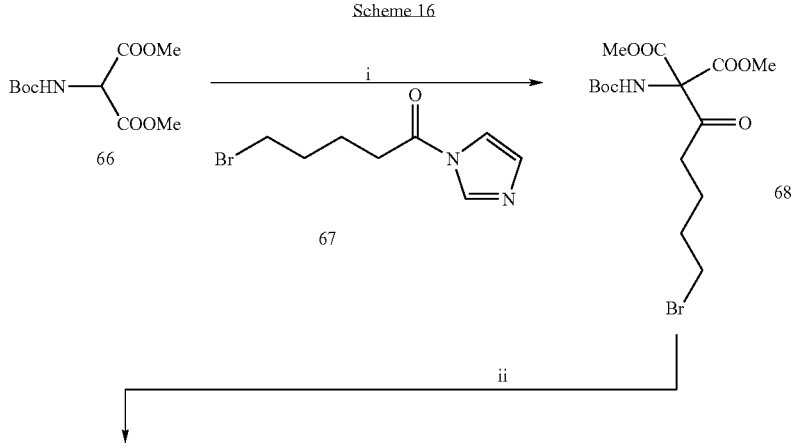

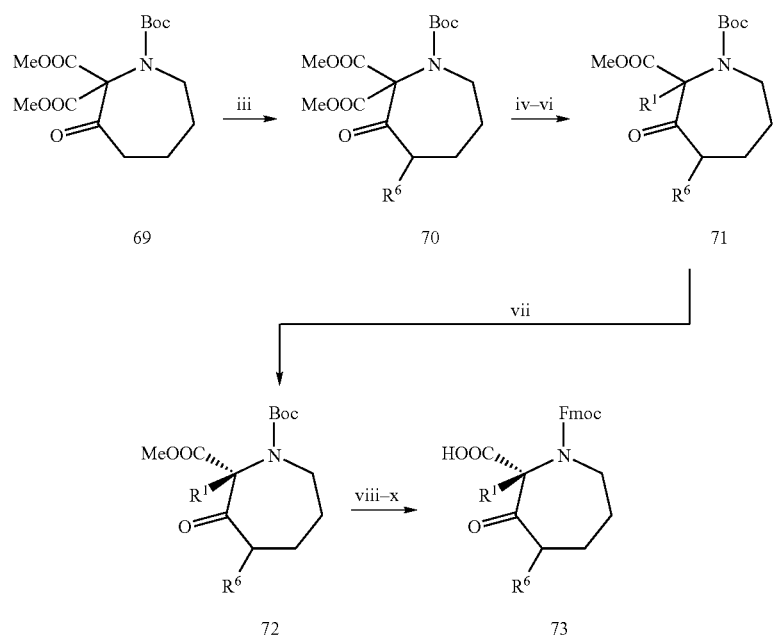

i: iBuMgCl, THF; ii: NaH, THF; iii: lithium hexamethyldisilazide, THF, chlorotrimetylsilane, -78°; then $R^6$—X, iv: NaOHaq., MeOH, 75°; then HClaq.; v: DBU, MeI, DMF; vi: lithium hexamethyl-disilazide,THF, chlorotrimetylsilane, -78°; then $R^1$—X; vii: resolution (e.g. lipase); then DBU, MeI, DMF; viii: LiOHx1H$_2$O, MeOH, H$_2$O; ix: TFA, CH$_2$Cl$_2$; x: FmocOSu, Na$_2$CO$_3$aq., dioxane Scheme 17

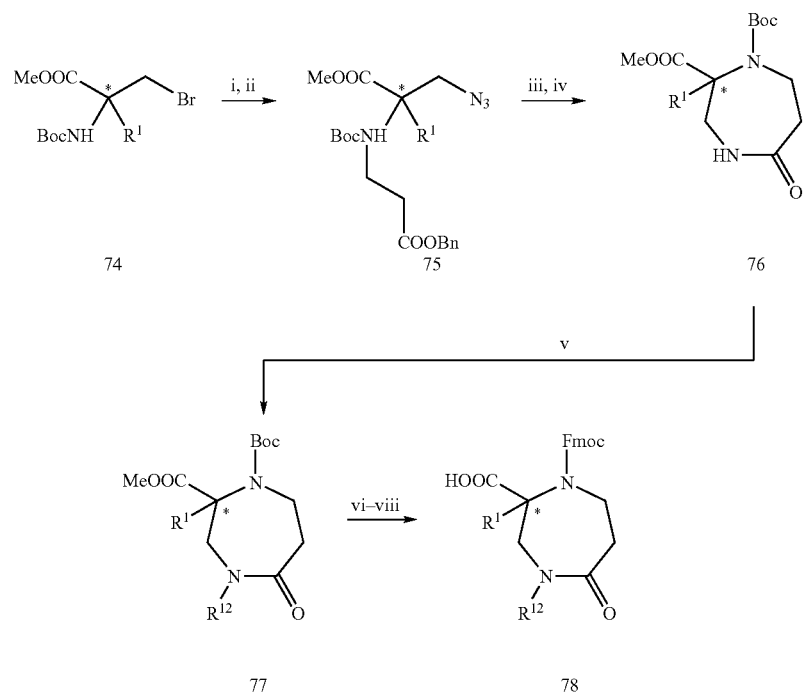

i: NaN$_3$, DMSO; ii: NaH, THF, CH$_2$=CHCOOBn; iii: Pd/C, H$_2$, EtOH; iv: EDCl, CH$_2$Cl$_2$, diisopropylethylamine; v: NaH, $R^{12}$—X, THF; vi: LiOHx1H$_2$O, MeOH, H$_2$O; vii: TFA, CH$_2$Cl$_2$; viii: FmocOSu, Na$_2$CO$_3$aq., dioxane A55 and A56: Compounds of this type can be prepared according to Schemes 18 and 19.

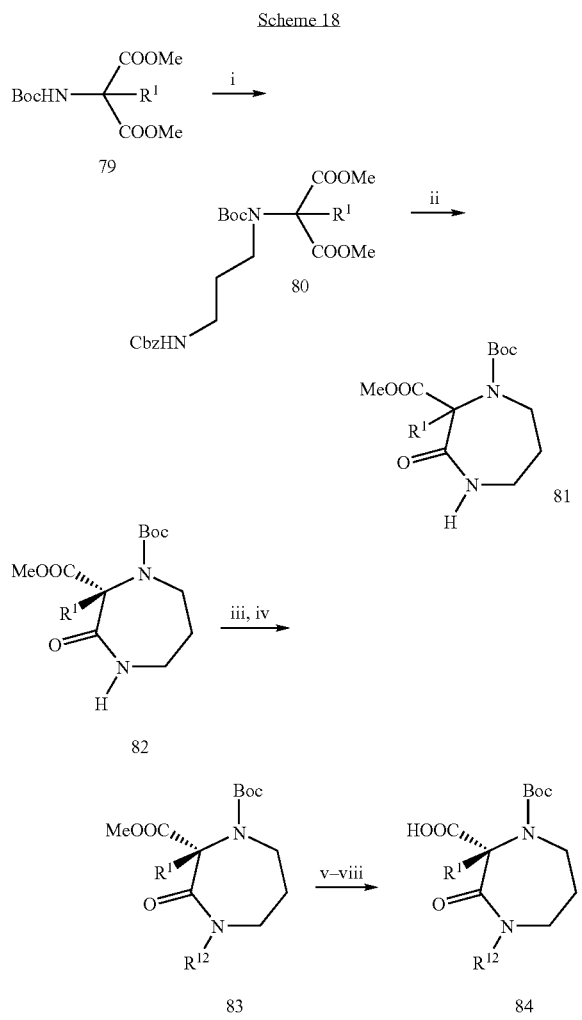

Scheme 18 i: NaH, THF, CbzNH(CH$_2$)$_3$Br; ii: Pd/C, H$_2$, EtOH; then toluene, heat; iii: resolution (e.g. lipase); iv: DBU, MeI, DMF; v: NaH, R$^{12}$—X THF; vi: LiOHx1H$_2$O, MeOH, H$_2$O; vii: TFA, CH$_2$Cl$_2$; viii: FmocOSu, Na$_2$CO$_3$aq., dioxane

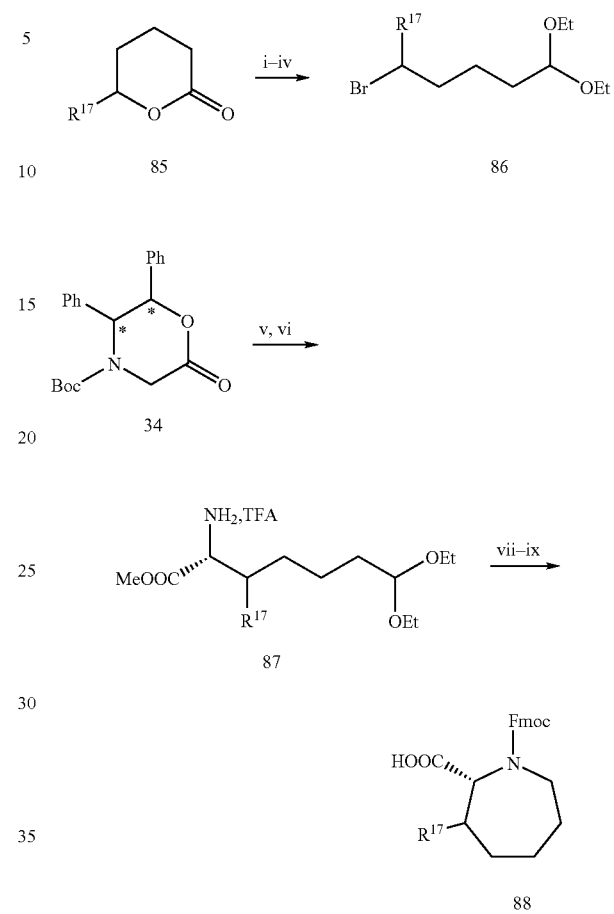

Scheme 19 i: HBr; ii: DBU, MeI, DMF; iii: DIBAL-H, THF; iv: EtOH, pyridinium p-toluenesulfonate, mol. sieves 4A; v: lithium hexamethyldisilazide, THF, -78°, 86; vi: Pd/C, H$_2$, EtOH; then DBU, MeI, DMF; then TFA, CH$_2$Cl$_2$; vii: HClaq., THF; then Na(OAc)$_3$BH, AcOH, dichloroethane; viii: LiOHx1H$_2$O, MeOH, H$_2$O; ix: FmocOSu, Na$_2$CO$_3$aq., dioxane A57: Compounds of this type can be prepared according to Scheme 20.

Scheme 20

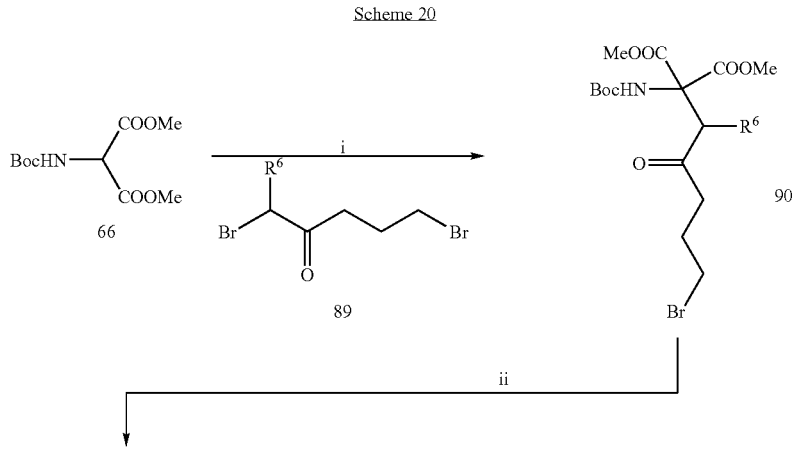

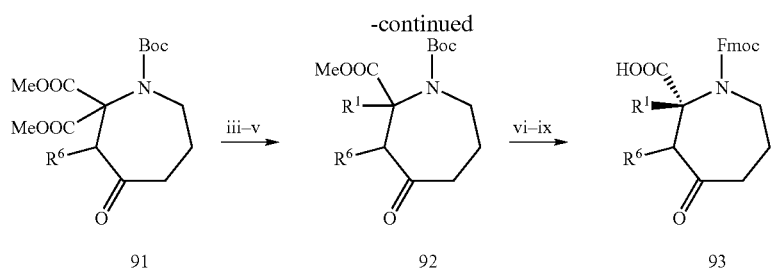

i: NaOMe, MeOH; ii: NaH, THF; iii: NaOHaq., MeOH, 75°; then HClaq.; iv: DBU, MeI, DMF; v: lithium hexamethyldisilazide, THF, chlorotrimethylsilane, -78°; then $R^1$—X; vi: resolution (e.g. lipase); then isolation of methylester: DBU, MeI, DMF; vii: LiOHx1H$_2$O, MeOH, H$_2$O; viii: TFA, CH$_2$Cl$_2$; ix: FmocOSu, Na$_2$CO$_3$aq., dioxane A58: See C.-H. Lee, H. Kohn, *J. Org. Chem.* 1990, 55, 6098–6104 ($R^1$=$R^8$=H).

A59: can be prepared according to Scheme 21.

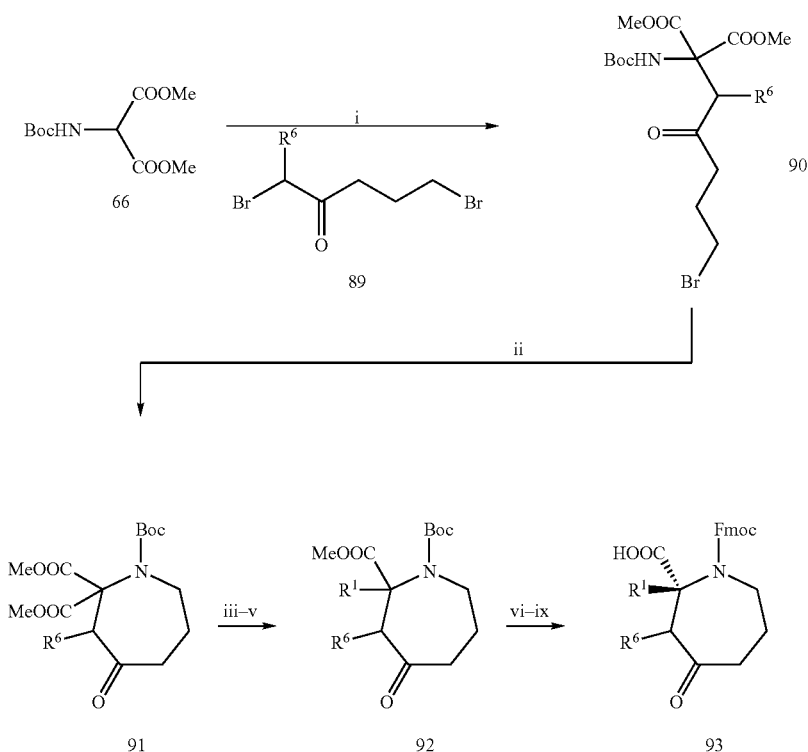

i: NaOMe, MeOH; ii: NaH, THF; iii: NaOH aq., MeOH, 75°; then HCl aq.; iv: DBU, MeI, DMF; v: lithium hexamethyldisilazide, THF, chlorotrimethylsilane, -78°; then $R^1$—X; vi: resolution (e.g. lipase); then isolation of methylester: DBU, MeI, DMF; vii: LiOHx1H$_2$O, MeOH, H$_2$O; viii: TFA, CH$_2$Cl$_2$; ix: FmocOSu, Na$_2$CO$_3$ aq., dioxane A60: Compounds of this type can be prepared according to Scheme 22.

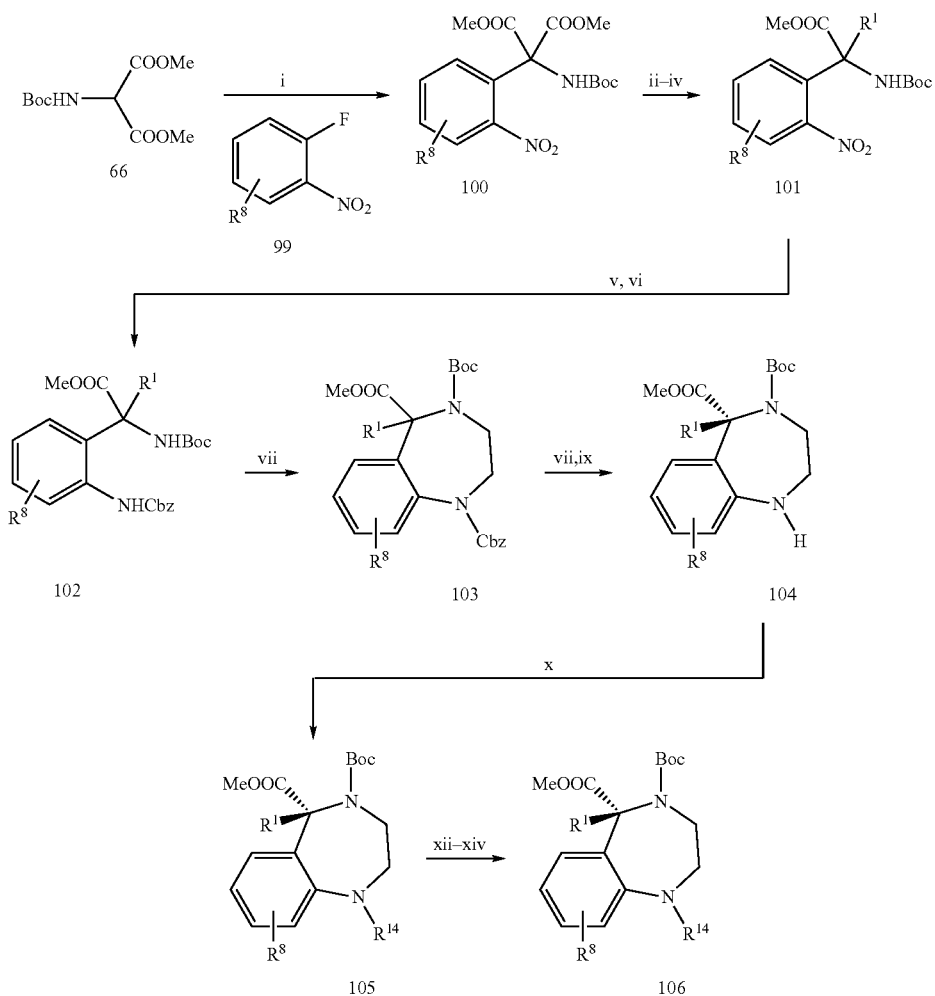

i: NaH, DMSO; ii: NaOH aq., MeOH, 75°; then HCl aq,; iii: DBU, MeI, DMF; iv: NaOMe (2.2 equiv.), R¹—X; v: Raney-Ni, H₂, EtOH; vi: CbzCl, Et₃N, CH₂Cl₂; vii: NaH, Br(CH₂)₂Br, THF; viii: resolution (e.g. lipase); then DBU, MeI, DMF; ix: Pd/C, H₂, EtOH; x: NaH, R¹⁴—X, THF; xi: LiOHx1H₂O, MeOH, H₂O; xii: TFA, CH₂Cl₂; xiii: FmocOSu, Na₂CO₃ aq., dioxane A61: See D. R. Armour, K. M. Morriss, M. S. Congreve, A. B. Hawcock, *Bioorg. Med. Chem. Lett.* 1997, 7, 2037–2042 ($R^1=R^{12}=H$).

A62: Compounds of this type can be prepared according to Scheme 23.

Scheme 23

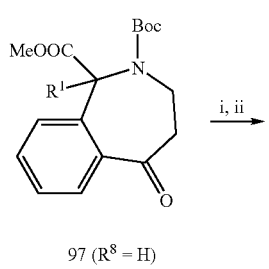

97 ($R^8 = H$)

-continued

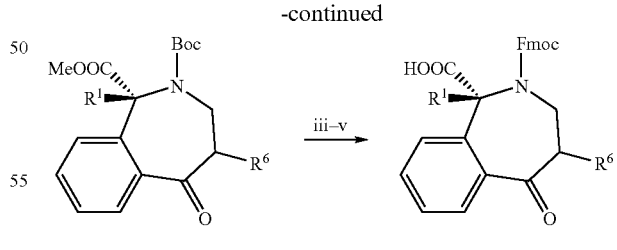

i: resolution (e.g. lipase); then DBU, MeI, DMF; ii: lithium hexamethyldisilazide, THF, chlorotrimethylsilane, -78°; then $R^6$—X;
iii: LiOHx1H₂O, MeOH, H₂O; iv: TFA, CH₂Cl₂; v: FmocOSu, Na₂CO₃ aq., dioxane A63: See S. E. Gibson, N. Guillo, R. J. Middleton, A. Thuiliez, M. J. Tozer, *J. Chem. Soc. Perkin Trans.* 1, 1997, 4, 447–456; S. E. Gibson, N. Guillo, S. B. Kalindjan, M. J.

Tozer, *Bioorg. Med. Chem. Lett,.* 1997, 7, 1289–1292 ($R^1$=H; $R^8$=H); Beilstein Registry Number: 459155 ($R^1$=H; $R^8$=4,5-MeO$_2$).

A64: Compounds of this type can be prepared according to Scheme 24.

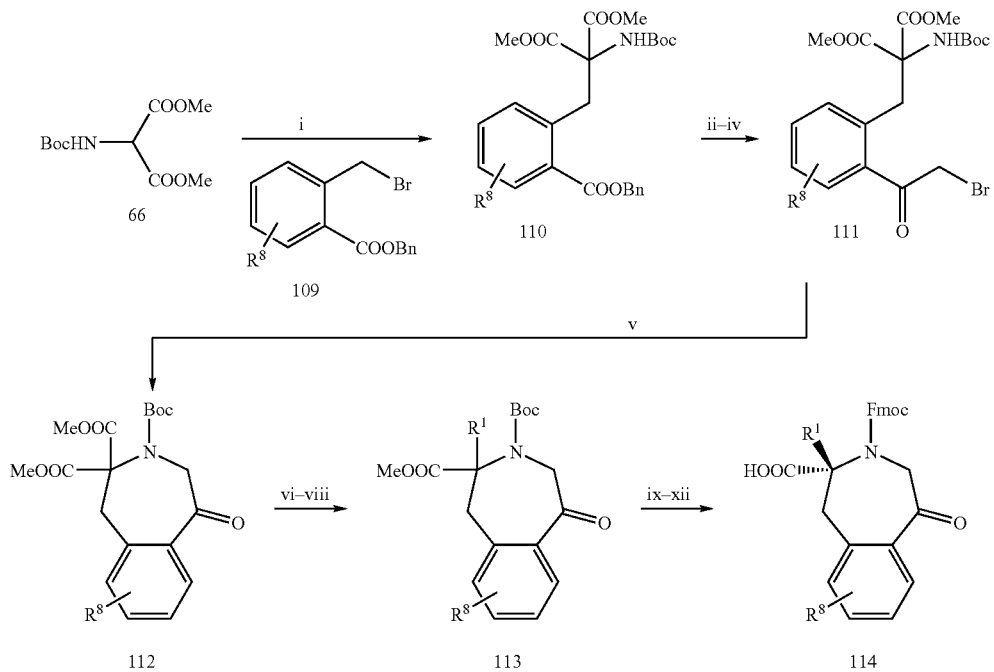

i: NaH, DMSO; ii: Pd/C, H$_2$, EtOH; iii: iBuOCOCl, diisopropylethylamine, CH$_2$Cl$_2$; then diazomethane; iv: HBr, CH$_2$Cl$_2$; v: NaH, THF; vi: NaOH aq., MeOH, 75°; then HCl aq.; vii: DBU, MeI DMF; viii: lithium diisopropylamide, THF, chlorotrimethylsilane, -78°; then $R^1$-X; ix: resolution (e.g. lipase); the isolation of methylester: DBU, MeI, DMF; x: LiOHx1H$_2$O, MeOH, H$_2$O; xi: TFA, CH$_2$Cl$_2$; xii: FmocOSu, Na$_2$CO$_3$ aq., dioxane A65 and A67: Compounds of these types can be prepared according to Schemes 25 and 26.

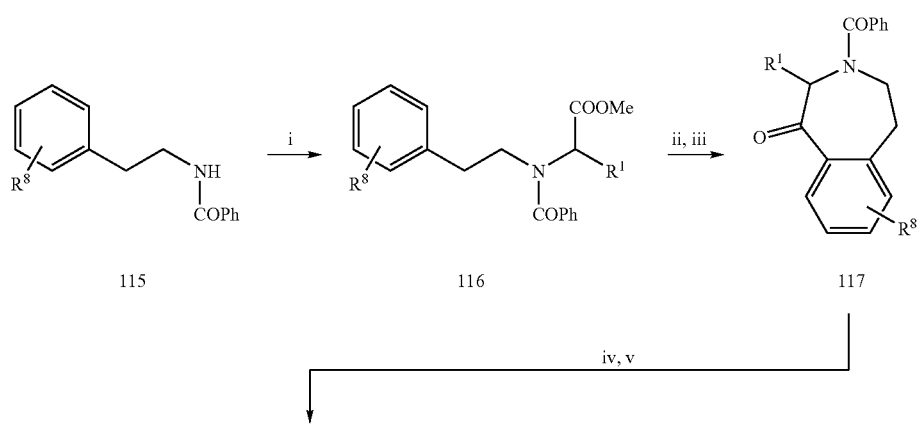

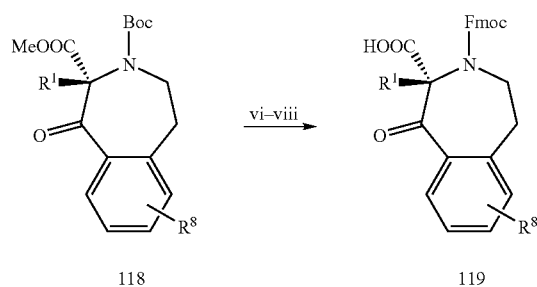

i: NaH, DMSO, BrCH(R¹)COOMe; ii: LiOHx1H₂O, MeOH, H₂O; iii: polyphosphoric acid; iv: NaH, ClCOOMe, THF; v: resolution (e.g. lipase); then isolation as methylester: DBU, MeI, DMF; vi: LiOHx1H₂O, MeOH, H₂O; vii: TFA, CH₂Cl₂; vii: FmocOSu, Na₂CO₃ aq., dioxane

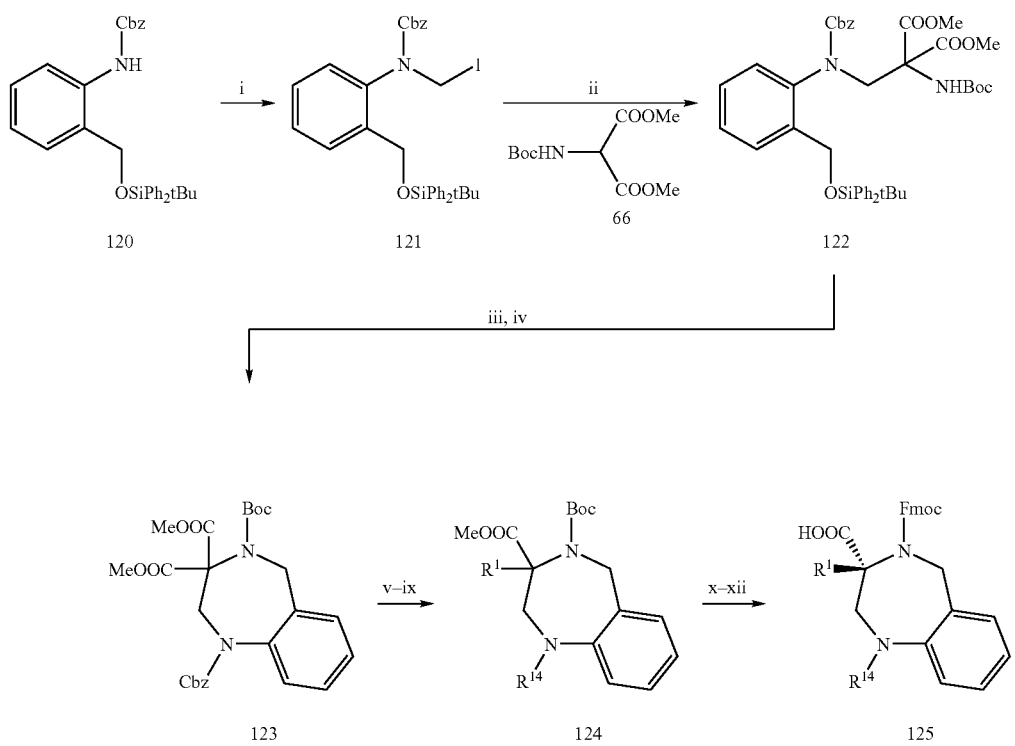

i: NaH, THF, CH₂I₂; ii: NaH, DMSO; iii: Bu₄NFx10H₂O, THF; iv: methanesulfonylchloride, Et₃N, CH₂Cl₂; then NaH, THF; v: NaOH aq., MeOH, 75°; then HCl aq.; vi: DBU, MeI, DMF; vii: lithium hexamethyldisilazide, THF, chlorotrimethylsilane, -78°; then R¹-X; viii: Pd/C, H₂, EtOH; ix: NaH, THF, R¹⁴-X; x: resolution (e.g. lipase); then isolation of methylester: DBU, MeI, DMF; xi: LiOHx1H₂O, MeOH, H₂O; xii: TFA, CH₂Cl₂; xiii: FmocOSu, Na₂CO₃ aq., dioxane A66: See G. L. Grunewald, L. H. Dahanukar, *J. Heterocycl. Chem*. 1994, 31, 1609–1618 ($R^1$=H; $R^8$=H, 8-$NO_2$; C(1)=O).

A68: See Griesbeck, H. Mauder, I. Müller, *Chem. Ber*. 1992, 11, 2467–2476; ($R^1$=$R^8$=H; C(1)=O).

A69: R. Kreher, W. Gerhardt, *Liebigs Ann. Chem*. 1981, 240–247 ($R^1$=$R^8$=H).

As explained above, building blocks A70 belong to the class of open-chain α-substituted α-amino acids, A71 and A72 to the class of the the corresponding β-amino acid analogues and A73–A104 to the class of the cyclic analogues of A70.

Building blocks of types A70 and A73–A104 have been synthesized by several different general methods: by [2+2] cycloaddition of ketenes with imines (I. Ojima, H. J. C. Chen, X. Quin, *Tetrahedron Lett*. 1988, 44, 5307–5318); by asymmetric aldol reaction (Y. Ito, M. Sawamura, E. Shirakawa, K. Hayashikazi, T. Hayashi, *Tetrahedron Lett*. 1988, 29, 235–238; by the oxazolidinone method (J. S. Amato, L. M. Weinstock, S. Karady, U.S. Pat. No. 4,508,921 A; M. Gander-Coquoz, D. Seebach, *Helv. Chem. Acta* 1988, 71, 224–236; A. K. Beck, D. Seebach, *Chimia* 1988, 42, 142–144; D. Seebach, J. D. Aebi, M. Gander-Coquoz, R. Naef, *Helv. Chim. Acta* 1987, 70, 1194–1216; D. Seebach, A. Fadel, *Helv. Chim. Acta* 1995, 68, 1243–1250; J. D. Aebi, D. Seebach, *Helv. Chim. Acta* 1985, 68, 1507–1518; A. Fadel, J. Salaun, *Tetrahedron Lett*. 1987, 28, 2243–2246); by Schmidt- rearrangement of α,α-disubstituted α-ketoesters (G. I. Georg, X. Guan, J. Kant, *Tetrahedron Lett*. 1988, 29, 403–406); asymmetric synthesis via chiral Ni(II)-derived Schiff-bases (Y. N. Belokon, V. I. Baktmutov, N. I. Chemoglazova, K. A. Kochetov, S. V. Vitt, N. S. Garbalinskaya, V. M. Belikov, *J. Chem. Soc. Perkin Trans*. 1, 1988, 305–312; M. Kolb, J. Barth, *Liebigs Ann. Chem*. 1983, 1668–1688); by the bis-lactim ether synthesis (U. Schöllkopf, R. Hinrichs, R. Lonsky, *Angew. Chem*. 1987, 99, 137–138); by microbial resolution (K. Sakashita, I. Watanabe, JP 62/253397 A2) and by the hydantoin method combined with resolution of the racemic amino acids with chiral auxilliaries derived from L-phenylalanine amides (D. Obrecht, C. Spiegler, P. Schönholzer, K. Müller, H. Heimgartner, F. Stierli, *Helv. Chim. Acta* 1992, 75, 1666–1696; D. Obrecht, U. Bohdal, J. Daly, C. Lehmann, P. Schönholzer, K. Müller, *Tetrahedron* 1995, 51, 10883–10900; D. Obrecht, C. Lehmann, C. Ruffieux, P. Schönholzer, K. Müller, *Helv. Chim. Acta* 1995, 78, 1567–1587; D. Obrecht, U. Bohdal, C. Broger, D. Bur, C. Lehmann, R. Ruffieux, P. Schönholzer, C. Spiegler, *Helv. Chim. Acta* 1995, 78, 563–580; D. Obrecht, H. Karajiannis, C. Lehmann, P. Schönholzer, C. Spiegler, *Helv. Chim. Acta* 1995, 78, 703–714; D. Obrecht, M. Altorfer, C. Lehmann, P. Schönholzer, K. Müller, *J. Org. Chem*. 1996, 61, 4080–4086; D. Obrecht, C. Abrecht, M. Altorfer, U. Bohdal, A. Grieder, P. Pfyffer, K. Müller, *Helv. Chim. Acta* 1996, 79, 1315–1337). The latter method has been especially useful in preparing both enantiomers of building blocks of type A70 (see Scheme 27) and A73–A104 (see Scheme 28) in pure form.

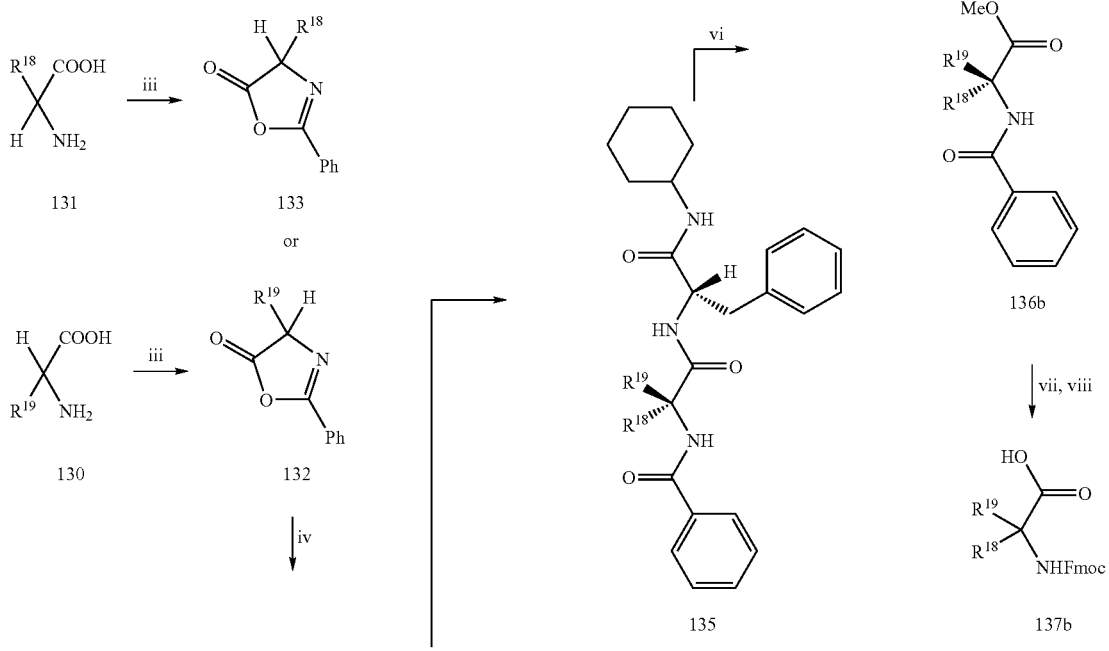

Scheme 27

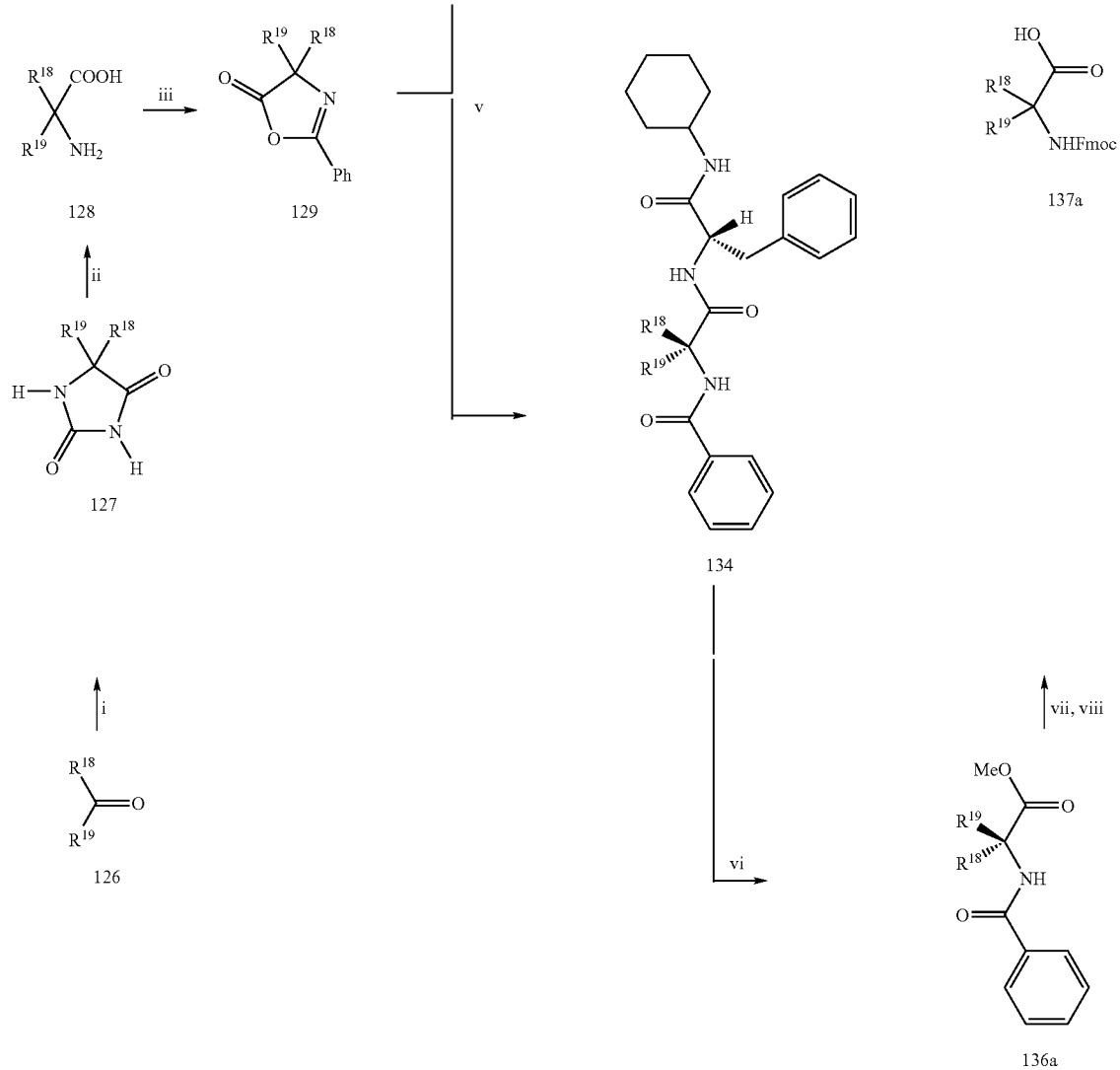

i: KCN, (NH$_4$)$_2$CO$_3$, EtOH/H$_2$O; ii: Ba(OH)$_2$, H$_2$O; iii: aq. NaOH, PhCOCl, dioxane; then DCC, CH$_2$Cl$_2$; iv: NaH, DMF, $R^{18}$—X or $R^{18}$—X; v: L-phenylalanine cyclohexylamide, N-methylpyrrolldone, 70°; vi: CH$_3$SO$_3$H, MeOH, 80°; vii: 6N HCl aq., dioxane, 100°; viii: Me$_3$SiCl, DIEA, CH$_2$Cl$_2$; then FmocCl The method depicted in Scheme 27 consists in treatment of the appropriate ketones 126 with KCN, (NH$_4$)$_2$CO$_3$ in a mixture of ethanol/water (E. Ware, *J. Chem. Res.* 1950, 46, 403; L. H. Goodson, I. L. Honigberg, J. J. Lehmann, W. H. Burton, *J. Org. Chem.* 1960, 25, 1920; S. N. Rastogi, J. S. Bindra, N. Anand, *Ind. J. Chem.* 1971, 1175) to yield the corresponding hydantoins 127, which were hydrolyzed with Ba(OH) in water at 120–140° (R. Sarges, R. C. Schur, J. L. Belletire, M. J. Paterson, *J. Med. Chem.* 1988, 31, 230) to give 128 in high yields. Schotten-Baumann acylation (Houben-Weyl, 'Methoden der Organischen Chemie', Volume XI/2, Stickstoff-Verbindungen II und III', Georg Tieme Verlag, Stuttgart, pp 339) followed by cyclization with N,N'-dicyclohexyl carbodiimide gave azlactones 129 (D. Obrecht, U. Bohdal, C. Broger, D. Bur, C. Lehmann, R. Ruffieux, P. Schönholzer, C. Spiegler, *Helv. Chim. Acta* 1995, 78, 563–580; D. Obrecht, C. Spiegler, P. Schönholzer, K. Müller, H. Heimgartner, F. Stierli, *Helv. Chim. Acta* 1992, 75, 1666–1696). Alternatively, azlactones 129 could also be prepared starting from amino acids 130 and 131, Schotten-Baumann acylation and cyclization with N,N'-dicyclohexyl carbodimide to azlactones 132 and 133 and alkylation to yield 129 (D. Obrecht, U. Bohdal, C. Broger, D. Bur, C. Lehmann, R. Ruffieux, P. Schönholzer, C. Spiegler, *Helv. Chim. Acta* 1995, 78, 563–580; D. Obrecht, C. Spiegler, P. Schönholzer, K. Müller, H. Heimgartner, F. Stierli, *Helv. Chim. Acta* 1992, 75, 1666–1696)(see Scheme 1). Treatment of 129 with L-phenylalanine cyclohexylamide (D. Obrecht, U. Bohdal, C. Broger, D. Bur, C. Lehmann, R. Ruffieux, P. Schönholzer, C. Spiegler, *Helv. Chim. Acta* 1995, 78, 563–580) gave diastereomeric peptides 134 and 135, which could be conveniently separated by flash-chromatography or crystallisation. Treatment of 134 and 135 with methanesulphonic acid in methanol at 80° gave esters 136a and 136b which were converted into the corresponding Fmoc-protected final building blocks 137a and 137b.

Scheme 28
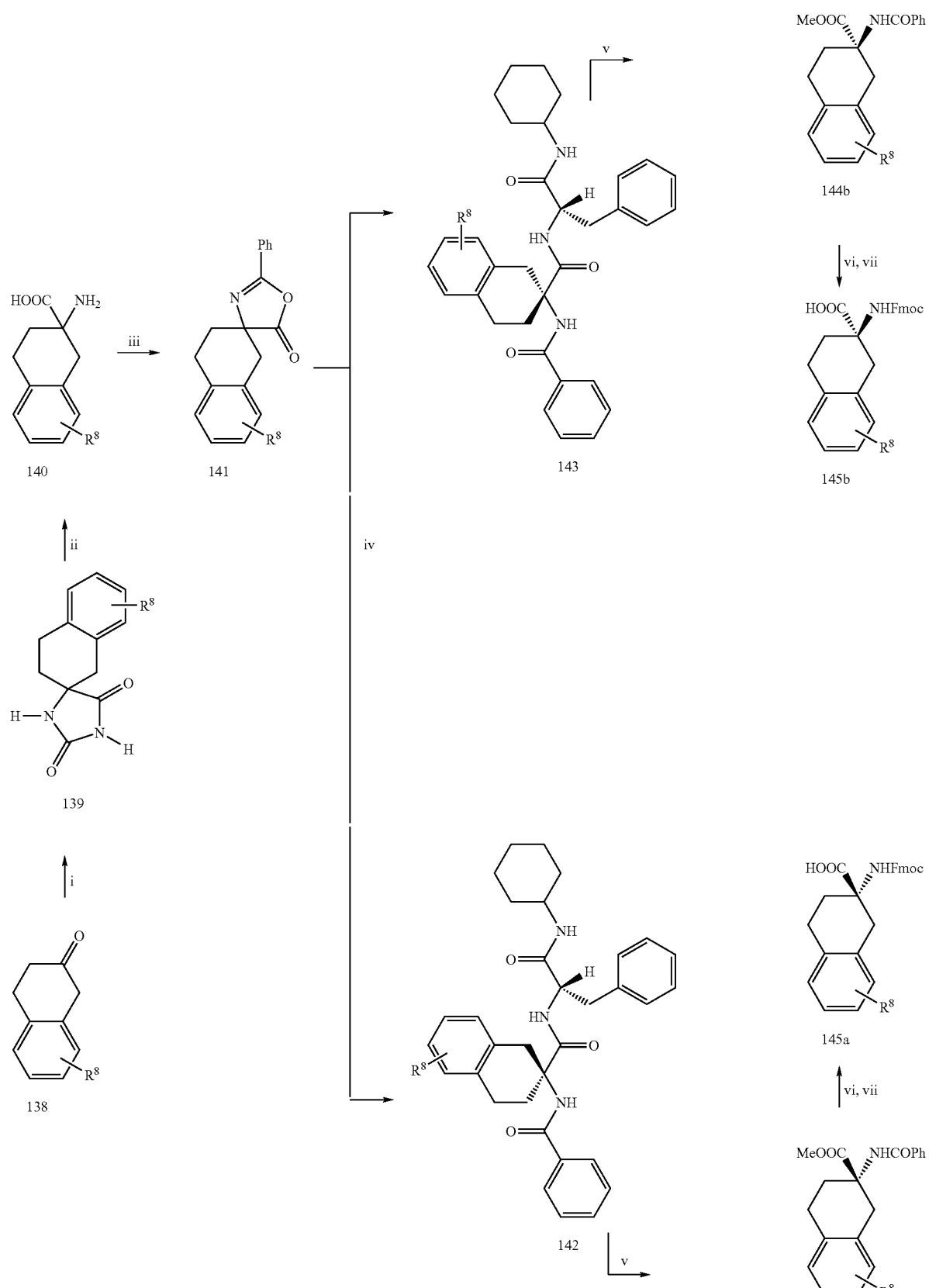
i: KCN, (NH$_4$)$_2$CO$_3$, EtOH/H$_2$O; ii: Ba(OH)$_2$, H$_2$O; iii: aq. NaOH, PhCOCl, dioxane; then DCC, CH$_2$Cl$_2$; iv: L-phenylalanine cyclohexylamide, N-methylpyrrolidone, 70°; v: CH$_3$SO$_3$H, MeOH, 80°; vi: 6N HCl aq., dioxane, 100°; vii: Me$_3$SiCl, DIEA, CH$_2$Cl$_2$; then FmocCl According to the general method described in Scheme 28 (D. Obrecht, U. Bohdal, C. Broger, D. Bur, C. Lehmann, R. Ruffieux, P. Schönholzer, C. Spiegler, *Helv. Chim. Acta* 1995, 78, 563–580; D. Obrecht, C. Spiegler, P. Schönholzer, K. Müller, H. Heimgartner, F. Stierli, *Helv. Chim. Acta* 1992, 75, 1666–1696) A73–A104 can be prepared starting from the corresponding ketones 138, hydantoin formation (139) (E. Ware, *J. Chem. Res.* 1950, 46, 403; L. H. Goodson, I. L. Honigberg, J. J. Lehmann, W. H. Burton, *J. Org. Chem.* 1960, 25, 1920; S. N. Rastogi, J. S. Bindra, N. Anand, *Ind. J. Chem.* 1971, 1175; D. Obrecht, U. Bohdal, C. Broger, D. Bur, C. Lehmann, R. Ruffieux, P. Schönholzer, C. Spiegler, *Helv. Chim. Acta* 1995, 78, 563–580) and saponification $(Ba(OH)_2)$ to yield the racemic amino acids 140, which upon Schotten-Baumann-acylation and cyclization with N,N'-dicyclohexylcarbodiimide gave azlactones 141. Reaction with L-phenylalanine cyclohexylamide (D. Obrecht, U. Bohdal, C. Broger, D. Bur, C. Lehmann, R. Ruffieux, P. Schönholzer, C. Spiegler, *Helv. Chim. Acta* 1995, 78, 563–580) gave the diastereomeric peptides 142 and 143, which were separated by flash-chromatography or crystallization. Treatment of 142 and 143 with methanesulphonic acid in methanol at 80° gave esters 144a and 144b which were converted into the corresponding suitably protected amino acid precursors 145a and 145b, ready for peptide synthesis.

A71: Amino acid building blocks of this type (see formula 147) can be conveniently prepared from the corresponding disubstituted succinates 146 by Curtius-rearrangement as shown in Scheme 29.

Scheme 29

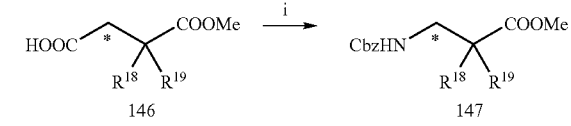

146 147 i: diphenylphosporyl azide, toluene, 80°; then benzyl alcohol

A71: See D. Seebach, S. Abele, T. Sifferlen, M. Haenggi, S. Gruner, P. Seiler, *Helv. Chim. Acta* 1998, 81, 2218–2243 ($R^{18}$ and $R^{19}$ form: $—(CH_2)_2—$; $—(CH_2)_3—$; $—(CH_2)_4—$; $—(CH_2)_5—$; $R^{20}=H$); L. Ducrie, S. Reinelt, P. Seiler, F. Diederich, D. R. Bolin, R. M. Campbell, G. L. Olson, *Helv. Chim. Acta* 1999, 82, 2432–2447; C. N. C. Drey, R. J. Ridge, *J. Chem. Soc. Perkin Trans.* 1, 1981, 2468–2471; U. P. Dhokte, V. V. Khau, D. R. Hutchinson, M. J. Martinelli, *Tetrahedron Lett.* 1998, 39, 8771–8774 ($R^{18}=R^{19}=Me$; $R^{20}=H$); D. L. Varie, D. A. Hay, S. L. Andis, T. H. Corbett, *Bioorg. Med. Chem. Lett.* 1999, 9, 369–374 ($R^{18}=R^{19}=Et$); Testa, *J. Org. Chem.* 1959, 24, 1928–1936 ($R^{18}=Et$; $R^{19}=Ph$); M. Haddad, C. Wakselman, *J. Fluorine Chem.* 1995, 73, 57–60 ($R^{18}=Me$; $R^{19}=CF_3$; $R^{20}=H$); T. Shono, K. Tsubata, N. Okinaga, *J. Org. Chem.* 1984, 49, 1056–1059 ($R^{18}=R^{19}=R^{20}=Me$); K. Ikeda, Y. Terao, M. Seldya, *Chem. Pharm. Bull.* 1981, 29, 1747–1749 ($R^{18}$ and $R^{19}$ form: $—(CH_2)_5—$; $R^{20}=Me$).

Amino acid building blocks of type A72 can be conveniently prepared by Arndt-Eistert C1-homologation of compounds of type A70 according to Scheme 30.

Scheme 30

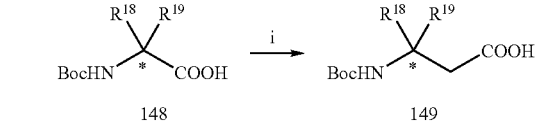

148 149 i: iBuOCOCl, diisopropylethylamine, $CH_2Cl_2$; then diazomethane, hv or Cu(I)

A72: See Y. V. Zeifman, *J. Gen. Chem. USSR* (Engl. Trans.) 1967, 37, 2355–2363 ($R^{18}=R^{19}=CF_3$); W. R. Schoen, J. M. Pisano, K. Pendergast, M. J. Wyvratt, M. H. Fisher, *J. Med. Chem.* 1994, 37, 897–906; S. Thaisrivongs, D. T. Pals, D. W. DuCharme, S. Turner, G. L. DeGraaf, *J. Med. Chem.* 1991, 34, 655–642; T. K. Hansen, H. Thoegersen, B. S. Hansen, *Bioorg. Med. Chem. Lett.* 1997, 7, 2951–2954; R. J. DeVita, R. Bochis, A. J. Frontier, A. Kotliar, M. H. Fisher, *J. Med. Chem.* 1998, 41, 1716–1728; D. Seebach, P. E. Ciceri, M. Overhand, B. Jaun, D. Rigo, *Helv. Chim. Acta* 1996, 79, 2043–2066; R. P. Nargund, K. H. Barakat, K. Cheng, W. Chan, B. R. Butler, A. A. Patchett, *Bioorg. Med. Chem. Lett.* 1996, 6, 1265–1270 ($R^{18}=R^{19}=Me$); E. Altmann, K. Nebel, M. Mutter, *Helv. Chim. Acta* 1991, 74, 800–806 ($R^{18}=Me$; $R^{19}=COOMe$).

A73: Compounds of this type can be prepared according to C. Mapelli, G. Tarocy, F. Schwitzer, C. H. Stammer, *J. Org. Chem.* 1989, 54, 145–149 ($R^{21}=4\text{-}OHC_6H_4$); F. Elrod, E. M. Holt, C. Mapelli, C. H. Stammer, *J. Chem. Soc. Chem. Commun.* 1988, 252–253 ($R^{21}=CH_2COOMe$); R. E. Mitchell, M. C. Pirrung, G. M. McGeehan, *Phytochemistry* 1987, 26, 2695 ($R^{21}=CH_2OH$), J. Bland, A. Batolussi, C. H. Stammer, *J. Org. Chem.* 1988, 53, 992–995 $R^{21}=CH_2NH_2$). Additional derivatives of A73 have been described by T. Wakamiya, Y. Oda, H. Fujita, T. Shiba, *Tetrahedron Lett.* 1986, 27, 2143–2134; U. Schöllkopf, B. Hupfeld, R Gull, *Angew. Chem.* 1986, 98, 755–756; J. E. Baldwin, R. M. Adlington, B. J. Rawlings, *Tetrahedron Lett.* 1985, 26, 481–484; D. Kalvin, K. Ramalinggar, R. Woodard, *Synth. Comm.* 1985, 15, 267–272 and L. M. Izquierdo, I. Arenal, M. Bemabe, E. Alvarez, *Tetrahedron Lett.* 1985, 41, 215–220.

A74: Compounds of this type can be prepared according to general method described in Scheme 28 starting from the corresponding cyclobutanones.

A75 and A76: Compounds of this type can be prepared using the following methods: P. Hughes, J. Clardy, *J. Org. Chem.* 1988, 53, 4793–4796; E. A. Bell, M. Y. Qureshi, R. J. Pryce, D. H. Janzen, P. Lemke, J. Clardy, *J. Am. Chem. Soc.* 1980, 102, 1409; Y. Gaoni, *Tetrahedron Lett.* 1988, 29, 1591–1594; R. D. Allan, J. R. Haurahan, T. W. Hambley, G. A. R. Johnston, K. N. Mewett, A. D. Mitrovic, *J. Med. Chem.* 1990, 33, 2905–2915 ($R^{23}=COOH$); G. W. Fleet, J. A. Seijas, M. Vasquez Tato, *Tetrahedron* 1988, 44, 2077–2080 ($R^{23}=CH_2OH$).

A77: Compounds of this type can be prepared according to J. H. Burcihalter, G. Schmied, *J. Pharm. Sci.* 1966, 55, 443–445 ($R^{23}$=aryl).

A78: Compounds of this type can be prepared according to J. C. Watkins, P. Kroosgard-Larsen, T. Honoré, *TIPS* 1990, 11, 25–33; F. Trigalo, D. Brisson, R. Azerad, *Tetrahedron Lett.* 1988, 29, 6109 ($R^{24}=COOH$).

A79: Compounds of this type can be prepared according to general method described in Scheme 28 starting from the corresponding pyrrolidine-3-ones.

A80–A82: Compounds of this type can be prepared according to D. M. Walker, E. W. Logusch, *Tetrahedron Lett.* 1989, 30, 1181–1184; Y. Morimoto, K. Achiwa, *Chem. Pharm. Bull.* 1989, 35, 3845–3849; J. Yoshimura, S. Kondo, M. Ihara, H. Hashimoto, *Carbohydrate Res.* 1982, 99, 129–142.

A83: Compounds of this type can be prepared according to general method described in Scheme 28 starting from the corresponding pyrazoline-4-ones.

A84: Compounds of this type can be prepared according to R. M. Pinder, B. H. Butcher, D. H. Buxton, D. J. Howells, *J. Med. Chem.* 1971, 14, 892–893; D. Obrecht, U. Bohdal, C. Broger, D. Bur, C. Lehmann, R. Ruffieux, P. Schönholzer, C. Spiegler, *Helv. Chim. Acta* 1995, 78, 563–580.

A85: Compounds of this type can be prepared according to general method described in Scheme 28 starting from the corresponding indane-1,3-diones.

A86: Compounds of this type can be prepared according to general method described in Scheme 28 starting from the corresponding indane-2-ones.

A87: Compounds of this type and analogues thereof can be prepared according to C. Cativiela, M. D. Diaz de Villegas, A. Avenoza, J. M. Peregrina, *Tetrahedron* 1993, 47, 10987–10996; C. Cativiela, P. Lopez, J. A. Mayoral, *Tetrahedron Assymmetry* 1990, 1, 379; C. Cativiela, J. A. Mayoral, A. Avenoza, M. Gonzalez, M. A. Rey, *Synthesis* 1990, 1114.

A87 and A88: Compounds of this type can be prepared according to L. Munday, *J. Chem. Soc.* 1961, 4372; J. Ansell, D. Morgan, H. C. Price, *Tetrahedron Lett.* 1978, 47, 4615–4616.

A89: Compounds of this type can be prepared according to general method described in Scheme 28 stating from the corresponding piperidine-3-ones.

A90: Compounds of this type can be prepared according to general method described in Scheme 28 starting from the corresponding tetrahydrothiapyran-3-ones.

A91: Compounds of this type can be prepared according to general method described in Scheme 28 starting from the corresponding tetrahydropyran-3-ones.

A92: Compounds of this type can be prepared according to general method described in Scheme 28 starting from the corresponding piperidine-2,5-diones.

A93: Compounds of this type can be prepared according to general method described in Scheme 28 starting from the corresponding cyclohexanones.

A94: Compounds of this type can be prepared according to *J. Org. Chem.* 1990, 55, 4208.

A95: Compounds of this type can be prepared according to N. J. Lewis, R. L. Inloes, J. Hes, R. H. Matthews, G. Milo, *J. Med. Chem.* 1978, 21, 1070–1073.

A96: Compounds of this type can be prepared according to general method described in Scheme 28 starting from the corresponding tetrahydropyran-4-ones.

A97: Compounds of this type can be prepared according to general method described in Scheme 28 starting from the corresponding piperidine-2,4-diones.

A98: Compounds of this type can be prepared according to general method described in Scheme 28 starting from the corresponding 1-tetralones (D. Obrecht, C. Spiegler, P. Schönholzer, K. Müller, H. Heimgartner, F. Stierli, *Helv. Chim. Acta* 1992, 75, 1666–1696).

A99: Compounds of this type can be prepared according to general method described in Scheme 28 starting from the corresponding tetraline-1,4-dione mono-diethylacetals.

A100: Compounds of this type can be prepared according to general method described in Scheme 28 starting from the corresponding tetrahydroquinolin-4-ones.

A101: Compounds of this type can be prepared according to general method described in Scheme 28 starting from the corresponding tetrahydroquinoline-2,4-diones.

A102: Compounds of this type can be prepared according to K. Ishizumi, N. Ohashi, N. Tanno, *J. Org. Chem.* 1987, 52, 4477–4485; D. Obrecht, U. Bohdal, C. Broger, D. Bur, C. Lehmann, R. Ruffieux, P. Schönholzer, C. Spiegler, *Helv. Chim. Acta* 1995, 78, 563–580; D. Obrecht, C. Spiegler, P. Schönholzer, K. Müller, H. Heimgartner, F. Stierli, *Helv. Chim. Acta* 1992, 75, 1666–1696; D. R. Haines, R. W. Fuller, S. Ahmad, D. T. Vistica, V. E. Marquez, *J. Med. Chem.* 1987, 30, 542–547; T. Decks, P. A. Crooks, R. D. Waigh, *J. Pharm. Sci* 1984, 73, 457–460; I. A. Blair, L. N. Mander, *Austr. J. Chem.* 1979, 32, 1055–1065.

Overviews dealing with building blocks of types (b)–(p) are: S. Hanessian, G. McNaughton-Smith, H.-G. Lombart, W. D. Lubell, *Tetrahedron* 1997, 38, 12789–12854; D. Obrecht, M. Altorfer, J. A. Robinson, "Novel Peptide Mimetic Building Blocks and Strategies for Efficient Lead Finding", *Adv. Med. Chem.* 1999, Vol. 4, 1–68

Templates of type (b1) can be prepared according to Schemes 31 and 32.

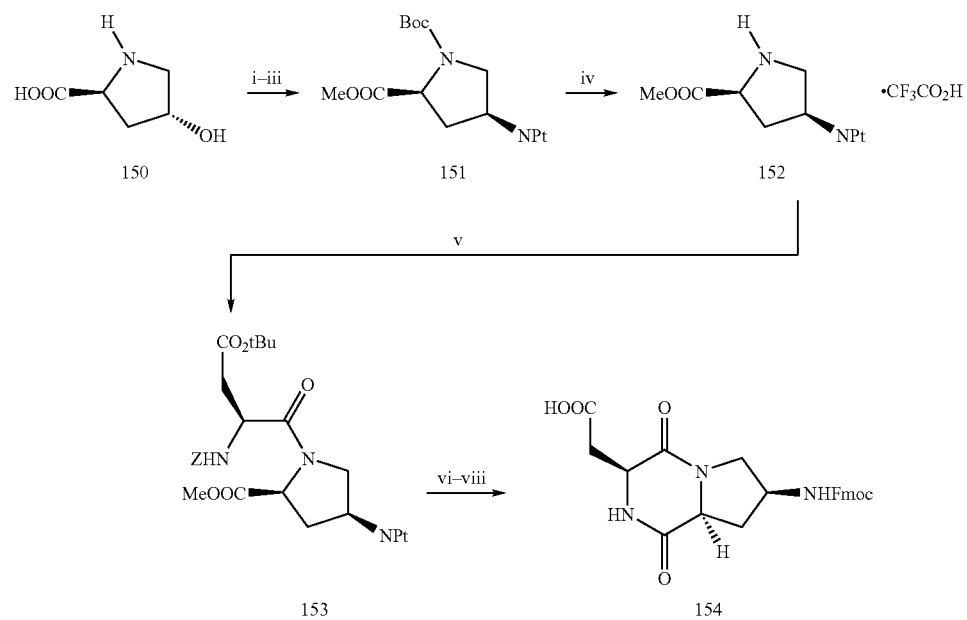

Scheme 31 i: Treatment of 150 with a dehydrating reagent such as thionylchloride in methanol at an elevated temperature, conveniently at reflux.

ii: Introduction of Boc, e.g. using di-tert.butyl dicarbonate and triethylamine in a suitable solvent such as dichloromethane; any other suitable N-protecting group (not shown in Reaction Scheme 31) can be introduced in an analogous manner.

iii: Reaction of formed product with phthalimide, diethyl diazodicarboxylate and triphenylphoshine under standard Mitsunobu conditions (Mitsunobu, O.; Wada, M.; Sano, T. J. *J. Am. Chem. Soc.* 1972, 94, 672) to conveniently yield 151.

iv: Treatment of 151 with trifluoracetic acid in dichloromethane.

v: 152 is coupled under standard peptide coupling conditions with Cbz-Asp(tBu)OH in DMF with reagents such as HBTU and 1-hydroxybenztriazole (HOBt) with a base such as diisopropylethylamine to yield 153.

vi: Removal of the Cbz-group, conveniently by hydrogenation using $H_2$ and a catalyst such as Palladium on charcoal, in solvents such as ethanol, DMF and ethyl acetate.

vii: The phthalimide group is cleaved off from the resulting product, conveniently by treatment with hydrazine in a suitable solvent such as ethanol at an elevated temperature, suitably at about 80° C. and cleavage of the formed product with trifluoracetic acid in $CH_2Cl_2$.

viii: The formed amino acid is conveniently protected with reagents such as 9-fluorenylmethoxcarbonyl chloride or 9-fluorenylmethoxcarbonyl succininide using a base such as sodium carbonate or triethylamine in a suitable solvent or mixture of solvents such as dioxane and water, or dichloromethane to yield 154 as described by Bisang, C.; Weber, C.; Robinson, J. A. *Helv. Chim. Acta* 1996, 79, 1825–1842.

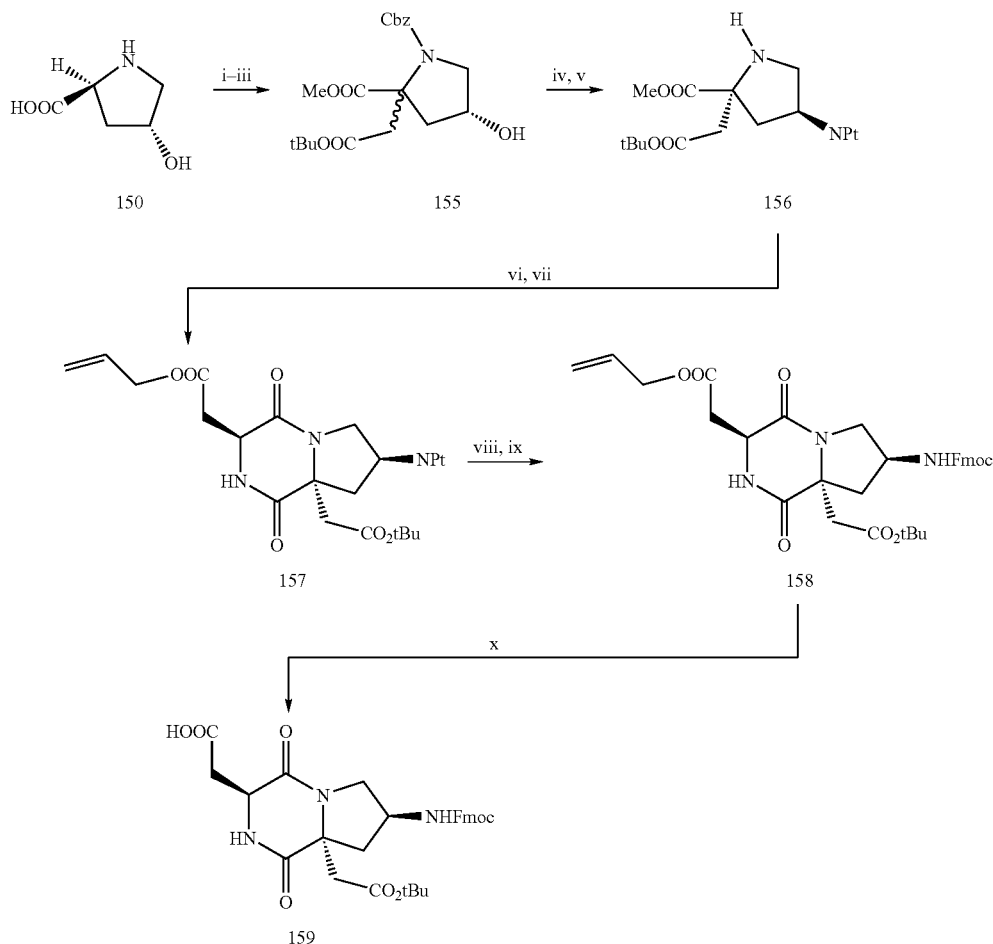

Scheme 32 i: Treatment of 150 with a dehydrating reagent such as thionyl chloride in a suitable solvent such as methanol at an elevated temperature, conveniently at reflux.

ii: The resulting amino acid ester is N-protected under standard conditions for introducing the Cbz-group, e.g. using benzyloxycarbonyl chloride and triethylamine in a suitable solvent such as dichloromethane.

iii: The Cbz-protected amino acid methyl ester is treated with trimethylsilylchloride and a base such as triethylamine in a solvent such as tetrahydrofuran, cooled, conveniently to about −78° C., followed by reaction with a strong base such as lithium diisopropylamide or lithium hexamethyldisilylazide and tert.-butyl bromoacetate yielding 155 as a mixture of diastereomers as described by Bisang, C.; Jiang, L.; Freund, E.; Emery, F.; Bauch, C.; Matile, H,; Pluschke, G.; Robinson, J. A. *J. Am. Chem. Soc.* 1998, 120, 7439–7449; Emery, F.; Bisang, C.; Favre, M.; Jiang, L.; Robinson, J. A. *J. Chem. Soc. Chem. Commun.* 1996, 2155–2156.

iv: Reaction of 155 with phthalimide, diethyl diazodicarboxylate and triphenylphosphine under standard Mitsunobu conditions (Mitsunobu, O.; Wada, M.; Sano, T. J. *J. Am. Chem. Soc.* 1972, 94, 672).

v: The resulting product is hydrogenated using H$_2$ and a suitable catalyst such as palladium on charcoal in a solvent such as ethyl acetate, DMF or ethanol; subsequently separation of diastereomers takes place and yields 156.

vi: 156 is coupled with Fmoc-Asp(alkyl)OH under standard peptide coupling conditions using reagents such as HATU, HOAt and a base such as diisopropylethylamine in a suitable solvent such as DMF.

vii: Cyclization, conveniently with DBU in DMF to yield 157.

viii: The phthalimide group is cleaved off from resulting product, conveniently by hydrazinolysis, e.g. treatment with methylhydrazine in a suitable solvent such as DMF.

ix: The formed product is conveniently protected with reagents such as 9-fluorenylmethoxcarbonyl chloride or 9-fluorenylmethoxcarbanyl succinimide using a base such as sodium carbonate or triethylamine in a suitable solvent or mixture of solvents such as dioxane and water, or dichloromethane to yield 158.

x: Standard removal of an alkyl ester group using e.g. palladium(0) as catalyst gives 159.

Templates of type (b2) can be prepared according to Scheme 33.

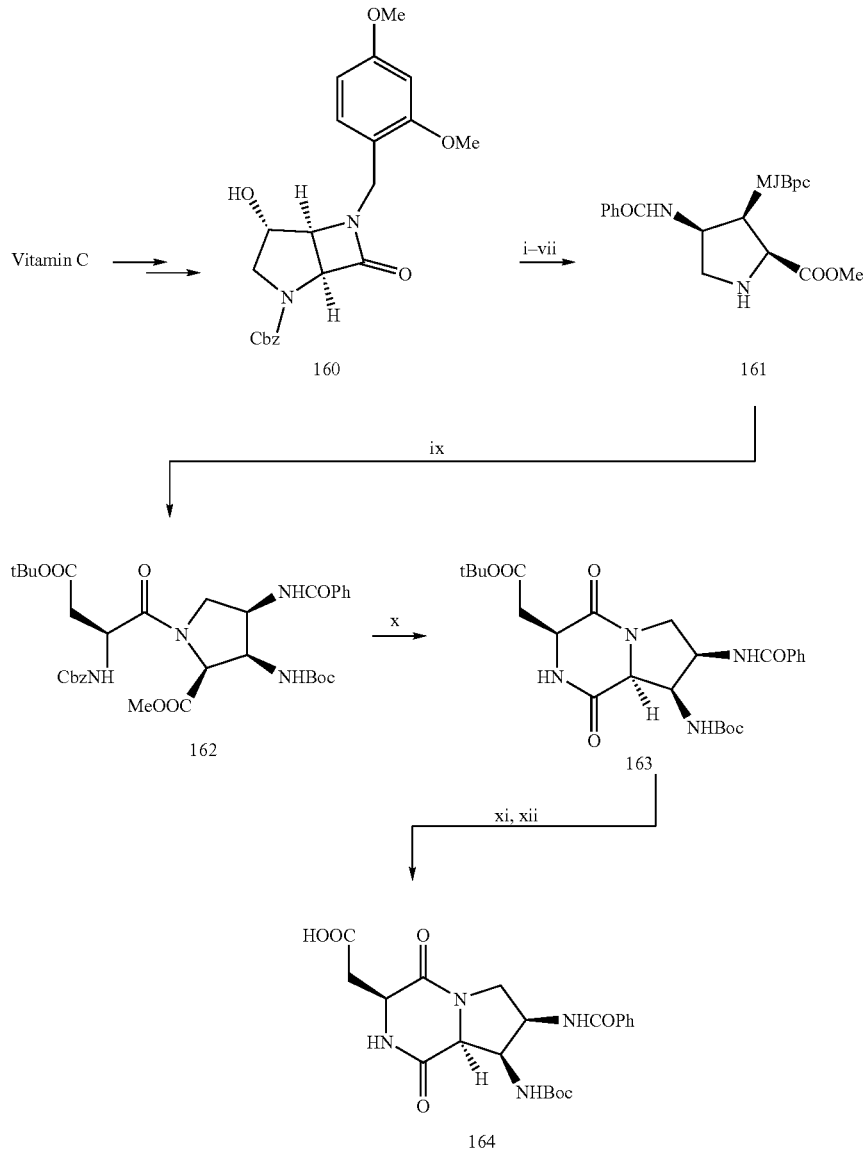

i: 160 (obtainable from Vitamin C as described by Hubschwerlen, C. (*Synthesis* 1986, 962) is treated with phthalimide, diethyl diazodicarboxylate and triphenylphoshine under standard Mitsunobu conditions (Mitsunobu, O.; Wada, M.; Sano, T. J. *J. Am. Chem. Soc.* 1972, 94, 672).

ii: The phthalimide group is cleaved off from the product, conveniently by hydrazinolysis, e.g. by treatment with methylhydrazine in a suitable solvent such as DMF.

iii: The amino group is protected by treatment with a benzoylating reagent such as benzoic acid anhydride or benzoylchloride and a base such as triethylamine or 4-dimethylaminopyridine in a suitable solvent such as dichloromethane or DMF.

iv: Removal of the 2,4-dimethoxybenzyl group, e.g. with $K_2S_2O_8$ and $Na_2HPO_4$ in aqueous acetonitrile at an elevated temperature, e.g. at about 80° C.

v: Introduction of a tert.-butoxycarbonyl group using e.g. di-tert.-butyloxycarbonyl dicarbonate, triethylamine and a catalytic amount of 4-dimethylaminopyridine in a suitable solvent such as dichloromethane.

vi: Reaction with aqueous sodium carbonate in tetrahydrofuran followed by acidification.

vii: Esterification of the carboxylic acid group, conveniently with diazomethane in a suitable solvent such as diethylether yielding 161.

viii Removal of the Cbz-group, conveniently by hydrogenation with $H_2$ in the presence of a catalyst such as palladium on charcoal in a solvent such as DMF to yield 161 as described by Pfeifer, M.; Robinson, J. A. *J. Chem. Soc. Chem. Commun.* 1998, 1977.

ix: 161 is coupled under standard peptide coupling conditions with Cbz-Asp(tBu)OH in DMF with reagents such as HBTU and 1-hydroxybenztriazole with a base such as diisopropylethylamine to yield 162 as described by Pfeifer, M.; Robinson, J. A. *J. Chem. Soc. Chem. Commun.* 1998, 1977.

x: Removal of the Cbz-group, e.g. by hydrogenation using $H_2$ and a catalyst such as palladium on charcoal under standard conditions, yields 163 as described by Pfeifer, M.; Robinson, J. A, *J. Chem. Soc. Chem. Commun.* 1998, 1977.

xi: Cleavage of the tert.-butyl ester and tert.-butyloxycarbonyl groups, conveniently using trifluoracetic acid in dichloromethane or 4N hydrochloric acid in dioxane.

xii: The intermediate free amino acid formed is conveniently protected with reagents such as 9-fluorenylmethoxcarbonyl chloride or 9-fluorenylmethoxycarbonyl succinimide using a base such as sodium carbonate or triethylamine in a suitable solvent or mixture of solvents such as dioxane and water, or dichloromethane to yield 164 as described by Pfeifer, M.; Robinson, J. A. *J. Chem. Soc. Chem. Commun.* 1998, 1977.

Templates of type (c1) can be prepared according to Schemes 34 to 37.

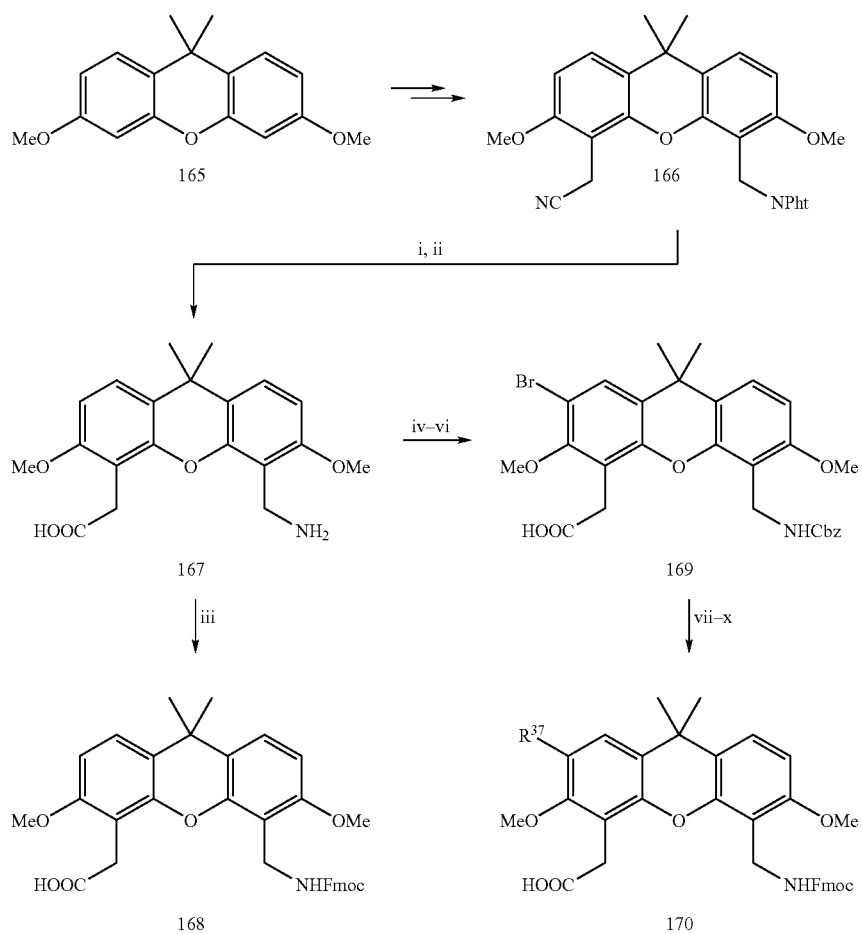

Scheme 34 i: 166 can be synthesized from 165 according to P. Waldmeier, "Solid-supported synthesis of highly substituted xanthene-derived templates for the synthesis of β-turn stabilized cyclic peptide libraries", PhD-thesis, University of Zurich, 1996. For cleaving the phthalimide group 166 is conveniently submitted to hydrazinolysis, e.g. by treatment with hydrazine hydrate in a suitable solvent such as ethanol at an elevated temperature, e.g. at about 80° C.

ii: The intermediate aminonitrile is saponified, conveniently under basic conditions, e.g. with aqueous sodium hydroxide in a suitable solvent such as ethanol at an elevated temperature, conveniently under reflux, to yield 167.

iii: The intermediate free amino acid formed is conveniently protected with reagents such as 9-fluorenylmethoxcarbonyl chloride or 9-fluorenylmethoxcarbonyl succinimide using a base such as sodium carbonate or triethylamine in a suitable solvent or mixture of solvents such as dioxane and water, or dichloromethane to yield 168 as described by P. Waldmeier, "Solid-supported synthesis of highly substituted xanthene-derived templates for the synthesis of β-turn stabilized cyclic peptide libraries", PhD-thesis, University of Zurich, 1996.

iv: Regioselective bromination of 167 is performed preferably with bromine in acetic acid and dichloromethane. In a similar fashion $R^{37}$=$NO_2$ can be introduced by treatment with $HNO_3$ in acetic acid and $R^{37}$=$CH_2$—NPht by treatment with hydroxymethyl phthalimide in $H_2SO_4$.

v: The amino group is conveniently Cbz-protected with reagents such as benzyloxycarbonyl chloride or succinimide in a suitable solvent such as dioxane in presence of a base such as aqueous sodium hydroxide.

vi: The carboxylic acid group is esterified, preferably with DBU and methyl iodide in DMF to yield 169.

vii: Introduction of lower alkyl, substituted lower alkyl and aryl substituents ($R^{37}$), conveniently by palladium(0)-catalyzed Stille-(Stille, J. K. *Angew. Chem.* 1986, 68, 504) and Suzuki-couplings (Oh-e, T.; Mijaura, N.; Suzuki, A. *J. Org. Chem.* 1993, 58, 2201). Any other functionalization known for aryl bromides can be employed for introduction of substituents $R^{37}$.

viii: Removal of the Cbz-group, e.g. by hydrogenation using $H^2$ and a catalyst such as palladium on charcoal in a suitable solvent such as ethanol, DMF and ethyl acetate.

ix: Hydrolysis of the ester group, conveniently under acidic conditions, e.g. with 25% aqueous hydrochloric acid in a suitable solvent such as dioxane at an elevated temperature, preferably at about 100° C.

x: The intermediate free amino acid formed is conveniently protected with reagents such as 9-fluorenylmethoxcarbonyl chloride or 9-fluorenylmethoxcarbonyl succinimide using a base such as sodium carbonate or triethylamine in a suitable solvent or mixture of solvents such as dioxane and water, or dichloromethane to yield 170.

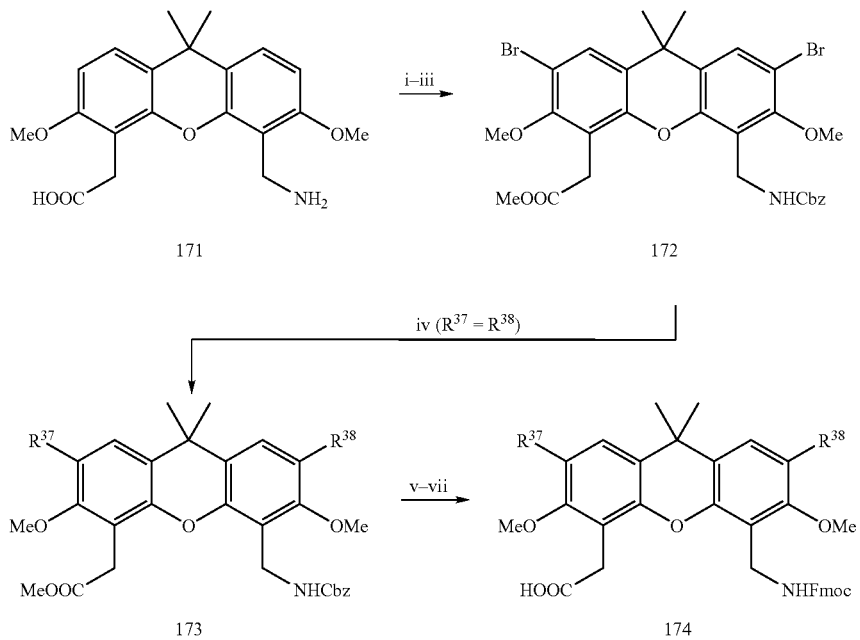

Scheme 35 i: Double ortho-bromination of 171 is performed preferably with excess bromine in acetic acid and dichloromethane. In a similar fashion $R^{37}$=$R^{38}$=$NO_2$ can be introduced by treatment with $HNO_3$ in acetic acid and $R^{37}$=$R^{38}$=$CH_2$—NPht by treatment with hydroxymethyl phthalimide in $H_2SO_4$.

ii: The amino group is protected, conveniently Cbz-protected, with reagents such as benzyloxycarbonyl chloride or succinimide in a suitable solvent such as dioxane in the presence of a base such as aqueous sodium hydroxide.

iii: The carboxylic acid group is esterified, preferably with DBU and methyl iodide in DMF to yield 172.

iv: Introduction of lower alkyl, substituted lower alkyl and aryl substituents ($R^{37}$=$R^{38}$), e.g. by palladium(0)-catalyzed Stille-(Stifle, J. K. *Angew. Chem.* 1986, 68, 504) and Suzuki-couplings (Oh-e, T.; Mijaura, N.; Suzuki, A. *J. Org. Chem.* 1993, 58, 2201). Any other functionalization known for aryl brormides can be employed for introduction of substituents $R^{37}$ and $R^{38}$.

v: Removal of the Cbz-group of 173, e.g. by hydrogenation using $H_2$ and a catalyst such as palladium on charcoal in a suitable solvent such as ethanol, DMF or ethyl acetate.

vi: Hydrolysis of the ester group, conveniently under acidic conditions, e.g. with 25% aqueous hydrochloric acid in a suitable solvent such as dioxane at an elevated temperature, conveniently at about 100° C.

vii: The intermediate free amino acid formed is conveniently protected with reagents such as 9-fluorenylmethoxcarbonyl chloride or 9-fluorenylmethoxycarbonyl succinimide using a base such as sodium carbonate or triethylamine in a suitable solvent or mixture of solvents such as dioxane and water, or dichloromethane to yield 174.

iv: Treatment of 175 with an appropriate triflating reagent, preferably trifluoromethanesulfonic acid anhydride in the presence of a base such as 2,6-di-tert.-butyl-pyridine in a suitable solvent such as dichloromethane.

v: Heating of the intermediate, conveniently in a suitable solvent such as methanol.

vi: Introduction of lower alkyl or aryl-lower alkyl ($R^{35}$) by alkylation to yield 177. Any other functionalization known for phenol groups can be employed for introduction of substituents $R^{35}$.

vii: Introduction of lower alkyl or aryl ($R^{36}$), conveniently by palladium(0)-catalyzed Suzuki-coupling (Ohe, T.; Mijaura, N.; Suzuki, A. *J. Org. Chem.* 1993, 58, 2201) to

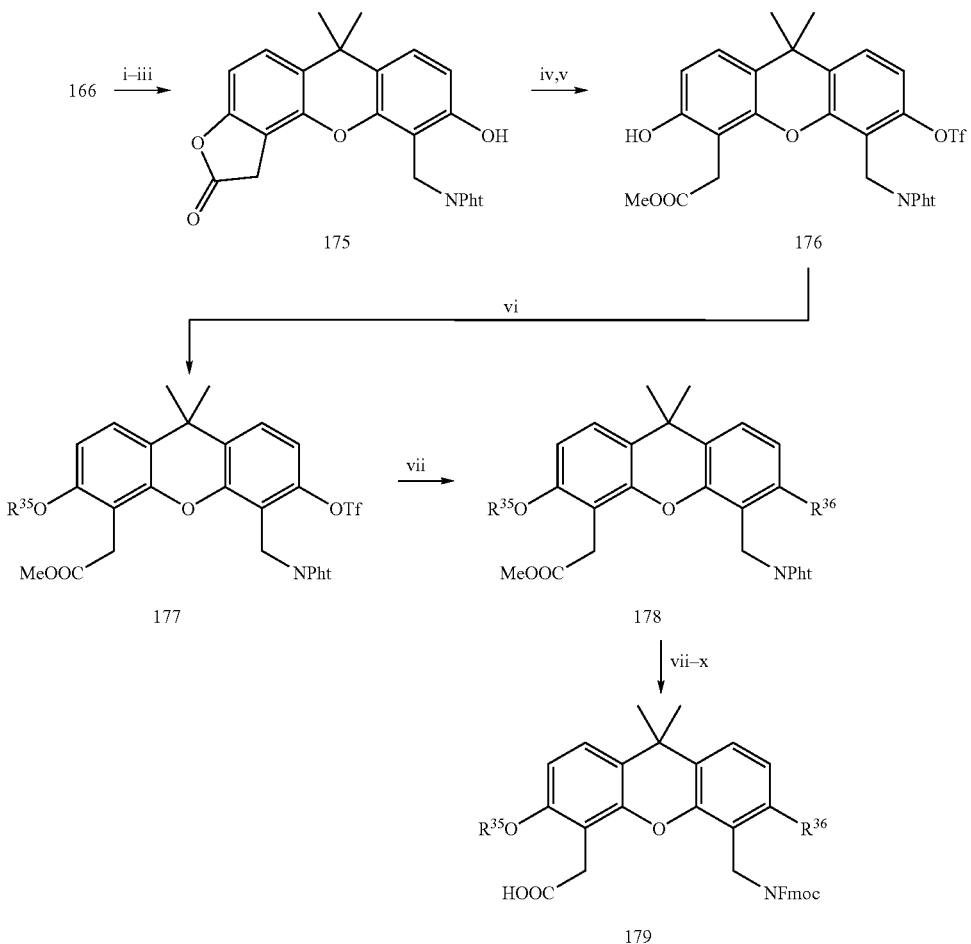

Scheme 36 i: Cleavage of the methoxy groups of 166, preferably by treatment with an excess of boron tribromide in a suitable solvent such as dichloromethane.

ii: Hydrolysis of the cyano group under acidic conditions, preferably with 25% aqueous hydrochloric acid in a suitable solvent such as dioxane at an elevated temperature, conveniently at about 100° C.

iii: The resulting acid is treated with a dehydrating agent such as thionyl chloride in a suitable solvent such as dioxane to yield 175.

yield 178. Any other functionalization known for aryl bromides can be employed for introduction of substituents $R^{36}$.

viii: Hydrolysis of the ester group under acidic conditions, conveniently with 25% aqueous hydrochloric acid in a suitable solvent such as dioxane at an elevated temperature, e.g. at about 100° C.

ix: Cleavage of the phthalimido group, conveniently by hydrazinolysis, e.g. with hydrazine hydrate in a suitable solvent such as ethanol.

x: The intermediate free amino acid formed is conveniently protected with reagents such as 9-fluorenylmethoxcarbonyl chloride or 9-fluorenylmethoxcarbonyl succinimide using a base such as sodium carbonate or triethylamine in a suitable solvent or mixture of solvents such as dioxane and water, or dichloromethane to yield 179.

Stille-(Stille, J. K. *Angew. Chem.* 1986, 68, 504) and Suzuki-couplings (Oh-e, T.; Mijaura, N.; Suzuki, A. *J. Org. Chem.* 1993, 58, 2201). Any other functionalization known for aryl bromides can be employed for introduction of substituents $R^{38}$.

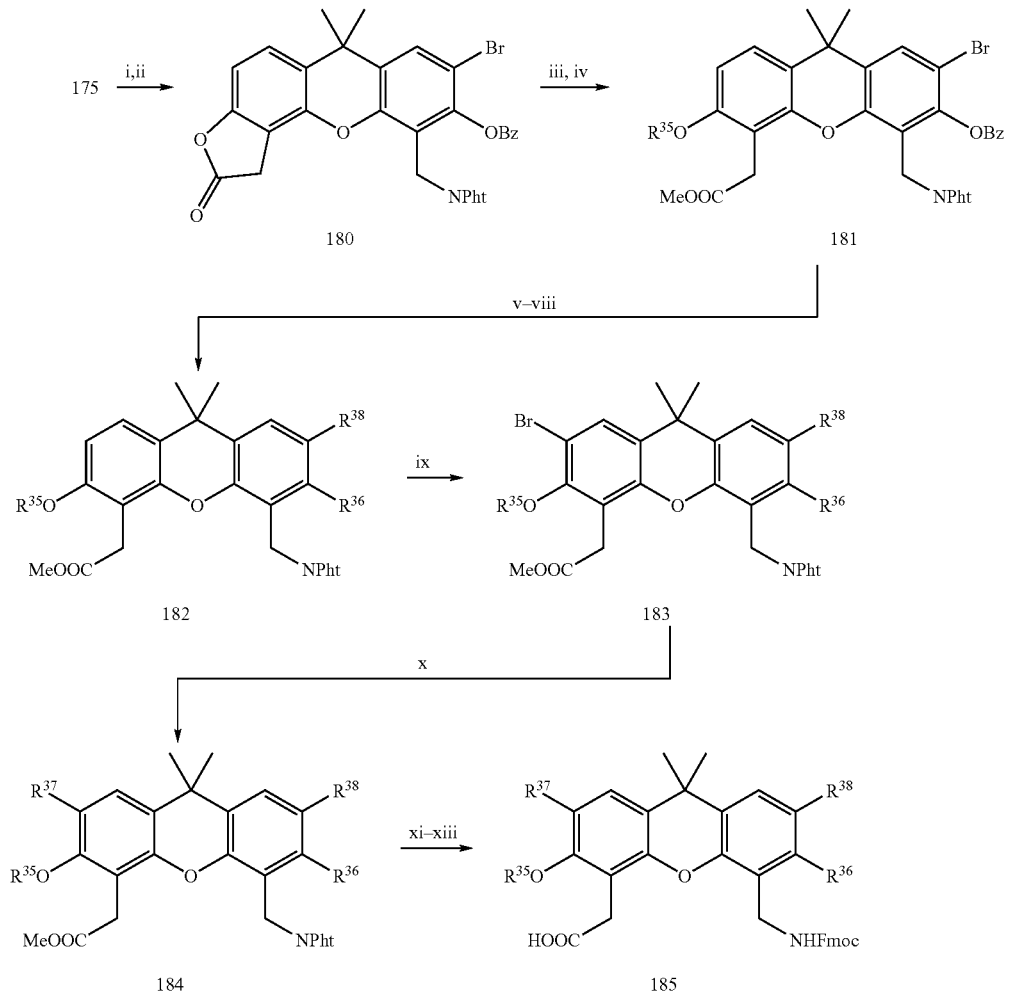

Scheme 37 i: Bromination of 175 using reagents such as bromine in a mixture of acetic acid and dichloromethane at temperatures ranging from about 0° C. to about room temperature.

ii: Benzoylation of the hydroxy group using an appropriate acylating agent such as benzoyl chloride or benzoic acid anhydride, a base such as pyridine or triethylamine and a suitable solvent such as dichloromethane to yield 180.

iii: 180 is treated with methanol and a catalytic amount of an acidic catalyst such as camphor sulfonic acid under heating.

iv: Introduction of lower alkyl or aryl-lower alkyl ($R^{35}$) by alkylation using a base such as sodium hydride or potassium tert.-butoxide in a solvent such as tetrahydrofuran, dimethoxyethane or DMF gives 181.

v: Lower alkyl, substituted lower alkyl and aryl substituents ($R^{38}$) are introduced, e.g. by palladium(0)-catalyzed vi: For cleaving the benzyloxy group the intermediate is conveniently heated with sodium cyanide adsorbed on aluminum oxide and methanol.

vii: Treatment with an appropriate triflating reagent, preferably trifluoromethanesulfonic acid anhydride, in the presence of a base such as 2,6-di-tert-butyl-pyridine in a suitable solvent such as dichloromethane.

viii: Introduction of lower alkyl and aryl substituents ($R^{36}$), e.g. by palladium(0)-catalyzed Stille-(Stille, J. K. *Angew. Chem.* 1986, 68, 504) and Suzuki-couplings (Oh-e, T.; Mijaura, N.; Suzuki, A. *J. Org. Chem.* 1993, 58, 2201) yields 182. Any other functionalization known for aryl bromides can be employed for introduction of substituents $R^{36}$.

ix: Bromination under standard conditions such as using bromine in acetic acid and dichloromethane at temperatures ranging from about 0° C. to about room temperature.

x: Lower alkyl, substituted lower alkyl and aryl substituents ($R^{37}$) are introduced, e.g. by palladium(0)-catalyzed Stille-(Stille, J. K. *Angew. Chem.* 1986, 68, 504) and Suzuki-couplings (Oh-e, T.; Mijaura, N.; Suzuki, A. *J. Org. Chem.* 1993, 58, 2201) to yield 184. Any other functionalization known for aryl bromides can be employed for introduction of substituents $R^{37}$.

xi: The ester group is hydrolyzed under acidic conditions, conveniently with 25% aqueous hydrochloric acid in a suitable solvent such as dioxane at an elevated temperature, e.g. at about 100° C.

xii: The phthalimido group is cleaved, e.g. by hydrazinolysis, conveniently with hydrazine hydrate in a suitable solvent such as ethanol.

xiii: The intermediate free amino acid formed is conveniently protected with reagents such as 9-fluorenylmethoxcarbonyl chloride or 9-fluorenylmethoxcarbonyl succinimide using a base such as sodium carbonate or triethylamine in a suitable solvent or mixture of solvents such as dioxane and water, or dichloromethane to yield 185.

Templates of type (c2) can be prepared as shown in Schemes 38 and 39.

i: 3,7-Dimethoxyphenothiazine 186 is prepared and converted into 187 according to Müller, K.; Obrecht, D.; Knierzinger, A.; Spiegler, C.; Bannwarth, W.; Trzeciak, A.; Englert, G.; Labhardt, A.; Schönholzer, P. *Perspectives in Medicinal Chemistry*, Editor Testa, B.; Kyburz, E.; Fuhrer, W.; Giger, R., Weinheim, New York, Basel, Cambridge: Verlag Helvetica Chimica Acta, 1993, 513–531; Bannwarth, W.; Gerber, F.; Grieder, A.; Knierzinger, A.; Müller, K.; Obrecht. D.; Trzeciak, A. *Can. Pat. Appl.* CA2101599(131 pages). The benzyl group is cleaved off from 187 conveniently by hydrogenation, e.g. with $H_2$ and a catalyst such as palladium on charcoal in a suitable solvent such as ethanol, DMF or ethyl acetate.

ii: Introduction of lower alkyl ($R^{43}$) by alkylation using an appropriate alkylating agent ($R^{43}$—X'; X'=OTf, Br, I) and strong bases such as sodium amide in liquid ammonia or sodium hydride in tetrahydrofuran, dioxan or DMF in the presence of a phase transfer catalyst such as TDA-I. In a similar manner substituted lower alkyl ($R^{43}$) can be

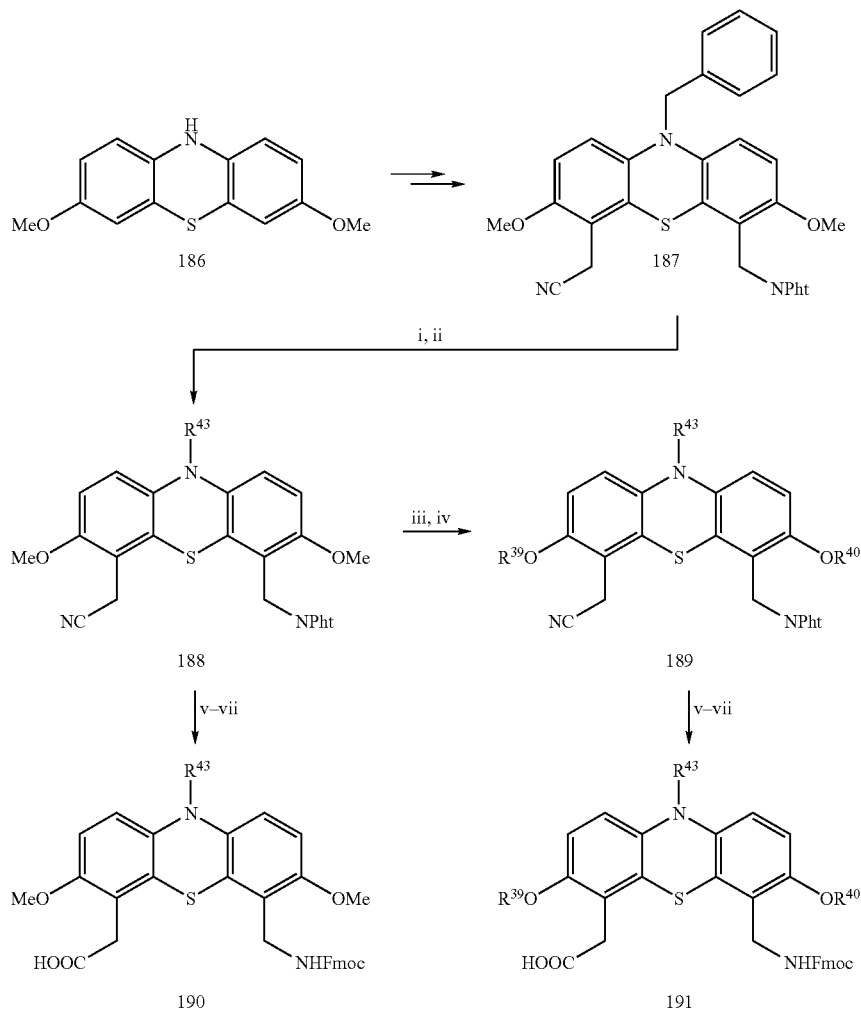

Scheme 38 introduced; thus, for example $R^{43}=CH_2COOR^{55}$ and $CH_2CH_2COOR^{55}$ can be introduced by treatment with the appropriate 2-halo acetic and, respectively, 3-halo propionic acid derivatives. Any other functionalization known for diarylamines can be employed for introduction of substituents $R^{43}$.

iii: Cleavage of the methoxy groups of 188, conveniently by treatment with an excess of boron tribromide in a suitable solvent such as dichloromethane at temperatures ranging from about −20° C. to about room temperature.

iv: For the introduction of lower alkyl, substituted lower alkyl or aryl-lower alkyl substituents ($R^{39}$ and $R^{40}$) the intermediate bis-phenol derivative is conveniently reacted with a reagent of the formula $R^{39}$— and $R^{40}$—X' (X'=OTf, Br, I) in the presence of strong bases such as sodium hydride in tetrahydrofuran, dioxan or DMF in the presence of a phase transfer catalyst such as TDA-I. Any other functionalization known for phenol groups can be employed for introduction of substituents $R^{39}$ and $R^{40}$.

v: The cyano group of 188 and, respectively, 189 is hydrolyzed, conveniently under acidic conditions, e.g. with 25% aqueous hydrochloric acid in a suitable solvent such as dioxane at an elevated temperature, e.g. at about 100° C.

vi: The phthalimide group of the intermediate is cleaved, conveniently by hydrazinolysis, e.g. with hydrazine hydrate in a suitable solvent such as ethanol.

vii: The free amino group is conveniently protected with reagents such as 9-fluorenylmethoxcarbonyl chloride or 9-fluorenylmethoxcarbonyl succinimide using a base such as sodium carbonate or triethylamine in a suitable solvent or mixture of solvents such as dioxane and water, or dichloromethane to yield 190 and, respectively, 191.

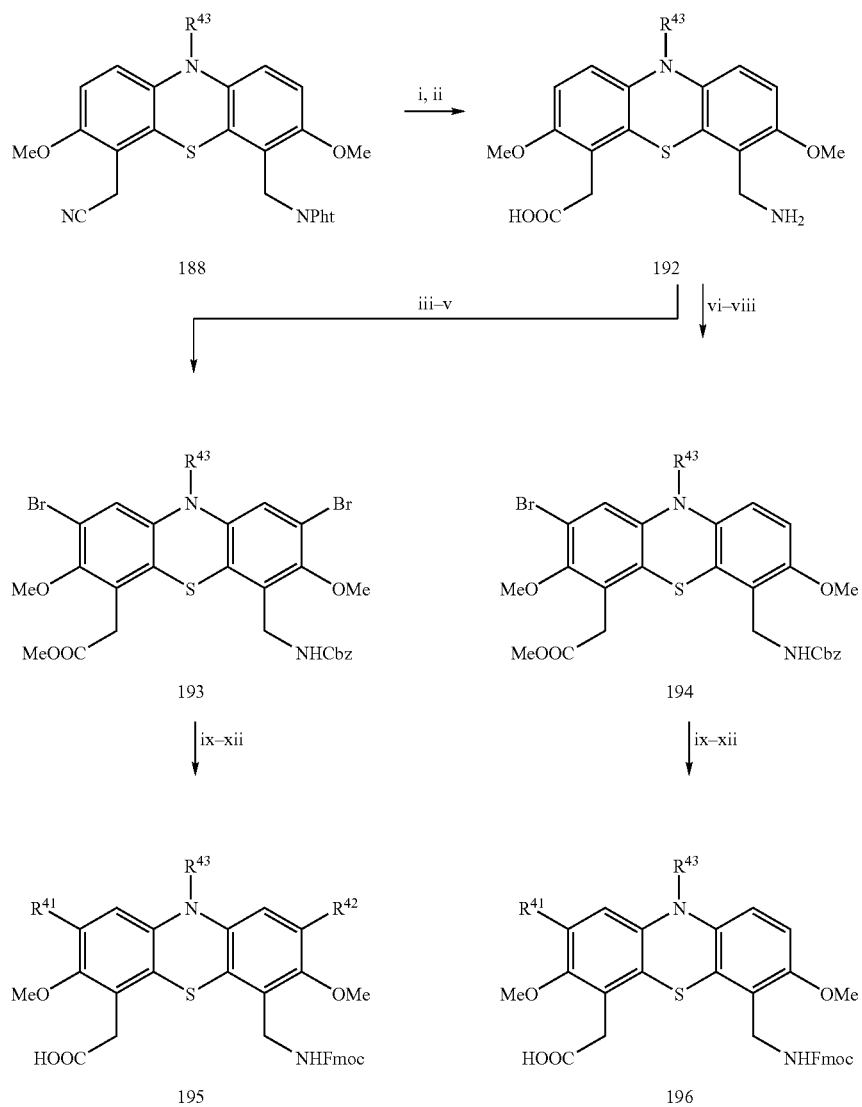

Scheme 39 i: The cyano group of 188 is hydrolyzed, conveniently under acidic conditions, e.g. with 25% aqueous hydrochloric acid in a suitable solvent such as dioxane at an elevated temperature, e.g. at about 100° C.

ii: The phthalimide group of the intermediate is cleaved, conveniently by hydrazinolysis, e.g. with hydrazine hydrate in a suitable solvent such as ethanol to yield 192.

iii: Double ortho-bromination of 192 is performed preferably with excess bromine in acetic acid and dichloromethane. In a similar fashion $R^{41}=R^{42}=NO_2$ can be introduced by treatment with $HNO_3$ in acetic acid and $R^{41}=R^{42}=CH_2-NPht$ by treatment with hydroxymethyl phthalimide in $H_2SO_4$. Any other functionalization by electrophilic aromatic substitution known can be employed for introduction of substituents $R^{41}$ and $R^{42}$.

iv: The amino group is protected, conveniently Cbz-protected, with reagents such as benzyloxycarbonyl chloride or succinimide in a suitable solvent such as dioxane in the presence of a base such as aqueous sodium hydroxide.

v: The carboxylic acid group is esterified, preferably with DBU and methyl iodide in DMF to yield 193.

vi: Regioselective bromination of 192 is performed preferably with bromine in acetic acid and dichloromethane. In a similar fashion $R^{41}=NO_2$ can be introduced by treatment with $HNO_3$ in acetic acid and $R^{41}=CH_2-NPt$ by treatment with hydroxymethyl phthalimide in $H_2SO_4$. Any other functionalization by electrophilic aromatic substitution known can be employed for introduction of substituents $R^{41}$.

vii: The amino group is conveniently Cbz-protected with reagents such as benzyloxycarbonyl chloride or succinimide in a suitable solvent such as dioxane in presence of a base such as aqueous sodium hydroxide.

viii: The carboxylic acid group is esterified, preferably with DBU and methyl iodide in DMF to yield 194.

ix: Introduction of lower alkyl, substituted lower alkyl and aryl substituents ($R^{41}$) for 194 and ($R^{41}$ and $R^{42}$) for 193, conveniently by palladium(0)-catalyzed Stille-(Stille, J. K. Angew. Chem. 1986, 68, 504) and Suzuki-couplings (Oh-e, T.; Mijaura, N.; Suzuki, A. J. Org. Chem. 1993, 58, 2201). Any other functionalization known for aryl bromides can be employed for introduction of substituents $R^{41}$ and $R^{42}$.

x: Removal of the Cbz-group, e.g. by hydrogenation using $H_2$ and a catalyst such as palladium on charcoal in a suitable solvent such as ethanol, DMF and ethyl acetate.

xi: Hydrolysis of the ester group, conveniently under acidic conditions, e.g. with 25% aqueous hydrochloric acid in a suitable solvent such as dioxane at an elevated temperature, preferably at about 100° C.

xii: The intermediate free amino acid formed is conveniently protected with reagents such as 9-fluorenylmethoxcarbonyl chloride or 9-fluorenylmethoxcarbonyl succinimide using a base such as sodium carbonate or triethylamine in a suitable solvent or mixture of solvents such as dioxane and water, or dichloromethane to yield 195 and 196.

Templates of type (c3) can be prepared as shown in Schemes 40 and 41.

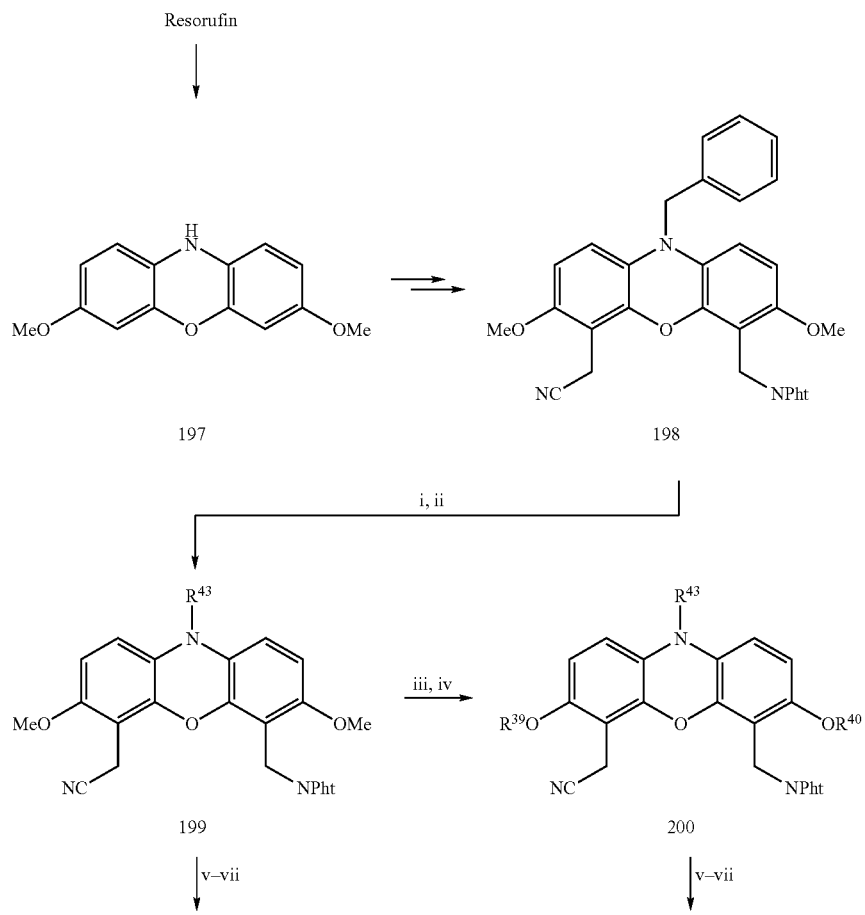

Scheme 40

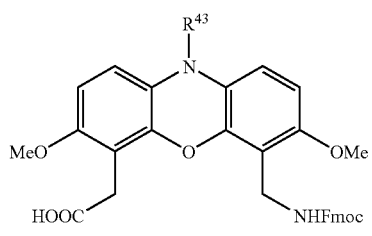

201

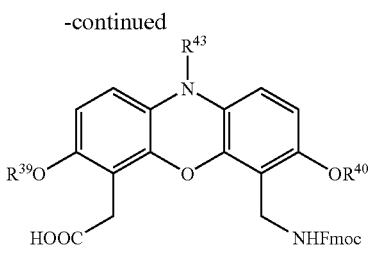

202 i: 197 can be prepared from commercial resorufin and coverted into 198 according to Müller, K.; Obrecht, D.; Knierzinger, A.; Spiegler, C.; Bannwarth, W.; Trzeciak, A.; Englert, G.; Labhardt, A.; Schönholzer, P. *Perspectives in Medicinal Chemistry*, Editor Testa, B.; Kyburz, E.; Fubrer, W.; Giger, R., Weinheim, New York, Basel, Cambridge: Verlag Helvetica Chimica Acta, 1993, 513–531; Bannwarth, W.; Gerber, F.; Grieder, A.; Knierzinger, A.; Müller, K.; Obrecht. D.; Trzeciak, A. *Can. Pat. Appl.* CA2101599(131 pages). For splitting off the benzyl group 198 is conveniently hydrogenated e.g. with $H_2$ and a catalyst such as palladium on charcoal in a suitable solvent such as ethanol, DMF or ethyl acetate.

ii: Introduction of lower alkyl ($R^{43}$) by alkylation with $R^{43}$—X' (X'=OTf, Br, I) using strong bases such as sodium amide in liquid ammonia or sodium hydride in tetrahydrofuran, dioxan or DMF in the presence of a phase transfer catalyst such as TDA-I to yield 199. In a similar manner substituted lower alkyl ($R^{43}$) can be introduced; thus, for example, $R^{43}$=$CH_2COOR^{55}$ and $CH^2CH_2COOR^{55}$ can be introduced by treatment with the appropriate 2-halo acetic and, respectively, 3-halo propionic acid derivatives. Any other functionalization of diarylamino groups known can be employed for introduction of substituents $R^{43}$.

iii: Cleavage of the methoxy groups of 199, conveniently by treatment with excess boron tribromide in dichloromethane at temperatures ranging from about −20° to about room temperature.

iv: The intermediate bis-phenol derivative is preferably reacted with $R^{39}$ and $R^{40}$—X' (X'=OTf, Br, I) in the presence of strong bases such as sodium hydride in tetrahydrofuran, dioxan or DMF in the presence of a phase transfer catalyst such as TDA-I. Any other functionalization for phenol groups can be employed for introduction of substituents $R^{39}$ and $R^{40}$.

v: The cyano group of 199 and, respectively, 200 is hydrolyzed under acidic conditions, e.g. with 25% aqueous hydrochloric acid in a suitable solvent such as dioxane at an elevated temperature, conveniently at about 100° C.

vi: The phthalimide group is cleaved, conveniently by hydrazinolysis, e.g. with hydrazine hydrate in suitable solvent such as ethanol.

vii: The free amino group is conveniently protected with reagents such as 9-fluorenylmethoxycarbonyl chloride or 9-fluorenylmethoxycarbonyl succinimide using a base such as sodium carbonate or triethylamine in suitable solvent or mixture of solvents such as dioxane and water, or dichloromethane to yield 201 and, respectively, 202.

Scheme 41

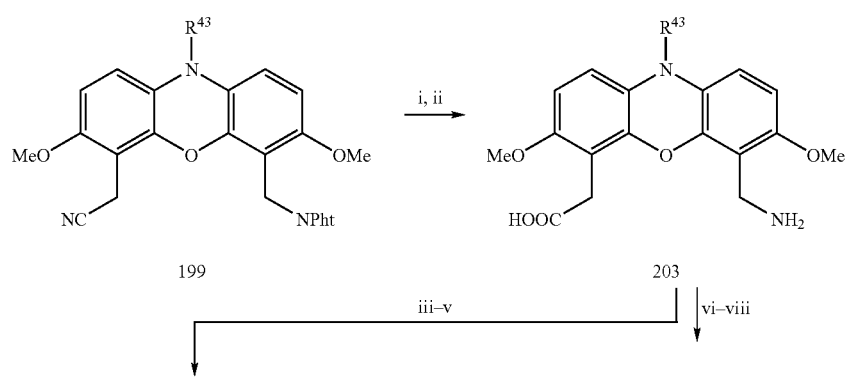

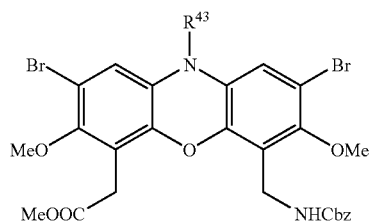

204

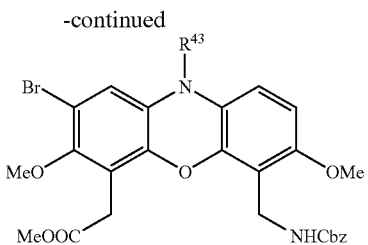

205

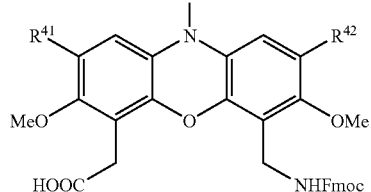

206

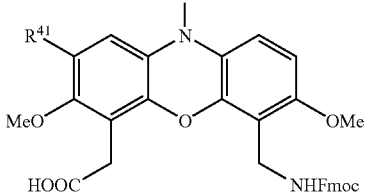

207 i: The cyano group of 199 is hydrolyzed, conveniently under acidic conditions, e.g. with 25% aqueous hydrochloric acid in a suitable solvent such as dioxane at an elevated temperature, e.g. at about 100° C.

ii: The phthalimide group of the intermediate is cleaved, conveniently by hydrazinolysis, e.g. with hydrazine hydrate in a suitable solvent such as ethanol to yield 203.

iii: Double ortho-bromination of 203 is performed preferably with excess bromine in acetic acid and dichloromethane. In a similar fashion $R^{41}=R^{42}=NO_2$ can be introduced by treatment with $HNO_3$ in acetic acid and $R^{41}=R^{42}=CH_2-NPht$ by treatment with hydroxymethyl phthalimide in $H_2SO_4$. Any other functionalization by electrophilic aromatic substitution can be employed for introduction of substituents $R^{41}$ and $R^{42}$.

iv: The amino group is protected, conveniently Cbz-protected, with reagents such as benzyloxycarbonyl chloride or succinimide in a suitable solvent such as dioxane in the presence of a base such as aqueous sodium hydroxide.

v: The carboxylic acid group is esterified, preferably with DBU and methyl iodide in DMF to yield 204.

vi: Regioselective bromination of 203 is performed preferably with bromine in acetic acid and dichloromethane. In a similar fashion $R^{41}=NO_2$ can be introduced by treatment with $HNO_3$ in acetic acid and $R^{41}=CR_2-NPht$ by treatment with hydroxymethyl phthalimide in $H_2SO_4$.

vii: The amino group is conveniently Cbz-protected with reagents such as benzyloxycarbonyl chloride or succinimide in a suitable solvent such as dioxane in presence of a base such as aqueous sodium hydroxide.

viii: The carboxylic acid group is esterified, preferably with DBU and methyl iodide in DMF to yield 205.

ix: Introduction of lower alkyl, substituted lower alkyl and aryl substituents ($R^{41}$) for 205 and ($R^{41}$ and $R^{42}$) for 204, conveniently by palladium(0)-catalyzed Stille-(Stille, J. K. Angew. Chem. 1986, 68, 504) and Suzuki-couplings (Oh-e, T.; Mijaura, N.; Suzuki, A. J. Org. Chem. 1993, 58, 2201). Any other functionalization known for aryl bromides can be employed for introduction of substituents $R^{41}$ and $R^{42}$.

x: Removal of the Cbz-group, e.g. by hydrogenation using $H_2$ and a catalyst such as palladium on charcoal in a suitable solvent such as ethanol, DMF and ethyl acetate.

xi: Hydrolysis of the ester group, conveniently under acidic conditions, e.g. with 25% aqueous hydrochloric acid in a suitable solvent such as dioxane at an elevated temperature, preferably at about 100° C.

xii: The intermediate free amino acid formed is conveniently protected with reagents such as 9-fluorenylmethoxycarbonyl chloride or 9-fluorenylmethoxycarbonyl succinimide using a base such as sodium carbonate or triethylamine in a suitable solvent or mixture of solvents such as dioxane and water, or dichloromethane to yield 206 and 207.

Templates(d) can be prepared according to D. Obrecht, U. Bohdal, C. Lehmann, P. Schönholzer, K. Müller, Tetrahedron 1995, 51, 10883; D. Obrecht, C. Abrecht, M. Altorfer, U. Bohdal, A. Grieder, M. Kleber, P. Pfyffer, K. Müller, Helv. Chim. Acta 1996, 79, 1315–1337.

Templates (e1) and (e2): See R. Mueller, L. Revesz, Tetrahedron Lett. 1994, 35, 4091; H.-G. Lubell, W. D. Lubell, J. Org. Chem. 1996, 61, 9437; L. Colombo, M. DiGiacomo, G. Papeo, O. Carugo, C. Scolastico, L. Manzoni, Tetrahedron Lett. 1994, 35, 4031.

Templates (e3): See S. Hanessian, B. Ronan, A. Laoui, Bioorg. Med. Chem. Lett. 1994, 4, 1397.

Templates (e4): See S. Hanessian, G. McNaughton-Smith, Bioorg. Med. Chem. Lett. 1996, 6, 1567.

Templates (f): See T. P. Curran, P. M. McEnay, Tetrahedron Lett. 1995, 36, 191–194.

Templates (g): See D. Gramberg, C. Weber, R. Beeli, J. Inglis, C. Bruns, J. A. Robinson, Helv. Chem. Acta 1995, 78, 1588–1606; K. H. Kim, J. P. Dumas, J. P. Germanas, J. Org. Chem. 1996, 61, 3138–3144.

Templates (h): See S. de Lombart, L. Blanchard, L. B. Stamford, D. M. Sperbeck, M. D. Grim, T. M. Jenson, H. R. Rodriguez, Tetrahedron Lett. 1994, 35, 7513–7516.

Templates (i1): See J. A. Robl, D. S. Karanewski, M. M. Asaad, Tetrahedron Lett. 1995, 5, 773–758.

Templates (i2): See T. P. Burkholder, T.-B. Le, E. L. Giroux, G. A. Flynn, Bioorg. Med. Chem. Lett. 1992, 2, 579.

Templates (i3) and (i4): See L. M. Simpkins, J. A. Robl, M. P. Cimarusti, D. E. Ryono, J. Stevenson, C.-Q. Sun, E. W. Petrillo, D. S. Karanewski, M. M. Asaad, J. E. Bird, T. R. Schaeffer, N. C. Trippodo, Abstracts of papers, 210$^{th}$ Am. Chem. Soc Meeting, Chicago, Ill., MEDI 064 (1995).

Templates (k): See D. BenIshai, A. R. McMurray, *Tetrahedron* 1993, 49, 6399.

Templates (l): See E. G. von Roedern, H. Kessler, *Angew. Chem. Int. Ed. Engl.* 1994, 33, 687–689.

Templates (m): See R. Gonzalez-Muniz, M. J. Dominguez, M. T. Garcia-Lopez, *Tetrahedron* 1992, 48, 5191–5198.

Templates (n): See F. Esser, A. Carpy, H. Briem, H. Köppen, K.-H. Pook, *Int. J. Pept. Res.* 1995, 45, 540–546.

Templates (o): See N. De la Figuera, I. Alkorta, T. Garcia-Lopez, R. Herranz, R. Gonzalez-Muniz, *Tetrahedron* 1995, 51, 7841.

Templates (p): See U. Slomcynska, D. K. Chalmers, F. Cornille, M. L. Smythe, D. D. Benson, K. D. Moeller, G. R. Marshall, *J. Org. Chem.* 1996, 61, 1198–1204.

The β-hairpin peptidomimetics of the invention can be used in a wide range of applications in order to inhibit the growth of or to kill microorganisms and/or cancer cells.

They can be used for example as disinfectants or as preservatives for materials such as foodstuffs, cosmetics, medicaments and other nutrient-containing materials or for preventing surfaces from microbial colonization [J. M. Schierholz, C. Fleck, J. Beuth, G. Pulverer, *J. Antimicrob. Chemother.*, 2000, 46, 45–50]. The β-hairpin peptidomimetics of the invention can also be used to treat or prevent diseases related to microbial infection in plants and animals.

For use as disinfectants or preservatives the β-hairpin peptidomimetics can be added to the desired material singly, as mixtures of several β-hairpin peptidomimetics or in combination with other antimicrobial agents. The β-hairpin peptidomimetics may be administered per se or may be applied as an appropriate formulation together with carriers, diluents or excipients well known in the art, expediently in a form suitable for oral, topical, transdermal, injection, buccal, transmucosal, pulmonary or inhalation administration, such as tablets, dragees, capsules, solutions, liquids, gels, plasters, creams, ointments, syrups, slurries, suspensions, sprays, nebulisers or suppositories.

When used to treat or prevent infections or diseases related to such infections or cancer, the β-hairpin peptidomimetics can be administered singly, as mixtures of several β-hairpin peptidomimetics, in combination with other antimicrobial, antibiotic or anicancer agents or in combination with other pharmaceutically active agents. The β-hairpin peptidomimetics can be administered per se or as pharmaceutical compositions.

Pharmaceutical compositions comprising β-hairpin peptidomimetics of the invention may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxilliaries which facilitate processing of the active β-hairpin peptidomimetics into preparations which can be used pharmaceutically. Proper formulation depends upon the method of administration chosen.

For topical administration the β-hairpin peptidomimetics of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the β-hairpin peptidomimetics of the invention may be formulated in adequate solutions, preferably in physiologically compatible buffers such as Hink's solution, Ringer's solution, or physiological saline buffer. The solution may contain formulatory agents such as suspending, stabilizing and/or dispersing agents. Alternatively, the β-hairpin peptidomimetics of the invention may be in powder form for combination with a suitable vehicle, e.g., sterile pyrogen-free water, before use.

For transmucosal administration, penetrants appropriate to the barrier to be permeated are used in the formulation as known in the art.

For oral administration, the compounds can be readily formulated by combining the active β-hairpin peptidomimetics of the invention with pharmaceutically acceptable carriers well known in the art. Such carriers enable the β-hairpin peptidomimetics of the invention to be formulated as tablets, pills, dragees, capsules, liquids, gels, syrups, slurries, suspensions etc., for oral ingestion of a patient to be treated. For oral formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP); granulating agents; and binding agents. If desired, desintegrating agents may be added, such as cross-linked polyvinylpyrrolidones, agar, or alginic acid or a salt thereof, such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. In addition, flavoring agents, preservatives, coloring agents and the like may be added.

For buccal administration, the composition may take the form of tablets, lozenges, etc. formulated as usual.

For administration by inhalation, the β-hairpin peptidomimetics of the invention are conveniently delivered in form of an aeorosol spray from pressurized packs or a nebulizer, with the use of a suitable propellant, e.g. dichlorodifluoromethane, trichlorofluromethane, carbon dioxide or another suitable gas. In the case of a pressurized aerosol the dose unit may be determined by providing a valve to deliver a metered amount Capsules and cartridges of e.g. gelatin for use in an inhaler or insufflator may be formulated containing a powder mix of the β-hairpin peptidomimetics of the invention and a suitable powder base such as lactose or starch.

The compounds may also be formulated in rectal or vaginal compositions such as suppositories together with appropriate suppository bases such as cocoa butter or other glycerides.

In addition to the formulation described previously, the β-hairpin peptidomimetics of the invention may also be formulated as depot preparations. Such long acting formulations may be administered by implantation (e.g. subcutaneously or intramuscularly) or by intramuscular injection. For the manufacture of such depot preparations the β-hairpin peptidomimetics of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well known in the art. Certain organic solvents such as dimethylsulfoxide also may be employed. Additionally, the β-hairpin peptidomimetics of the invention may be delivered using a sustained-release system, such as semipermeable matrices of solid polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic agent, additional strategies for protein stabilization may be employed.

As the β-hairpin pepdidomimetics of the invention may contain charged residues, they may be included in any of the above-described formulations as free bases or as pharmaceutically acceptable salts. Pharmaceutically acceptable salts tend to be more soluble in aqueous and other protic solvents than are the corresponding free base forms.

The β-hairpin peptidomimetics of the invention, or compositions thereof, will generally be used in an amount effective to achieve the intended purpose. It is to be understood that the amount used will depend on a particular application.

For example, for use as a desinfectant or preservative, an antimicrobially effective amount of a β-hairpin peptidomimetic of the invention, or a composition thereof, is applied or added to the material to be desinfected or preserved. By antimicrobially effective amount is meant an amount of a β-hairpin peptidomimetic of the invention or composition that inhibits the growth of, or is lethal to, a target microbe population. While the antimicrobially effective amount will depend on a particular application, for use as desinfectants or preservatives the β-hairpin peptidomimetics of the invention, or compositions thereof, are usually added or applied to the material to be desinfected or preserved in relatively low amounts. Typically, the β-hairpin peptidomimetics of the invention comprise less than about 5% by weight of a desinfectant solution or material to be preserved, preferably less than 1% by weight and more preferably less than 0.1% by weight. An ordinary skilled expert will be able to determine antimicrobially effective amounts of particular β-hairpin pepdidomimetics of the invention for particular applications without undue experimentation using, for example, the in vitro assays provided in the examples.

For use to treat or prevent microbial infections or diseases related thereto and cancer, the β-hairpin pepidomimetics of the invention, or compositions thereof, are administered or applied in a therapeutically effective amount. By therapeutically effective amount is meant an amount effective in ameliorating the symptoms of, or ameliorate, treat or prevent microbial infections or diseases related thereto. Determination of a therapeutically effective amount is well within the capacities of those skilled in the art, especially in view of the detailed disclosure provided herein.

As in the case of desinfectants and preservatives, for topical administration to treat or prevent bacterial, yeast, fungal or other infections a therapeutically effective dose can be determined using, for example, the in vitro assays provided in the examples. The treatment may be applied while the infection is visible, or even when it is not visible.

An ordinary skilled expert will be able to determine therapeutically effective amounts to treat topical infections without undue experimentation.

For systemic administration, a therapeutically effective dose can be estimated initially from in vitro assays. For example, a dose can be formulated in animal models to achieve a circulating β-hairpin peptidomimetic concentration range that includes the $IC_{50}$ as determined in the cell culture (i.e. the concentration of a test compound that is lethal to 50% of a cell culture), the MIC, as determined in cell culture (i.e. the concentration of a test compound that is lethal to 100% of a cell culture). Such information can be used to more accurately determine useful doses in humans.

Initial dosages can also be determined from in vivo data, e.g. animal models, using techniques that are well known in the art. One having ordinary skills in the art could readily optimize administration to humans based on animal data.

Dosage amount for applications as antimicrobial agents may be adjusted individually to provide plasma levels of the β-hairpin peptidomimetics of the invention which are sufficient to maintain the therapeutic effect. Usual patient dosages for administration by injection range from about 0.1–5 mg/kg/day, preferably from about 0.5 to 1 mg/kg/day. Therapeutically effective serum levels may be achieved by administering multiple doses each day.

In cases of local administration or selective uptake, the effective local concentration of the β-hairpin peptidomimetics of the invention may not be related to plasma concentration. One having the skills in the art will be able to optimize therapeutically effective local dosages without undue experimentation.

The amount of β-hairpin peptidomimetics administered will, of course, be dependent on the subject being treated, on the subject's weight, the severity of the affliction, the manner of administration and the judgement of the prescribing physician.

The antimicrobial therapy may be repeated intermittently while infections are detectable or even when they are not detectable. The therapy may be provided alone or in combination with other drugs, such as for example antibiotics or other antimicrobial agents.

Normally, a therapeutically effective dose of the β-hairpin peptidomimetics described herein will provide therapeutic benefit without causing substantial toxicity.

Hemolysis of red blood cells is often employed for assessment of toxicity of related compounds such as protegrin or tachyplesin. Values are given as %-lysis of red blood cells observed at a concentration of 100 μg/ml. Typical values determined for cationic peptides such as protegrin and tachyplesin range between 30–40% with average MIC-values of 1–5 μg/ml over a wide range of pathogens. Normally, β-hairpin peptidomimetics of the invention will show hemolysis in a range of 0.5–10%, often in a range of 1–5%, at activity levels comparable to those mentioned above for protegrin and tachyplesin. Thus preferred compounds exhibit low MIC-values and low %-hemolysis of red blood cells observed at a concentration of 100 μg/ml.

Toxicity of the β-hairpin peptidomimetics of the invention herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in humans. The dosage of the β-hairpin peptidomimetics of the invention lies preferably within a range of circulating concentrations that include the effective dose with little or no toxicity. The dosage may vary within the range depending upon the dosage form employed and the route of administration utilized. The exact formulation, route of administration and dose can be chosen by the individual physician in view of the patient's condition (see, e.g. Fingl et at. 1975, In: *The Pharmacological Basis of Therapeutics*, Ch. 1, p. 1).

The following Examples illustrate the invention in more detail but are not intended to limit its scope in any way. The following abbreviations are used in these Examples:

HBTU: 1-benzotriazol-1-yl-tetramethylurounium hexafluorophosphate (Knorr et al. *Tetrahedron Lett*. 1989, 30, 1927–1930)
HOBt: 1-hydroxybenzotriazole
DIEA: diisopropylethylamine
HOAT: 7-aza-1-hydroxybenzotriazole
HATU: O-(7-aza-benzotriazole-1-yl)-N,N,N',N'-tetramethyluronoium hexafluorophosphate Carpino et al. *Tetrahedron Lett*. 1994, 35, 2279–2281)

EXAMPLES

1. Peptide Synthesis

Coupling of the First Protected Amino Acid Residue 0.5 g of 2-chlorotritylchloride resin (Barlos et al. *Tetrahedron Lett*. 1989, 30, 3943–3946) (0.83 mMol/g, 0.415 mmol) was filled into a dried flask The resin was suspended in $CH_2Cl_2$ (2.5 ml) and allowed to swell at room temperature under constant stirring. The resin was treated with 0.415 mMol (1 eq) of the first suitably protected amino acid residue (see below) and 284 μl (4 eq) of diisopropylethylamine (IDEA) in $CH_2Cl_2$ (2.5 ml), the mixture was shaken at 25° C. for 15 minutes, poured onto the pre-swollen resin and stirred at 25° C. for 18 hours. The resin colour changed to purple and the solution remained yellowish. The resin was washed extensively ($CH_2Cl_2$/MeOH/DIEA: 17/2/1; $CH_2Cl_2$, DMF; $CH_2Cl_2$; $Et_2O$, 3 times each) and dried under vacuum for 6 hours.

Loading was typically 0.6–0.7 mMol/g.

The following preloaded resins were prepared: Fmoc-GlyO-chlorotritylresin; Fmoc-Arg(Pbf)O-chlorotritylresin; Fmoc-Lys(Boc)O-chlorotritylresin.

1.1. Procedure 1

The synthesis was carried out using a Syro-peptide synthesizer (Multisyntech) using 24 to 96 reaction vessels. In each vessel was placed 60 mg (weight of the resin before loading) of the above resin. The following reaction cycles were programmed and carried out:

| Step | Reagent | Time |
|---|---|---|
| 1 | $CH_2Cl_2$, wash and swell (manual) | 3 × 1 min. |
| 2 | DMF, wash and swell | 1 × 5 min. |
| 3 | 40% piperidine/DMF | 1 × 5 min. |
| 4 | DMF, wash | 5 × 2 min. |
| 5 | 5 equiv. Fmoc amino acid/DMF + 5 eq. HBTU + 5 eq. HOBt + 5 eq. DIEA | 1 × 120 min. |
| 6 | DMF, wash | 4 × 2 min. |
| 7 | $CH_2Cl_2$, wash (at the end of the synthesis) | 3 × 2 min. |

Steps 3 to 6 are repeated to add each amino-acid.

Cleavage of the Fully Protected Peptide Fragment

After completion of the synthesis, the resin was suspended in 1 ml (0.39 mMol) of 1% TFA in $CH_2Cl_2$ (v/v) for 3 minutes, filtered and the filtrate was neutralized with 1 ml (1.17 mMol, 3 eq.) of 20% DIEA in $CH_2Cl_2$ (v/v). This procedure was repeated twice to ensure completion of the cleavage. The filtrate was evaporated to dryness and the product was fully deprotected to be analyzed by reverse phase-HPLC (column $C_{18}$) to monitor the efficiency of the linear peptide synthesis.

Cyclization of the Linear Peptide 100 mg of the fully protected linear peptide were dissolved in DMF (9 ml, conc. 10 mg/ml). Then 41.8 mg (0.110 mMol, 3 eq.) of HATU, 14.9 mg (0.110 mMol, 3 eq) of HOAt and 1 ml (0.584 mMol) of 10% DIEA in DMF (v/v) were added and the mixture vortexed at 20° C. for 16 hours and subsequently concentrated under high vacuum. The residue was partitioned between $CH_2Cl_2$ and $H_2O/CH_3CN$ (90/10: v/v). The $CH_2Cl_2$ phase was evaporated to yield the fully protected cyclic peptide.

Deprotection and Purification of the Cyclic Peptide

The cyclic peptide obtained was dissolved in 1 ml of the cleavage mixture containing 95% trifluoroacetic acid (TFA), 2.5% water and 2.5% triisopropylsilane (TIS). The mixture was left to stand at 20° C. for 2.5 hours and then concentrated under vacuum. The residue was dissolved in a solution of $H_2O$/acetic acid (75/25: v/v) and the mixture extracted with di-isopropylether.

The water phase was dried under vacuum and then the product purified by preparative reverse phase HPLC.

After lyophilisation products were obtained as a white powder and analysed by ESI-MS. The analytical data comprising HPLC retention times and ESI-MS are shown in tables 1–7. Analytical HPLC retension times (RT, in minutes) were determined using a VYDAC 218TP104 (length 25 cm) column with gradient A: (10% $CH_3CN$+0.1% TFA and 90% $H_2O$+0.1% TFA to 98% $CH_3CN$+0.1% TFA and 2% $H_2O$+0.1% TFA in 20 minutes) and with gradient B: (10% $CH_3CN$+0.1% TFA and 90% $H_2O$+0.1% TFA to 98% $CH_3CN$+0.1% TFA and 2% $H_2O$+0.1% TFA in 21 minutes).

Examples ex.1–7 (n=8) are shown in table 1. The peptides were synthesized starting with the amino acid at position P4 which was coupled to the resin. Starting resins were Fmoc-Arg(Pbf)O-chlorotritylresin and Fmoc-Lys(Boc)O-chlorotritylresin, which were prepared as described above. The linear peptides were synthesized on solid support according to procedure 1 in the following sequence: P5-P6-P7-P8-$^D$Pro-P1-P2-P3-P4-resin, cleaved, cyclized, deprotected and purified as indicated. HPLC-retension times (minutes) were determined using gradient A.

Examples ex.831 (n=9) are shown in table 2. The peptides were synthesized starting with the amino acid at position P5 which was coupled to the resin. Starting resin was Fmoc-Arg(Pbf)O-chlorotritylresin, which was prepared as described above. The linear peptides were synthesized on solid support according to procedure 1 in the following sequence: P6-P7-P8-P9-$^D$Pro-Pro-P1-P2-P3-P4-P5-resin, cleaved, cyclized, deprotected and purified as indicated. HPLC-retension times (minutes) were determined using gradient A.

Examples ex.32–58 (n=10) are shown in table 3. The peptides were synthesized staring with the amino acid at position P5 which was coupled to the resin. Starting resin was Fmoc-Arg(Pbf)O-chlorotr;tykesin, which was prepared as described above. The linear peptides were synthesized on solid support according to procedure 1 in the following sequence: P6-P7-P8-P9-P10-$^D$Pro-Pro-P1-P2-P3-P4-P5- resin, cleaved, cyclized, deprotected and purified as indicated. HPLC-retension times (minutes) were determined using gradient A.

Examples ex.59–70 (n=11) are shown in table 4. The peptides were synthesized starting with the amino acid at position P5 which was coupled to the resin. Starting resin was Fmoc-Arg(Pbf)O-chlorotritylresin, which was prepared as described above. The linear peptides were synthesized on solid support according to procedure 1 in the following sequence: P6-P7-P8-P9-P10-P11-$^D$Pro-Pro-P1-P2-P3-P4-P5-resin, cleaved, cyclized, deprotected and purified as indicated. HPLC-retension times (minutes) were determined using gradient A.

Examples ex.71–84 (n=14) are shown in table 5. The peptides were synthesized starting with the amino acid at position P7 which was coupled to the resin. Starting resin was Fmoc-Arg(Pbf)O-chlorotritylresin, which was prepared as described above. The linear peptides were synthesized on solid support according to procedure 1 in the following sequence: P8-P9-P10-P11-P12-P13-P14-$^D$Pro-P1-P2-P3-P4-P5-P6-P7-resin, cleaved, cyclized, deprotected and purified as indicated. HPLC-retension times (minutes) were determined using gradient A.

Examples ex.85–95 (n=16) are shown in table 6. The peptides were synthesized staring with the amino acid at position P8 which was coupled to the resin. Starting resins were Fmoc-Arg(Pbf)O-chlorotritylresin and Fmoc-Lys(Boc)O-chlorotritylresin, which were prepared as described above. The linear peptides were synthesized on solid support according to procedure 1 in the following sequence: P9-P10-P11-P12-P13-P13-P15-P16-$^D$Pro-P1-P2-P3-P4-P5-P6-P7-P8-resin, cleaved, cyclized, deprotected and purified as indicated. HPLC-retension times (minutes) were determined using gradient A.

Examples ex.96–246, ex.276 (n=12) are shown in table 7. The peptides (exept ex.177 and ex.181) were synthesized starting with the amino acid at position P6 which was grafted to the resin. Starting resins were Fmoc-Arg(Pbf)O-chlorotritylresin and Fmoc-Lys(Boc)O-chlorotritylresin, which were prepared as described above. The linear peptides were synthesized on solid support according to procedure 1 in the following sequence: P7-P8-P9-P10-P11-P12-$^D$Pro-Pro-P1-P2-P3-P4-P5-P6-resin, cleaved, cyclized, deprotected and purified as indicated. HPLC-retension times (minutes) were determined using gradient A.

Examples ex.177 to ex.181 (n=12) are shown in table 7. The peptides were synthesized starting with the amino acid at position P7 which was coupled to the resin. Starting resin was Fmoc-Arg(Pbf)O-chlorotritylresin, which were prepared as described above. The linear peptides were synthesized on solid support according to procedure 1 in the following sequence: P8-P9-P10-P11-P12-$^D$Pro-Pro-P1-P2-P3-P4-P5-P6-P7-resin, cleaved, cyclized, deprotected and purified as indicated HPLC-retension times (minutes) were determined using gradient A.

Examples ex.247–277 (n=12) are shown in table 7. The peptides were synthesized starting with the amino acid at position P6 which was grafted to the resin. Starting resins were Fmoc-Arg(Pbf)O-chlorotritylresin and Fmoc-Lys(Boc)O-chlorotritylresin, which were prepared as described above. The linear peptides were synthesized on solid support according to procedure 1 in the following sequence: P7-P8-P9-P10-P11-P12-$^D$Pro-BB-P1-P2-P3-P4-P5-P6-resin, cleaved, cyclized, deprotected and purified as indicated.

BB: Gly (ex.247); Arg(Pmc) (ex.248); Y (Bzl) (ex.249); Phe (ex250); Trp (ex.251); Leu (ex.252); Ile (ex.253); Cha (ex.254); 2-Nal (ex.255); 219a (ex.256); 219b (ex.257); 219c (ex.258); 219d (ex.259); 219e (ex.260); 219f (ex.261); 219g (ex.262); 219h (ex.263); 219i (ex.264); 219k (ex.265); 219l (ex.266); 219m (ex267); 219n (ex.268); 219o (ex.269); 219p (ex.270); 219q (ex.271); 219r (ex.272); 219s (ex.273); 219t (ex.274), 219u (ex.275).

Building blocks 219a–u are described below.

Example ex.277 (n=12) is shown in table 7. The peptide was synthesized starting with the amino acid at position P6 which was grafted to the resin. Starting resin was Fmoc-Arg(Pbf)O-chlorotritylresin, which were prepared as described above. The linear peptide was synthesized on solid support according to procedure 1 in the following sequence: P7-P5-P9-P10-P11-P12-(c1-1)-P1-P2-P3-P4-P5-P6-resin, cleaved, cyclized, deprotected and purified as indicated.

Building block (c1-1) is described below.

Examples ex.278–300 (n=12) are shown in table 7. The peptides were synthesized starting with the amino acid at position P6 which was grafted to the resin. Starting resins were Fmoc-Arg(Pbf)O-chlorotritylresin, Fmoc-Tyr(Bzl)O-chlorotrityl resin and Fmoc-)Tyr(Bzl)O-chlorotrityl resin which were prepared as described above. The linear peptide was synthesized on solid support according to procedure 1 in the following sequence: P7-P8-P9-P10-P11-P12-$^D$Pro-Pro-P1-P2-P3-P4-P5-P6-resin, cleaved, cyclized, deprotected and purified as indicated. Analytical HPLC-retention times (RT, in minutes) were determined using a VYDAC 218TP104 (length 25 cm) column with gradient B (10% $CH_3CN+0.1\%$ TFA and 90% $H_2O+0.1\%$ TFA to 98% $CH_3CN+0.1\%$ TFA and 2% $H_2O+0.1\%$ TFA in 21 minutes).

Retention times (minutes) were the following: ex.278 (11.43); ex.279 (11.64); ex.280 (10.57); ex.281 (10.04); ex282 (10.63); ex.283 (10.00); ex.284 (9.21).

Retention times (minutes) for examples 285–300 were determined with gradient C: VYDAC $C_{18}$-column (length 15 cm); (8% $CH_3CN+0.1\%$ TFA and 92% $H_2O+0.1\%$ TFA to 62.8% $CH_3CN+0.1\%$ TFA and 37.2% $H_2O+0.1\%$ TFA in 8 minutes to 100% $CH_3CN+0.1\%$ TFA in 9 minutes).

ex.285 (5.37; 5.57)*; ex.286 (5.17); ex.287 (5.0); ex.288 (4.15;4.37)*; ex.289 (4.47; 4.72)*; ex.290 (3.45; 3.72)*; ex.291 (3.65; 3.82)*; ex.292 (4.27); ex.293 (4.10); ex.294 (3.83; 4.13)*; ex.296 (4.38; 4.67)*; ex.297 (4.10; 4.32)*; ex.298 (4.12); ex.299 (4.47); ex.300 (5.03).

* double peaks which show both correct MS and chiral amino acid analysis. At 60° only one peak is observed.

TABLE 1

Examples ex. 1–7 (n = 8)

| Example | SEQ. ID | P1 | P2 | P3 | P4 | P5 | P6 | P7 | P8 | Template | RT(') | %[a)] | MS |
|---|---|---|---|---|---|---|---|---|---|---|---|---|---|
| 1. | SEQ ID NO: 1 | Tyr | Val | Arg | Arg | Arg | Phe | Leu | Val | $^D$Pro$^L$Pro | 18.6 | 76 | 1284.6 |
| 2. | SEQ ID NO: 2 | Tyr | Val | Arg | Lys | Gly | Phe | Leu | Val | $^D$Pro$^L$Pro | 18.8 | 86 | 1157.4 |
| 3. | SEQ ID NO: 3 | Trp | Val | Arg | Lys | Gly | Phe | Leu | Trp | $^D$Pro$^L$Pro | 22.0 | 70 | 1263.8 |

TABLE 1-continued

Examples ex. 1–7 (n = 8)

| Example | SEQ. ID | P1 | P2 | P3 | P4 | P5 | P6 | P7 | P8 | Template | RT(') | %[a] | MS |
|---|---|---|---|---|---|---|---|---|---|---|---|---|---|
| 4. | SEQ ID NO: 4 | Tyr | Val | Arg | Arg | Arg | Trp | Leu | Val | $^D$Pro$^L$Pro | 19.1 | 35 | 1323.6 |
| 5. | SEQ ID NO: 5 | Tyr | Val | Tyr | Arg | Arg | Phe | Leu | Val | $^D$Pro$^L$Pro | 20.7 | 81 | 1287.6 |
| 6. | SEQ ID NO: 6 | Lys | Val | Tyr | Arg | Arg | Phe | Leu | Val | $^D$Pro$^L$Pro | 16.7 | 75 | 1256.6 |
| 7. | SEQ ID NO: 7 | Lys | Val | Tyr | Lys | Gly | Phe | Leu | Trp | $^D$Pro$^L$Pro | 19.5 | 64 | 1216.5 |

[a] %-purity of crude product. All compounds were purified by preparative HPLC-chromatography as indicated. Purities > 90%.

TABLE 2

Examples ex. 8–29 (n = 9)

| Example | SEQ. ID | P1 | P2 | P3 | P4 | P5 | P6 | P7 | P8 | P9 | Template | RT(') | %[a] | MS |
|---|---|---|---|---|---|---|---|---|---|---|---|---|---|---|
| 8. | SEQ ID NO: 8 | Arg | Phe | Leu | Arg | Arg | Arg | Leu | Phe | Arg | $^D$Pro$^L$Pro | 10.5 | 35 | 1495.9 |
| 9. | SEQ ID NO: 9 | Arg | Tyr | Leu | Arg | Arg | Arg | Leu | Tyr | Arg | $^D$Pro$^L$Pro | 8.8 | 46 | 1527.9 |
| 10. | SEQ ID NO: 10 | Arg | Phe | Phe | Arg | Arg | Arg | Leu | Phe | Arg | $^D$Pro$^L$Pro | 10.0 | 26 | 1529.9 |
| 11. | SEQ ID NO: 11 | Arg | Tyr | Tyr | Arg | Arg | Arg | Leu | Tyr | Arg | $^D$Pro$^L$Pro | 8.0 | 90 | 1577.9 |
| 12. | SEQ ID NO: 12 | Leu | Phe | Phe | Arg | Arg | Arg | Leu | Phe | Arg | $^D$Pro$^L$Pro | 10.2 | 52 | 1502.9 |
| 13. | SEQ ID NO: 13 | Leu | Tyr | Tyr | Arg | Arg | Arg | Leu | Tyr | Arg | $^D$Pro$^L$Pro | 8.4 | 30 | 1550.9 |
| 14. | SEQ ID NO: 14 | Arg | Phe | Leu | Phe | Arg | Arg | Leu | Leu | Arg | $^D$Pro$^L$Pro | 10.1 | 51 | 1468.9 |
| 15. | SEQ ID NO: 15 | Arg | Tyr | Leu | Tyr | Arg | Arg | Leu | Leu | Arg | $^D$Pro$^L$Pro | 8.8 | 55 | 1500.9 |
| 16. | SEQ ID NO: 16 | Leu | Phe | Leu | Phe | Arg | Arg | Leu | Phe | Arg | $^D$Pro$^L$Pro | 9.7 | 38 | 1459.9 |
| 17. | SEQ ID NO: 17 | Leu | Tyr | Leu | Tyr | Arg | Arg | Leu | Tyr | Arg | $^D$Pro$^L$Pro | 11.8 | 67 | 1507.9 |
| 18. | SEQ ID NO: 18 | Arg | Phe | Leu | Phe | Arg | Arg | Leu | Phe | Leu | $^D$Pro$^L$Pro | 10.3 | 57 | 1459.9 |
| 19. | SEQ ID NO: 19 | Arg | Tyr | Leu | Tyr | Arg | Arg | Leu | Tyr | Leu | $^D$Pro$^L$Pro | 11.7 | 66 | 1507.9 |
| 20. | SEQ ID NO: 20 | Phe | Leu | Leu | Phe | Arg | Arg | Leu | Phe | Arg | $^D$Pro$^L$Pro | 9.9 | 67 | 1459.9 |
| 21. | SEQ ID NO: 21 | Tyr | Leu | Leu | Tyr | Arg | Arg | Leu | Tyr | Arg | $^D$Pro$^L$Pro | 11.9 | 57 | 1507.9 |
| 22. | SEQ ID NO: 22 | Arg | Leu | Leu | Phe | Arg | Arg | Leu | Phe | Phe | $^D$Pro$^L$Pro | 10.1 | 68 | 1459.9 |
| 23. | SEQ ID NO: 23 | Arg | Leu | Leu | Tyr | Arg | Arg | Leu | Tyr | Tyr | $^D$Pro$^L$Pro | 11.5 | 63 | 1507.9 |
| 24. | SEQ ID NO: 24 | Arg | Phe | Leu | Arg | Phe | Arg | Leu | Phe | Arg | $^D$Pro$^L$Pro | 8.5 | 33 | 1502.9 |
| 25. | SEQ ID NO: 25 | Arg | Phe | Leu | Arg | Arg | Phe | Phe | Leu | Arg | $^D$Pro$^L$Pro | 10.3 | 30 | 1502.9 |
| 26. | SEQ ID NO: 26 | Arg | Tyr | Leu | Arg | Arg | Tyr | Tyr | Leu | Arg | $^D$Pro$^L$Pro | 12.6 | 65 | 1550.9 |
| 27. | SEQ ID NO: 27 | Leu | Tyr | Leu | Arg | Arg | Tyr | Leu | Tyr | Arg | $^D$Pro$^L$Pro | 10.1 | 29 | 1491.8 |
| 28. | SEQ ID NO: 28 | Leu | Leu | Phe | Phe | Arg | Arg | Leu | Phe | Arg | $^D$Pro$^L$Pro | 12.1 | 35 | 1443.8 |
| 29. | SEQ ID NO: 29 | Leu | Leu | Tyr | Tyr | Arg | Arg | Leu | Tyr | Arg | $^D$Pro$^L$Pro | 10.3 | 33 | 1491.8 |
| 30. | SEQ ID NO: 30 | Arg | Leu | Phe | Phe | Arg | Arg | Leu | Phe | Leu | $^D$Pro$^L$Pro | 12.1 | 35 | 1459.9 |
| 31. | SEQ ID NO: 31 | Arg | Leu | Tyr | Tyr | Arg | Arg | Leu | Tyr | Leu | $^D$Pro$^L$Pro | 10.3 | 33 | 1507.8 |

[a] %-purity of crude product. All compounds were purified by preparative HPLC-chromatography as indicated. Purities obtained > 90%.

TABLE 3

Examples ex. 32–58 (n = 10)

| Example | Sequ. ID | P1 | P2 | P3 | P4 | P5 | P6 | P7 | P8 | P9 | P10 | Template | RT(') | %[a] | MS |
|---|---|---|---|---|---|---|---|---|---|---|---|---|---|---|---|
| 32. | SEQ ID NO: 32 | Arg | Phe | Leu | Phe | Arg | Arg | Arg | Leu | Phe | Arg | $^D$Pro$^L$Pro | 10.2 | 37 | 1643.0 |
| 33. | SEQ ID NO: 33 | Arg | Tyr | Leu | Tyr | Arg | Arg | Arg | Leu | Tyr | Arg | $^D$Pro$^L$Pro | 8.3 | 41 | 1691.0 |
| 34. | SEQ ID NO: 34 | Arg | Phe | Phe | Phe | Arg | Arg | Arg | Leu | Leu | Arg | $^D$Pro$^L$Pro | 10.1 | 45 | 1643.0 |
| 35. | SEQ ID NO: 35 | Arg | Tyr | Tyr | Tyr | Arg | Arg | Arg | Leu | Leu | Arg | $^D$Pro$^L$Pro | 8.87 | 70 | 1691.0 |
| 36. | SEQ ID NO: 36 | Arg | Leu | Phe | Phe | Arg | Arg | Arg | Leu | Phe | Arg | $^D$Pro$^L$Pro | 10.4 | 56 | 1643.0 |
| 37. | SEQ ID NO: 37 | Leu | Tyr | Leu | Tyr | Arg | Arg | Arg | Leu | Tyr | Arg | $^D$Pro$^L$Pro | 9.6 | 35 | 1648.0 |
| 38. | SEQ ID NO: 38 | Arg | Phe | Leu | Phe | Arg | Arg | Arg | Leu | Phe | Leu | $^D$Pro$^L$Pro | 11.1 | 50 | 1600.0 |
| 39. | SEQ ID NO: 39 | Arg | Tyr | Leu | Tyr | Arg | Arg | Arg | Leu | Tyr | Leu | $^D$Pro$^L$Pro | 9.81 | 41 | 1648.0 |
| 40. | SEQ ID NO: 40 | Leu | Leu | Phe | Phe | Arg | Arg | Arg | Leu | Phe | Arg | $^D$Pro$^L$Pro | 11.8 | 58 | 1600.0 |
| 41. | SEQ ID NO: 41 | Arg | Leu | Phe | Phe | Arg | Arg | Arg | Leu | Phe | Leu | $^D$Pro$^L$Pro | 11.6 | 54 | 1600.0 |
| 42. | SEQ ID NO: 42 | Leu | Tyr | Tyr | Tyr | Arg | Arg | Arg | Leu | Leu | Arg | $^D$Pro$^L$Pro | 9.9 | 51 | 1648.0 |
| 43. | SEQ ID NO: 43 | Arg | Phe | Phe | Phe | Arg | Arg | Arg | Leu | Leu | Leu | $^D$Pro$^L$Pro | 11.3 | 49 | 1600.0 |
| 44. | SEQ ID NO: 44 | Arg | Tyr | Tyr | Tyr | Arg | Arg | Arg | Leu | Leu | Leu | $^D$Pro$^L$Pro | 9.9 | 63 | 1648.0 |
| 45. | SEQ ID NO: 45 | Arg | Leu | Leu | Phe | Arg | Gly | Arg | Phe | Phe | Arg | $^D$Pro$^L$Pro | 10.6 | 78 | 1543.9 |
| 46. | SEQ ID NO: 46 | Arg | Leu | Leu | Tyr | Arg | Gly | Arg | Tyr | Tyr | Arg | $^D$Pro$^L$Pro | 9.1 | 45 | 1591.9 |
| 47. | SEQ ID NO: 47 | Arg | Phe | Phe | Phe | Arg | Gly | Arg | Leu | Leu | Arg | $^D$Pro$^L$Pro | 10.4 | 43 | 1543.9 |
| 48. | SEQ ID NO: 48 | Arg | Tyr | Tyr | Tyr | Arg | Gly | Arg | Leu | Leu | Arg | $^D$Pro$^L$Pro | 8.8 | 48 | 1591.9 |
| 49. | SEQ ID NO: 49 | Leu | Phe | Leu | Phe | Arg | Gly | Arg | Leu | Phe | Arg | $^D$Pro$^L$Pro | 12.4 | 65 | 1500.9 |
| 50. | SEQ ID NO: 50 | Leu | Tyr | Leu | Tyr | Arg | Gly | Arg | Leu | Tyr | Arg | $^D$Pro$^L$Pro | 10.3 | 58 | 1548.9 |
| 51. | SEQ ID NO: 51 | Arg | Phe | Leu | Phe | Arg | Gly | Arg | Leu | Phe | Leu | $^D$Pro$^L$Pro | 12.3 | 42 | 1500.9 |
| 52. | SEQ ID NO: 52 | Arg | Tyr | Leu | Tyr | Arg | Gly | Arg | Leu | Tyr | Leu | $^D$Pro$^L$Pro | 10.6 | 20 | 1548.9 |
| 53. | SEQ ID NO: 53 | Leu | Arg | Phe | Phe | Arg | Leu | Arg | Leu | Phe | Arg | $^D$Pro$^L$Pro | 11.9 | 51 | 1600.0 |
| 54. | SEQ ID NO: 54 | Leu | Arg | Tyr | Tyr | Arg | Leu | Arg | Leu | Tyr | Arg | $^D$Pro$^L$Pro | 9.9 | 50 | 1648.0 |
| 55. | SEQ ID NO: 55 | Leu | Leu | Phe | Phe | Arg | Gly | Arg | Leu | Phe | Arg | $^D$Pro$^L$Pro | 12.5 | 50 | 1500.9 |

TABLE 3-continued

Examples ex. 32–58 (n = 10)

| Example | Sequ. ID | P1 | P2 | P3 | P4 | P5 | P6 | P7 | P8 | P9 | P10 | Template | RT(') | %[a] | MS |
|---|---|---|---|---|---|---|---|---|---|---|---|---|---|---|---|
| 56. | SEQ ID NO: 56 | Leu | Leu | Tyr | Tyr | Arg | Gly | Arg | Leu | Tyr | Arg | $^D$Pro$^L$Pro | 10.1 | 38 | 1548.9 |
| 57. | SEQ ID NO: 57 | Arg | Phe | Leu | Phe | Arg | Gly | Arg | Phe | Arg | Leu | $^D$Pro$^L$Pro | 11.3 | 57 | 1543.9 |
| 58. | SEQ ID NO: 58 | Arg | Tyr | Leu | Tyr | Arg | Gly | Arg | Tyr | Arg | Leu | $^D$Pro$^L$Pro | 10.8 | 56 | 1591.9 |

[a]%-purity of crude product. All compounds were purified by preparative HPLC-chromatography as indicated. Purities obtained > 90%.

TABLE 4

Examples ex. 59–70 (n = 11)

| Example | SEQ. ID | P1 | P2 | P3 | P4 | P5 | P6 | P7 | P8 | P9 | P10 | P11 | Template | RT(') | % | MS |
|---|---|---|---|---|---|---|---|---|---|---|---|---|---|---|---|---|
| 59. | SEQ ID NO: 59 | Arg | Leu | Phe | Leu | Arg | Arg | Arg | Phe | Phe | Arg | Leu | $^D$Pro$^L$Pro | 11.1 | 75 | 1756.2 |
| 60. | SEQ ID NO: 60 | Arg | Leu | Tyr | Leu | Arg | Arg | Arg | Tyr | Tyr | Arg | Leu | $^D$Pro$^L$Pro | 9.5 | 28 | 1804.2 |
| 61. | SEQ ID NO: 61 | Leu | Leu | Phe | Leu | Arg | Arg | Arg | Phe | Phe | Arg | Arg | $^D$Pro$^L$Pro | 10.8 | 65 | 1756.2 |
| 62. | SEQ ID NO: 62 | Arg | Leu | Phe | Leu | Arg | Arg | Arg | Leu | Phe | Arg | Phe | $^D$Pro$^L$Pro | 11.3 | 57 | 1756.2 |
| 63. | SEQ ID NO: 63 | Phe | Leu | Phe | Leu | Arg | Arg | Arg | Leu | Phe | Arg | Arg | $^D$Pro$^L$Pro | 11.1 | 76 | 1756.2 |
| 64. | SEQ ID NO: 64 | Tyr | Leu | Tyr | Leu | Arg | Arg | Arg | Leu | Tyr | Arg | Arg | $^D$Pro$^L$Pro | 9.5 | 70 | 1804.2 |
| 65. | SEQ ID NO: 65 | Arg | Leu | Phe | Leu | Arg | Gly | Arg | Phe | Phe | Leu | Arg | $^D$Pro$^L$Pro | 9.8 | 36 | 1700.1 |
| 66. | SEQ ID NO: 66 | Leu | Leu | Tyr | Tyr | Arg | Arg | Leu | Tyr | Tyr | Arg | Arg | $^D$Pro$^L$Pro | 9.9 | 47 | 1811.2 |
| 67. | SEQ ID NO: 67 | Leu | Tyr | Leu | Tyr | Arg | Arg | Tyr | Leu | Tyr | Arg | Arg | $^D$Pro$^L$Pro | 9.9 | 47 | 1811.2 |
| 68. | SEQ ID NO: 68 | Arg | Arg | Phe | Phe | Arg | Arg | Leu | Phe | Phe | Leu | Leu | $^D$Pro$^L$Pro | 12.4 | 46 | 1747.2 |
| 69. | SEQ ID NO: 69 | Arg | Leu | Tyr | Tyr | Arg | Arg | Leu | Tyr | Tyr | Arg | Leu | $^D$Pro$^L$Pro | 9.9 | 51 | 1811.2 |
| 70. | SEQ ID NO: 70 | Arg | Leu | Phe | Phe | Arg | Gly | Arg | Phe | Phe | Arg | Leu | $^D$Pro$^L$Pro | 10.5 | 26 | 1691.1 |

[a]%-purity of crude product. All compounds were purified by preparative HPLC-chromatography as indicated. Purities > 90%.

TABLE 5

Examples ex. 71–84 (n = 14)

| Example | SEQ. ID | P1 | P2 | P3 | P4 | P5 | P6 | P7 | P8 | P9 | P10 |
|---|---|---|---|---|---|---|---|---|---|---|---|
| 71. | SEQ ID NO: 71 | Arg | Tyr | Leu | Leu | Tyr | Arg | Arg | Arg | Tyr | Leu |
| 72. | SEQ ID NO: 72 | Arg | Leu | Leu | Tyr | Tyr | Arg | Arg | Arg | Tyr | Leu |
| 73. | SEQ ID NO: 73 | Arg | Leu | Leu | Leu | Tyr | Arg | Arg | Arg | Tyr | Leu |
| 74. | SEQ ID NO: 74 | Arg | Phe | Leu | Phe | Leu | Arg | Arg | Arg | Phe | Phe |
| 75. | SEQ ID NO: 75 | Arg | Tyr | Leu | Tyr | Leu | Arg | Arg | Arg | Tyr | Tyr |
| 76. | SEQ ID NO: 76 | Arg | Phe | Leu | Phe | Leu | Arg | Arg | Arg | Phe | Leu |
| 77. | SEQ ID NO: 77 | Arg | Tyr | Leu | Tyr | Leu | Arg | Arg | Arg | Tyr | Leu |
| 78. | SEQ ID NO: 78 | Arg | Arg | Leu | Leu | Phe | Arg | Arg | Arg | Phe | Leu |
| 79. | SEQ ID NO: 79 | Arg | Arg | Leu | Leu | Tyr | Arg | Arg | Arg | Tyr | Leu |
| 80. | SEQ ID NO: 80 | Arg | Arg | Leu | Tyr | Tyr | Arg | Arg | Arg | Tyr | Leu |
| 81. | SEQ ID NO: 81 | Arg | Arg | Leu | Leu | Tyr | Arg | Arg | Arg | Tyr | Leu |
| 82. | SEQ ID NO: 82 | Arg | Arg | Leu | Phe | Leu | Arg | Arg | Arg | Phe | Phe |
| 83. | SEQ ID NO: 83 | Arg | Arg | Leu | Tyr | Leu | Arg | Arg | Arg | Tyr | Tyr |
| 84. | SEQ ID NO: 84 | Arg | Arg | Leu | Tyr | Leu | Arg | Arg | Arg | Tyr | Leu |

| Example | SEQ. ID | P11 | P12 | P13 | P14 | Template | RT(') | % | MS |
|---|---|---|---|---|---|---|---|---|---|
| 71. | SEQ ID NO: 71 | Leu | Tyr | Arg | Arg | $^D$Pro$^L$Pro | 9.4 | 48 | 2236.7 |
| 72. | SEQ ID NO: 72 | Leu | Tyr | Arg | Arg | $^D$Pro$^L$Pro | 9.4 | 29 | 2236.7 |
| 73. | SEQ ID NO: 73 | Tyr | Tyr | Arg | Arg | $^D$Pro$^L$Pro | 9.4 | 50 | 2236.7 |
| 74. | SEQ ID NO: 74 | Leu | Phe | Arg | Arg | $^D$Pro$^L$Pro | 10.9 | 78 | 2206.7 |
| 75. | SEQ ID NO: 75 | Leu | Tyr | Arg | Arg | $^D$Pro$^L$Pro | 9.1 | 51 | 2286.7 |
| 76. | SEQ ID NO: 76 | Phe | Leu | Arg | Arg | $^D$Pro$^L$Pro | 10.6 | 79 | 2172.7 |
| 77. | SEQ ID NO: 77 | Tyr | Leu | Arg | Arg | $^D$Pro$^L$Pro | 9.1 | 53 | 2236.7 |
| 78. | SEQ ID NO: 78 | Leu | Phe | Phe | Arg | $^D$Pro$^L$Pro | 11.0 | 42 | 2172.7 |
| 79. | SEQ ID NO: 79 | Leu | Tyr | Tyr | Arg | $^D$Pro$^L$Pro | 9.4 | 91 | 2236.7 |
| 80. | SEQ ID NO: 80 | Leu | Tyr | Tyr | Arg | $^D$Pro$^L$Pro | 9.3 | 72 | 2286.7 |
| 81. | SEQ ID NO: 81 | Tyr | Tyr | Leu | Arg | $^D$Pro$^L$Pro | 9.5 | 65 | 2236.7 |
| 82. | SEQ ID NO: 82 | Leu | Phe | Phe | Arg | $^D$Pro$^L$Pro | 11.1 | 34 | 2206.7 |
| 83. | SEQ ID NO: 83 | Leu | Tyr | Tyr | Arg | $^D$Pro$^L$Pro | 9.3 | 89 | 2286.7 |
| 84. | SEQ ID NO: 84 | Tyr | Leu | Tyr | Arg | $^D$Pro$^L$Pro | 9.3 | 47 | 2236.7 |

[a]%-purity of crude product. All compounds were purified by preparative HPLC-chromatography. Purities > 90%.

TABLE 6

| Examples ex. 85–95 (n = 16) | | | | | | | | | | | | |
|---|---|---|---|---|---|---|---|---|---|---|---|---|
| Example | Sequ. ID | P1 | P2 | P3 | P4 | P5 | P6 | P7 | P8 | P9 | P10 | P11 |
| 85. | SEQ ID NO: 85 | Lys | Arg | Leu | Lys | Tyr | Val | Arg | Arg | Arg | Trp | Leu |
| 86. | SEQ ID NO: 86 | Lys | Arg | Leu | Lys | Tyr | Val | Arg | Arg | Gly | Trp | Leu |
| 87. | SEQ ID NO: 87 | Lys | Arg | Leu | Lys | Tyr | Trp | Arg | Arg | Arg | Trp | Tyr |
| 88. | SEQ ID NO: 88 | Lys | Arg | Leu | Tyr | Tyr | Trp | Arg | Arg | Arg | Trp | Tyr |
| 89. | SEQ ID NO: 89 | Lys | Arg | Leu | Lys | Tyr | Trp | Arg | Arg | Gly | Trp | Tyr |
| 90. | SEQ ID NO: 90 | Lys | Arg | Leu | Tyr | Tyr | Trp | Arg | Arg | Gly | Trp | Tyr |
| 91. | SEQ ID NO: 91 | Lys | Arg | Leu | Tyr | Tyr | Trp | Arg | Arg | Arg | Trp | Lys |
| 92. | SEQ ID NO: 92 | Lys | Arg | Leu | Lys | Tyr | Trp | Arg | Arg | Gly | Trp | Lys |
| 93. | SEQ ID NO: 93 | Tyr | Lys | Leu | Arg | Leu | Lys | Tyr | Arg | Arg | Trp | Lys |
| 94. | SEQ ID NO: 94 | Tyr | Lys | Leu | Gln | Leu | Lys | Trp | Arg | Arg | Phe | Lys |
| 95. | SEQ ID NO: 95 | Tyr | Lys | Leu | Gln | Leu | Gln | Lys | Lys | Gly | Trp | Gln |

| Example | Sequ. ID | P12 | P13 | P14 | P15 | P16 | Template | RT(') | % | MS |
|---|---|---|---|---|---|---|---|---|---|---|
| 85. | SEQ ID NO: 85 | Val | Lys | Val | Leu | Arg | $^D$Pro$^L$Pro | 13.7 | 70 | 2346.0 |
| 86. | SEQ ID NO: 86 | Val | Lys | Val | Leu | Arg | $^D$Pro$^L$Pro | 13.9 | 38 | 2246.8 |
| 87. | SEQ ID NO: 87 | Val | Lys | Val | Leu | Arg | $^D$Pro$^L$Pro | 13.6 | 34 | 2483.1 |
| 88. | SEQ ID NO: 88 | Val | Phe | Val | Leu | Arg | $^D$Pro$^L$Pro | 14.3 | 35 | 2537.1 |
| 89. | SEQ ID NO: 89 | Val | Lys | Val | Leu | Arg | $^D$Pro$^L$Pro | 13.7 | 27 | 2383.9 |
| 90. | SEQ ID NO: 90 | Val | Phe | Val | Leu | Arg | $^D$Pro$^L$Pro | 14.6 | 39 | 2437.9 |
| 91. | SEQ ID NO: 91 | Val | Phe | Val | Leu | Arg | $^D$Pro$^L$Pro | 13.9 | 22 | 2402.1 |
| 92. | SEQ ID NO: 92 | Val | Lys | Val | Leu | Arg | $^D$Pro$^L$Pro | 13.4 | 26 | 2348.9 |
| 93. | SEQ ID NO: 93 | Tyr | Arg | Val | Lys | Phe | $^D$Pro$^L$Pro | 12.5 | 34 | 2402.1 |
| 94. | SEQ ID NO: 94 | Tyr | Gln | Val | Lys | Phe | $^D$Pro$^L$Pro | 12.1 | 21 | 2348.9 |
| 95. | SEQ ID NO: 95 | Tyr | Gln | Val | Lys | Phe | $^D$Pro$^L$Pro | 11.1 | 84 | 2383.9 | a)%-purity of crude product. All compounds were purified by preparative HPLC-chromatography. Purities > 90%.

TABLE 7

| Example | Sequ. ID | P1 | P2 | P3 | P4 | P5 | P6 | P7 | P8 | P9 | P10 | P11 | P12 | Template | RT(') | % | MS |
|---|---|---|---|---|---|---|---|---|---|---|---|---|---|---|---|---|---|
| | | | | | | | Examples ex. 96-128 (n = 12); | | | | | | | | | | |
| 96. | SEQ ID NO: 96 | Leu | Arg | Leu | Val | Tyr | Lys | Gly | Phe | Leu | Tyr | Arg | Val | DPro-LPro | 21.6 | 92 | 1703.1 |
| 97. | SEQ ID NO: 97 | Leu | Arg | Phe | Val | Tyr | Lys | Gly | Phe | Leu | Tyr | Arg | Val | DPro-LPro | 21.6 | 95 | 1737.1 |
| 98. | SEQ ID NO: 98 | Leu | Arg | Thr | Val | Tyr | Lys | Gly | Phe | Leu | Tyr | Arg | Val | DPro-LPro | 20.0 | 93 | 1691.1 |
| 99. | SEQ ID NO: 99 | Leu | Arg | Lys | Val | Arg | Lys | Gly | Arg | Leu | Tyr | Arg | Val | DPro-LPro | 15.7 | 99 | 1720.2 |
| 100. | SEQ ID NO: 100 | Leu | Arg | Lys | Trp | Tyr | Lys | Gly | Phe | Trp | Tyr | Arg | Val | DPro-LPro | 17.6 | 60 | 1878.3 |
| 101. | SEQ ID NO: 101 | Leu | Arg | Lys | Val | Tyr | Arg | Gly | Phe | Leu | Tyr | Arg | Val | DPro-LPro | 17.8 | 61 | 1845.3 |
| 102. | SEQ ID NO: 102 | Leu | Lys | Lys | Val | Tyr | Arg | Arg | Phe | Leu | Lys | Lys | Val | DPro-LPro | 15.9 | 59 | 1754.3 |
| 103. | SEQ ID NO: 103 | Leu | Arg | Leu | Lys | Tyr | Arg | Arg | Phe | Lys | Tyr | Arg | Val | DPro-LPro | 20.5 | 36 | 1874.3 |
| 104. | SEQ ID NO: 104 | Leu | Arg | Leu | Glu | Tyr | Arg | Arg | Phe | Glu | Tyr | Arg | Val | DPro-LPro | 21.5 | 99 | 1876.2 |
| 105. | SEQ ID NO: 105 | Leu | Arg | Leu | Gln | Tyr | Arg | Arg | Phe | Gln | Tyr | Arg | Val | DPro-LPro | 21.5 | 58 | 1874.2 |
| 106. | SEQ ID NO: 106 | Leu | Arg | Leu | Lys | Lys | Arg | Arg | Trp | Lys | Tyr | Arg | Val | DPro-LPro | 18.1 | 51 | 1879.7 |
| 107. | SEQ ID NO: 107 | Leu | Arg | Leu | Lys | Trp | Arg | Arg | Lys | Lys | Tyr | Arg | Val | DPro-LPro | 20.2 | 28 | 1879.7 |
| 108. | SEQ ID NO: 108 | Leu | Arg | Trp | Phe | Tyr | Arg | Arg | Phe | Leu | Tyr | Arg | Val | DPro-LPro | 20.9 | 40 | 1948.7 |
| 109. | SEQ ID NO: 109 | Lys | Val | Arg | Gln | Arg | Arg | Arg | Lys | Leu | Lys | Leu | Val | DPro-LPro | 15.7 | 75 | 1833.7 |
| 110. | SEQ ID NO: 110 | Leu | Arg | Leu | Gln | Tyr | Arg | Arg | Trp | Leu | Tyr | Arg | Val | DPro-LPro | 21.9 | 30 | 1913.3 |
| 111. | SEQ ID NO: 111 | Leu | Arg | Leu | Gln | Trp | Arg | Arg | Trp | Gln | Tyr | Arg | Val | DPro-LPro | 22.6 | 75 | 1897.3 |
| 112. | SEQ ID NO: 112 | Leu | Arg | Leu | Gln | Lys | Arg | Arg | Lys | Gln | Tyr | Arg | Val | DPro-LPro | 18.9 | 49 | 1878.3 |
| 113. | SEQ ID NO: 113 | Leu | Arg | Leu | Gln | Trp | Arg | Arg | Phe | Gln | Tyr | Arg | Val | DPro-LPro | 21.2 | 75 | 1878.3 |
| 114. | SEQ ID NO: 114 | Phe | Arg | Leu | Gln | Tyr | Arg | Arg | Phe | Gln | Tyr | Arg | Val | DPro-LPro | 22.3 | 50 | 1908.3 |
| 115. | SEQ ID NO: 115 | Leu | Arg | Leu | Gln | Tyr | Arg | Arg | Phe | Gln | Tyr | Arg | Phe | DPro-LPro | 22.4 | 99 | 1908.3 |
| 116. | SEQ ID NO: 116 | Phe | Arg | Leu | Gln | Tyr | Arg | Arg | Phe | Gln | Tyr | Arg | Phe | DPro-LPro | 22.9 | 99 | 1956.3 |
| 117. | SEQ ID NO: 117 | Leu | Arg | Leu | Gln | Tyr | Arg | Arg | Phe | Gln | Trp | Arg | Val | DPro-LPro | 22.7 | 15 | 1897.3 |
| 118. | SEQ ID NO: 118 | Leu | Arg | Trp | Gln | Tyr | Arg | Arg | Phe | Gln | Tyr | Arg | Val | DPro-LPro | 21.9 | 21 | 1947.3 |
| 119. | SEQ ID NO: 119 | Gln | Val | Arg | Phe | Arg | Arg | Arg | Lys | Leu | Gln | Leu | Arg | DPro-LPro | 17.2 | 46 | 1831.3 |
| 120. | SEQ ID NO: 120 | Phe | Arg | Leu | Lys | Lys | Arg | Arg | Trp | Lys | Tyr | Arg | Val | DPro-LPro | 10.5 | 52 | 1912.4 |
| 121. | SEQ ID NO: 121 | Cha | Arg | Leu | Lys | Lys | Arg | Arg | Trp | Lys | Tyr | Arg | Val | DPro-LPro | 10.6 | 36 | 1918.4 |
| 122. | SEQ ID NO: 122 | hPhe | Arg | Leu | Lys | Lys | Arg | Arg | Trp | Lys | Tyr | Arg | Val | DPro-LPro | 9.6 | 95 | 1926.4 |
| 123. | SEQ ID NO: 123 | 2Nal | Arg | Leu | Lys | Lys | Arg | Arg | Trp | Lys | Tyr | Arg | Val | DPro-LPro | 9.6 | 69 | 1962.4 |
| 124. | SEQ ID NO: 124 | 1Nal | Arg | Leu | Lys | Lys | Arg | Arg | Trp | Lys | Tyr | Arg | Val | DPro-LPro | 11.8 | 47 | 1962.4 |
| 125. | SEQ ID NO: 125 | Nle | Arg | Leu | Lys | Lys | Arg | Arg | Trp | Lys | Tyr | Arg | Val | DPro-LPro | 10.3 | 63 | 1878.4 |
| 126. | SEQ ID NO: 126 | Leu | Arg | Phe | Lys | Lys | Arg | Arg | Trp | Lys | Tyr | Leu | Val | DPro-LPro | 10.6 | 44 | 1912.4 |
| 127. | SEQ ID NO: 127 | Leu | Arg | Cha | Lys | Lys | Arg | Arg | Trp | Lys | Tyr | Arg | Val | DPro-LPro | 10.8 | 41 | 1918.4 |
| 128. | SEQ ID NO: 128 | Leu | Arg | Y(bzl) | Lys | Lys | Arg | Arg | Trp | Lys | Tyr | Arg | Val | DPro-LPro | 11.5 | 23 | 2018.5 |
| | | | | | | | Examples ex. 129-161 (n = 12) | | | | | | | | | | |
| 129. | SEQ ID NO: 129 | Leu | Arg | Trp | Lys | Lys | Arg | Arg | Trp | Lys | Tyr | Arg | Val | DPro-LPro | 10.5 | 41 | 1951.4 |
| 130. | SEQ ID NO: 130 | Leu | Arg | hPhe | Lys | Lys | Arg | Arg | Trp | Lys | Tyr | Arg | Val | DPro-LPro | 10.6 | 32 | 1926.4 |
| 131. | SEQ ID NO: 131 | Leu | Arg | 2Nal | Lys | Lys | Arg | Arg | Trp | Lys | Tyr | Arg | Val | DPro-LPro | 11.0 | 42 | 1962.4 |
| 132. | SEQ ID NO: 132 | Leu | Arg | 1Nal | Lys | Lys | Arg | Arg | Trp | Lys | Tyr | Arg | Val | DPro-LPro | 10.9 | 43 | 1962.4 |
| 133. | SEQ ID NO: 133 | Leu | Arg | Val | Lys | Lys | Arg | Arg | Trp | Lys | Tyr | Arg | Val | DPro-LPro | 10.0 | 47 | 1864.3 |
| 134. | SEQ ID NO: 134 | Leu | Arg | Ile | Lys | Lys | Arg | Arg | Trp | Lys | Tyr | Arg | Val | DPro-LPro | 10.3 | 34 | 1878.4 |
| 135. | SEQ ID NO: 135 | Leu | Arg | Nle | Lys | Lys | Arg | Arg | Trp | Lys | Tyr | Arg | Val | DPro-LPro | 10.3 | 90 | 1878.4 |
| 136. | SEQ ID NO: 136 | Leu | Arg | Leu | Lys | Lys | Arg | Arg | Tyr | Lys | Tyr | Arg | Val | DPro-LPro | 9.9 | 48 | 1855.3 |

TABLE 7-continued

| # | SEQ ID NO | | | | | | | | | | | | | | |
|---|---|---|---|---|---|---|---|---|---|---|---|---|---|---|---|
| 137. | SEQ ID NO: 137 | Leu | Arg | Leu | Lys | Lys | Arg | Arg | Trp | Lys | Tyr | Y(Bzl) | Arg | DPro-LPro | 11.0 | 33 | 1945.4 |
| 138. | SEQ ID NO: 138 | Leu | Arg | Leu | Lys | Lys | Arg | Arg | Trp | Lys | Tyr | hPhe | Arg | DPro-LPro | 10.3 | 52 | 1853.3 |
| 139. | SEQ ID NO: 139 | Leu | Arg | Leu | Lys | Lys | Arg | Arg | Trp | Lys | Tyr | 2Nal | Arg | DPro-LPro | 10.5 | 53 | 1889.4 |
| 140. | SEQ ID NO: 140 | Leu | Arg | Leu | Lys | Lys | Arg | Arg | Trp | Lys | Tyr | 1Nal | Arg | DPro-LPro | 10.5 | 34 | 1889.4 |
| 141. | SEQ ID NO: 141 | Leu | Arg | Leu | Lys | Lys | Arg | Arg | Trp | Lys | Tyr | Val | Arg | DPro-LPro | 9.9 | 49 | 1791.3 |
| 142. | SEQ ID NO: 142 | Leu | Arg | Leu | Lys | Lys | Arg | Arg | Trp | Lys | Tyr | Ile | Arg | DPro-LPro | 10.0 | 32 | 1805.3 |
| 143. | SEQ ID NO: 143 | Leu | Arg | Leu | Lys | Lys | Arg | Arg | Trp | Lys | Tyr | Leu | Arg | DPro-LPro | 10.1 | 46 | 1805.3 |
| 144. | SEQ ID NO: 144 | Leu | Arg | Leu | Lys | Lys | Arg | Arg | Trp | Lys | Tyr | Nle | Arg | DPro-LPro | 10.1 | 43 | 1805.3 |
| 145. | SEQ ID NO: 145 | Leu | Arg | Leu | Lys | Lys | Arg | Arg | Trp | Lys | Tyr | His | Arg | DPro-LPro | 9.8 | 56 | 1829.3 |
| 146. | SEQ ID NO: 146 | Leu | Arg | Leu | Lys | Lys | Arg | Arg | Trp | Lys | Tyr | Trp | Arg | DPro-LPro | 10.9 | 45 | 1862.3 |
| 147. | SEQ ID NO: 147 | Leu | Arg | Leu | Lys | Lys | Arg | Arg | Trp | Lys | Phe | Y(Bzl) | Arg | DPro-LPro | 11.4 | 15 | 1968.5 |
| 148. | SEQ ID NO: 148 | Leu | Arg | Leu | Lys | Lys | Arg | Arg | Trp | Lys | Trp | Trp | Arg | DPro-LPro | 10.8 | 56 | 1901.4 |
| 149. | SEQ ID NO: 149 | Leu | Arg | Leu | Lys | Lys | Arg | Arg | Trp | Lys | hPhe | Trp | Arg | DPro-LPro | 11.3 | 32 | 1876.4 |
| 150. | SEQ ID NO: 150 | Leu | Arg | Leu | Lys | Lys | Arg | Arg | Trp | Lys | 1Nal | Trp | Arg | DPro-LPro | 11.6 | 24 | 1912.4 |
| 151. | SEQ ID NO: 151 | Leu | Arg | Leu | Lys | Lys | Arg | Arg | Trp | Lys | Val | Trp | Arg | DPro-LPro | 10.6 | 48 | 1814.3 |
| 152. | SEQ ID NO: 152 | Leu | Arg | Leu | Lys | Lys | Arg | Arg | Trp | Lys | Ile | Trp | Arg | DPro-LPro | 10.9 | 40 | 1828.3 |
| 153. | SEQ ID NO: 153 | Leu | Arg | Leu | Lys | Lys | Arg | Arg | Trp | Lys | Leu | Trp | Arg | DPro-LPro | 10.7 | 18 | 1828.3 |
| 154. | SEQ ID NO: 154 | Leu | Arg | Leu | Lys | Lys | Arg | Arg | Trp | Lys | Nle | Trp | Arg | DPro-LPro | 11.2 | 40 | 1828.3 |
| 155. | SEQ ID NO: 155 | Leu | Arg | Leu | Lys | Lys | Arg | Arg | Trp | Lys | Tyr | Phe | Arg | DPro-LPro | 10.6 | 35 | 1926.4 |
| 156. | SEQ ID NO: 156 | Leu | Arg | Leu | Lys | Lys | Arg | Arg | Trp | Lys | Tyr | Cha | Arg | DPro-LPro | 11.2 | 60 | 1932.5 |
| 157. | SEQ ID NO: 157 | Leu | Arg | Leu | Lys | Lys | Arg | Arg | Trp | Lys | Tyr | Y(Bzl) | Arg | DPro-LPro | 11.7 | 37 | 2032.5 |
| 158. | SEQ ID NO: 158 | Leu | Arg | Leu | Lys | Lys | Arg | Arg | Trp | Lys | Tyr | Trp | Arg | DPro-LPro | 10.4 | 69 | 1965.4 |
| 159. | SEQ ID NO: 159 | Leu | Arg | Leu | Lys | Lys | Arg | Arg | Trp | Lys | Tyr | hPhe | Arg | DPro-LPro | 10.8 | 95 | 1940.4 |
| 160. | SEQ ID NO: 160 | Leu | Arg | Leu | Lys | Lys | Arg | Arg | Trp | Lys | Tyr | 2Nal | Arg | DPro-LPro | 11.2 | 30 | 1976.5 |
| 161. | SEQ ID NO: 161 | Leu | Arg | Leu | Lys | Lys | Arg | Arg | Trp | Lys | Tyr | 1Nal | Arg | DPro-LPro | 11.3 | 89 | 1976.5 |

Examples ex. 162–194 (n = 12)

| # | SEQ ID NO | | | | | | | | | | | | | | |
|---|---|---|---|---|---|---|---|---|---|---|---|---|---|---|---|
| 162. | SEQ ID NO: 162 | Leu | Arg | Leu | Lys | Lys | Arg | Arg | Trp | Lys | Tyr | Ile | Arg | DPro-LPro | 10.5 | 56 | 1892.4 |
| 163. | SEQ ID NO: 163 | Leu | Arg | Leu | Lys | Lys | Arg | Arg | Trp | Lys | Tyr | Nle | Arg | DPro-LPro | 10.5 | 91 | 1892.4 |
| 164. | SEQ ID NO: 164 | Leu | Arg | Leu | Lys | Lys | Arg | Arg | Trp | Lys | Tyr | His | Arg | DPro-LPro | 8.6 | 88 | 1916.4 |
| 165. | SEQ ID NO: 165 | Leu | Trp | Leu | Lys | Lys | Arg | Arg | Trp | Lys | Tyr | Val | Arg | DPro-LPro | 10.4 | 55 | 1908.4 |
| 166. | SEQ ID NO: 166 | Leu | Leu | Leu | Lys | Lys | Arg | Arg | Trp | Lys | Tyr | Val | Arg | DPro-LPro | 10.6 | 88 | 1835.3 |
| 167. | SEQ ID NO: 167 | Leu | Thr | Leu | Lys | Lys | Arg | Arg | Trp | Lys | Tyr | Val | Arg | DPro-LPro | 10.4 | 94 | 1823.3 |
| 168. | SEQ ID NO: 168 | Leu | Gln | Leu | Lys | Lys | Arg | Arg | Trp | Lys | Tyr | Val | Arg | DPro-LPro | 10.4 | 55 | 1850.3 |
| 169. | SEQ ID NO: 169 | Leu | Arg | Leu | Leu | Lys | Arg | Arg | Trp | Lys | Tyr | Val | Arg | DPro-LPro | 10.9 | 62 | 1863.3 |
| 170. | SEQ ID NO: 170 | Leu | Arg | Leu | Arg | Lys | Arg | Arg | Trp | Lys | Tyr | Val | Arg | DPro-LPro | 10.3 | 45 | 1906.4 |
| 171. | SEQ ID NO: 171 | Leu | Arg | Leu | Thr | Lys | Arg | Arg | Trp | Lys | Tyr | Val | Arg | DPro-LPro | 10.4 | 94 | 1851.3 |
| 172. | SEQ ID NO: 172 | Leu | Arg | Leu | Gln | Lys | Arg | Arg | Trp | Lys | Tyr | Val | Arg | DPro-LPro | 10.3 | 76 | 1878.3 |
| 173. | SEQ ID NO: 173 | Leu | Arg | Leu | Lys | Leu | Arg | Arg | Trp | Lys | Tyr | Val | Arg | DPro-LPro | 11.9 | 43 | 1863.3 |
| 174. | SEQ ID NO: 174 | Leu | Arg | Leu | Lys | His | Arg | Arg | Trp | Lys | Tyr | Val | Arg | DPro-LPro | 10.5 | 53 | 1887.3 |
| 175. | SEQ ID NO: 175 | Leu | Arg | Leu | Lys | Arg | Arg | Arg | Trp | Lys | Tyr | Val | Arg | DPro-LPro | 10.4 | 37 | 1906.4 |
| 176. | SEQ ID NO: 176 | Leu | Arg | Leu | Lys | Thr | Arg | Arg | Trp | Lys | Tyr | Val | Arg | DPro-LPro | 11.4 | 45 | 1851.3 |
| 177. | SEQ ID NO: 177 | Leu | Leu | Leu | Lys | Lys | Arg | Arg | Trp | Lys | Tyr | Val | Arg | DPro-LPro | 10.8 | 58 | 1835.3 |
| 178. | SEQ ID NO: 178 | Leu | His | Leu | Lys | Lys | Arg | Arg | Trp | Lys | Tyr | Val | Arg | DPro-LPro | 10.2 | 46 | 1859.3 |
| 179. | SEQ ID NO: 179 | Leu | Lys | Leu | Lys | Lys | Arg | Arg | Trp | Lys | Tyr | Val | Arg | DPro-LPro | 10.3 | 53 | 1850.3 |
| 180. | SEQ ID NO: 180 | Leu | Thr | Leu | Lys | Lys | Arg | Arg | Trp | Lys | Tyr | Val | Arg | DPro-LPro | 10.4 | 82 | 1823.3 |
| 181. | SEQ ID NO: 181 | Leu | Arg | Leu | Lys | Lys | Arg | Arg | Trp | Lys | Tyr | Val | Arg | DPro-LPro | 10.4 | 36 | 1850.3 |

TABLE 7-continued

| # | SEQ ID NO | P1 | P2 | P3 | P4 | P5 | P6 | P7 | P8 | P9 | P10 | P11 | Template | | | Mass |
|---|---|---|---|---|---|---|---|---|---|---|---|---|---|---|---|---|
| 182. | SEQ ID NO: 182 | Leu | Arg | Leu | Lys | Lys | Arg | Trp | Lys | Tyr | Arg | Val | DPro-LPro | 10.8 | 70 | 1908.4 |
| 183. | SEQ ID NO: 183 | Leu | Arg | Leu | Lys | Lys | Arg | His | Lys | Tyr | Arg | Val | DPro-LPro | 10.3 | 74 | 1859.3 |
| 184. | SEQ ID NO: 184 | Leu | Arg | Leu | Lys | Lys | Arg | Lys | Lys | Tyr | Arg | Val | DPro-LPro | 10.2 | 50 | 1850.3 |
| 185. | SEQ ID NO: 185 | Leu | Arg | Bip | Lys | Lys | Arg | Arg | Lys | Tyr | Arg | Val | DPro-LPro | 11.4 | 39 | 1988.5 |
| 186. | SEQ ID NO: 186 | Leu | Arg | 4ClPhe | Lys | Lys | Arg | Arg | Lys | Tyr | Arg | Val | DPro-LPro | 11.1 | 53 | 1946.8 |
| 187. | SEQ ID NO: 187 | Leu | Arg | AmPhe | Lys | Lys | Arg | Arg | Lys | Tyr | Arg | Val | DPro-LPro | 8.6 | 83 | 1927.4 |
| 188. | SEQ ID NO: 188 | Leu | Arg | S(Bzl) | Lys | Lys | Arg | Arg | Lys | Tyr | Arg | Val | DPro-LPro | 10.4 | 66 | 1942.4 |
| 189. | SEQ ID NO: 189 | Leu | Arg | T(Bzl) | Lys | Lys | Arg | Arg | Lys | Tyr | Arg | Val | DPro-LPro | 10.8 | 51 | 1956.4 |
| 190. | SEQ ID NO: 190 | Leu | Arg | Orn | Lys | Lys | Arg | Arg | Lys | Tyr | Arg | Val | DPro-LPro | 8.4 | 84 | 1879.3 |
| 191. | SEQ ID NO: 191 | Leu | Arg | Leu | Lys | Lys | Arg | Bip | Lys | Tyr | Arg | Val | DPro-LPro | 11.3 | 39 | 1988.5 |
| 192. | SEQ ID NO: 192 | Leu | Arg | Leu | Lys | Lys | Arg | 4ClPhe | Lys | Tyr | Arg | Val | DPro-LPro | 10.9 | 50 | 1946.8 |
| 193. | SEQ ID NO: 193 | Leu | Arg | Leu | Lys | Lys | Arg | AmPhe | Lys | Tyr | Arg | Val | DPro-LPro | 9.2 | 82 | 1927.4 |
| 194. | SEQ ID NO: 194 | Leu | Arg | Leu | Lys | Lys | Arg | S(Bzl) | Lys | Tyr | Arg | Val | DPro-LPro | 10.7 | 80 | 1942.4 |

Examples ex. 195–227 (n = 12)

| # | SEQ ID NO | P1 | P2 | P3 | P4 | P5 | P6 | P7 | P8 | P9 | P10 | P11 | Template | | | Mass |
|---|---|---|---|---|---|---|---|---|---|---|---|---|---|---|---|---|
| 195. | SEQ ID NO: 195 | Leu | Arg | T(Bzl) | Lys | Lys | Arg | Trp | Lys | Tyr | Arg | Val | DPro-LPro | 10.7 | 37 | 1956.4 |
| 196. | SEQ ID NO: 196 | Leu | Arg | Orn | Lys | Lys | Arg | Trp | Lys | Tyr | Arg | Val | DPro-LPro | 9.2 | 48 | 1879.3 |
| 197. | SEQ ID NO: 197 | Leu | Arg | Leu | Lys | Lys | Arg | Bip | Lys | Tyr | Arg | Val | DPro-LPro | 10.8 | 57 | 1915.4 |
| 198. | SEQ ID NO: 198 | Leu | Arg | Leu | Lys | Lys | Arg | 4ClPhe | Lys | Tyr | Arg | Val | DPro-LPro | 10.4 | 49 | 1873.8 |
| 199. | SEQ ID NO: 199 | Leu | Arg | Leu | Lys | Lys | Arg | AmPhe | Lys | Tyr | Arg | Val | DPro-LPro | 9.8 | 43 | 1854.3 |
| 200. | SEQ ID NO: 200 | Leu | Arg | Leu | Lys | Lys | Arg | S(Bzl) | Lys | Tyr | Arg | Val | DPro-LPro | 10.3 | 48 | 1869.3 |
| 201. | SEQ ID NO: 201 | Leu | Arg | Leu | Lys | Lys | Arg | T(Bzl) | Lys | Tyr | Arg | Val | DPro-LPro | 10.2 | 87 | 1883.4 |
| 202. | SEQ ID NO: 202 | Leu | Arg | Leu | Lys | Lys | Arg | Orn | Lys | Tyr | Arg | Val | DPro-LPro | 9.7 | 31 | 1806.3 |
| 203. | SEQ ID NO: 203 | Leu | Arg | Leu | Lys | Lys | Arg | Trp | Lys | Bip | Arg | Val | DPro-LPro | 11.6 | 46 | 1938.5 |
| 204. | SEQ ID NO: 204 | Leu | Arg | Leu | Lys | Lys | Arg | Trp | Lys | 4ClPhe | Arg | Val | DPro-LPro | 11.21 | 48 | 1896.8 |
| 205. | SEQ ID NO: 205 | Leu | Arg | Leu | Lys | Lys | Arg | Trp | Lys | S(Bzl) | Arg | Val | DPro-LPro | 11.5 | 32 | 1892.4 |
| 206. | SEQ ID NO: 206 | Leu | Arg | Leu | Lys | Lys | Arg | Trp | Lys | T(Bzl) | Arg | Val | DPro-LPro | 11.5 | 36 | 1906.4 |
| 207. | SEQ ID NO: 207 | Leu | Arg | Leu | Lys | Lys | Arg | Trp | Lys | Orn | Arg | Val | DPro-LPro | 9.4 | 49 | 1829.3 |
| 208. | SEQ ID NO: 208 | Leu | Arg | Leu | Lys | Lys | Arg | Trp | Lys | Tyr | Arg | Bip | DPro-LPro | 11.7 | 37 | 2002.5 |
| 209. | SEQ ID NO: 209 | Leu | Arg | Leu | Lys | Lys | Arg | Trp | Lys | Tyr | Arg | 4ClPhe | DPro-LPro | 11.0 | 32 | 1960.8 |
| 210. | SEQ ID NO: 210 | Leu | Arg | Leu | Lys | Lys | Arg | Trp | Lys | Tyr | Arg | AmPhe | DPro-LPro | 8.6 | 88 | 1941.4 |
| 211. | SEQ ID NO: 211 | Leu | Arg | Leu | Lys | Lys | Arg | Trp | Lys | Tyr | Arg | T(Bzl) | DPro-LPro | 10.9 | 51 | 1970.5 |
| 212. | SEQ ID NO: 212 | Leu | Arg | Leu | Lys | Lys | Arg | Trp | Lys | Tyr | Arg | Orn | DPro-LPro | 8.3 | 75 | 1893.4 |
| 213. | SEQ ID NO: 213 | Leu | Arg | Leu | Lys | Lys | Arg | Trp | Lys | Tyr | Arg | Val | DPro-LPro | 10.3 | 63 | 1836.3 |
| 214. | SEQ ID NO: 214 | Leu | Orn | Leu | Lys | Lys | Arg | Trp | Lys | Tyr | Arg | Val | DPro-LPro | 10.4 | 44 | 1864.3 |
| 215. | SEQ ID NO: 215 | Leu | Arg | Leu | Orn | Lys | Arg | Trp | Lys | Tyr | Arg | Val | DPro-LPro | 10.2 | 44 | 1836.3 |
| 216. | SEQ ID NO: 216 | Leu | Arg | Leu | Lys | Orn | Arg | Trp | Lys | Tyr | Arg | Val | DPro-LPro | 10.3 | 44 | 1864.3 |
| 217. | SEQ ID NO: 217 | Leu | Arg | Leu | Lys | Lys | Orn | Trp | Lys | Tyr | Arg | Val | DPro-LPro | 10.3 | 40 | 1836.3 |
| 218. | SEQ ID NO: 218 | Leu | Arg | Leu | Lys | Lys | Arg | Trp | Orn | Tyr | Arg | Val | DPro-LPro | 10.2 | 92 | 1836.3 |
| 219. | SEQ ID NO: 219 | Leu | Arg | Leu | Lys | Lys | Arg | Trp | Gln | Tyr | Arg | Val | DPro-LPro | 10.4 | 92 | 1850.3 |
| 220. | SEQ ID NO: 220 | Leu | Arg | Leu | Lys | Lys | Arg | Trp | Tyr | Tyr | Arg | Val | DPro-LPro | 10.5 | 88 | 1913.4 |
| 221. | SEQ ID NO: 221 | Leu | Arg | Leu | Lys | Lys | Arg | Trp | His | Tyr | Arg | Val | DPro-LPro | 10.4 | 49 | 1887.3 |
| 222. | SEQ ID NO: 222 | Leu | Arg | Leu | Lys | Lys | Arg | Trp | Arg | Tyr | Arg | Val | DPro-LPro | 10.3 | 53 | 1906.4 |
| 223. | SEQ ID NO: 223 | Leu | Arg | Leu | Lys | Lys | Arg | Trp | Thr | Tyr | Arg | Val | DPro-LPro | 10.5 | 84 | 1851.3 |
| 224. | SEQ ID NO: 224 | Leu | Arg | Leu | Lys | Lys | Arg | Trp | Gln | Tyr | Arg | Val | DPro-LPro | 10.5 | 52 | 1878.3 |
| 225. | SEQ ID NO: 225 | Leu | Arg | Leu | Lys | Lys | Arg | Trp | Lys | Tyr | Tyr | Val | DPro-LPro | 10.6 | 54 | 1885.3 |
| 226. | SEQ ID NO: 226 | Leu | Arg | Leu | Lys | Lys | Arg | Trp | Lys | Tyr | Trp | Val | DPro-LPro | 10.9 | 47 | 1908.4 |
| 227. | SEQ ID NO: 227 | Leu | Arg | Leu | Lys | Lys | Arg | Bip | Lys | Bip | Arg | Val | DPro-LPro | 12.3 | 50 | 1975.5 |

TABLE 7-continued

Examples ex. 228–255 (n = 12)

| Example | Sequ. ID | P1 | P2 | P3 | P4 | P5 | P6 | P7 | P8 | P9 | P10 | P11 | P12 | Template | | MS |
|---|---|---|---|---|---|---|---|---|---|---|---|---|---|---|---|---|
| 228. | SEQ ID NO: 228 | Leu | Leu | Arg | Lys | Arg | Lys | Arg | Bip | Tyr | Lys | Arg | Val | $^D$Pro-$^L$Pro | 10.9 | 46 | 1943.4 |
| 229. | SEQ ID NO: 229 | Leu | Leu | Lys | Lys | Lys | Arg | Bip | Arg | Tyr | Lys | Arg | Val | $^D$Pro-$^L$Pro | 10.9 | 41 | 1943.4 |
| 230. | SEQ ID NO: 230 | Trp | Leu | Lys | Lys | Lys | Arg | Bip | Lys | Tyr | Lys | Arg | Val | $^D$Pro-$^L$Pro | 11.0 | 73 | 1945.4 |
| 231. | SEQ ID NO: 231 | Trp | Leu | Arg | Lys | Lys | Arg | Bip | Lys | Tyr | Lys | Arg | Val | $^D$Pro-$^L$Pro | 11.0 | 71 | 1973.5 |
| 232. | SEQ ID NO: 232 | Trp | Leu | Lys | Lys | Arg | Bip | Lys | Arg | Tyr | Lys | Arg | Val | $^D$Pro-$^L$Pro | 11.0 | 71 | 1973.5 |
| 233. | SEQ ID NO: 233 | Trp | Leu | Lys | Lys | Lys | Bip | Lys | Arg | Tyr | Lys | Arg | Val | $^D$Pro-$^L$Pro | 12.4 | 60 | 2033.6 |
| 234. | SEQ ID NO: 234 | Trp | Leu | Lys | Lys | Arg | Bip | Lys | Arg | Tyr | Lys | Arg | Val | $^D$Pro-$^L$Pro | 12.4 | 85 | 2033.6 |
| 235. | SEQ ID NO: 235 | Leu | Leu | Arg | Lys | Arg | Bip | Lys | Arg | Tyr | Lys | Arg | Val | $^D$Pro-$^L$Pro | 11.6 | 50 | 2185.7 |
| 236. | SEQ ID NO: 236 | 4ClPhe | Leu | Arg | Lys | Arg | Bip | Lys | Tyr | Bip | Lys | Arg | Val | $^D$Pro-$^L$Pro | 10.7 | 39 | 1983.9 |
| 237. | SEQ ID NO: 237 | 4ClPhe | Leu | Lys | Lys | Arg | Bip | Lys | Tyr | Bip | Lys | Arg | Val | $^D$Pro-$^L$Pro | 13.0 | 36 | 2043.9 |
| 238. | SEQ ID NO: 238 | 4ClPhe | Leu | Lys | Lys | Arg | Bip | Lys | Bip | Tyr | Lys | Arg | Bip | $^D$Pro-$^L$Pro | 12.9 | 52 | 2108.0 |
| 239. | SEQ ID NO: 239 | 4ClPhe | Leu | Lys | Lys | Arg | Bip | Lys | Bip | Bip | Lys | Arg | Bip | $^D$Pro-$^L$Pro | 12.6 | 68 | 2168.1 |
| 240. | SEQ ID NO: 240 | 4ClPhe | Leu | Arg | Lys | Arg | Bip | Arg | Tyr | Val | Lys | Arg | Val | $^D$Pro-$^L$Pro | 11.7 | 46 | 2011.9 |
| 241. | SEQ ID NO: 241 | 4ClPhe | Leu | Lys | Lys | Arg | Bip | Arg | Tyr | Val | Lys | Arg | Val | $^D$Pro-$^L$Pro | 11.8 | 41 | 2011.9 |
| 242. | SEQ ID NO: 242 | Trp | Leu | Lys | Lys | Arg | Bip | Lys | Tyr | Val | Lys | Arg | Val | $^D$Pro-$^L$Pro | 11.8 | 48 | 2013.9 |
| 243. | SEQ ID NO: 243 | 4ClPhe | Leu | Arg | Lys | Arg | Bip | Arg | Tyr | Val | Lys | Arg | Val | $^D$Pro-$^L$Pro | 11.9 | 38 | 2041.9 |
| 244. | SEQ ID NO: 244 | Trp | Leu | Arg | Lys | Arg | Bip | Arg | Tyr | Val | Lys | Arg | Val | $^D$Pro-$^L$Pro | 11.9 | 74 | 2041.9 |
| 245. | SEQ ID NO: 245 | Trp | Leu | Arg | Lys | Arg | Bip | Lys | Bip | Val | Lys | Arg | Val | $^D$Pro-$^L$Pro | 13.2 | 66 | 2102.0 |
| 246. | SEQ ID NO: 246 | Trp | Leu | Lys | Lys | Arg | Bip | Lys | Bip | Val | Lys | Arg | Val | $^D$Pro-$^L$Pro | 13.2 | 49 | 2102.0 |
| 247. | SEQ ID NO: 247 | Leu | Leu | Lys | Lys | Arg | Trp | Lys | Tyr | Val | Lys | Arg | Val | $^D$Pro-Gly | 9.5 | 58 | 1838.3 |
| 248. | SEQ ID NO: 248 | Arg | Leu | Lys | Lys | Arg | Trp | Lys | Tyr | Val | Lys | Arg | Val | $^D$Pro-Arg | 9.3 | 57 | 1937.4 |
| 249. | SEQ ID NO: 249 | Arg | Leu | Lys | Lys | Arg | Trp | Lys | Tyr | Val | Lys | Arg | Val | $^D$Pro-Tyr | 9.9 | 29 | 1944.4 |
| 250. | SEQ ID NO: 250 | Arg | Leu | Lys | Lys | Arg | Trp | Lys | Tyr | Val | Lys | Arg | Val | $^D$Pro-Phe | 9.9 | 34 | 1928.4 |
| 251. | SEQ ID NO: 251 | Arg | Leu | Lys | Lys | Arg | Trp | Lys | Tyr | Val | Lys | Arg | Val | $^D$Pro-Trp | 10.7 | 25 | 1967.5 |
| 252. | SEQ ID NO: 252 | Arg | Leu | Lys | Lys | Arg | Trp | Lys | Tyr | Val | Lys | Arg | Val | $^D$Pro-Leu | 10.5 | 21 | 1894.4 |
| 253. | SEQ ID NO: 253 | Arg | Leu | Lys | Lys | Arg | Trp | Lys | Tyr | Val | Lys | Arg | Val | $^D$Pro-Ile | 10.4 | 42 | 1894.4 |
| 254. | SEQ ID NO: 254 | Arg | Leu | Lys | Lys | Arg | Trp | Lys | Tyr | Val | Lys | Arg | Val | $^D$Pro-Cha | 11.2 | 36 | 1934.5 |
| 255. | SEQ ID NO: 255 | Arg | Leu | Lys | Lys | Arg | Trp | Lys | Tyr | Val | Lys | Arg | Val | $^D$Pro-2Nal | 11.4 | 27 | 1978.5 |

All products were purified by preparative HPLC-chromatography. Purities > 90%.

Examples ex. 256–286 (n = 12)

| Example | Sequ. ID | P1 | P2 | P3 | P4 | P5 | P6 | P7 | P8 | P9 | P10 | P11 | P12 | Template | MS |
|---|---|---|---|---|---|---|---|---|---|---|---|---|---|---|---|
| 256. | SEQ ID NO: 256 | Leu | Arg | Leu | Lys | Lys | Arg | Arg | Trp | Lys | Tyr | Arg | Val | $^D$Pro-A8'-1 | 1990.5 |
| 257. | SEQ ID NO: 257 | Leu | Arg | Leu | Lys | Lys | Arg | Arg | Trp | Lys | Tyr | Arg | Val | $^D$Pro-A8'-2 | 2018.3 |
| 258. | SEQ ID NO: 258 | Leu | Arg | Leu | Lys | Lys | Arg | Arg | Trp | Lys | Tyr | Arg | Val | $^D$Pro-A8'-3 | 2086.4 |
| 259. | SEQ ID NO: 259 | Leu | Arg | Leu | Lys | Lys | Arg | Arg | Trp | Lys | Tyr | Arg | Val | $^D$Pro-A8'-4 | 2086.4 |
| 260. | SEQ ID NO: 260 | Leu | Arg | Leu | Lys | Lys | Arg | Arg | Trp | Lys | Tyr | Arg | Val | $^D$Pro-A8'-5 | 1978.3 |
| 261. | SEQ ID NO: 261 | Leu | Arg | Leu | Lys | Lys | Arg | Arg | Trp | Lys | Tyr | Arg | Val | $^D$Pro-A8'-6 | 2023.3 |
| 262. | SEQ ID NO: 262 | Leu | Arg | Leu | Lys | Lys | Arg | Arg | Trp | Lys | Tyr | Arg | Val | $^D$Pro-A8'-7 | 1934.3 |
| 263. | SEQ ID NO: 263 | Leu | Arg | Leu | Lys | Lys | Arg | Arg | Trp | Lys | Tyr | Arg | Val | $^D$Pro-A8'-8 | 1948.2 |
| 264. | SEQ ID NO: 264 | Leu | Arg | Leu | Lys | Lys | Arg | Arg | Trp | Lys | Tyr | Arg | Val | $^D$Pro-A8'-9 | 1962.2 |
| 265. | SEQ ID NO: 265 | Leu | Arg | Leu | Lys | Lys | Arg | Arg | Trp | Lys | Tyr | Arg | Val | $^D$Pro-A8'-10 | 1976.3 |
| 266. | SEQ ID NO: 266 | Leu | Arg | Leu | Lys | Lys | Arg | Arg | Trp | Lys | Tyr | Arg | Val | $^D$Pro-A8'-11 | 1962.2 |
| 267. | SEQ ID NO: 267 | Leu | Arg | Leu | Lys | Lys | Arg | Arg | Trp | Lys | Tyr | Arg | Val | $^D$Pro-A8'-12 | 2002.3 |

TABLE 7-continued

| | | | | | | | | | | | |
|---|---|---|---|---|---|---|---|---|---|---|---|
| 268. | SEQ ID NO: 268 | Leu | Arg | Leu | Lys | Lys | Arg | Trp | Lys | Tyr | Arg | Val | DPro-A8-13 | 2016.3 |
| 269. | SEQ ID NO: 269 | Leu | Arg | Leu | Lys | Lys | Arg | Trp | Lys | Tyr | Arg | Val | DPro-A8-14 | 1976.3 |
| 270. | SEQ ID NO: 270 | Leu | Arg | Leu | Lys | Lys | Arg | Trp | Lys | Tyr | Arg | Val | DPro-A8-15 | 1996.2 |
| 271. | SEQ ID NO: 271 | Leu | Arg | Leu | Lys | Lys | Arg | Trp | Lys | Tyr | Arg | Val | DPro-A8-16 | 2011.4 |
| 272. | SEQ ID NO: 272 | Leu | Arg | Leu | Lys | Lys | Arg | Trp | Lys | Tyr | Arg | Val | DPro-A8-17 | 2049.3 |
| 273. | SEQ ID NO: 273 | Leu | Arg | Leu | Lys | Lys | Arg | Trp | Lys | Tyr | Arg | Val | DPro-A8-18 | 2063.4 |
| 274. | SEQ ID NO: 274 | Leu | Arg | Leu | Lys | Lys | Arg | Trp | Lys | Tyr | Arg | Val | DPro-A8-19 | 2072.3 |
| 275. | SEQ ID NO: 275 | Leu | Arg | Leu | Lys | Lys | Arg | Trp | Lys | Tyr | Arg | Val | DPro-A8-20 | 2046.4 |
| 276. | SEQ ID NO: 276 | Leu | Arg | Leu | Lys | Lys | Gly | Trp | Lys | Tyr | Arg | Val | DPro-LPro | 1779.2 |
| 277. | SEQ ID NO: 277 | Leu | Tyr | Leu | Lys | Lys | Arg | Trp | Lys | Tyr | Tyr | Val | (c1)-1 | 2023.2 |
| 278. | SEQ ID NO: 278 | Leu | Trp | Leu | Lys | Lys | Arg | Trp | Lys | Tyr | Tyr | Val | DPro-LPro | 1892.3 |
| 279. | SEQ ID NO: 279 | Leu | Trp | Leu | Lys | Lys | Arg | Trp | Lys | Tyr | Trp | Val | DPro-LPro | 1915.4 |
| 280. | SEQ ID NO: 280 | Arg | Trp | Leu | Lys | Lys | Arg | Trp | Lys | Tyr | Tyr | Val | DPro-LPro | 1981.4 |
| 281. | SEQ ID NO: 281 | Arg | Trp | Leu | Lys | Lys | Arg | Trp | Lys | Tyr | Tyr | Val | DPro-LPro | 1958.4 |
| 282. | SEQ ID NO: 282 | Leu | Trp | Leu | Lys | Lys | Arg | Trp | Lys | Tyr | Tyr | Val | DPro-LPro | 1995.5 |
| 283. | SEQ ID NO: 283 | Leu | Trp | Leu | Lys | Lys | Arg | Trp | Lys | Tyr | Tyr | Arg | DPro-LPro | 1972.4 |
| 284. | SEQ ID NO: 284 | Arg | Trp | Leu | Lys | Lys | Arg | Trp | Lys | Tyr | Tyr | Arg | DPro-LPro | 2015.5 |
| 285. | SEQ ID NO: 285 | Leu | Arg | Leu | Lys | Lys | Y(Bzl) | Trp | Lys | Tyr | Arg | Val | DPro-LPro | 1975.5 |
| 286. | SEQ ID NO: 286 | Leu | Arg | Leu | Lys | Lys | DY(Bzl) | Trp | Lys | Tyr | Arg | Val | DPro-LPro | 1975.5 |

Examples ex. 287–300 (n = 12)

All products were purified by preparative HPLC-chromatography. Purities > 90%.

| | | | | | | | | | | | |
|---|---|---|---|---|---|---|---|---|---|---|---|
| 287. | SEQ ID NO: 287 | Bip | Trp | Leu | Lys | Lys | Arg | Trp | Lys | Tyr | Tyr | Arg | DPro-LPro | 2082.6 |
| 288. | SEQ ID NO: 288 | Thr | Thr | Leu | Lys | Lys | Arg | Trp | Lys | Tyr | Tyr | Arg | DPro-LPro | 1960.4 |
| 289. | SEQ ID NO: 289 | Arg | Bip | Leu | Lys | Lys | Arg | Trp | Lys | Tyr | Tyr | Arg | DPro-LPro | 2052.5 |
| 290. | SEQ ID NO: 290 | Arg | Thr | Thr | Lys | Lys | Arg | Trp | Lys | Tyr | Tyr | Arg | DPro-LPro | 1930.4 |
| 291. | SEQ ID NO: 291 | Arg | Arg | Leu | Lys | Lys | Arg | Trp | Lys | Tyr | Tyr | Arg | DPro-LPro | 2003.4 |
| 292. | SEQ ID NO: 292 | Arg | Arg | Leu | Lys | Arg | Arg | Trp | Lys | Tyr | Tyr | Arg | DPro-LPro | 2043.5 |
| 293. | SEQ ID NO: 293 | Arg | Arg | Leu | Gln | Lys | Arg | Trp | Lys | Tyr | Tyr | Arg | DPro-LPro | 2015.4 |
| 294. | SEQ ID NO: 294 | Lys | Arg | Leu | Lys | Lys | Arg | Trp | Lys | Tyr | Tyr | Arg | DPro-LPro | 1987.5 |
| 295. | SEQ ID NO: 295 | Tyr | Tyr | Leu | Lys | Lys | Arg | Trp | Lys | Tyr | Tyr | Arg | DPro-LPro | 2022.5 |
| 296. | SEQ ID NO: 296 | Trp | Trp | Leu | Lys | Lys | Arg | Trp | Lys | Tyr | Tyr | Arg | DPro-LPro | 2045.5 |
| 297. | SEQ ID NO: 297 | Val | Val | Leu | Lys | Lys | Arg | Trp | Lys | Tyr | Tyr | Arg | DPro-LPro | 2082.4 |
| 298. | SEQ ID NO: 298 | Gln | Gln | Leu | Lys | Lys | Arg | Trp | Lys | Tyr | Tyr | Arg | DPro-LPro | 1987.4 |
| 299. | SEQ ID NO: 299 | Cha | Trp | Leu | Lys | Lys | Arg | Trp | Lys | Tyr | Tyr | Arg | DPro-LPro | 2012.5 |
| 300. | SEQ ID NO: 300 | Y(bzl) | Trp | Leu | Lys | Lys | Arg | Trp | Lys | Tyr | Tyr | Arg | DPro-LPro | 2112.6 |

[a] %-purity of crude product. Purities of all compounds after prep. HPLC > 90%.

1.2. Procedure 2

Examples ex.256–275 were also synthesized using procedure 2.

The peptide synthesis was carried out by solid phase method using standard Fmoc chemistry on a peptide synthesizer-ABI 433A.

The first amino acid, Fmoc-Arg(Pbf)-OH (1.29 g, 1.2 equiv.) was coupled to the 2-chlorotritylchloride resin (Barlos et al. *Tetrahedron Lett.* 1989, 30, 3943–3946) (2 g, 0.83 mmol/g) in presence of DIEA (1.12 mL, 4 equiv.) in $CH_2Cl_2$ (20 mL), with swirling for 3 hr at room temperature. The resin was then washed with $3 \times CH_2Cl_2$/MeOH/DIEA(17:2:1), $3 \times CH_2Cl_2$, $2 \times DMF$, $2 \times CH_2Cl_2$, $2 \times MeOH$. Finally, the resin was dried under vacuum and the substitution level was measured by weight increase (~0.6 mmol/g)

The resin with the synthesized linear peptide, Fmoc-Arg(Pbf)-Trp(Boc)-Lys(Boc)-Tyr(tBu)-Arg(Pbf)-Val-$^D$Pro-212-Leu-Arg(Pbf)-Leu-Lys(Boc)Lys(Boc)-Arg(Pbf)-resin, was preferably divided into equal parts and placed in different reaction vessels in order to carry out the acylation reaction in parallel format. The coupling and deprotection reactions in the following steps were monitored by Kaiser's test (Kaiser et al. *Anal. Biochemistry* 1970, 43, 595).

Removal of Alloc Protecting Group:

To the linear peptide resin (100 mg in each reaction vessel) was added $Pd(PPh_3)_4$ (15 mg, 0.5 equiv.) under argon followed by dry $CH_2Cl_2$ (10 mL) and phenylsilane (17 μL, 30 equiv.). The reaction mixture was left for 1 hour in the dark, filtered, and the resin was washed twice with $CH_2Cl_2$, DMF, and $CH_2Cl_2$.

Acylation of 4-amino-proline Group:

To the resin was added the corresponding acylating agent (usually a carboxyxlic acid ($R^{64}$COOH, 3 equiv.), HBTU (22.3 mg, 4 equiv.), HOBt (8 mg, 4 equiv.) and DIEA (125 μL, 6 equiv.) in DMF (2 mL) for 1.5–2 hrs at room temperature. The resin was filtered, washed with $2 \times DMF$, $3 \times CH_2Cl_2$, $2 \times DMF$.

Deprotection of $N^\alpha$-Fmoc Group:

Deprotection of the Fmoc-group was achieved by treating the resin with 20% piperidine in DMF for 20 min. The resin was subsequently filtered and washed three times with DMF, and $CH_1Cl_2$, and twice with DMF, and $CH_2Cl_2$.

Cleavage of Peptide from the Resin:

The linear side-chain protected peptide was cleaved from the resin using $AcOH:TFE:CH_2Cl_2$ (2:2:6, v/v/v) for 2 hrs at room temperature. The resin was filtered off and washed twice with a mixture of AcOH:TFE:DCM and once with $CH_2Cl_2$. The filtrate was subsequently diluted with hexane (14 times by vol.) and concentrated. Evaporation was repeated twice with hexane to remove traces of AcOH. The residue was dried under vacuum. Yield of the linear protected peptide was generally about 40–50 mg.

Cyclization of the Linear Protected Peptide:

Cyclization was carried out in DMF at a concentration of 5 mg/mL using HATU (13.12 mg, 3 equiv.), HOAT (4.7 mg, 3 equiv.), DIEA (153 μL, 6 equiv.). The reaction mixture was stirred for 16 hrs at room temperature and the completion of reaction was monitored by HPLC. After the evaporation of DMF, $CH_3CN/H_2O$ (90/10, v/v) was added to the residue and extracted with DCM. The organic layer was washed once with water and evaporated to dryness. Dried under vacuum.

Cleavage of Side Chain Protecting Groups:

The final deprotection of the side-chain protecting groups was carried out by treating the peptide with TFA:triisopropylsilane:$H_2O$ (95:2.5:2.5, v/v/v) at room temperature for 3 hrs. TFA was then evaporated and the residue triturated with cold ether.

Purification:

The crude peptides thus obtained were analyzed and purified by HPLC on a VYDAC C18 preparative column using 5–60% $CH_3CN/H_2O+0.1\%$ TFA in 30 min as gradient and a flow rate of 10 ml/min. The purity of the final peptide was checked by analytical HPLC and by ESI-MS. Analytical data are shown in table 7.

1.3. Procedure 3

Procedure 3 describes the synthesis of peptides having disulfide β-strand linkages.

a) n=8::The peptides are synthesized according to procedure 1 starting with the amino acid at position P4, coupled to the resin. The linear peptides are synthesized on solid support according to procedure 1 in the following sequence: P5-P6-P7-P8-$^D$Pro-Pro-P1-P2-P3-P4-resin, where at positions P2 and P7 Fmoc-Cys(Acm)OH or Fmoc-hCys(Acm)OH are incorporated. The linear peptides are cleaved and cyclized as described in procedure 1. The cyclized side chain protected β-hairpin mimetics are dissolved in methanol (0.5 ml) to which is added dropwise a solution of iodine in methanol (1N, 1.5 equiv.) at room temperature. The reaction mixture is stirred for 4 hours at room temperature and the solvent evaporated. The crude product is subsequently deprotected and purified as described in procedure 1.

b) n=9::The peptides are synthesized according to procedure 1 starting with the amino acid at position P5, coupled to the resin. The linear peptides are synthesized on solid support according to procedure 1 in the following sequence: P6-P7-P8-P9-$^D$Pro-Pro-P1-P2-P3-P4-P5-resin, where at positions P2 and P8 Fmoc-Cys(Acm)OH or Fmoc-hCys(Acm)OH are incorporated. The linear peptides are cleaved and cyclized as described in procedure 1. The cyclized side chain protected β-hairpin mimetics are dissolved in methanol (0.5 ml) to which is added dropwise a solution of iodine in methanol (1N, 1.5 equiv.) at room temperature. The reaction mixture is stirred for 4 hours at room temperature and the solvent evaporated. The crude product is subsequently deprotected and purified as described in procedure 1.

c) n=10::The peptides are synthesized according to procedure 1 starting with the amino acid at position P5, coupled to the resin. The linear peptides are synthesized on solid support according to procedure 1 in the following sequence: P6-P7-P8-P9-P10-$^D$Pro-Pro-P1-P2-P3-P4-P5-resin, where at positions P3 and P8 Fmoc-Cys(Acm)OH or Fmoc-hCys(Acm)OH are incorporated. The linear peptides are cleaved and cyclized as described in procedure 1. The cyclized side chain protected β-hairpin mimetics are dissolved in methanol (0.5 ml) to which is added dropwise a solution of iodine in methanol (1N, 1.5 equiv.) at room temperature. The reaction mixture is stirred for 4 hours at room temperature and the solvent evaporated. The crude product is subsequently deprotected and purified as described in procedure 1.

d) n=11::The peptides are synthesized according to procedure 1 starting with the amino acid at position P5, coupled to the resin. The linear peptides are synthesized on solid support according to procedure 1 in the following sequence: P6-P7-P8-P9-P10-P11-$^D$Pro-Pro-P1-P2-P3-P4-P5-resin, or P6-P7-P8-P9-P10-P11-$^D$Pro-Pro-P1-P2-P3-P4, or P5-P6-

P7-P8-P9-P10-P11-$^D$Pro-Pro-P1-P2-P3-P4-P5-resin, where at positions P2, P4, P8 and P10 Fmoc-Cys(Acm)OH or Fmoc-hCys(Acm)OH are incorporated. The linear peptides are cleaved and cyclized as described in procedure 1. The cyclized side chain protected β-hairpin mimetics are dissolved in methanol (0.5 ml) to which is added dropwise a solution of iodine in methanol (1N, 1.5 equiv.) at room temperature. The reaction mixture is stirred for 4 hours at room temperature and the solvent evaporated. The crude product is subsequently deprotected and purified as described in procedure 1.

e) n=12::The peptides are synthesized according to procedure 1 starting with the amino acid at position P6, coupled to the resin. The linear peptides are synthesized on solid support according to procedure 1 in the following sequence; P7-P8-P9-P10-P11-P12-$^D$Pro-Pro-P1-P2-P3-P4-P5-P6-resin, or P7-P8-P9-P10-P11-$^D$Pro-Pro-P1-P2-P3-P4-P5-P6-resin, or P7-P8-P9-P10-P11-$^D$Pro-Pro-P1-P2-P3-P4-P5-P6-resin, where at positions P2, P4, P9 and P11 Fmoc-Cys(Acm)OH or Fmoc-hCys(Acm)OH are incorporated. The linear peptides are cleaved and cyclized as described in procedure 1. The cyclized side chain protected β-hairpin mimetics are dissolved in methanol (0.5 ml) to which is added dropwise a solution of iodine in methanol (1N, 1.5 equiv.) at room temperature. The reaction mixture is stirred for 4 hours at room temperature and the solvent evaporated. The crude product is subsequently deprotected and purified as described in procedure 1.

Ex.301:

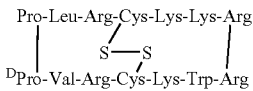

Following procedure 3 NH$_2$Arg(Pbf)-Lys(Boc)-Lys(Boc)-Cys(Acm)-Arg(Pbf)-Leu-Pro-$^D$Pro-Val-Arg-Cys(Acm)-Lys(Boc)-Trp(Boc)-Arg(Pbf)-[SEQ ID NO:301], coupled to the resin, was synthesized on the resin, the linear side-chain protected peptide cleaved and cyclized, followed by disulfide formation, deprotection and preparative HPLC chromatography yielding the above product [SEQ ID NO:302] as a white amorphous powder. ESI-MS: 1806.2 ([M+H]+).

f) n=14::The peptides are synthesized according to procedure 1 starting with the amino acid at position P7, coupled to the resin. The linear peptides are synthesized on solid support according to procedure 1 in the following sequence: P8-P9-P10-P11-P12-P13-P14-$^D$Pro-Pro-P1-P2-P3-P4-P5-P6-P7-resin, or P8-P9-P10-P11-P12-P13-P14-$^D$Pro-Pro-P1-P2-P3-P4-P5-P6-P7-resin, or P8-P9-P10-P11-P12-P14-$^D$Pro-Pro-P1-P2-P3-P4-P5-P6-P7-resin, where at positions P3, P5, P10 and P12 Fmoc-Cys(Acm)OH or Fmoc-hCys(Acm)OH are incorporated. The linear peptides are cleaved and cyclized as described in procedure 1. The cyclized side chain protected β-hairpin mimetics are dissolved in methanol (0.5 ml) to which is added dropwise a solution of iodine in methanol (1N, 1.5 equiv.) at room temperature. The reaction mixture is stirred for 4 hours at room temperature and the solvent evaporated. The crude product is subsequently deprotected and purified as described in procedure 1.

g) n=16::The peptides are synthesized according to procedure 1 starting with the amino acid at position P8, coupled to the resin. The linear peptides are synthesized on solid support according to procedure 1 in the following sequence: P9-P10-P11-P12-P13-P14-P15-P16-$^D$Pro-Pro-P1-P2-P3-P4-P5-P6-P7-P8-resin, or P9-P10-P11-P12-P13-P14-P15-P16-$^D$Pro-Pro-P1-P2-P3-P4-P5-P6-P7-P8-resin, or P9-P10-P11-P12-P13-P14-P15-P16-$^D$Pro-Pro-P1-P2-P3-P4-P5-P6-P7-P8-resin, or P9-P10-P11-P12-P13-P14-P15-P16-$^D$Pro-Pro-P1-P2-P3-P4-P5-P6-P7-P8-resin, or P9-P10-P11-P12-P13-P14-P51-P16-$^D$Pro-Pro-P1-P2-P3-P4-P5-P6-P7-P8-resin, or P9-P10-P11-P12-P13-P14-P15-P16-$^D$Pro-Pro-P1-P2-P3-P4-P5-P6-P7-P8-resin, or P9-P10-P11-P12-P13-P14-P15-P16-$^D$Pro-Pro-P1-P2-P3-P4-P5-P6-P7-P8-resin, where at positions P2, P4, P6, P11, P13 and P15 Fmoc-Cys(Acm)OH or Fmoc-hCys(Acm)OH are incorporated. The linear peptides are cleaved and cyclized as described in procedure 1. The cyclized side chain protected β-hairpin mimetics are dissolved in methanol (0.5 ml) to which is added dropwise a solution of iodine in methanol (1N, 1.5 equiv.) at room temperature. The reaction mixture is stirred for 4 hours at room temperature and the solvent evaporated. The crude product is subsequently deprotected and purified as described in procedure 1.

1.4. Procedure 4

Procedure 4 describes the synthesis of peptides having amide β-strand linkages.

a) n=8::The peptides are synthesized according to procedure 1 starting with the amino acid at position P4, coupled to the resin. The linear peptides are synthesized on solid support according to procedure 1 in the following sequence: P5-P6-P7-P8-$^D$Pro-Pro-P1-P2-P3-P4-resin, where at position P2 Fmoc-Asp(OAllyl)OH or Fmoc-Glu(OAllyl)OH, and at position P7 Fmoc-Orn(Alloc)OH or Fmoc-Lys(Alloc)OH are incorporated. Alternatively, at position P2 Fmoc-Orn(Alloc)OH or Fmoc-Lys(Alloc)OH, and at position P7 Fmoc-Asp(OAllyl)OH or Fmoc-Glu(OAllyl)OH are incorporated. The linear peptides are cleaved and cyclized, and the alkyl groups are removed as described in procedure 2. The amide linkage is subsequently performed as described for the cyclization according to procedures 1 and 2, the side chain protective groups are removed and the products are purified as described in procedures 1 and 2.

b) n—9::The peptides are synthesized according to procedure 1 starting with the amino acid at position P5, coupled to the resin. The linear peptides are synthesized on solid support according to procedure 1 in the following sequence: P6-P7-P8-P9-$^D$Pro-Pro-P1-P2-P3-P4-P5-resin, where at position P2 Fmoc-Asp(OAllyl)OH or Fmoc-Glu(OAllyl)OH, and at position P8 Fmoc-Orn(Alloc)OH or Fmoc-Lys(Alloc)OH are incorporated. Alternatively, at position P2 Fmoc-Orn(Alloc)OH or Fmoc-Lys(Alloc)OH, and at position P8 Fmoc-Asp(OAllyl)OH or Fmoc-Glu(OAllyl)OH are incorporated. The linear peptides are cleaved and cyclized, and the alkyl groups are removed as described in procedure 2. The amide linkage is subsequently performed as described for the cyclization according to procedures 1 and 2, the side chain protective groups are removed and the products are purified as described in procedures 1 and 2.

c) n=10::The peptides are synthesized according to procedure 1 starting with the amino acid at position P5, coupled to the resin. The linear peptides are synthesized on solid support according to procedure 1 in the following sequence: P6-P7-P5-P9-P10-$^D$Pro-Pro-P1-P2-P3-P4-P5-resin, where at position P3 Fmoc-Asp(OAllyl)OH or Fmoc-Glu(OAllyl)OH, and at position P8 Fmoc-Orn(Alloc)OH or Fmoc-Lys(Alloc)OH are incorporated. Alternatively, at position P3 Fmoc-Orn(Alloc)OH or Fmoc-Lys(Alloc)OH, and at position P8 Fmoc-Asp(OAllyl)OH or Fmoc-Glu(OAllyl)OH are incorporated. The linear peptides are cleaved and cyclized, and the alkyl groups are removed as described in procedure 2. The amide linkage is subsequently performed as described for the cyclization according to procedures 1 and 2, the side chain protective groups are removed and the products are purified as described in procedures 1 and 2.

d) n=11::The peptides are synthesized according to procedure 1 starting with the amino acid at position P5, coupled to the resin. The linear peptides are synthesized on solid support according to procedure 1 in the following sequence: P6-P7-P8-P9-P10-P11-$^D$Pro-Pro-P1-P2-P3-P4-P5-resin, or P6-P7-P8-P9-P10-P11-$^D$Pro-Pro-P1-P2-P3-P4-P5-resin, or P6-P7-P8-P9-P10-P11-$^D$Pro-Pro-P1-P2-P3-P4-P5-resin; where at positions P2 and/or P4 Fmoc-Asp(OAllyl)OH or Fmoc-Glu(OAllyl)OH, and at positions P8 and/or P10 Fmoc-Orn(Alloc)OH or Fmoc-Lys(Alloc)OH are incorporated. Alternatively, at positions P2 and/or P4 Fmoc-Orn(Alloc)OH or Fmoc-Lys(Alloc)OH, and at positions P8 and/or P10 Fmoc-Asp(OAllyl)OH or Fmoc-Glu(OAllyl)OH are incorporated. The linear peptides are cleaved and cyclized, and the alkyl groups are removed as described in procedure 2. The amide linkage is subsequently performed as described for the cyclization according to procedures 1 and 2, the side chain protective groups are removed and the products are purified as described in procedures 1 and 2.

e) n=12::The peptides are synthesized according to procedure 1 starting with the amino acid at position P6, coupled to the resin. The linear peptides are synthesized on solid support according to procedure 1 in the following sequence: P7-P8-P9-P10-P11-P12-$^D$Pro-Pro-P1-P2-P3-P4-P5-P6-resin, or P7-P8-P9-P10-P11-P12-$^D$Pro-Pro-P1-P2-P3-P4-P5-P6-resin, or P7-P8-P9-P10-P11-P12-$^D$Pro-Pro-P1-P2-P3-P4-P5-P6-resin; where at positions P2 and/or P4 Fmoc-Asp(OAllyl)OH or Fmoc-Glu(OAllyl)OH, and at positions P9 and/or P11 Fmoc-Orn(Alloc)OH or Fmoc-Lys(Alloc)OH are incorporated. Alternatively, at positions P2 and/or P4 Fmoc-Orn(Alloc)OH or Fmoc-Lys(Alloc)OH, and at positions P9 and/or P11 Fmoc-Asp(OAllyl)OH or Fmoc-Glu(OAllyl)OH are incorporated. The linear peptides are cleaved and cyclized, and the alkyl groups are removed as described in procedure 2. The amide linkage is subsequently performed as described for the cyclization according to procedures 1 and 2, the side chain protective groups are removed and the products are purified as described in procedures 1 and 2.

f) n=14::The peptides are synthesized according to procedure 1 starting with the amino acid at position P7, coupled to the resin. The linear peptides are synthesized on solid support according to procedure 1 in the following sequence: P8-P9-P10-P11-P12-P3-P14-$^D$Pro-Pro-P1-P2-P3-P4-P5-P6-P7-resin, or P8-P9-P10-P11-P12-P13-P14-$^D$Pro-Pro-P1-P2-P3-P4-P5-P6-P7-resin, or P8-P9-P10-P11-P12-R14-$^D$Pro-Pro-P1-P2-P3-P4-P5-P6-P7-resin; where at positions P3 and/or P5 Fmoc-Asp(OAllyl)OH or Fmoc-Glu(OAllyl)OH, and at positions P10 and/or P12 Fmoc-Orn(Alloc)OH or Fmoc-Lys(Alloc)OH are incorporated. Alternatively, at positions P3 and/or P5 Fmoc-Orn(Alloc)OH or Fmoc-Lys(Alloc)OH, and at positions P10 and/or P12 Fmoc-Asp(OAllyl)OH or Fmoc-Glu(OAllyl)OH are incorporated. The linear peptides are cleaved and cyclized, and the alkyl groups are removed as described in procedure 2. The amide linkage was subsequently performed as described for the cyclization according to procedures 1 and 2, the side chain protective groups are removed and the products are purified as described in procedures 1 and 2.

g) n=16::The peptides are synthesized according to procedure 1 starting with the amino acid at position P7, coupled to the resin. The linear peptides are synthesized on solid support according to procedure 1 in the following sequence: P8-P9-P10-P11-P12-P13-P14-P15-P16-$^D$Pro-Pro-P1-P2-P3-P4-P5-P6-P7-resin, or P8-P9-P10-P11-P12-P13-P14-P15-P16-$^D$Pro-Pro-P1-P2-P3-P4-P5-P6-P7-resin, or P9-P9-P10-P11-P12-P4-P5-P16-$^D$Pro-Pro-P1-P2-P3-P4-P5-P6-P7-resin, or P8-P9-P10-P11-P12-P13-P14-P15-P16-$^D$Pro-Pro-P1-P2-P3-P4-P5-P6-P7-resin, or P8-P9-P10-P11-P12-P13-P14-P15-P16-$^D$Pro-Pro-P1-P2-P3-P4-P5-P6-P7-resin, or P8-P9-P10-P11-P12-P13-P14-P15-P16-$^D$Pro-Pro-P1-P2-P3-P4-P5-P6-P7-resin, or P8-P9-P10-P11-P12-P13-P14-P15-P16-$^D$Pro-Pro-P1-P2-P3-P4-P5-P6-P7-resin; where at positions P2 and/or P4 and/or P6 Fmoc-Asp(OAllyl)OH or Fmoc-Glu(OAllyl)OH, and at positions P11 and/or P13 and/or P15 Fmoc-Orn(Alloc)OH or Fmoc-Lys(Alloc)OH are incorporated. Alternatively, at positions P2 and/or P4 and/or P6 Fmoc-Orn(Alloc)OH or Fmoc-Lys(Alloc)OH, and at positions P11 and/or P13 and/or P15 Fmoc-Asp(OAllyl)OH or Fmoc-Glu(OAllyl)OH are incorporated. The linear peptides are cleaved and cyclized, and the alkyl groups are removed as described in procedure 2. The amide linkage is subsequently performed as described for the cyclization according to procedures 1 and 2, the side chain protective groups are removed and the products are purified as described in procedures 1 and 2.

Ex.302:

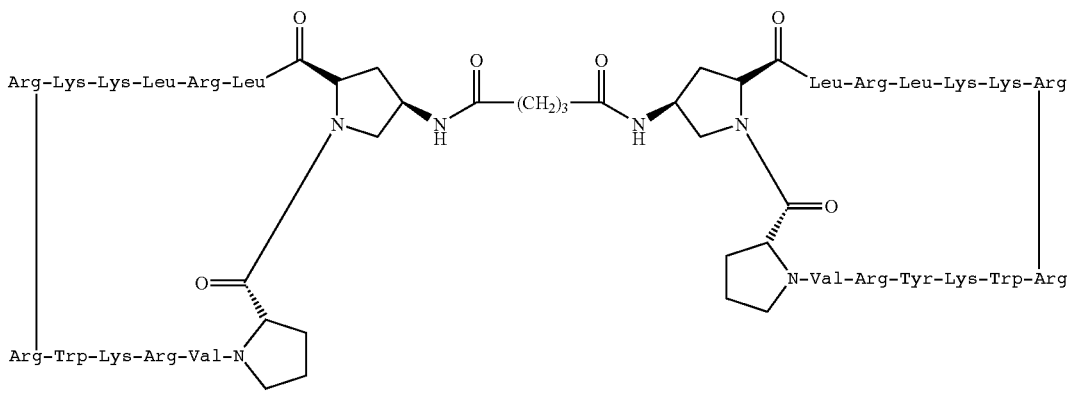

Following procedure 2 NH₂Arg(Pbf)-Trp(Boc)-Lys(Boc)-Tyr(tBu)-Arg(Pbf-ᴅPro-212-Leu-Arg(Pbf)-Leu-Lys(Boc)-Lys(Boc)-Arg(Pbf)-[SEQ ID NO:303], coupled to the resin, was prepared, the linear peptide cleaved and cyclized. The Alloc-group was removed from building block 212 as described in procedure 2, half of the resulting amine reacted with excess glutaric anhydride in pyridine and DMAP and the solvents were removed. The resulting acid was coupled with the second half of the above mentioned amine in DMF and in the presence of TATU, HOAt and DIEA. The protective groups were removed as described in procedure 2 and the product purified by preparative HPLC chromatography as described in procedure 2 to yield the above product [SEQ ID NO:304] as a white amorphous powder. ESI-MS: 3882.3 ([M+H]⁺).

2. Synthesis of Templates 2.1. The synthesis of (2S,4S)-4-[(Allyloxy)carbonylamino]-1-[(9H-fluoren-9-yl)methoxycarbonyl]-proline (212) and (2S,4R)-4-[(Allyloxy)carbonylamino]-1-[(9H-fluoren-9-yl)methoxy-carbonyl]proline (217) are shown in Schemes 42 and 43.

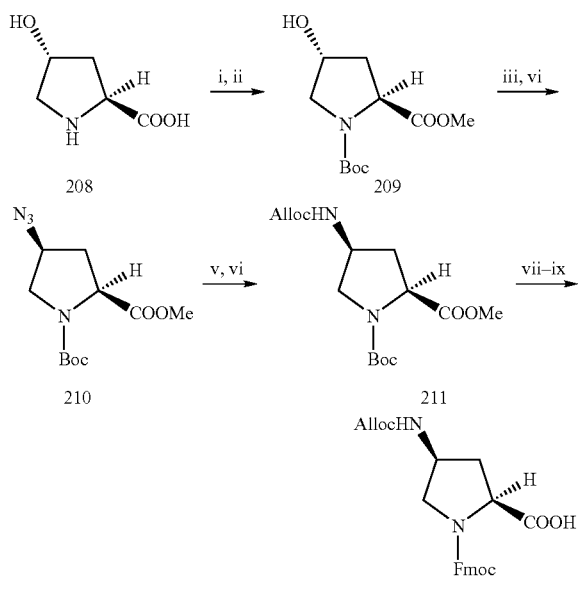

Scheme 42 i: SOCl₂, MeOH; ii: Boc₂O, DMAP, Et₃N; iii: pNO₂C₆H₄SO₂Cl, Et₃N; iv: NaN₃, DMF; v: SnCl₂, dioxane/H₂O; vi: ClCOOCH₂CH=CH₂ aq. NaHCO₃, dioxane: vii: LiOH, MeOH, H₂O; viii: TFA, CH₂Cl₂; ix: Fmoc—Osu, DIEA (2S,4S)-4-[(Allyloxy)carbonylamino]-1-[(9H-fluoren-9-yl)methoxycarbonyl]-proline (212)

i,ii: To a solution of (2S,4R)-4-hydroxyproline (30 g, 0.18 mol) in abs. methanol (300 ml) at 0° C. thionyl chloride (38 ml, 2.5 eq, 0.45 mol) was added dropwise. The solution was heated to reflux and stirred for 3 h under nitrogen. Then the solution was concentrated by rotary evaporation and the ester precipitated by adding diethylether. After filtration the white solid was washed with diethylether, then dried at HV: (2S,4R)-4-hydroxyproline-methylester.hydrochloride as a white solid (29.9 g, 90%). %). TLC (CH₂Cl₂/MeOH/water 70:28:2): R_f 0.82. [α]_D²⁰=−24.5 (c=1.01, MeOH). IR (KBr): 3378s (br.), 2950m, 2863w, 1745s, 1700s, 1590 m, 1450s, 1415s, 1360s, 1215s, 1185s, 1080m, 700m. ¹H-NMR (300 MHz, MeOH-d₄) 4.66–4.55 (m, 2H, H—C(4), H—C(2)); 3.85 (s, 3H, H₃—CO); 3.45 (dd, J=12.2, 3.8, 1H, H—C(5)); 3.37–3.25 (m, 1H, H—C(5)); 2.44–2.34 (m, 1H, H—C(3)), 2.27–2.12 (m, 1H, H—C(3)). ¹³C-NMR (75 MHz, MeOH-d₄): 170.8 (s, COOMe); 70.8 (d, C(4)); 59.6 (d, C(2)); 55.2 (t, C(5)); 54.2 (q, Me); 38.7 (t, C(3)). CI-MS (NH₃): 146.1 ([M-Cl]⁺).

30 g (0.17 mmol) of the above intermediate was dissolved in CH₂Cl₂ (300 ml), cooled to 0° C. and triethylamine (45 ml, 1.5 eq, 0.25 mol) was added dropwise. Then di-tert.-butyldicarbonate (54.0 g, 1.5 eq, 0.25 mmol) in CH₁Cl₂ (15 ml) and 4-N,N-dimethylaminopyridine (2.50 g, 0.1 eq, 17 mmol) was added and the solution stirred at room temperature overnight. Then the solution was washed with 1N aq. citric acid solution, sat. aq. NaHCO₃ solution, dried (Na₂SO₄), evaporated and the residue dried at high vaccum: (2S,4R)-4-Hydroxy-1-[(tert-butoxy)carbonyl]proline-methylester (209) as a white solid (39.6 g, 78%). TLC (CH₂Cl₂/MeOH 9:1): R_f 0.55. [α]_D²⁴=−55.9 (c=0.983, CHCl₃). IR (KBr): 3615w, 3440w (br.), 2980m, 2950m, 2880m, 1750s, 1705s, 1680s, 1480 m, 1410s, 1370s, 1340m, 1200s, 1160s, 1130m, 1090m, 1055w, 960w, 915w, 895w, 855m, 715m. ¹H-NMR (300 MHz, CDCl₃): 4.47–4.37 (m, 2H, H—C(4), H—C(2)); 3.73 (s, 3H, H₃C—O)); 3.62 (dd, J=11.8, 4.1, 1H, H—C(5)); 3.54–3.44 (m, 1H, H—C(5)); 2.32–2.25 (m, 1H, H—C(3)); 2.10–2.03 (m, 1H, H—C(3)); 1.46+1.41 (2s, 9H, tBu). ¹³C-NMR (75 MHz, CDCl₃): 173.6 (s, COOMe); 154.3+153.9 (2s, COOtBu); 80.3 (s, C-tBu); 70.0+69.3 (2d, C(4)); 57.9+57.4 (2d, C(2)); 54.6 (t, C(5)); 51.9 (q, Me); 39.0+38.4 (2t, C(3)); 28.1+27.6 (2q, tBu). CI-MS: 246.2 ([M+H]⁺); 190.1 ([M-tBu+H]⁺); 146.1 ([M-BOC+H]⁺).

iii,iv: 39 g (0.16 mol) of 209 was dissolved in CH₂Cl₂ (300 ml) followed by addition of 4-nitrobenzenesulfonyl chloride (46 g, 1.3 eq, 0.21 mol) and Et₃N (33 ml, 1.5 eq, 0.24 mol) at 0° C. Then the solution was stirred overnight and brought gradually to room temperature, washed with 1N hydrochloric acid, sat. aq. NaHCO₃ solution and dried (Na₂SO₄). The solvents were evaporated and the crude product was purified by filtration on silica gel with (2:1) hexane/AcOEt. The product was crystallized from hexane/AcOEt (2S,4S)-4-[(p-nitrobenzyl)sulfonyloxy]-1-[(tert-butoxy)carbonyl]proline methylester as white crystals (46.4 g, 65%). TLC (hexane/AcOEt 1:1): R_f 0.78. M.p.: 93–95° C. [α]_D²⁰=−32.3° (c=0.907, CHCl₃). IR (KBr): 3110w, 3071w, 2971w, 1745s, 1696s, 1609s, 1532s, 1414s, 1365s, 1348m, 1289m, 1190m, 1173m, 1122w, 1097w, 1043w, 954w, 912w, 755w, 578w. ¹H-NMR (600 MHz, CDCl₃): 8.42–8.34 (m, 2H, H-C(Nos)); 8.11–8.04 (m, 2H, H—C(Nos)); 5.14 (s, 1H, H—C(4)); 4.39–4.28 (m, 1H, H—C(2)); 3.70–3.56 (m, 5H, H₂—C(5), H₃C—O); 2.58–2.38 (m, 1H, H—C(3)); 2.25–2.11 (m, 1H, H—C(3)); 1.37+1.33 (2s, 9H, tBu). ¹³C-NMR (150 MHz, CDCl₃): 172.4+172.2 (2s, COOMe); 153.6+153.0 (2s, COOtBu); 150.8+142.0 (2s, C(Nos)); 129.0+124.6 (2d, C(Nos)); 80.4 (s, C-tBu); 80.8+79.9 (2d, C(4)); 57.1+56.9 (2d, C(2)); 52.2+51.7 (2t, C(5)); 52.3 (q, Me); 37.1+35.9 (2t, C(3)); 28.0 (q, tBu). ESI-MS (MeOH+NaI): 453.0 ([M+Na]⁺).

38 g (88 mmol) of the above intermediate was dissolved in DMF (450 ml) then heated to 40° C. when sodium azide (34 g, 6 eq, 0.53 mol) was added and the solution stirred overnight. DMF was evaporated and the solid suspended in diethylether. The suspension was washed with water and dried (Na₂SO₄). The solvent was evaporated and the product dried at high vacuum: (2S,4S)-4-Azido-1-[(tert-butoxy)carbonyl]proline methylester (210) yellow oil (21.1 g, 88%). [α]_D²⁰=−36.9 (c=0.965, CHCl₃). ¹H-NMR (600 MHz, CDCl₃): 4.46–4.25 (2m, 1H, H—C(2)); 4.20–4.10 (m, 1H, H—C(4)); 3.80–3.65 (m, 4H, H—C(5), H₃C—O); 3.53–3.41 (m, 1H, H—C(5)); 2.54–2.39 (m, 1H, H—C(3)); 2.21–2.12 (m, 1H, H—C(3)); 1.47+1.41 (2s, 9H, tBu). ¹³C-NMR (150 MHz, CDCl₃): 172.2+171.9 (2s, COOMe); 153.9+153.4 (2s, COOtBu); 80.5 (s, C-tBu); 59.2+58.2 (2d, C(4)); 57.7+57.3 (2d, C(2)); 52.4+52.2 (2q, Me); 51.2+50.7 (2t, C(5)); 36.0+35.0 (2t, C(3)); 28.3+28.2 (2q, tBu). EI-MS (70ev): 270.1 ([M]⁺); 227.1 ([M-CO₂+H]⁺); 169.1 ([M-BOC+H]⁺);.

v,vi: 21.1 g (78 mmol) of the above intermediate was dissolved in a (3:1)-mixture of dioxane/water (500 ml) and SnCl₂ (59.2 g, 4 eq, 0.31 mol) was added at 0° and the solution stirred for 30 min. and gradually brought to room temperature and stirred for another 5 h. After adjusting the pH to 8 with solid NaHCO₃, alkyl chloroformate (41.5 ml, 5 eq, 0.39 mol) was added and the solution stirred at room temperature overnight. The reaction mixture was evaporated and extracted with AcOEt. The organic phase was washed with brine, dried (Na₂SO₄), the solvent evaporated and the product was dried at high vacuum: (2S,4S)-4-[(Allyloxy)carbonylamino]-1-[(tert-butoxy)carbonyl]proline methylester (211) as a clear thick oil (22.3 g, 87%). [α]$_D^{20}$=–30.2° (c=1.25, CHCl₃). ¹H-NMR (300 MHz, CDCl₃): 5.98–5.77 (m, 1H, H—C(β)(Alloc)); 5.32–5.12 (m, 2H, H₂—C(γ)(Alloc); 4.59–4.46 (m, 2H, H₂—C(α)(Alloc)); 4.40–4.16 (m, 2H, H—C(4), H—C(2)); 3.80–3.53 (m, 4H, H—C(5), H₃C—O); 3.53–3.31 (m, 1H, H—C(5)); 2.54–2.17 (m, 1H, H—C(3)); 1.98–1.84 (m, 1H, H—C(3)); 1.41+1.37 (2s, 9H, tBu). ESI-MS (MeOH+CH₂Cl₂): 351.2 ([M+Na]⁺); 229.0 ([M-BOC+H]⁺).

vii-ix: 22 g, 67 mmol) of 211 was dissolved in a (4:1)-mixture of methanol/water (100 ml) and LiOH (5 g, 2 eq, 134 mmol) was added at room temperature and the solution stirred for 3.5 h. The reaction mixture was evaporated and extracted with 1N hydrochloric acid (100 ml) and AcOEt. The solvent was removed and the resulting solid dissolved in 1:1 TFA/CH₂Cl₂ (200 ml) and stirred for 2 h. The solvents were evaporated and the product dried at high vacuum: (2S,4S)-4-[(Allyloxy)carbonylamino]proline as a clear oil (21 g, 96%) ¹H-NMR (600 MHz, MeOH-d₄): 5.98–5.85 (m, 1H, H—C(β)(Alloc)); 5.30 (dd, J=17.1, 1.5 Hz, 1H, H—C(γ)(Alloc)); 5.12 (d, J=10.7 Hz, 1H, H—C(γ)(Alloc)); 4.54 (d, J=4.4 Hz, 2H, H₂—C(α)(Alloc)); 4.44 (t, J=8.9 Hz, 1H, H—C(2)); 4.36–4.27 (m, 1H, H—C(4)); 3.58 (dd, 3=12.2, 7.3 Hz, 1H, H—C(5)); 3.34–3.32 (m, 1H, H—C(5)); 2.73 (ddd, J=13.6, 8.7, 7.2 Hz, 1H, H—C(3)); 2.23–2.15 (m, 1H, H—C(3)). ¹³C-NMR (150 MHz, MeOH-d₄): 171.3 (s, COOMe); 158.3 (s, COOAllyl); 134.1 (d, C(β)(Alloc)); 118.0 (t, C(γ)(Alloc)); 66.8 (t, C(α)(Alloc)); 59.7 (d, C(2)); 51.3 (d, C(4)); 51.1 (t, C(5)); 34.9 (t, C(3)). ESI-MS (DCM+MeOH): 237.0 ([M+Na]⁺); 215.0 ([M+H]⁺).

15 g (70 mmol) of the above intermediate and 9-fluorenylmethoxycarbonylsuccinimid (28 g, 1.2 eq, 84 mmol) were dissolved in DCM (700 ml) and DIEA (48 ml, 6 eq, 0.42 mol) was added and the solution stirred overnight at room temperature. The solvent was removed and the residue dissolved in AcOEt and washed with 1N hydrochloric acid and dried (Na₂SO₄). After evaporation, the crude product was purified by filtration on silica gel with a gradient of (3:1) hexane/AcOEt to AcOEt. The solvent was evaporated and the residue crystallized from hexane at –20° C. The product was dried at high vacuum: (2S,4S)-4-[(Allyloxy)carbonylamino]-1-[(9H-fluoren-9-yl)methoxycarbonyl]-proline (212) as a white solid (23.8 mg, 78%) [α]$_D^{20}$=–27.0 (c=1.1, CHCl₃). IR (KBr): 3321w (br.), 3066w, 2953w, 1707s, 1530m, 1451s, 1422s, 1354m, 1250m, 1205m, 1173m, 1118m, 1033m, 977m, 936m, 759m, 739s, 621m, 597w, 571w, 545s. ¹H-NMR (300 MHz, MeOH-d₄): 7.88–7.78 (m, 2H, H—C(4')(Fmoc)); 7.71–7.61 (m, 2H, H—C(1')(Fmoc)); 7.49–7.29 (m, 4H, H—C(3')(Fmoc), H—C(2')(Fmoc)); 6.08–5.68 (m, 1H, H—C(β)(Alloc)); 5.41–5.17 (m, 2H, H₂—C(γ)(Alloc); 4.58 (s, 2H, H₂C(α)(Alloc)); 4.74–4.17 (m, 5H, H₂-(10')(Fmoc), H—C(9')(Fmoc), H—C(4), H—C(2)); 3.94–3.73 (m, 1H, H—C(5)); 3.41–3.26 (m, 1H, H—C(5)); 2.74–2.54 (m, 1H, H—C(3)); 2.12–1.92 (m, 1H, H—C(3)). ESI-MS (DCM+MeOH): 459.3 ([M+Na]⁺); 437.3 ([M+H]⁺).

Scheme 43

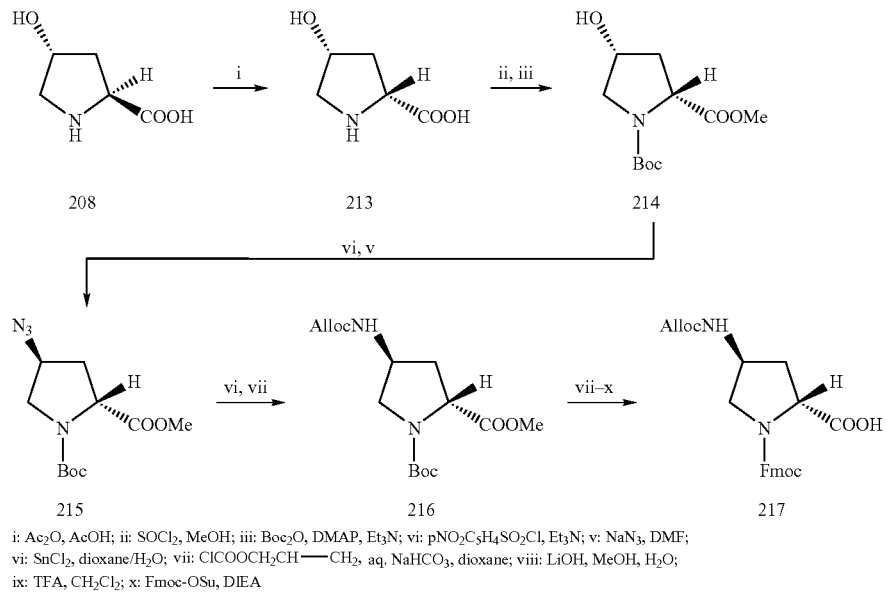

i: Ac₂O, AcOH; ii: SOCl₂, MeOH; iii: Boc₂O, DMAP, Et₃N; vi: pNO₂C₅H₄SO₂Cl, Et₃N; v: NaN₃, DMF; vi: SnCl₂, dioxane/H₂O; vii: ClCOOCH₂CH═CH₂, aq. NaHCO₃, dioxane; viii: LiOH, MeOH, H₂O; ix: TFA, CH₂Cl₂; x: Fmoc-OSu, DIEA

2.2. (2R,4S)-4-[(Allyloxy)carbonylamino]-1-[(9H-fluoren-9-yl)methoxycarbonyl]-proline (217)

i: A solution of acetic anhydride (1.02 kg, 5.3 eq, 10 mol) in glacial acetic acid (3 l) was heated to 50° C. and (2S,4R)-4-hydroxyproline (208) (247 g, 1.88 mol) was added in one portion. The solution was refluxed for 5.5 h, cooled to room temperature and the solvent was removed under reduced pressure giving a thick oil. The oil was then dissolved in 2N hydrochloric acid (3.5 l) and heated to reflux for 4 h and treated with charcoal and filtered through Celite. As the solution was evaporated, white needles formed, which were filtered. The product was dried at high vacuum: (2R,4R)-4-hydroxyproline.hydrochloride (213) white cryst. needles (220.9 g, 70%). M.p.: 117° C. $[\alpha]_D^{20}$=+19.3° (c=1.04, water). IR (KBr): 3238s 3017s, 2569m, 1712s, 1584m, 1376s, 1332m, 1255s, 1204s, 1181w, 1091w, 1066w, 994w, 725m, 499s. $^1$H-NMR (600 MHz, MeOH-d$_4$): 9.64 (s, 1H, H—N); 8.89 (s, 1H, H—N); 4.55–4.53 (m, 1H, H—C(4)); 4.51 (dd, J=10.4, 3.6 Hz, 1H, H—C(2)); 3.44–3.35 (m, 2H, H$_2$—C(5)); 2.54–2.48 (m, 1H, H—C(3)); 2.40–2.34 (m, 1H, H—C(3)). $^{13}$C-NMR (150 MHz, MeOH-d$_4$): 171.9 (s, COOH); 70.3 (d, C(4)); 59.6 (d, C(2)); 55.0 (t, C(5)); 38.5 (t, C(3)). EI-MS (NH$_3$): 132.1 ([M-Cl]$^+$). The filtrate was further concentrated to give an additional 59.5 g (19%).

ii,iii: To a solution of 213 (30 g, 0.18 mol) in abs. methanol (550 ml) was added dropwise at 0° C. thionyl chloride (38 ml, 2.5 eq, 0.45 mol). The solution refluxed for 3 h under nitrogen atmosphere. The solution was evaporated and the ester hydrochloride precipitated by adding diethylether. After filtration the white solid was washed with diethylether and dried at high vacuum: (2R,4R)-4-hydroxyproline methylester.hydrochloride white solid (29 g, 89%). $[\alpha]_D^{20}$=+8.6° (c=0.873, MeOH). IR (KBr): 3388s (br.), 2980s (r.), 1730s, 1634m, 1586s, 1384s, 1248s, 1095s, 1064s, 1030m, 877m. $^1$H-NMR (300 MHz, MeOH d): 4.59–4.44 (m, 2H, H—C(4), H—C(2)); 3.81 (s, 3H, H$_3$C-0); 3.37–3.31 (m, 2H, H$_2$—C(5)); 2.50–2.37 (m, 1H, H—C(3)), 2.37–2.27 (m, 1H, H—C(3)). $^{13}$C-NMR (75 MHz, MeOH-d$_4$): 170.9 (s, COOMe); 70.2 (d, C(4)); 59.8 (d, C(2)); 55.1 (t, C(5));)); 54.1 (q, C(Me)); 38.4 (1, C(3)). EI-MS (NH$_3$): 146.1 ([M-Cl]$^+$).

10 g (55 mmol) of the above intermediate was dissolved in CH$_2$Cl$_2$ (100 ml), cooled to 0° C. and triethylamine (15.2 ml, 2 eq, 0.11 mol) was added dropwise. Then di-tert-butyldicarbonate (18.0 g, 1.5 eq, 83 mmol) in CH$_2$Cl$_2$ (10 ml) and 4-N,N-dimethylaminopyridine (0.67 g, 0.1 eq, 5 mmol) were added and the solution was stirred at RT overnight. The solution was washed with 1M aq. citric acid solution and sat. aqueous NaHCO$_3$ solution, dried (Na$_2$SO$_4$), the solvents evaporated and dried at high vaccum: (2R,4R)-4-hydroxy-1-[(tert-butoxy)-carbonyl]prolinemethylester (214) as a white solid (13 g, 97%). $[\alpha]_D^{20}$=+13.0° (c=1.06, CHCl$_3$). IR (KBr): 3466s (br.), 2985s, 2930m, 1729s, 1679s, 1424s, 1283m, 1262m, 1122s, 1089s, 969m, 770m. $^1$H-NMR (300 MHz, CDCl$_3$): 4.43–4.26 (m, 2H, H—C(4), H—C(2)); 3.80+3.79 (2s, 3H, H$_3$C—O)); 3.76–3.47 (m, 2H, H$_2$—C(5)); 2.44–2.24 (m, 1H, H—C(3)); 2.16–2.03 (m, 1H, H—C(3)); 1.47+1.43 (2s, 9H, tBu). ESI-MS: 268.1 ([M+Na]$^+$).

iv,v: 214 (12.2 g, 50 mmol) was dissolved in CH$_2$Cl$_2$ (130 ml), cooled to 0° C. and 4-nitrobenzenesulfonyl chloride (14.3 g, 1.3 eq, 65 mmol) and Et$_3$N (10.3 ml, 1.5 eq, 75 mmol) were added The reaction mixture was stirred overnight and gradually brought to room temperature. The solution was washed with 1N hydrochloric acid and saturated aqueous NaHCO$_3$ solution, dried (Na$_2$SO$_4$), the solvents were evaporated and the crude product was purified by filtration on silica gel with (2:1)-mixture of hexane/AcOEt: 18 g (84%). The product was then recrystallized from hexane/AcOEt: (2R,4R)-4-[(p-nitrobenzyl)sulfonyloxy]-1-[(tert-butoxy)carbonyl]proline-methylester as white crystals (13.7 g, 64%). TLC (hexane/AcOEt 1:1): R$_f$ 0.76. M.p.: 113–115° C. $[\alpha]_D^{20}$=+21.6° (c=0.924, CHCl$_3$). IR (KBr): 3112s (br.), 2981s, 2955s, 2882m, 1755s, 1683s, 1532s, 1413s, 1375s, 1348s, 1192s, 928s, 911s, 759m, 745s, 610s. $^1$H-NMR (600 MHz, CDCl$_3$): 8.45–8.35 (m, 2H, H—C(Nos)); 8.15–8.06 (m, 2H, H—C(Nos)); 5.27–5.16 (m, 1H, H—C(4)); 4.53–4.32 (m, 1H, H—C(2)); 3.75–3.60 (m, 5H, H$_2$—C(5), H$_3$C—O); 2.59–2.35 (m, 2H, H$_2$C(3)); 1.42+1.39 (2s, 9H, tBu). $^{13}$C-NMR (150 MHz, CDCl$_3$): 171.8+171.6 (s, COOMe); 153.8+153.4 (s, COOtBu); 151.0+142.6 (s, C(Nos)); 129.2+124.7 (d, C(Nos)); 81.0 (s, C-tBu); 80.8+79.7 (d, C(4)); 57.4+57.1 (d, C(2)); 52.6+52.5+52.3+51.8 (t, C(5), q, Me); 37.2+36.3 (t, C(3)); 28.5+28.3 (q, tBu). ESI-MS (DCM+MEOH+NaI): 453.2 ([M+Na]$^+$).

13 g (30 mmol) of the above intermediate was dissolved in DMF (200 ml), heated to 40° C. and sodium azide (14.3 g, 6 eq, 180 mmol) was added and the reaction mixture stirred over-night. The reaction mixture was evaporated and the residue suspended in diethylether. The suspension was filtered, the filtrate washed with water and the organic phase dried(Na$_2$SO$_4$). The solvent was evaporated and the product dried at high vacuum: (2R,4S)-4-azido-1-[(tert-butoxy)carbonyl]prolinemethylester (215) as a yellow oil (8.15 g, 99%). $[\alpha]_D^{20}$=+42.8° (c=1.05, CHCl$_3$). $^1$H-NMR (300 MHz, CDCl$_3$): 4.58–4.37 (n, 1H, H—C(2)); 4.34–4.23 (m, 1H, H—C(4)); 3.92–3.51 (m, 5H, H$_2$—C(5), H$_3$C—O); 2.52–2.33 (m, 1H, H—C(3)); 2.33–2.20 (m, 1H, H—C(3)); 1.56+1.51 (2s, 9H, tBu). CI-MS (NH$_3$): 288.2 ([M+NH$_4$]$^+$); 271.1 ([M+H]$^+$).

vi,vii: 215 (8 g, 30 mmol) was dissolved in a (3:1)-mixture of dioxane/water (400 ml), cooled to 0° C. and SnCl$_2$ (22.4 g, 4 eq, 120 mmol) was added and the reaction mixture stirred for 30 min. at 0°, gradually warmed to room temperature and stirred for another 5 h. After adjusting the pH of the solution to 8 with solid NaHCO$_3$, alkyl chloroformate (15.7 ml, 5 eq, 150 mmol) was added. The reaction mixture was stirred overnight at room temperature, evaporated and extracted with AcOEt and the organic phase washed with brine. After drying the organic phase (Na$_2$SO$_4$), the solvent was evaporated and the product dried at high vacuum: (2R,4S)-4-[(Allyloxy)carbonylamino]-1-[(tert-butoxy)carbonyl]proline-methylester as a clear thick oil (216) (8.7 g, 89%). $[\alpha]_D^{20}$=+41.9° (c=0.928, CHCl$_3$). $^1$H-NMR (300 MHz CDCl$_3$): 5.98–5.87 (m, 1H, H—C($\beta$)(Alloc)); 5.34–5.02 (m, 2H, H$_2$—C($\gamma$)(Alloc); 4.62–4.49 (m, 2H, H$_2$—C($\alpha$)(Alloc)); 4.4–14.23 (m, 2H, H—C(4), H—C(2)); 3.82–3.66 (m, 4H, H—C(5), H$_3$C—O); 3.43–3.20 (m, 1H, H—C(5)); 2.33–2.07 (m, 2H, H$_2$—C(3)); 1.43+1.39 (2s, 9H, tBu). CI-MS (NH$_3$): 329.1 ([M+H]$^+$).

vii-x: 216 (8.4 g, 25 mmol) was dissolved in (4:1)-mixture of methanol/water (100 ml) at room temperature, LiOH (2.2 g, 2 eq, 50 mmol) added and the solution stirred overnight. Methanol was evaporated and the residue poured onto 1N hydrochloric acid (100 ml) and extracted with AcOEt. The solvent was removed and the residue dissolved in (1:1)-mixture of TFA/CH$_2$Cl$_2$ (200 ml) and stirred for 2 h. The solvents were evaporated and the product dried at high vaccum: (2R,4R)-4-[(Allyloxy)carbonylamino]proline as a clear oil (5.2 g, 96%) $^1$H-NMR (300 MHz MeOH-d$_4$): 6.04–5.88 (m, 1H, H$_2$—C($\beta$)(Alloc)); 5.38–5.19 (m, 2H, H$_2$—C($\gamma$)(Alloc); 4.64–4.54 (m, 3H, H$_2$C($\alpha$)(Alloc), H—C(4)); 4.39–4.22 (m, 1H, H—C(2)); 3.71–3.60 (m, 1H, H—C (5)); 3.45–3.32 (m, 1H, H—C(5)); 2.51–2.41 (m, 2H, H₂C (3)). CI-MS (NH₃): 215.1 ([M+H]⁺).

200 mg (0.86 mmol) of the above intermediate and 9-fluorenylmethoxycarbonylsuccinimide (440 mg, 1.5 eq, 1.3 mmol) were dissolved in CH₂Cl₂ (10 ml) and DIEA (466 µl, 4 eq, 3.44 mmol) was added, and the solution stirred overnight at room temperature. The solvent was removed and the residue dissolved in AcOEt, washed with 1N hydrochloric acid dried (Na₂SO₄). After evaporation, the crude product was purified by filtration over silica gel with first a gradient of (3:1) hexane/AcOEt to AcOEt. The solvent was coevaporated with CH₂Cl₂ and the product dried at high vacuum: (2R,4S)-4-[(Allyloxy)carbonylamino]-1-[(9H-fluoren-9-yl)methoxycarbonyl]-proline (217) white solid (90 mg, 33%) [α]$_D^{20}$=+29.3° (c=1.08, CHCl₃). IR (KBr): 3314s (br.), 3066s (br.), 2952s (br.), 1708s (br.), 1536m, 1424s, 1353s, 1126m, 1030 m, 909m, 759m, 738s, 620m. ¹H-NMR (300 MHz, CDCl₃): 8.74 (s, 1H, H—N); 7.79–7.66 (m, 2H, H—C(4')(fmoc)); 7.62–7.49 (m, 2H, H—C(1')(fmoc)); 7.44–7.22 (m, 4H, H—C(3')(fmoc), H—C(2')(fmoc)); 6.03–5.74 (m, 1H, H—C(β)(Alloc)); 5.41–5.07 (m, 2H, H₂—C(γ)(Alloc); 4.74–4.17 (m, 7H, H₂—C(10')(fmoc), H—C(9')(fmoc), H—C(4), H—C(2), H₂—C(α)(Alloc)); 3.91–3.76 (m, 1H, H—C(5)); 3.48–3.25 (m, 1H, H—C(5)); 2.45–2.08 (m, 2H, H₂—C(3)). ESI-MS (MeOH): 437.3 ([M+H]⁺); ESI-MS (MeOH+Na): 459.1 ([M+Na]⁺).

2.3. Starting from derivatives 210 and 215 the key precursors 219a–u and 221a–u can be prepared according to Scheme 44.

R⁶⁴: n-hexyl (219a, 221a); n-heptyl (219b, 221b); 4-(phenyl)benzyl (219c, 221c); diphenylmethyl (219d, 221d); 3-amino-propyl (219e, 221e); 5-amino-pentyl (219f, 221f); methyl (219 g, 221g); ethyl (219h, 221h); isopropyl (219I, 221i); isobutyl (219k, 221k); n-propyl (219l, 221l); cyclohexyl (219m, 221m); cyclohexylmethyl (219n, 221n); n-butyl (219o, 221o); phenyl (219p, 221p); benzyl (219q, 221q); (3-indolyl)methyl (219r, 221r); 2-(3-indolyl)ethyl (219s, 221s); (4phenyl)phenyl (219t, 221t); n-nonyl (219u, 221u).

Scheme 44

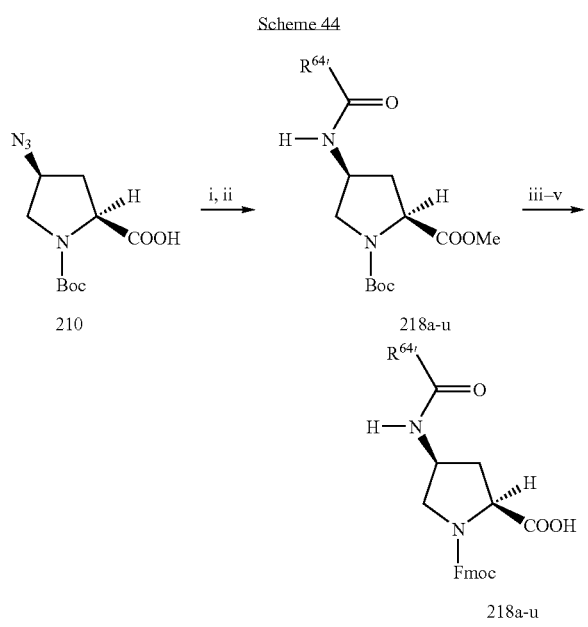

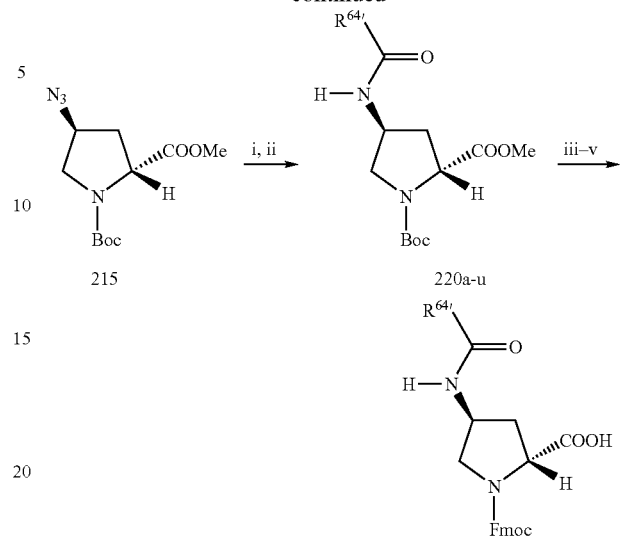

i: SnCl₂, dioxane/H₂O; ii: R⁶⁴COCl, diisopropylethylamine, CH₂Cl₂; iii: LiOHx1H₂O, MeOH, H₂O; iv: TFA, CH₂Cl₂; v: FmocOSu, Na2CO3 aq., dioxane i,ii: Typical Procedures:

To a solution of 78 mmol of azides 210 and 215 in a (3:1)-mixture of dioxane/water (500 ml) was added at 0° C. SnCl₂ (59.2 g, 4 eq, 0.31 mol) and the solution was stirred for 30 minutes. The reaction mixture was gradually warmed up to room temperature and stirred for another 5 hours. After adjusting the pH to 8 with solid NaHCO₃, the reaction mixture was extracted with CH₂Cl₂, the organic fraction dried (MgSO₄), evaporated and the residue dried under reduced pressure. The residue was dissolved in CH₂Cl₂ (300 ml), cooled to 4° with an ice bath, followed by addition of DIEA (20.0 ml, 117 mmol) and a solution of the appropriate acid chloride R⁶⁴'COCl (101.0 mmol) in CH₂Cl₂ (50 ml) at 4° C. The reaction mixture was stirred for 1 hour at 4° and for 18 hours at room temperature and extracted with HCl aq. (0.5N, 200 ml) and CH₂Cl₂. The organic fraction was dried (MgSO₄), evaporated and the residue chromatographed on SiO₂ with gradients of ethylacetate/hexane yielding 218a–u and 220a–u, which were converted into the final products 219a–u and 221a–u as described for the conversion of 216 into 217. The overall yields were 50–60%.

Templates (b1):

Synthesis of (2S,6S,8aR)-8a-{[(tert.-butyl)oxycarbonyl]methyl}perhydro-5,8-dioxo-{[(9H-fluoren-9-yl)methoxycarbonyl]amino}-pyrrolo[1,2-a]pyrazine-6-acetic acid (222):

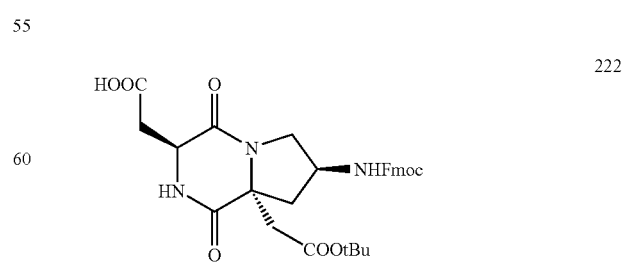

To a stirred solution of 250 mg (0.414 mmol) of alkyl {(2S,6S,8aR)-8a-[(tert.-butyl)oxycarbonyl]

methyl}perhydro-5,8-dioxo-{[(9H-fluoren-9-yl)methoxy-carbonyl]amino}-pyrrolo[1,2-a]pyrazin-6-acetate in a degassed mixture of dichloromethane/methanol (9:1, 3 ml) were added under argon 25 mg (0.0216 mmol) of tetrakis (triphenylphosphine)palladium, 0.05 ml of acetic acid and 0.025 ml of N-methylmorpholine. The reaction mixture was stirred for 48 hours at room temperature and poured onto water and dichloromethane. The organic phase was dried (MgSO$_4$), evaporated and the residue chromatographed on SiO$_2$ with dichloromethane/methanol (9:1) to yield 180 mg (77%) of (2S,6S,8aR)-8a-{[(tert.-butyl)oxycarbonyl] methyl}perhydro-5,8-dioxo-{[(9H-fluoren-9-yl)-methoxy-carbonyl]amino}-pyrrolo[1,2-a]pyrazine-6-acetic acid (222) as a white powder.

$^1$H-NMR(300 MHz, DMSO-d$_6$): 8.30 (s, 1H); 7.88 (d, J=7.2, 2H); 7.67 (d, J=7.4, 2H); 7.62 (br.s, 1H); 7.41 (t, J=7.2, 2H); 7.33 (t, J=7.4, 2H); 4.35–4.2 (m, 5H); 3.55 (br.d, J=6.3, 2H); 2.8–2.55 (m, 3H); 2.45–2.25 (m, 2H); 2.1–1.95 (m, 1H); 1.35 (s, 9H); MS(ESI): 586.1 (M+Na)$^+$, 564.1 (M+H)$^+$.

Templates (c1):

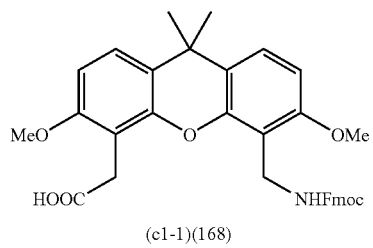

(c1-1)(168)

Experimental procedure described in W. Bannwarth, A. Knierzinger, K. Müller, D. Obrecht, A. Trzeciak EP 0 592 791 A2, 1993.

3. Biological Methods 3.1. Preparation of the Peptides

Lyophilized peptides were weighed on a Microbalance (Mettler MT5) and dissolved in sterile water containing 0.01% acetic acid Tachyplesin was purchased from Bachem Ltd. (Bubendorf Switzerland).

3.2. Antimicrobial Activity of the Peptides

The antimicrobial activities of the peptides were determined by the standard NCCLS broth microdilution method (see ref 1, below) and examined in sterile 96-wells plates (Nunclon polystyrene microtiter plates) in a total volume of 100 μl. Innocula of the microorganisms were prepared with 0.5 Mcfarland standard and then diluted into Mueller-Hinton (MH) broth to give appr. 10$^6$ colony forming units (CFU)/ml for bacteria or 5×10$^5$ CFU/ml for *Candida*. Aliquots (50 μl) of the innocula were added to 50 μl of MH broth containing the peptide in serial twofold dilutions. The microorganisms used were *Escherichia coli* (ATCC 25922), *Pseudomnonas aeruginosa* (*P. aeruginosa*) (ATCC 27853), *Stahylococcus aureus* (ATCC 29213 and ATCC 25923) and *Candida albicans*. A selected number of peptides were screened for activity against a larger panel of gram-negative strains. These strains were; *Escherichia coli* ATCC 43827 and clinical isolates of Pseudomonas (*P. aeruginosa* V07 14482, *P. aeruginosa* 15288, *P. aeruginosa* V02 15328 and *P. aeruginosa* V09 16085) and *Acinetobacter* (*Acinetobacter* V04 19905/1, *Acinetobacter* V12 21143/1 and *Acinetobacter* V12 21193/1). Antimicrobial activities of the peptides were expressed as the minimal inhibitory concentration (MIC) in jig/min at which no visible growth was observed after 18–20 hours of incubation of the microtiter plates at 37° C.

3.3. Antimicrobial Activity of the Peptides in 1% Salt

Salt sensitivity of the peptides was tested by the microtiter serial dilution assay as described above. Only MH broth was replaced by MH broth containing 1% NaCl.

3.4. Antimicrobial Activity of the Peptides in Human Serum

Serum binding of the peptides was tested by microtiter serial dilution assay as described above. Only MH broth was replaced by MH broth containing 90% human serum (Bio-Whittaker).

3.5. Hemolysis

The peptides were tested for their hemolytic activity against human red blood cells (hRBC). Fresh hRBC were washed three times with phosphate buffered saline (PBS) by centrifugation for 10 min at 2000×g. Peptides at a concentration of 100 μg/ml were incubated with 20% v/v hRBC for 1 hour at 37° C. The final erythrocyte concentration was appr. 0.9×10$^9$/ml. A value of 0% resp. 100% cell lysis was determined by incubation of the hRBC in the presence of PBS alone and resp. 0.1% Triton X-100 in H$_2$O. The samples were centrifuged and the supernatant was 20 fold diluted in PBS buffer and the optical density (OD) of the sample at 540 nM was measured. The 100% lysis value (OD$_{540}$H$_2$O) gave an OD of approximately 1.6–2.0. Percent hemolysis was calculated as follows: (OD$_{540}$peptide/OD$_{540}$H$_2$O)×100%.

3.6. Cytotoxicity Assay

The cytotoxicity of the peptides to HELA cells (Acc57) and MCF-7 cells (Acc115) was determined using the MTT reduction assay (see ref 2 and 3, below). Briefly the method is as follows; HELA cells and MCF-7 cells were grown in RPMI1640 plus 5% fetal calf serum in microtiter plates for 48 hours at 37° C. at 5% CO$_2$. The total number of cells was finally 10$^6$ cells per well. The supernatant of the cell cultures was discarded and fresh RPMI1640 medium containing 5% fetal calf serum and the peptides in serial dilutions of 12.5, 25 and 50 μg/ml were pipeted into the wells. Each peptide concentration was assayed in triplicate. Incubation of the cells was continued for 20–24 hours at 37° C. at 5% CO$_2$. Wells were then washed three times with fresh RPMI medium and finally 100 μl MTT reagent (0.5 mg/ml in RPMI1640) was added to each well. This was incubated at 37° C. for 2 hours and subsequently the wells were washed once with PBS. 100 μl isopropanol was added to each well and the absorbance at 595 nm of the solubilized product was measured (OD$_{595}$peptide). The 100 percent growth value (OD$_{595}$Medium) was determined from wells containing HELA or MCF-7 cells with RPMI1640 plus 5% fetal calf serum but no peptides. The zero percent growth value (OD$_{595}$Empty well) was extracted from wells that did not contain HELA or MCF-7 cells. The percentage MTT reduction for a certain peptide concentration was calculated as follows: (OD$_{595}$peptide-OD$_{595}$Empty well)/(OD$_{595}$Medium-OD$_{595}$Empty well)×100% and was plotted for each peptide concentration. The EC$_{50}$ of a peptide is defined as the concentration at which 50% inhibition of MTT reduction was observed and was calculated for each peptide.

REFERENCES

1. National Committee for Clinical Laboratory Standards. 1993. Methods for dilution antimicrobial susceptibility tests for bacteria that grow aerobically, 3rd ed. Approved standard M7-A3. National Committee for Clinical laboratory standards, Villanova, Pa.
2. Mossman T. J Immunol Meth 1983, 65, 55–63
3. Berridge M V, Tan A S. *Archives of Biochemistry & Biophysics* 1993, 303, 474–482

3.7. Results

TABLE 8

Minimal inhibitory concentrations (MIC in μg/ml) and percentage hemolyses at a concentration of 100 μg/ml of peptide

| Ex. | Escherichia coli ATCC 25922 | Pseudomonas putida ATCC 27853 | Staphylococcus aureus ATCC 29213 | Staphylococcus aureus ATCC 25923 | Candida albicans | Hemolyses hRBC |
|---|---|---|---|---|---|---|
| 11 | 25 | 100 | 100 | 100 | 100 | 0.2 |
| 36 | 25 | 25 | 25 | 50 | 25 | 0.5 |
| 40 | 25 | 50 | 25 | 50 | 25 | 1.2 |
| 59 | 4.7 | 50 | 25 | 50 | 25 | 3.0 |
| 63 | 6.2 | 50 | 12.5 | 25 | 12.5 | 3.0 |
| 71 | 12.5 | 100 | 12.5 | 12.5 | 50 | 1.2 |
| 87 | 6.2 | 6.2 | 9.4 | 9.4 | 12.5 | 3.7 |
| 101 | 12.5 | 50 | >50 | >50 | 50 | 0.2 |
| 103 | 9.4 | 25 | 25 | 25 | 12.5 | 18.3 |
| 105 | 6.2 | 9.4 | 12.5 | 6.2 | 6.2 | 31.0 |
| 106 | 12.5 | 6.2 | 25 | 12.5 | 12.5 | 1.4 |
| 107 | 25 | 6.2 | 12.5 | 9.4 | 12.5 | 10.4 |
| 109 | 50 | 25 | 50 | 50 | 12.5 | 3.2 |
| 112 | 25 | 50 | 25 | 25 | 25 | 2.6 |
| 113 | 50 | 100 | 100 | 100 | 100 | 9.2 |
| 119 | 50 | 25 | >100 | 100 | 50 | 3.5 |
| 120 | 18.8 | 9.4 | 18.8 | 9.4 | 12.5 | 1.1 |
| 121 | 25 | 25 | 6.2 | 6.2 | 6.2 | 7.1 |
| 126 | 25 | 25 | 25 | 50 | 25 | 2.6 |
| 128 | 6.2 | 12.5 | 6.2 | 6.2 | 12.5 | 13.9 |
| 133 | 6.2 | 6.2 | 12.5 | 25 | 12.5 | 1.1 |
| 134 | 12.5 | 6.2 | 12.5 | 25 | 12.5 | 1.2 |
| 137 | 25 | 6.2 | 6.2 | 6.2 | 6.2 | 3.1 |
| 139 | 25 | 6.2 | 12.5 | 9.4 | 6.2 | 3.5 |
| 140 | 12.5 | 6.2 | 12.5 | 12.5 | 6.2 | 2.7 |
| 141 | 25 | 12.5 | 25 | 25 | 12.5 | 2.0 |
| 142 | 25 | 12.5 | 50 | 25 | 12.5 | 2.3 |
| 146 | 12.5 | 12.5 | 25 | 12.5 | 6.2 | 30.1 |
| 147 | 50 | 25 | 25 | 25 | 12.5 | 1.9 |
| 148 | 25 | 12.5 | 12.5 | 9.4 | 6.2 | 3.9 |
| 150 | 25 | 12.5 | 12.5 | 12.5 | 12.5 | 29.3 |
| 151 | 50 | 50 | 100 | 50 | 25 | 4.9 |
| 152 | 25 | 25 | 50 | 25 | 12.5 | 29.1 |
| 154 | 12.5 | 12.5 | 25 | 12.5 | 12.5 | 31.5 |
| 155 | 6.2 | 12.5 | 6.2 | 12.5 | 6.2 | 10.1 |
| 156 | 50 | 12.5 | 12.5 | 6.2 | 12.5 | 35.2 |
| 158 | 12.5 | 6.2 | 12.5 | 12.5 | 12.5 | 10.5 |
| 159 | 12.5 | 12.5 | 12.5 | 12.5 | 12.5 | 21.7 |
| 161 | 25 | 12.5 | 6.2 | 6.2 | 12.5 | 3.7 |
| 163 | 12.5 | 12.5 | 12.5 | 12.5 | 12.5 | 24.6 |
| 165 | 6.2 | 12.5 | 25 | 18 | 12.5 | 0.2 |
| 168 | 12.5 | 12.5 | 25 | 25 | 12.5 | 1.1 |
| 172 | 6.2 | 25 | 25 | 25 | 12.5 | 1.0 |
| 173 | 12.5 | 25 | 6.2 | 12.5 | 12.5 | 27.4 |
| 175 | 12.5 | 6.2 | 12.5 | 12.5 | 12.5 | 2.4 |
| 177 | 25 | 12.5 | 25 | 25 | 12.5 | 4.1 |
| 182 | 12.5 | 6.2 | 6.2 | 25 | 12.5 | 6.2 |
| 185 | 12.5 | 6.2 | 6.2 | 6.2 | 12.5 | 17.6 |
| 186 | 6.2 | 3.1 | 6.2 | 6.2 | 6.2 | 11.5 |
| 187 | 12.5 | 100 | 50 | 100 | 25 | 0.3 |
| 197 | 12.5 | 3.1 | 6.2 | 6.2 | 6.2 | 3.4 |
| 203 | 6.2 | 6.2 | 6.2 | 6.2 | 6.2 | 33.0 |
| 205 | 6.2 | 6.2 | 12.5 | 6.2 | 6.2 | 27.0 |
| 206 | 6.2 | 6.2 | 12.5 | 12.5 | 6.2 | 8.5 |
| 207 | 50 | 50 | 25 | 50 | 25 | 0.1 |
| 208 | 12.5 | 6.2 | 6.2 | 6.2 | 12.5 | 18.4 |
| 209 | 12.5 | 6.2 | 12.5 | 12.5 | 18.8 | 6.4 |
| 210 | 12.5 | 6.2 | 25 | 25 | 25 | 1.9 |
| 214 | 12.5 | 6.2 | 12.5 | 12.5 | 12.5 | 1.0 |
| 216 | 12.5 | 6.2 | 12.5 | 25 | 12.5 | 1.4 |
| 217 | 18.8 | 6.2 | 12.5 | 25 | 12.5 | 1.7 |
| 218 | 25 | 6.2 | 25 | 25 | 25 | 2.2 |

TABLE 8-continued

Minimal inhibitory concentrations (MIC in µg/ml) and percentage hemolyses at a concentration of 100 µg/ml of peptide

| Ex. | Escherichia coli ATCC 25922 | Pseudomonas putida ATCC 27853 | Staphylococcus aureus ATCC 29213 | Staphylococcus aureus ATCC 25923 | Candida albicans | Hemolyses hRBC |
|---|---|---|---|---|---|---|
| 219 | 12.5 | 12.5 | 50 | 50 | 25 | 2.6 |
| 220 | 12.5 | 18.8 | 25 | 25 | 12.5 | 2.3 |
| 222 | 12.5 | 6.2 | 12.5 | 12.5 | 6.2 | 2.2 |
| 223 | 6.2 | 12.5 | 12.5 | 25 | 12.5 | 2.7 |
| 224 | 6.2 | 12.5 | 18.8 | 25 | 12.5 | 3.7 |
| 225 | 6.2 | 12.5 | 12.5 | 25 | 12.5 | 4.4 |
| 228 | 12.5 | 6.2 | 6.2 | 6.2 | 12.5 | 6.3 |
| 229 | 12.5 | 6.2 | 3.1 | 6.2 | 6.2 | 4.8 |
| 230 | 6.2 | 6.2 | 6.2 | 9.4 | 12.5 | 1.7 |
| 232 | 6.2 | 12.5 | 9.4 | 6.2 | 9.4 | 1.5 |
| 233 | 9.4 | 12.5 | 9.4 | 6.2 | 12.5 | 37 |
| 234 | 6.2 | 12.5 | 6.2 | 3.1 | 12.5 | 33.9 |
| 242 | 6.2 | 12.5 | 6.2 | 12.5 | 12.5 | 19.4 |
| 244 | 3.1 | 12.5 | 6.2 | 6.2 | 12.5 | 22.7 |
| 250 | 6.2 | 6.2 | 12.5 | 12.5 | 12.5 | 0.7 |
| 251 | 6.2 | 9.4 | 6.2 | 12.5 | 12.5 | 4.1 |
| 254 | 12.5 | 6.2 | 6.2 | 12.5 | 12.5 | 11.7 |
| 256 | 3.1 | 3.1 | 6.2 | 6.2 | 6.2 | 2.7 |
| 257 | 6.2 | 6.2 | 6.2 | 6.2 | 25 | 19.6 |
| 258 | 6.2 | 6.2 | 6.2 | 6.2 | 12.5 | 23.6 |
| 259 | 6.2 | 6.2 | 6.2 | 6.2 | 12.5 | 18.0 |
| 267 | 12.5 | 6.2 | 6.2 | 12.5 | 12.5 | 3.4 |
| 277 | 25 | 18.8 | 3.1 | 6.2 | 6.2 | 12.7 |
| 278 | 12.5 | 25 | 50 | 50 | 50 | 5.3 |
| 279 | 12.5 | 12.5 | 50 | 50 | 50 | 4.9 |
| 280 | 12.5 | 12.5 | 50 | 100 | 25 | 1.8 |
| 281 | 12.5 | 4.7 | 100 | 100 | 50 | 1.1 |
| 282 | 12.5 | 12.5 | 25 | 50 | 25 | 1.6 |
| 283 | 12.5 | 4.7 | 100 | 100 | 50 | 1.0 |
| 284 | 6.2 | 1.6 | 12.5 | 12.5 | 12.5 | 0.7 |
| 287 | 25 | 50 | 12.5 | 25 | 25 | 28.5 |
| 288 | 25 | 1.5 | 100 | 100 | 100 | 1.1 |
| 289 | 50 | 3.1 | 25 | 25 | 25 | 1.7 |
| 292 | 25 | 6.2 | 50 | 100 | 25 | 1.3 |
| 293 | 25 | 12.5 | 100 | 100 | 100 | 1.3 |
| 294 | 25 | 3.1 | 100 | 100 | 50 | 1.5 |
| 295 | 25 | 6.5 | 50 | 100 | 50 | 2.0 |
| 296 | 12.5 | 6.2 | 25 | 50 | 25 | 1.9 |
| 297 | 25 | 3.1 | 100 | 100 | 50 | 0.9 |
| 298 | 25 | 3.1 | 100 | 200 | 50 | 1.0 |
| 299 | 50 | 6.2 | 25 | 100 | 50 | 2.5 |
| 300 | 25 | 12.5 | 12.5 | 25 | 50 | 6.5 |
| 301 | 25 | 50.0 | 50.0 | 25 | 50.0 | 0.5 |
| 302 | 6.2 | 3.1 | 3.1 | 6.2 | 6.2 | 3.4 |

TABLE 9

Minimal inhibitory concentration (MIC in µg/ml) in Mueller-Hinton broth containing 1% NaCl

| Ex. | Escherichia coli ATCC 25922 | Pseudomonas putida ATCC 27853 | Staphylococcus aureus ATCC 29213 | Staphylococcus aureus ATCC 25923 | Candida albicans |
|---|---|---|---|---|---|
| 106 | 100 | 50 | 100 | 100 | 100 |
| 197 | 12.5 | 6.2 | 18.8 | 12.5 | 12.5 |
| 230 | 25 | 50 | 50 | 50 | 18.8 |
| 250 | 12.5 | 50 | 100 | 50 | 50 |
| 229 | 50 | 18.8 | 25 | 25 | 12.5 |
| 256 | 6.2 | 6.2 | 25 | 25 | 25 |

Several compounds which showed a preference towards Gram-negative bacteria were tested against several *pseudomonas* strains as shown in Table 10.

TABLE 10

Minimal inhibitory concentrations (MIC in µg/ml) against pseudomonas strains

| MIC (µg/ml) | ex. 197 | ex. 284 | ex. 283 | ex. 288 | ex. 289 | ex. 292 | ex. 296 | ex. 297 | ex. 298 |
|---|---|---|---|---|---|---|---|---|---|
| *Escherichia coli* ATCC 25922 | 12.5 | 6.2 | 25 | 25 | 25 | 25 | 12.5 | 25 | 25 |
| *Escherichia coli* ATCC 43827 | 12.5 | 12.5 | 12.5 | 12.5 | 25 | 25 | 12.5 | 12.5 | 12.5 |
| *P. aeruginosa* ATCC 278853 | 3.1 | 1.6 | 3.1 | 3.1 | 6.2 | 6.2 | 3.1 | 3.1 | 3.1 |
| *P. aeruginosa* VO7 14482 | 12.5 | 3.1 | 4.7 | 3.1 | 6.2 | 12.5 | 12.5 | 4.7 | 3.1 |
| *P. aeruginosa* 15288 | 12.5 | 3.1 | 2.5 | 6.2 | 6.2 | 12.5 | 12.5 | 6.2 | 4.7 |
| *P. aeruginosa* V02 15328 | 12.5 | 3.1 | 6.2 | 3.1 | 6.2 | 12.5 | 12.5 | 6.2 | 3.1 |
| *P. aeruginosa* V09 16085 | 9.4 | 1.6 | 3.1 | 6.2 | 6.2 | 6.2 | 6.2 | 3.1 | 3.1 |
| Acinetobacter V04 19905/1 | 12.5 | 6.2 | 6.2 | 6.2 | 12.5 | 12.5 | 6.2 | 6.2 | 6.2 |
| Acinetobacter V12 21143/1 | 12.5 | 3.1 | 6.2 | 6.2 | 6.2 | 6.2 | 6.2 | 6.2 | 9.4 |
| Acinetobacter V12 21193/1 | 12.5 | 3.1 | 3.1 | 6.2 | 3.1 | 6.2 | 3.1 | 6.2 | 6.2 |

TABLE 11

Anticancer activity ($EC_{50}$-values) in µg/ml

| Example ex. | Hela (µg/ml) | MCF (µg/ml) | Hemolysis hRBC |
|---|---|---|---|
| 80 | 337 | nd | nd |
| 106 | 43 | 39 | 1.4 |
| 170 | 24 | 41 | nd |
| 197 | 20 | 23 | 3.4 |
| 229 | 13 | 25 | 4.8 |
| 230 | 23 | 32 | 1.7 |
| 285 | 11 | 11 | 4.2 |
| 286 | nd | 23 | 17.1 |

The invention claimed is:
1. Compounds of the general formulae

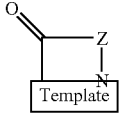

(Ia)

wherein

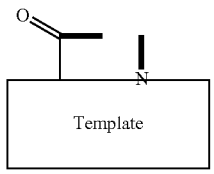

is a group of the formulae

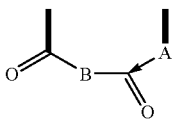

(a1)

wherein

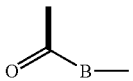

is the residue of an L-α-amino acid with B being the enantiomer of one of the groups A5, A8 or A10 as defined hereinafter;

is a group of one of the formulae
$R^1$ is H; lower alkyl; or aryl-lower alkyl;
$R^2$ is H; alkyl; alkenyl; $-(CH_2)_m(CHR^{61})_sOR^{55}$; $-(CH_2)_m(CHR^{61})_sSR^{56}$; $-(CH_2)_m(CHR^{61})_sNR^{33}R^{34}$; $-(CH_2)_m(CHR^{61})_sOCONR^{33}R^{75}$; $-(CH_2)_m(CHR^{61})_sNR^{20}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_sPO(OR^{60})_2$; $-(CH_2)_o(CHR^{61})_sSO_2R^{62}$; or $-(CH_2)_o(CHR^{61})_sC_6H_4R^8$;
$R^5$ is alkyl; alkenyl; $-(CH_2)_o(CHR^{61})_sOR^{55}$; $-(CH_2)_o(CHR^{61})_sSR^{56}$; $-(CH_2)_o(CHR^{61})_sNR^{33}R^{34}$; $-(CH_2)_o(CHR^{61})_sOCONR^{33}R^{75}$; $-(CH_2)_o(CHR^{61})_sNR^{20}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_sPO(OR^{60})_2$; $-(CH_2)_o(CHR^{61})_sSO_2R^{62}$; or $-(CH_2)_o(CHR^{61})_sC_6H_4R^8$;
$R^7$ is alkyl; alkenyl; $-(CH_2)_q(CHR^{61})_sOR^{55}$; $-(CH_2)_q(CHR^{61})_sNR^{33}R^{34}$; $-(CH_2)_q(CHR^{61})_sOCONR^{33}R^{75}$; $-(CH_2)_q(CHR^{61})_sNR^{20}CONR^{33}R^{82}$; $-(CH_2)_r(CHR^{61})_sCOOR^{57}$; $-(CH_2)_r(CHR^{61})_sCONR^{58}R^{59}$; $-(CH_2)_r(CHR^{61})_sPO(OR^{60})_2$; $-(CH_2)_r(CHR^{61})_sSO_2R^{62}$; or $-(CH_2)_r(CHR^{61})_sC_6H_4R^8$;
$R^8$ is H; Cl; F; $CF_3$; $NO_2$; lower alkyl; lower alkenyl; aryl; aryl-lower alkyl; $-(CH_2)_o(CHR^{61})_sOR^{55}$; $-(CH_2)_o(CHR^{61})_sSR^{56}$; $-(CH_2)_o(CHR^{61})NR^{33}R^{34}$; $-(CH_2)_o(CHR^{61})_sOCONR^{33}R^{75}$; $-(CH_2)_o(CHR^{61})_sNR^{20}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_sPO(OR^{60})_2$; $-(CH_2)_o(CHR^{61})_sSO_2R^{62}$; or $-(CH_2)_o(CHR^{61})_sCOR^{64}$;
$R^{20}$ is H; alkyl; alkenyl; or aryl-lower alkyl;
$R^{33}$ is H; alkyl, alkenyl; $-(CH_2)_m(CHR^{61})_sOR^{55}$; $-(CH_2)_m(CHR^{61})_sNR^{34}R^{63}$; $-(CH_2)_m(CHR^{61})_sOCONR^{75}R^{82}$; $-CH_2)_m(CHR^{61})_sNR^{20}CONR^{78}R^{82}$; $-(CH_2)_o(CHR^{61})_sCOR^{64}$; $-(CH_2)_o(CHR^{61})_s-CONR^{58}R^{59}$, $-(CH_2)_o(CHR^{61})_sPO(OR^{60})_2$; $-(CH_2)_o(CHR^{61})_sSO_2R^{62}$; or $-(CH_2)_o(CHR^{61})_sC_6H_4R^8$;
$R^{34}$ is H; lower alkyl; aryl, or aryl-lower alkyl;
$R^{33}$ and $R^{34}$ taken together can form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$;
$R^{55}$ is H; lower alkyl; lower alkenyl; aryl-lower alkyl; $-(CH_2)_m(CHR^{61})_sOR^{57}$; $-(CH_2)_m(CHR^{61})_sNR^{34}R^{63}$; $-(CH_2)_m(CHR^{61})_sOCONR^{75}R^{82}$; $-(CH_2)_m(CHR^{61})_sNR^{20}CONR^{78}R^{82}$; $-(CH_2)_o(CHR^{61})_s-COR^{64}$; $-(CH_2)_o(CHR^{61})COOR^{57}$; or $-(CH_2)_o(CHR^{61})_sCONR^{58}R^{59}$;
$R^{56}$ is H; lower alkyl; lower alkenyl; aryl-lower alkyl; $-(CH_2)_m(CHR^{61})_sOR^{57}$; $-(CH_2)_m(CHR^{61})_sNR^{34}R^{63}$; $-(CH_2)_m(CHR^{61})_sOCONR^{75}R^{82}$; $-(CH_2)_m(CHR^{61})_sNR^{20}CONR^{78}R^{82}$; $-(CH_2)_o(CHR^{61})_s-COR^{64}$; or $-(CH_2)_o(CHR^{61})_sCONR^{58}R^{59}$;
$R^{57}$ is H; lower alkyl; lower alkenyl; aryl lower alkyl; or heteroaryl lower alkyl;
$R^{58}$ is H; lower alkyl; lower alkenyl; aryl; heteroaryl; aryl-lower alkyl; or heteroaryl-lower alkyl;
$R^{59}$ is H; lower alkyl; lower alkenyl; aryl; heteroaryl; aryl-lower alkyl; or heteroaryl-lower alkyl; or
$R^{58}$ and $R^{59}$ taken together can form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$;
$R^{60}$ is H; lower alkyl; lower alkenyl; aryl; or aryl-lower alkyl;
$R^{61}$ is alkyl; alkenyl; aryl; heteroaryl; aryl-lower alkyl; heteroaryl-lower alkyl; $-(CH_2)_mOR^{55}$; $-(CH_2)_mNR^{33}R^{34}$; $-(CH_2)_mOCONR^{75}R^{82}$; $-(CH_2)_mNR^{20}CONR^{78}R^{82}$; $-(CH_2)_oCOOR^{57}$; $-(CH_2)_oNR^{58}R^{59}$; or $-(CH_2)_oPO(COR^{60})_2$;
$R^{62}$ is lower alkyl; lower alkenyl; aryl, heteroaryl; or aryl-lower alkyl;
$R^{63}$ is H; lower alkyl; lower alkenyl; aryl, heteroaryl; aryl-lower alkyl; heteroaryl-lower alkyl; $-COR^{64}$; $-COOR^{57}$; $-CONR^{58}R^{59}$; $-SO_2R^{62}$; or $-PO(OR^{60})_2$;
$R^{34}$ and $R^{63}$ taken together can form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$;
$R^{64}$ is H; lower alkyl; lower alkenyl; aryl; heteroaryl; aryl-lower alkyl; heteroaryl-lower alkyl; $-(CH_2)_p(CHR^{61})_sOR^{65}$; $-(CH_2)_p(CHR^{61})_sSR^{66}$; or $-(CH_2)_p(CHR^{61})_sNR^{34}R^{63}$; $-(CH_2)_p(CHR^{61})_sOCONR^{75}R^{82}$; $-(CH_2)_p(CHR^{61})_sNR^{20}CONR^{78}R^{82}$;
m is 2–4; o is 0–4; p is 1–4; q is 0–2; r is 1 or 2; s is 0 or 1;
$R^{67}$ is H; Cl; Br; F; $NO_2$; $-NR^{34}COR^{57}$; lower alkyl; or lower alkenyl;

$R^{68}$ is H; Cl; Br; F; $NO_2$; $-NR^{34}COR^{57}$; lower; or lower alkenyl;

$R^{69}$ is H; Cl; Br; F; $NO_2$; $-NR^{34}COR^{57}$; lower alkyl; or lower alkenyl; and $R^{70}$ is H; Cl; Br; F; $NO_2$; $-NR^{34}COR^{57}$; lower alkyl; lower alkenyl;

Z is a chains of 12 α-amino acid residues, the positions of said amino acid residues in said chains being counted starting from the N-terminal amino acid, whereby these amino acid residues are, depending on their position in the chains, Gly, or of one of the types C: $-NR^{20}CH(R^{72})CO-$;
D: $-NR^{20}CH(R^{73})CO-$;
E: $-NR^{20}CH(R^{74})CO-$;
F: $-NR^{20}CH(R^{84})CO-$; and $R^{72}$ is H; lower alkyl; lower alkenyl; $-(CH_2)_p(CHR^{61})_sOR^{85}$; or $-(CH_2)_p(CHR^{61})_sSR^{85}$;

$R^{73}$ is $-(CH_2)_oR^{77}$; $-(CH_2)_rO(CH_2)_oR^{77}$; $-(CH_2)_rS(CH_2)_oR^{77}$; or $-(CH_2)_rNR^{20}(CH_2)_oR^{77}$;

$R^{74}$ is $-(CH_2)_pNR^{78}R^{79}$; $-(CH_2)_pNR^{77}R^{80}$; $-(CH_2)_pC(=NR^{80})NR^{78}R^{79}$; $-(CH_2)_pC(=NOR^{50})NR^{78}R^{79}$; $-(CH_2)_pC(=NNR^{78}R^{79})NR^{78}R^{79}$; $-(CH_2)_pNR^{80}C(=NR^{80})NR^{78}R^{79}$; $-(CH_2)_pN=C(NR^{78}R^{80})NR^{79}R^{80}$; $-(CH_2)_pC_6H_4NR^{78}R^{79}$; $-(CH_2)_pC_6H_4NR^{77}R^{80}$; $-(CH_2)_pC_6H_4C(=NR^{80})NR^{78}R^{79}$; $-(CH_2)_pC_6H_4C(=NOR^j)NR^{78}R^{79}$; $-(CH_2)_pC_6H_4C(=NNR^{78}R^{79})NR^{78R79}$; $-(CH_2)_pC_6H_4NR^{80}C(=NR^{80})NR^{78}R^{79}$; $-(CH_2)_pC_6H_4N=C(NR^{78}R^{80})NR^{79}R^{80}$; $-(CH_2)_rO(CH_2)_mNR^{78}R^{79}$; $-(CH_2)_rO(CH_2)_mNR^{77}R^{80}$; $-(CH_2)_rO(CH_2)_pC(=NR^{80})NR^{78}R^{79}$; $-(CH_2)_rO(CH_2)_pC(=NOR^j)NR^{78}R^{79}$; $-(CH_2)_rO(CH_2)_pC(=NNR^{78}R^{79})NR^{78}R^{79}$; $-(CH_2)_rO(CH_2)_mNR^{80}C(=NR^{80})NR^{78}R^{79}$; $-(CH_2)_rO(CH_2)_mN=C(NR^{78}R^{80})NR^{79}R^{80}$; $-(CH_2)_rO(CH_2)_pC_6H_4CNR^{78}R^{79}$; $-(CH_2)_rO(CH_2)_pC_6H_4C(=NR^{80})NR^{78}R^{79}$; $-(CH_2)_rO(CH_2)_pC_6H_4C(=NOR^j)NR^{78}R^{79}$; $-(CH_2)_rO(CH_2)_pC_6H_4C(=NNR^{78}R^{79})NR^{78}R^{79}$; $-(CH_2)_rO(CH_2)_pC_6H_4NR^{80}C(=NR^{80})NR^{78}R^{79}$; $-(CH_2)_rS(CH_2)_mNR^{78}R^{79}$; $-(CH_2)_rS(CH_2)_mNR^{77}R^{80}$; $-(CH_2)_rS(CH_2)_pC(=NR^{80})NR^{78}R^{79}$; $-(CH_2)_rS(CH_2)_pC(=NOR^j)NR^{78}R^{79}$; $-(CH_2)_rS(CH_2)_pC(=NNR^{78}R^{79})NR^{78}R^{79}$; $-(CH_2)_rS(CH_2)_mNR^{80}C(=NR^{80})NR^{78}R^{79}$; $-(CH_2)_rS(CH_2)_mN=C(NR^{78}R^{80})NR^{79}R^{80}$; $-(CH_2)_rS(CH_2)_pC_6H_4CNR^{78}R^{79}$; $-(CH_2)_rS(CH_2)_pC_6H_4C(=NR^{80})NR^{78}R^{79}$; $-(CH_2)_rS(CH_2)_pC_6H_4C(=NOR^j)NR^{78}R^{79}$; $-(CH_2)_rS(CH_2)_pC_6H_4C(=NNR^{78}R^{79})NR^{78}R^{79}$; $-(CH_2)_rS(CH_2)_pC_6H_4NR^{80}C(=NR^{80})NR^{78}R^{79}$; $-(CH_2)_pNR^{80}COR^{64}$; $-(CH_2)_pNR^{80}COR^{77}$; $-(CH_2)_pNR^{80}CONR^{78}R^{79}$; or $-(CH_2)_pC_6H_4NR^{80}CONR^{78}R^{79}$;

$R^{75}$ is lower alkyl; lower alkenyl; or aryl-lower alkyl;

$R^{33}$ and $R^{75}$ taken together can form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$;

$R^{75}$ and $R^{82}$ taken together can form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$;

$R^{76}$ is H; lower alkyl; lower alkenyl; aryl-lower alkyl; $-(CH_2)_oOR^{72}$; $-(CH_2)_oSR^{72}$; $-(CH_2)_oNR^{33}R^{34}$; $-(CH_2)_oOCONR^{33R75}$; $-(CH_2)_oNR^{20}CONR^{33}R^{82}$; $-(CH_2)_oCOOR^{75}$; $-(CH_2)_oCONR^{58}R^{59}$; $-(CH_2)_oPO(OR^{60})_2$; $-(CH_2)_pSO_2R^{62}$; or $-(CH_2)_oCOR^{64}$;

$R^{77}$ is $-C_6R^{67}R^{68}R^{69}R^{70}R^{76}$; or a heteroaryl group of one of the formulae

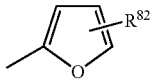 H1

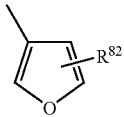 H2

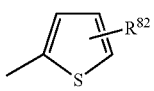 H3

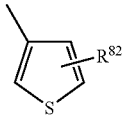 H4

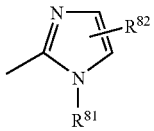 H5

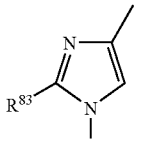 H6

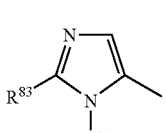 H7

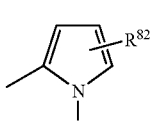 H8

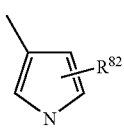 H9

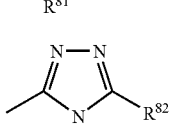 H10

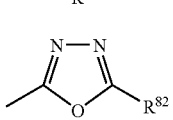 H11

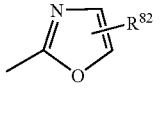 H12

-continued
H13 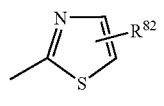
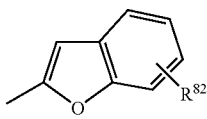 H26
H14 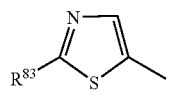
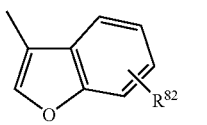 H27
H15 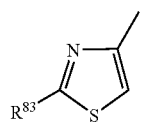
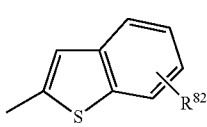 H28
H16 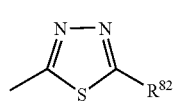
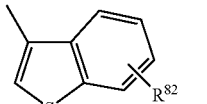 H29
H17 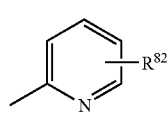
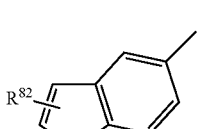 H30
H18 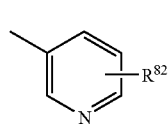
 H31
H19 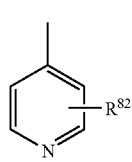
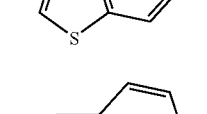 H32
H20 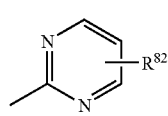
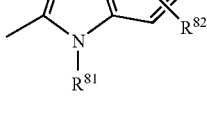 H33
H21 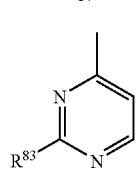
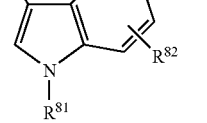 H34
H22 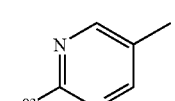
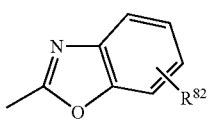 H35
H23 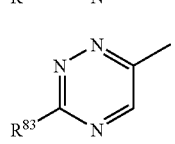
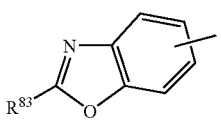 H36
H24 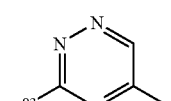
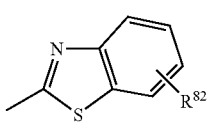
H25 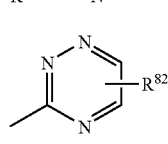

-continued

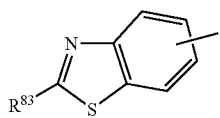
H37

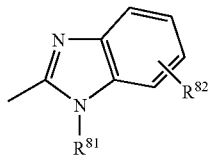
H38

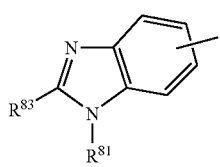
H39

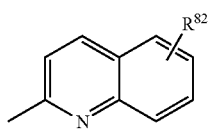
H40

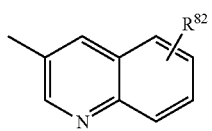
H41

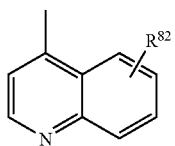
H42

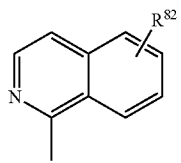
H43

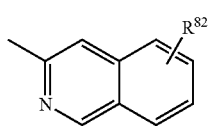
H44

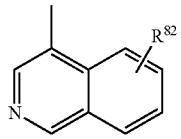
H45

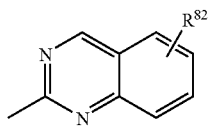
H46

-continued

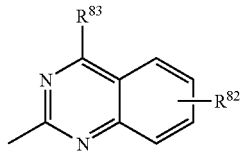
H47

H48

H49

H50

H51

H52

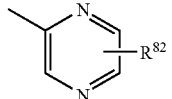
H53

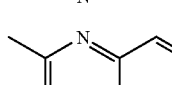
H54

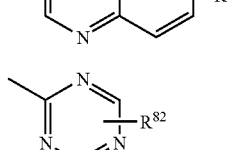

$R^{78}$ is H; lower alkyl; aryl; or aryl-lower alkyl;

$R^{78}$ and $R^{82}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;

$R^{79}$ is H; lower alkyl; aryl; or aryl-lower alkyl; or $R^{78}$ and $R^{79}$, taken together, can be —(CH$_2$)$_{2-7}$—; —(CH$_2$)$_2$O(CH$_2$)$_2$—; or —(CH$_2$)$_2$NR$^{57}$(CH$_2$)$_2$—;

$R^{80}$ is H; or lower alkyl;

$R^{81}$ is H; lower alkyl; or aryl-lower alkyl;

$R^{82}$ is H; lower alkyl; aryl; heteroaryl; or aryl-lower alkyl;

$R^{33}$ and $R^{82}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;

$R^{83}$ is H; lower alkyl; aryl; or —NR$^{78}$R$^{79}$;

$R^{84}$ is —(CH$_2$)$_m$(CHR$^{61}$)$_s$OH; —(CH$_2$)$_p$CONR$^{78}$R$^{79}$; —(CH$_2$)$_p$NR$^{80}$CONR$^{78}$R$^{79}$;

—(CH$_2$)$_p$C$_6$H$_4$CONR$^{78}$R$^{79}$; or —(CH$_2$)$_p$C$_6$H$_4$NR$^{80}$CONR$^{78}$R$^{79}$;

R$^{85}$ is lower alkyl; or lower alkenyl;

with the proviso that in said chain of 12 α-amino acid residues Z, the amino acid residues in positions 1 to 12 are:
  P1: of type C or of type D or of type E or of type F;
  P2: of type E or of type D;
  P3: of type C or of type D;
  P4: of type E or of type F or of type D;
  P5: of type E or of type D or of type C, or the residue is Gly;
  P6: of type E or of type F, or the residue is Gly;
  P7: of type E or of type F;
  P8: of type D or of type C;
  P9: of type E or of type D or of type F;
  P10: of type D or of type C;
  P11: of type E or of type D; and
  P12: of type C or of type D or of type E or of type F; and
  at P6 and P7 also D-isomers being possible;
and pharmaceutically acceptable salts thereof.

2. Compounds according to claim 1 wherein
  R$^2$ and R$^{76}$ are other than —(CH$_2$)$_m$(CHR$^{61}$)$_s$OCONR$^{33}$R$^{75}$ or —(CH$_2$)$_m$(CHR$^{61}$)$_s$NR$^{20}$CONR$^{33}$R$^{82}$;
  R$^{33}$, R$^{55}$, R$^{56}$, R$^{61}$ and R$^{64}$ are other than —(CH$^2$)$_m$(CHR$^{61}$)$_s$OCONR$^{75}$R$^{82}$ or —(CH$_2$)$_m$(CHR$^{61}$)$_s$NR$^{20}$CONR$^{78}$R$^{82}$;
  R$^{33}$ and R$^{34}$, or R$^{34}$ and R$^{63}$ are other than, taken together, —CH$_{2-6}$—; —(CH$_2$)$_2$O(CH$_2$)$_2$—, —(CH$_2$)$_2$S(CH$_2$)$_2$— or —(CH$_2$)$_2$NR$^{57}$(CH$_2$)$_2$—;
  R$^{57}$ in —(CH$_2$)$_2$NR$^{57}$(CH$_2$)$_2$— or —(CH$_2$)$_r$NR$^{57}$(CH$_2$)$_r$— is other than lower alkenyl or heteroaryl-lower alkyl;
  R$^{74}$ is other than —(CH$_2$)$_p$NR$^{77}$R$^{80}$, —(CH$_2$)$_p$C$_6$H$_4$NR$^{77}$R$^{80}$, —(CH$_2$)$_p$O(CH$_2$)$_m$NR$^{77}$R$^{80}$, —(CH$_2$)$_p$S(CH$_2$)$_m$NR$^{77}$R$^{80}$, —(CH$_2$)$_p$N=C(NR$^{78}$R$^{80}$)NR$^{79}$R$^{80}$, —(CH$_2$)$_p$C$_6$H$_4$N=C(NR$^{78}$R$^{80}$)NR$^{79}$R$^{80}$, —(CH$_2$)$_p$O(CH$_2$)$_m$N=C(NR$^{78}$R$^{80}$)NR$^{79}$R$^{80}$, —(CH$_2$)$_p$S(CH$_2$)$_m$N=C(NR$^{78}$R$^{80}$)NR$^{79}$R$^{80}$, —(CH$_2$)$_p$NR$^{80}$COR$^{64}$, or —(CH$_2$)$_p$NR$^{80}$COR$^{77}$;
  R$^{77}$ is other than H52, H53 and H54; and in Z the amino acid residues in positions 1, 5 and 12 are:
  P1: of type C or of type D or of type E;
  P5: of type E or of type D, or the residue is Gly; and
  P12: of type C or of type D or of type E.

3. Compounds according to claim 1 wherein
  R$^1$ is hydrogen or lower alkyl;
  R$^2$ is H; lower alkyl; lower alkenyl; —(CH$_2$)$_m$OR$^{55}$ (where R$^{55}$ is lower alkyl; or lower alkenyl); —CH$_2$)$_m$SR$^{56}$ (where R$^{56}$ is lower alkyl; or lower alkenyl); —(CH$_2$)$_m$NR$^{33}$R$^{34}$ (where R$^{33}$ is lower alkyl; or lower alkenyl; R$^{34}$ is H; or lower alkyl; or R$^{33}$ and R$^{34}$ taken together are —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$ is H; or lower alkyl); —(CH$_2$)$_m$OCONR$^{33}$R$^{75}$ (where R$^{33}$ is H; lower alkyl; or lower alkenyl; R$^{75}$ is lower alkyl; or R$^{33}$ and R$^{75}$ taken together are —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$ is H; or lower alkyl); —(CH$_2$)$_m$NR$^{20}$CONR$^{33}$R$^{82}$ (where R$^{20}$ is H; or lower alkyl; R$^{33}$ is H; or lower alkyl; or lower alkenyl; R$^{82}$ is H; or lower alkyl; or R$^{33}$ and R$^{82}$ taken together are —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$ is H; or lower alkyl); —(CH$_2$)$_o$N(R$^{20}$)COR$^{64}$ (where: R$^{20}$ is H; or lower alkyl; R$^{64}$ is lower alkyl; or lower alkenyl); (CH$_2$)$_o$COOR$^{57}$ (where R$^{57}$ is lower alkyl; or lower alkenyl); —(CH$_2$)$_o$CONR$^{58}$R$^{59}$ (where R$^{58}$ is lower alkyl; or lower alkenyl; and R$^{59}$ is H; or lower alkyl; or R$^{58}$ and R$^{59}$ taken together are —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$ is H; or lower alkyl); —(CH$_2$)$_o$PO(OR$^{60}$)$_2$ (where R$^{60}$ is lower alkyl; or lower alkenyl); —(CH$_2$)$_o$SO$_2$R$^{62}$ (where R$^{62}$ is lower alkyl; or lower alkenyl); or —(CH$_2$)$_q$C$_6$F$_4$R$^8$ (where R$^8$ is H; F; Cl; CF$_3$; lower alkyl; lower alkenyl; or lower alkoxy);

R$^5$ is lower alkyl; lower alkenyl; —(CH$_2$)$_o$OR$^{55}$ (where R$^{55}$ is lower alkyl; or lower alkenyl); —(CH$_2$)$_o$SR$^{56}$ (where R$^{56}$ is lower alkyl; or lower alkenyl); (CH$_2$)$_o$NR$^{33}$R$^{34}$ (where R$^{33}$ is lower alkyl; or lower alkenyl; R$^{34}$ is H; or lower alkyl; or R$^{33}$ and R$^{34}$ taken together are —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$ is H; or lower alkyl); —(CH$_2$)$_o$OCONR$^{33}$R$^{75}$ (where R$^{33}$ is H; or lower alkyl; or lower alkenyl; R$^{75}$ is lower alkyl; or R$^{33}$ and R$^{75}$ taken together are —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$ is H; or lower alkyl); —(CH$_2$)$_o$NR$^{20}$CONR$^{33}$R$^{82}$ (where R$^{20}$ is H; or lower alkyl; R$^{33}$ is H; or lower alkyl; or lower alkenyl; R$^{82}$ is H; or lower alkyl; or R$^{33}$ and R$^{82}$ taken together are —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$ is H; or lower alkyl); —(CH$_2$)$_o$N(R$^{20}$)COR$^{64}$ (where: R$^{20}$ is H; or lower alkyl; R$^{64}$ is alkyl; alkenyl; aryl; aryl-lower alkyl; or heteroaryl-lower alkyl); —(CH$_2$)$_o$COOR$^{57}$ (where R$^{57}$ is lower alkyl; or lower alkenyl); —(CH$_2$)$_o$CONR$^{58}$R$^{59}$ (where R$^{58}$ is lower alkyl; or lower alkenyl; and R$^{59}$ is H; or lower alkyl; or R$^{58}$ and R$^{59}$ taken together are —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$ is H; or lower alkyl); —(CH$_2$)$_o$PO(OR$^{60}$)$_2$ (where R$^{60}$ is lower alkyl; or lower alkenyl); —(CH$_2$)$_o$SO$_2$R$^{62}$ (where R$^{62}$ is lower alkyl; or lower alkenyl); or —(CH$_2$)$_q$C$_6$H$_4$R$^8$ (where R$^8$ is H; F; Cl; CF$_3$; lower alkyl; lower alkenyl; or lower alkoxy):

R$^7$ is lower alkyl; lower alkenyl; —(CH$_2$)$_q$OR$^{55}$ (where R$^{55}$ is lower alkyl; or lower alkenyl); —(CH$_2$)$_q$SR$^{56}$ (where R$^{56}$ is lower alkyl; or lower alkenyl); —(CH$_2$)$_q$NR$^{33}$R$^{34}$ (where R$^{33}$ is lower alkyl; or lower alkenyl; R$^{34}$ is H; or lower alkyl; or R$^{33}$ and R$^{34}$ taken together are —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$ is H; or lower alkyl); —(CH$_2$)$_q$OCONR$^{33}$R$^{75}$ (where R$^{33}$ is H; or lower alkyl; or lower alkenyl; R$^{75}$ is lower alkyl; or R$^{33}$ and R$^{75}$ taken together are —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$ is H; or lower alkyl); —(CH$_2$)$_q$NR$^{20}$CONR$^{33}$R$^{82}$ (where R$^{20}$ is H; or lower alkyl; R$^{33}$ is H; or lower alkyl; or lower alkenyl; R$^{82}$ is H; or lower alkyl; or R$^{33}$ and R$^{82}$ taken together are —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$ is H; or lower alkyl); —(CH$_2$)$_q$N(R$^{20}$)COR$^{64}$ (where: R$^{20}$ is H; or lower alkyl; R$^{64}$ is lower alkyl; or lower alkenyl); —(CH$^2$)$_r$COOR$^{57}$ (where R$^{57}$ is lower alkyl; or lower alkenyl); —(CH$_2$)$_q$CONR$^{58}$R$^{59}$ (where R$^{58}$ is lower alkyl; or lower alkenyl; and R$^{59}$ is H; or lower alkyl; or R$^{58}$ and R$^{59}$ taken together are —(CH$_2$)$_{2-6}$—; —(C H$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$ is H; or lower alkyl); —(CH$_2$)$_r$PO(OR$^{60}$)$_2$ (where R$^{60}$ is lower alkyl; or lower alkenyl); —(CH$_2$)$_r$SO$_2$R$^{62}$ (where R$^{62}$ is lower alkyl; or lower alkenyl); or —(CH$_2$)$_q$C$_6$H$_4$R$^8$ (where R$^8$ is H; F; Cl; CF$_3$; lower alkyl; lower alkenyl; or lower alkoxy); R$^8$ is H; F; Cl; CF$_3$; lower alkyl; lower alkenyl; —(CH$_2$)$_o$OR$^{55}$ (where R$^{55}$ is lower alkyl; or lower alkenyl); —(CH$_2$)$_o$SR$^{56}$ (where R$^{56}$ is lower alkyl; or lower alkenyl); —(CH$_2$)$_o$(NR$^{33}$R$^{34}$ (where R$^{33}$ is lower alkyl; or lower alkenyl; R$^{34}$ is H; or lower alkyl; or R$^{33}$ and R$^{34}$ taken together are —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$ is H; or lower alkyl); —(CH$_2$)$_o$OCONR$^{33}$R$^{75}$ (where R$^{33}$ is H; or lower alkyl; or lower alkenyl; R$^{75}$ is lower alkyl; or R$^{33}$ and R$^{75}$ taken together are —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$ is H; or lower alkyl); —(CH$_2$)$_o$NR$^{20}$CONR$^{33}$R$^{82}$ (where R$^{20}$ is H; or lower alkyl; R$^{33}$ is H; or lower alkyl; or lower alkenyl; R$^{82}$ is H; or lower alkyl; or R$^{33}$ and R$^{82}$ taken together are —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$ is H; or lower alkyl); —(CH$_2$)$_o$N(R$^{20}$)COR$^{64}$ (where R$^{20}$ is H; or lower alkyl; R$^{64}$ is lower alkyl; or lower alkenyl); —(CH$^p$)$_o$COOR$^{57}$ (where R$^{57}$ is lower alkyl; or lower alkenyl); —(CH$_2$)$_o$CONR$^{58}$R$^{59}$ (where R$^{58}$ is lower alkyl; or lower alkenyl; and R$^{59}$ is H; or lower alkyl; or R$^{58}$ and R$^{59}$ taken together are ——(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$ is H; or lower alkyl); —(CH$_2$)$_o$PO(OR$^{60}$)$_2$ (where R$^{60}$ is lower alkyl; or lower alkenyl); —(CH$_2$)$_o$SO$_2$R$^{62}$ (where R$^{62}$ is lower alkyl; or lower alkenyl); or —(CH$_2$)$_q$C$_6$H$_4$R$^8$ (where R$^8$ is H; F; Cl; CF$_3$; lower alkyl; lower alkenyl; or lower alkoxy).

4. Compounds according to claim 3 wherein A is a group of one of the formulae A5 (with R$^2$ being H); and A8.

5. Compounds according to claim 4 wherein A is a group of formula

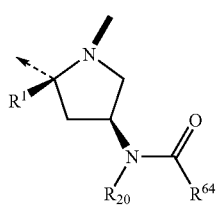

A8' wherein R$^{20}$ is H or lower alkyl; and R$^{64}$ is alkyl; alkenyl; aryl; aryl-lower alkyl; or heteroaryl-lower alkyl.

6. Compounds according to claim 5 wherein R$^{64}$ is n-hexyl; n-heptyl; 4-(phenyl)benzyl; diphenylmethyl, 3-amino-propyl; 5-amino-pentyl; methyl; ethyl; isopropyl; isobutyl; n-propyl; cyclohexyl; cyclohexylmethyl; n-butyl; phenyl; benzyl; (3-indolyl)methyl; 2-(3-indolyl)ethyl; (4-phenyl)phenyl; or n-nonyl.

7. Compounds according to claim 1 wherein B is an enantiomer of one of the groups A5 (with R$^2$ being H) and A8.

8. Compounds according to claim 7 wherein B is a group, having (L)-configuration, of formula

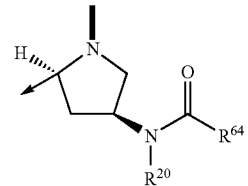

A8"

wherein R$^{20}$ is H; or lower alkyl; and R$^{64}$ is alkyl; alkenyl; aryl; aryl-lower alkyl; or heteroaryl-lower alkyl.

9. Compounds according to claim 8 wherein R$^{64}$ is n-hexyl; n-heptyl; 4-(phenyl)benzyl; diphenylmethyl, 3-amino-propyl; 5-amino-pentyl; methyl; ethyl; isopropyl; isobutyl; n-propyl; cyclohexyl; cyclohexylmethyl; n-butyl; phenyl; benzyl; (3-indolyl)methyl; 2-(3-indolyl)ethyl; (4-phenyl)phenyl; or n-nonyl.

10. Compounds according to claim 1 wherein in the chain of α-amino acid residues Z, the amino acid residues in position 1–12 are:
P1: of type C or of type E; or of type D; or of type F;
P2: of type E; or of type D;
P3: of type C or of type D;
P4: of type E;
P5: of type E; or of type C;
P6: of type E or of type F,
P7: of type E;
P8: of type D;
P9: of type E or of type D;
P10: of type D;
P11: of type E; or of type D and
P12: of type C or of type E; or of type D; or of type F;
at P6 and P7 also D-isomers being possible.

11. Compounds according to claim 10 wherein the amino acid residues in position 1–12 are:
P1: Leu; Arg; Lys; Tyr; Trp; Val; Gln; or 4-AmPhe;
P2: Mg; Trp; or Gln;
P3: Leu,; Val; Ile; or Phe;
P4: Lys; Arg; Gln; or Orn;
P5: Lys; or Arg;
P6: Arg; Tyr (Bzl); or $^D$Tyr (Bzl)
P7: Arg;
P8: Trp; Bip; 1-Nal; Tyr (Bzl); or Val;
P9: Lys; Arg; Orn; Tyr; Trp; or Gln;
P10: Tyr; Thr (Bzl); or Tyr (Bzl);
P11: Arg; or Tyr; and
P12: Val; Arg; 1-Nal; or 4-AmPhe.

12. A compound according to claim 1 wherein the template is $^D$Pro-$^L$Pro; and the amino acid residues in position 1–12 are:
P1: Leu;
P2: Arg;
P3: Leu;
P4: Lys;
P5: Lys;
P6: Arg;
P7: Arg;
P8: Trp;
P9: Lys;
P10: Tyr;
P11: Arg; and
P12: Val.

13. A compound according to claim 1 wherein the template is $^D$Pro-$^L$Pro; and the amino acid residues in position 1–12 are:
- P1: Leu;
- P2: Arg;
- P3: Leu;
- P4: Lys;
- P5: Lys;
- P6: Arg;
- P7: Arg;
- P8: Y(Bzl);
- P9: Lys;
- P10: Tyr;
- P11: Arg; and
- P12: Val.

14. A compound according to claim 1 wherein the template is $^D$Pro-$^L$Pro; and the amino acid residues in position 1–12 are:
- P1: Leu;
- P2: Arg;
- P3: Leu;
- P4: Lys;
- P5: Lys;
- P6: Arg;
- P7: Arg;
- P8: Trp;
- P9: Lys;
- P10: Tyr;
- P11: Arg; and
- P12: 1-Nal.

15. A compound according to claim 1 wherein the template is $^D$Pro-$^L$Pro; and the amino acid residues in position 1–12 are:
- P1: Leu;
- P2: Arg;
- P3: Leu;
- P4: Lys;
- P5: Lys;
- P6: Arg;
- P7: Arg;
- P8: Bip;
- P9: Lys;
- P10: Tyr;
- P11: Arg; and
- P12: Val.

16. A compound according to claim 1 wherein the template is $^D$Pro-$^L$Pro; and the amino acid residues in position 1–12 are:
- P1: Leu;
- P2: Arg;
- P3: Leu;
- P4: Lys;
- P5: Lys;
- P6: Arg;
- P7: Arg;
- P8: Trp;
- P9: Lys;
- P10: Thr (Bzl);
- P11: Arg; and
- P12: Val.

17. A compound according to claim 1 wherein the template is $^D$Pro-$^L$Pro; and the amino acid residues in position 1–12 are:
- P1: Leu;
- P2: Arg;
- P3: Leu;
- P4: Lys;
- P5: Lys;
- P6: Arg;
- P7: Arg;
- P8: Trp;
- P9: Arg;
- P10: Tyr;
- P11: Arg; and
- P12: Val.

18. A compound according to claim 1 wherein the template is $^D$Pro-$^L$Pro; and the amino acid residues in position 1–12 are:
- P1: Leu;
- P2: Trp;
- P3: Leu;
- P4: Lys;
- P5: Lys;
- P6: Arg;
- P7: Arg;
- P8: Bip;
- P9: Lys;
- P10: Tyr;
- P11: Arg; and
- P12: Val.

19. A compound according to claim 1 wherein the template is $^D$Pro-(2R,4S)-4-[n-hexylcarbonylamino]-$^L$pro; and the amino acid residues in position 1–12 are:
- P1: Leu;
- P2: Arg;
- P3: Leu;
- P4: Lys;
- P5: Lys;
- P6: Arg;
- P7: Arg;
- P8: Trp;
- P9: Lys;
- P10: Tyr;
- P11: Arg; and
- P12: Val.

20. A compound according to claim 1 wherein the template is $^D$Pro-(2R,4S)-4-[cyclohexylcarbonylamino]-$^L$Pro; and the amino acid residues in position 1–12 are:
- P1: Leu;
- P2: Arg;
- P3: Leu;
- P4: Lys;
- P5: Lys;
- P6: Arg;
- P7: Arg;
- P8: Trp;
- P9: Lys;
- P10: Tyr;
- P11: Arg; and
- P12: Val.

21. A compound according to claim 1 wherein the template is $^D$Pro-$^L$Pro; and the amino acid residues in position 1–12 are:
- P1: Arg;
- P2: Trp;
- P3: Leu;
- P4: Lys;
- P5: Lys;
- P6: Arg;
- P7: Arg;
- P8: Trp;
- P9: Lys;
- P10: Tyr;
- P11: Tyr; and
- P12: Val.

22. A compound according to claim 1 wherein the template is $^D$Pro-$^L$Pro; and the amino acid residues in position 1–12 are:

P1: Leu;
P2: Trp;
P3: Leu;
P4: Lys;
P5: Lys;
P6: Arg;
P7: Arg;
P8: Trp;
P9: Lys;
P10: Tyr;
P11: Tyr; and
P12: Arg.

23. A compound according to claim 1 wherein the template is $^D$Pro-$^L$Pro; and the amino acid residues in position 1–12 are:
P1: Arg;
P2: Trp;
P3: Leu;
P4: Lys;
P5: Lys;
P6: Arg;
P7: Arg;
P8: Trp;
P9: Lys;
P10: Tyr;
P11: Tyr; and
P12, Arg.

24. A compound according to claim 1 wherein the template is $^D$Pro-$^L$Pro; and the amino acid residues in position 1–12 are:
P1: Leu;
P2: Arg;
P3: Leu;
P4: Lys;
P5: Lys;
P6: $^D$Tyr (Bzl);
P7: Arg;
P8: Trp;
P9: Lys;
P10: Tyr;
P11, Arg; and
P12: Val.

25. A compound according to claim 1 wherein the template is $^D$Pro-$^L$Pro; and the amino acid residues in position 1–12 are:
P1: Arg;
P2: Bip;
P3: Leu;
P4: Lys;
P5: Lys;
P6: Arg;
P7: Arg;
P8: Trp;
P9: Lys;
P10: Tyr;
P11: Tyr; and
P12: Arg.

26. A compound according to claim 1 wherein the template is $^D$Pro-$^L$Pro; and the amino acid residues in position 1–12 are:
P1: Lys;
P2: Trp;
P3: Leu;
P4: Lys;
P5: Lys;
P6: Arg;
P7: Arg;
P8: Trp;
P9: Lys;
P10: Tyr;
P11: Tyr; and
P12: Arg.

27. A compound according to claim 1 wherein the template is $^D$Pro-$^L$Pro; and the amino acid residues in position 1–12 are:
P1: Tyr;
P2: Trp;
P3: Leu;
P4: Lys;
P5: Lys;
P6: Arg;
P7: Arg;
P8: Trp;
P9: Lys;
P10: Tyr;
P11: Tyr; and
P12: Arg.

28. A compound according to claim 1 wherein the template is $^D$Pro-$^L$Pro; and the amino acid residues in position 1–12 are:
P1: Trp;
P2: Trp;
P3: Leu;
P4: Lys;
P5: Lys;
P6: Arg;
P7: Arg;
P8: Trp;
P9: Lys;
P10: Tyr;
P11: Tyr; and
P12: Arg.

29. A compound according to claim 1 wherein the template is $^D$Pro-$^L$Pro; and the amino acid residues in position 1–12 are:
P1: Val;
P2: Trp;
P3: Leu;
P4: Lys;
P5: Lys;
P6: Arg;
P7: Arg;
P8: Trp;
P9: Lys;
P10: Tyr;
P11: Tyr; and
P12: Arg.

30. A compound according to claim 1 wherein the template is $^D$Pro-$^L$Pro; and the amino acid residues in position 1–12 are:
P1: Gln;
P2: Trp;
P3: Leu;
P4: Lys;
P5: Lys;
P6: Arg;
P7: Arg;
P8: Trp;
P9: Lys;
P10: Tyr;
P11: Tyr; and
P12: Arg.

31. A compound according to claim 1 wherein the template is $^D$Pro-$^L$Pro; and the amino acid residues in position 1–12 are:
P1: Leu;
P2: Arg;
P3: Leu;

P4: Lys;
P5: Lys;
P6: Tyr (Bzl);
P7: Arg;
P8: Trp;
P9: Lys;
P10: Tyr;
P11: Arg; and
P12: Val.

32. A pharmaceutical composition comprising a compound according to claim 1 and a pharmaceutically inert carrier.

33. A composition according to claim 32 in a form suitable for oral, topical, transdermal, injection, buccal, transmucosal, pulmonary or inhalation administration.

34. A composition according to claim 32 in form of tablets, dragees, capsules, solutions, liquids, gels, plasters, creams, ointments, syrups, slurries, suspensions, sprays, nebulisers or suppositories.

35. A process for the manufacture of compounds according to claim 1 comprising the steps of:
(a) coupling an appropriately functionalized solid support with an appropriately N-protected derivative of that amino acid which in the desired end-product is in position or 6, 7 or 5 any functional group which may be present in said N-protected amino acid derivative being likewise appropriately protected;
(b) removing the N-protecting group from the product thus obtained;
(c) coupling the product thus obtained with an appropriately N-protected derivative of that amino acid which in the desired end-product is one position nearer the N-terminal amino acid residue, any functional group which may be present in said N-protected amino acid derivative being likewise appropriately protected;
(d) removing the N-protecting group from the product thus obtained;
(e) repeating steps (c) and (d) until the N-terminal amino acid residue has been introduced;
(f) coupling the product thus obtained to a compound of the general formula $$O=C(OH)(X)\text{—Template} \quad \text{II}$$

wherein $$O=C(—)(—)\text{—Template}$$

is as defined above and X is an N-protecting group or, alternatively, (fa) coupling the product obtained in step (d) or (e) with an appropriately N-protected derivative of an amino acid of the general formula $$\text{HOOC—B—H} \quad \text{III}$$

or $$\text{HOOC-A-H} \quad \text{IV}$$

wherein B and A are as defined above, any functional group which may be present in said N-protected amino acid derivative being likewise appropriately protected;
(fb) removing the N-protecting group from the product thus obtained; and
(fc) coupling the product thus obtained with an appropriately N-protected derivative of an amino acid of the above general formula IV and, respectively, III, any functional group which may be present in said N-protected amino acid derivative being likewise appropriately protected;
(g) removing the N-protecting group from the product obtained in step (f) or (fc);
(h) coupling the product thus obtained to an appropriately N-protected derivative of that amino acid which in the desired end-product is in position 12, any functional group which may be present in said N-protected amino acid derivative being likewise appropriately protected;
(i) removing the N-protecting group from the product thus obtained;
(j) coupling the product thus obtained to an appropriately N-protected derivative of that amino acid which in the desired end-product is one position farther away from position 12, any functional group which may be present in said N-protected amino acid derivative being likewise appropriately protected;
(k) removing the N-protecting group from the product thus obtained;
(l) repeating steps (j) and (k) until all amino acid residues have been introduced;
(m) if desired, selectively deprotecting one or several protected functional group(s) present in the molecule and appropriately substituting the reactive group(s) thus liberated;
(o) detaching the product thus obtained from the solid support;
(p) cyclizing the product cleaved from the solid support;
(q) removing any protecting groups present on functional groups of any members of the chain of amino acid residues and, if desired, any protecting group(s) which may in addition be present in the molecule; and
(r) if desired, converting the product thus obtained into a pharmaceutically acceptable salt or converting a pharmaceutically acceptable, or unacceptable, salt thus obtained into the corresponding free compound of formula I or into a different, pharmaceutically acceptable, salt.

* * * * *

UNITED STATES PATENT AND TRADEMARK OFFICE
CERTIFICATE OF CORRECTION

PATENT NO.         : 7,253,146 B2
APPLICATION NO. : 10/469060
DATED                  : August 7, 2007
INVENTOR(S)        : Daniel Obrecht, John Anthony Robinson and Jan Wim Vrijbloed It is certified that error appears in the above-identified patent and that said Letters Patent is hereby corrected as shown below:

Column 345, claim 1, lines 39-50, of the printed patent incorrectly reads:

"is the residue of an L-α-amino acid with B being the enantiomer of one of the groups A5, A8 or A10 as defined hereinafter;

is a group of one of the formulae
   $R^1$ is H; lower alkyl; or aryl-lower alkyl;"

Signed and Sealed this

Third Day of August, 2010

David J. Kappos
*Director of the United States Patent and Trademark Office*

CERTIFICATE OF CORRECTION (continued)

Column 345, claim 1, lines 39-50, of the printed patent should read:

--is the residue of an L-α-amino acid with B being the enantiomer of one of the groups A5, A8 or A10 as defined hereinafter;

is a group of one of the formulae

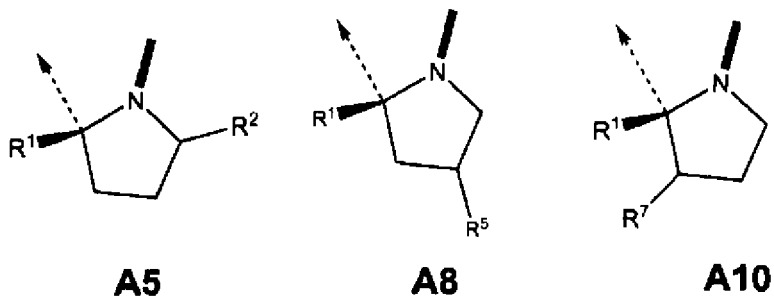

$R^1$ is  H; lower alkyl; or aryl-lower alkyl;--.

SEQUENCE LISTING

<160> NUMBER OF SEQ ID NOS: 304

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (9)..(9)
<223> OTHER INFORMATION: Xaa is D-Pro

<400> SEQUENCE: 1

Tyr Val Arg Arg Arg Phe Leu Val Xaa Pro
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (9)..(9)
<223> OTHER INFORMATION: Xaa is D-Pro

<400> SEQUENCE: 2

```
Tyr Val Arg Lys Gly Phe Leu Val Xaa Pro
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (9)..(9)
<223> OTHER INFORMATION: Xaa is D-Pro

<400> SEQUENCE: 3

Trp Val Arg Lys Gly Phe Leu Trp Xaa Pro
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (9)..(9)
<223> OTHER INFORMATION: Xaa is D-Pro

<400> SEQUENCE: 4

Tyr Val Arg Arg Arg Trp Leu Val Xaa Pro
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (9)..(9)
<223> OTHER INFORMATION: Xaa is D-Pro

<400> SEQUENCE: 5

Tyr Val Tyr Arg Arg Phe Leu Val Xaa Pro
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (9)..(9)
<223> OTHER INFORMATION: Xaa is D-Pro

<400> SEQUENCE: 6

Lys Val Tyr Arg Arg Phe Leu Val Xaa Pro
1               5                   10

<210> SEQ ID NO 7
<211> LENGTH: 10
<212> TYPE: PRT
```

```
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (9)..(9)
<223> OTHER INFORMATION: Xaa is D-Pro

<400> SEQUENCE: 7

Lys Val Tyr Lys Gly Phe Leu Trp Xaa Pro
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (10)..(10)
<223> OTHER INFORMATION: Xaa is D-Pro

<400> SEQUENCE: 8

Arg Phe Leu Arg Arg Arg Leu Phe Arg Xaa Pro
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (10)..(10)
<223> OTHER INFORMATION: Xaa is D-Pro

<400> SEQUENCE: 9

Arg Tyr Leu Arg Arg Arg Leu Tyr Arg Xaa Pro
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (10)..(10)
<223> OTHER INFORMATION: Xaa is D-Pro

<400> SEQUENCE: 10

Arg Phe Phe Arg Arg Arg Leu Phe Arg Xaa Pro
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (10)..(10)
```

```
<223> OTHER INFORMATION: Xaa is D-Pro

<400> SEQUENCE: 11

Arg Tyr Tyr Arg Arg Arg Leu Tyr Arg Xaa Pro
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (10)..(10)
<223> OTHER INFORMATION: Xaa is D-Pro

<400> SEQUENCE: 12

Leu Phe Phe Arg Arg Arg Leu Phe Arg Xaa Pro
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (10)..(10)
<223> OTHER INFORMATION: Xaa is D-Pro

<400> SEQUENCE: 13

Leu Tyr Tyr Arg Arg Arg Leu Tyr Arg Xaa Pro
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (10)..(10)
<223> OTHER INFORMATION: Xaa is D-Pro

<400> SEQUENCE: 14

Arg Phe Leu Phe Arg Arg Leu Leu Arg Xaa Pro
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (10)..(10)
<223> OTHER INFORMATION: Xaa is D-Pro

<400> SEQUENCE: 15

Arg Tyr Leu Tyr Arg Arg Leu Leu Arg Xaa Pro
1               5                   10
```

```
<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (10)..(10)
<223> OTHER INFORMATION: Xaa is D-Pro

<400> SEQUENCE: 16

Leu Phe Leu Phe Arg Arg Leu Phe Arg Xaa Pro
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (10)..(10)
<223> OTHER INFORMATION: Xaa is D-Pro

<400> SEQUENCE: 17

Leu Tyr Leu Tyr Arg Arg Leu Tyr Arg Xaa Pro
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (10)..(10)
<223> OTHER INFORMATION: Xaa is D-Pro

<400> SEQUENCE: 18

Arg Phe Leu Phe Arg Arg Leu Phe Leu Xaa Pro
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (10)..(10)
<223> OTHER INFORMATION: Xaa is D-Pro

<400> SEQUENCE: 19

Arg Tyr Leu Tyr Arg Arg Leu Tyr Leu Xaa Pro
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence:
```

```
                          Cyclic peptide
<220> FEATURE:
<221> NAME/KEY: MISC_FEATURE
<222> LOCATION: (10)..(10)
<223> OTHER INFORMATION: Xaa is D-Pro

<400> SEQUENCE: 20

Phe Leu Leu Phe Arg Arg Leu Phe Arg Xaa Pro
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence:
                          Cyclic peptide
<220> FEATURE:
<221> NAME/KEY: MISC_FEATURE
<222> LOCATION: (10)..(10)
<223> OTHER INFORMATION: Xaa is D-Pro

<400> SEQUENCE: 21

Tyr Leu Leu Tyr Arg Arg Leu Tyr Arg Xaa Pro
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence:
                          Cyclic peptide
<220> FEATURE:
<221> NAME/KEY: MISC_FEATURE
<222> LOCATION: (10)..(10)
<223> OTHER INFORMATION: Xaa is D-Pro

<400> SEQUENCE: 22

Arg Leu Leu Phe Arg Arg Leu Phe Phe Xaa Pro
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence:
                          Cyclic peptide
<220> FEATURE:
<221> NAME/KEY: MISC_FEATURE
<222> LOCATION: (10)..(10)
<223> OTHER INFORMATION: Xaa is D-Pro

<400> SEQUENCE: 23

Arg Leu Leu Tyr Arg Arg Leu Tyr Tyr Xaa Pro
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence:
                          Cyclic peptide
<220> FEATURE:
<221> NAME/KEY: MISC_FEATURE
<222> LOCATION: (10)..(10)
<223> OTHER INFORMATION: Xaa is D-Pro

<400> SEQUENCE: 24
```

Arg Phe Leu Arg Arg Phe Leu Phe Arg Xaa Pro
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (10)..(10)
<223> OTHER INFORMATION: Xaa is D-Pro

<400> SEQUENCE: 25

Arg Phe Leu Arg Arg Phe Phe Leu Arg Xaa Pro
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (10)..(10)
<223> OTHER INFORMATION: Xaa is D-Pro

<400> SEQUENCE: 26

Arg Tyr Leu Arg Arg Tyr Tyr Leu Arg Xaa Pro
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (10)..(10)
<223> OTHER INFORMATION: Xaa is D-Pro

<400> SEQUENCE: 27

Leu Tyr Leu Arg Arg Tyr Leu Tyr Arg Xaa Pro
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (10)..(10)
<223> OTHER INFORMATION: Xaa is D-Pro

<400> SEQUENCE: 28

Leu Leu Phe Phe Arg Arg Leu Phe Arg Xaa Pro
1               5                   10

<210> SEQ ID NO 29
<211> LENGTH: 11

```
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (10)..(10)
<223> OTHER INFORMATION: Xaa is D-Pro

<400> SEQUENCE: 29

Leu Leu Tyr Tyr Arg Arg Leu Tyr Arg Xaa Pro
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (10)..(10)
<223> OTHER INFORMATION: Xaa is D-Pro

<400> SEQUENCE: 30

Arg Leu Phe Phe Arg Arg Leu Phe Leu Xaa Pro
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (10)..(10)
<223> OTHER INFORMATION: Xaa is D-Pro

<400> SEQUENCE: 31

Arg Leu Tyr Tyr Arg Arg Leu Tyr Leu Xaa Pro
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (11)..(11)
<223> OTHER INFORMATION: Xaa is D-Pro

<400> SEQUENCE: 32

Arg Phe Leu Phe Arg Arg Arg Leu Phe Arg Xaa Pro
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
```

```
<222> LOCATION: (11)..(11)
<223> OTHER INFORMATION: Xaa is D-Pro

<400> SEQUENCE: 33

Arg Tyr Leu Tyr Arg Arg Arg Leu Tyr Arg Xaa Pro
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (11)..(11)
<223> OTHER INFORMATION: Xaa is D-Pro

<400> SEQUENCE: 34

Arg Phe Phe Phe Arg Arg Arg Leu Leu Arg Xaa Pro
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (11)..(11)
<223> OTHER INFORMATION: Xaa is D-Pro

<400> SEQUENCE: 35

Arg Tyr Tyr Tyr Arg Arg Arg Leu Leu Arg Xaa Pro
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (11)..(11)
<223> OTHER INFORMATION: Xaa is D-Pro

<400> SEQUENCE: 36

Arg Leu Phe Phe Arg Arg Arg Leu Phe Arg Xaa Pro
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (11)..(11)
<223> OTHER INFORMATION: Xaa is D-Pro

<400> SEQUENCE: 37

Leu Tyr Leu Tyr Arg Arg Arg Leu Tyr Arg Xaa Pro
1               5                   10
```

```
<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (11)..(11)
<223> OTHER INFORMATION: Xaa is D-Pro

<400> SEQUENCE: 38

Arg Phe Leu Phe Arg Arg Arg Leu Phe Leu Xaa Pro
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (11)..(11)
<223> OTHER INFORMATION: Xaa is D-Pro

<400> SEQUENCE: 39

Arg Tyr Leu Tyr Arg Arg Arg Leu Tyr Leu Xaa Pro
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (11)..(11)
<223> OTHER INFORMATION: Xaa is D-Pro

<400> SEQUENCE: 40

Leu Leu Phe Phe Arg Arg Arg Leu Phe Arg Xaa Pro
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (11)..(11)
<223> OTHER INFORMATION: Xaa is D-Pro

<400> SEQUENCE: 41

Arg Leu Phe Phe Arg Arg Arg Leu Phe Leu Xaa Pro
1               5                   10

<210> SEQ ID NO 42
<211> LENGTH: 12
<212> TYPE: PRT
<213> ORGANISM: Artificial Sequence
<220> FEATURE:
```

```
<223> OTHER INFORMATION: Description of Artificial Sequence:
                       Cyclic peptide
<220> FEATURE:
<221> NAME/KEY: MISC_FEATURE
<222> LOCATION: (11)..(11)
<223> OTHER INFORMATION: Xaa is D-Pro

<400> SEQUENCE: 42

Leu Tyr Tyr Tyr Arg Arg Arg Leu Leu Arg Xaa Pro
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence:
                       Cyclic peptide
<220> FEATURE:
<221> NAME/KEY: MISC_FEATURE
<222> LOCATION: (11)..(11)
<223> OTHER INFORMATION: Xaa is D-Pro

<400> SEQUENCE: 43

Arg Phe Phe Phe Arg Arg Arg Leu Leu Leu Xaa Pro
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence:
                       Cyclic peptide
<220> FEATURE:
<221> NAME/KEY: MISC_FEATURE
<222> LOCATION: (11)..(11)
<223> OTHER INFORMATION: Xaa is D-Pro

<400> SEQUENCE: 44

Arg Tyr Tyr Tyr Arg Arg Arg Leu Leu Leu Xaa Pro
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence:
                       Cyclic peptide
<220> FEATURE:
<221> NAME/KEY: MISC_FEATURE
<222> LOCATION: (11)..(11)
<223> OTHER INFORMATION: Xaa is D-Pro

<400> SEQUENCE: 45

Arg Leu Leu Phe Arg Gly Arg Phe Phe Arg Xaa Pro
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence:
                       Cyclic peptide
<220> FEATURE:
<221> NAME/KEY: MISC_FEATURE
<222> LOCATION: (11)..(11)
<223> OTHER INFORMATION: Xaa is D-Pro
```

```
<400> SEQUENCE: 46

Arg Leu Leu Tyr Arg Gly Arg Tyr Tyr Arg Xaa Pro
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (11)..(11)
<223> OTHER INFORMATION: Xaa is D-Pro

<400> SEQUENCE: 47

Arg Phe Phe Phe Arg Gly Arg Leu Leu Arg Xaa Pro
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (11)..(11)
<223> OTHER INFORMATION: Xaa is D-Pro

<400> SEQUENCE: 48

Arg Tyr Tyr Tyr Arg Gly Arg Leu Leu Arg Xaa Pro
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (11)..(11)
<223> OTHER INFORMATION: Xaa is D-Pro

<400> SEQUENCE: 49

Leu Phe Leu Phe Arg Gly Arg Leu Phe Arg Xaa Pro
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (11)..(11)
<223> OTHER INFORMATION: Xaa is D-Pro

<400> SEQUENCE: 50

Leu Tyr Leu Tyr Arg Gly Arg Leu Tyr Arg Xaa Pro
1               5                   10

<210> SEQ ID NO 51
```

```
<211> LENGTH: 12
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (11)..(11)
<223> OTHER INFORMATION: Xaa is D-Pro

<400> SEQUENCE: 51

Arg Phe Leu Phe Arg Gly Arg Leu Phe Leu Xaa Pro
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (11)..(11)
<223> OTHER INFORMATION: Xaa is D-Pro

<400> SEQUENCE: 52

Arg Tyr Leu Tyr Arg Gly Arg Leu Tyr Leu Xaa Pro
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (11)..(11)
<223> OTHER INFORMATION: Xaa is D-Pro

<400> SEQUENCE: 53

Leu Arg Phe Phe Arg Leu Arg Leu Phe Arg Xaa Pro
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (11)..(11)
<223> OTHER INFORMATION: Xaa is D-Pro

<400> SEQUENCE: 54

Leu Arg Tyr Tyr Arg Leu Arg Leu Tyr Arg Xaa Pro
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
```

```
<221> NAME/KEY: MISC_FEATURE
<222> LOCATION: (11)..(11)
<223> OTHER INFORMATION: Xaa is D-Pro

<400> SEQUENCE: 55

Leu Leu Phe Phe Arg Gly Arg Leu Phe Arg Xaa Pro
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (11)..(11)
<223> OTHER INFORMATION: Xaa is D-Pro

<400> SEQUENCE: 56

Leu Leu Tyr Tyr Arg Gly Arg Leu Tyr Arg Xaa Pro
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (11)..(11)
<223> OTHER INFORMATION: Xaa is D-Pro

<400> SEQUENCE: 57

Arg Phe Leu Phe Arg Gly Arg Phe Arg Leu Xaa Pro
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (11)..(11)
<223> OTHER INFORMATION: Xaa is D-Pro

<400> SEQUENCE: 58

Arg Tyr Leu Tyr Arg Gly Arg Tyr Arg Leu Xaa Pro
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (12)..(12)
<223> OTHER INFORMATION: Xaa is D-Pro

<400> SEQUENCE: 59

Arg Leu Phe Leu Arg Arg Arg Phe Phe Arg Leu Xaa Pro
```

```
1               5                   10
```

<210> SEQ ID NO 60
<211> LENGTH: 13
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (12)..(12)
<223> OTHER INFORMATION: Xaa is D-Pro

<400> SEQUENCE: 60

```
Arg Leu Tyr Leu Arg Arg Arg Tyr Tyr Arg Leu Xaa Pro
1               5                   10
```

<210> SEQ ID NO 61
<211> LENGTH: 13
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (12)..(12)
<223> OTHER INFORMATION: Xaa is D-Pro

<400> SEQUENCE: 61

```
Leu Leu Phe Leu Arg Arg Arg Phe Phe Arg Arg Xaa Pro
1               5                   10
```

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (12)..(12)
<223> OTHER INFORMATION: Xaa is D-Pro

<400> SEQUENCE: 62

```
Arg Leu Phe Leu Arg Arg Arg Leu Phe Arg Phe Xaa Pro
1               5                   10
```

<210> SEQ ID NO 63
<211> LENGTH: 13
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (12)..(12)
<223> OTHER INFORMATION: Xaa is D-Pro

<400> SEQUENCE: 63

```
Phe Leu Phe Leu Arg Arg Arg Leu Phe Arg Arg Xaa Pro
1               5                   10
```

<210> SEQ ID NO 64
<211> LENGTH: 13
<212> TYPE: PRT
<213> ORGANISM: Artificial Sequence

```
<220> FEATURE:
<223> OTHER INFORMATION: Description of Artificial Sequence:
      Cyclic peptide
<220> FEATURE:
<221> NAME/KEY: MISC_FEATURE
<222> LOCATION: (12)..(12)
<223> OTHER INFORMATION: Xaa is D-Pro

<400> SEQUENCE: 64

Tyr Leu Tyr Leu Arg Arg Arg Leu Tyr Arg Arg Xaa Pro
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (12)..(12)
<223> OTHER INFORMATION: Xaa is D-Pro

<400> SEQUENCE: 65

Arg Arg Phe Leu Arg Gly Arg Phe Phe Leu Arg Xaa Pro
1               5                   10

<210> SEQ ID NO 66
<211> LENGTH: 13
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (12)..(12)
<223> OTHER INFORMATION: Xaa is D-Pro

<400> SEQUENCE: 66

Leu Leu Tyr Tyr Arg Arg Leu Tyr Tyr Arg Arg Xaa Pro
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (12)..(12)
<223> OTHER INFORMATION: Xaa is D-Pro

<400> SEQUENCE: 67

Leu Tyr Leu Tyr Arg Arg Tyr Leu Tyr Arg Arg Xaa Pro
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (12)..(12)
<223> OTHER INFORMATION: Xaa is D-Pro
```

```
<400> SEQUENCE: 68

Arg Arg Phe Phe Arg Arg Leu Phe Phe Leu Leu Xaa Pro
1               5                   10

<210> SEQ ID NO 69
<211> LENGTH: 13
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (12)..(12)
<223> OTHER INFORMATION: Xaa is D-Pro

<400> SEQUENCE: 69

Arg Leu Tyr Tyr Arg Arg Leu Tyr Tyr Arg Leu Xaa Pro
1               5                   10

<210> SEQ ID NO 70
<211> LENGTH: 13
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (12)..(12)
<223> OTHER INFORMATION: Xaa is D-Pro

<400> SEQUENCE: 70

Arg Leu Phe Phe Arg Gly Arg Phe Phe Arg Leu Xaa Pro
1               5                   10

<210> SEQ ID NO 71
<211> LENGTH: 16
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (15)..(15)
<223> OTHER INFORMATION: Xaa is D-Pro

<400> SEQUENCE: 71

Arg Tyr Leu Leu Tyr Arg Arg Arg Tyr Leu Leu Tyr Arg Arg Xaa Pro
1               5                   10                  15

<210> SEQ ID NO 72
<211> LENGTH: 16
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (15)..(15)
<223> OTHER INFORMATION: Xaa is D-Pro

<400> SEQUENCE: 72

Arg Leu Leu Tyr Tyr Arg Arg Arg Tyr Leu Leu Tyr Arg Arg Xaa Pro
1               5                   10                  15
```

<210> SEQ ID NO 73
<211> LENGTH: 16
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (15)..(15)
<223> OTHER INFORMATION: Xaa is D-Pro

<400> SEQUENCE: 73

Arg Leu Leu Leu Tyr Arg Arg Arg Tyr Leu Tyr Tyr Arg Arg Xaa Pro
1               5                   10                  15

<210> SEQ ID NO 74
<211> LENGTH: 16
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (15)..(15)
<223> OTHER INFORMATION: Xaa is D-Pro

<400> SEQUENCE: 74

Arg Phe Leu Phe Leu Arg Arg Arg Phe Phe Leu Phe Arg Arg Xaa Pro
1               5                   10                  15

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (15)..(15)
<223> OTHER INFORMATION: Xaa is D-Pro

<400> SEQUENCE: 75

Arg Tyr Leu Tyr Leu Arg Arg Arg Tyr Tyr Leu Tyr Arg Arg Xaa Pro
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (15)..(15)
<223> OTHER INFORMATION: Xaa is D-Pro

<400> SEQUENCE: 76

Arg Phe Leu Phe Leu Arg Arg Arg Phe Leu Phe Leu Arg Arg Xaa Pro
1               5                   10                  15

<210> SEQ ID NO 77
<211> LENGTH: 16
<212> TYPE: PRT
<213> ORGANISM: Artificial Sequence
<220> FEATURE:
<223> OTHER INFORMATION: Description of Artificial Sequence:
      Cyclic peptide

```
<220> FEATURE:
<221> NAME/KEY: MISC_FEATURE
<222> LOCATION: (15)..(15)
<223> OTHER INFORMATION: Xaa is D-Pro

<400> SEQUENCE: 77

Arg Tyr Leu Tyr Leu Arg Arg Arg Tyr Leu Tyr Leu Arg Arg Xaa Pro
 1               5                  10                  15

<210> SEQ ID NO 78
<211> LENGTH: 16
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (15)..(15)
<223> OTHER INFORMATION: Xaa is D-Pro

<400> SEQUENCE: 78

Arg Arg Leu Leu Phe Arg Arg Arg Phe Leu Leu Phe Phe Arg Xaa Pro
 1               5                  10                  15

<210> SEQ ID NO 79
<211> LENGTH: 16
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (15)..(15)
<223> OTHER INFORMATION: Xaa is D-Pro

<400> SEQUENCE: 79

Arg Arg Leu Leu Tyr Arg Arg Arg Tyr Leu Leu Tyr Tyr Arg Xaa Pro
 1               5                  10                  15

<210> SEQ ID NO 80
<211> LENGTH: 16
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (15)..(15)
<223> OTHER INFORMATION: Xaa is D-Pro

<400> SEQUENCE: 80

Arg Arg Leu Tyr Tyr Arg Arg Arg Tyr Leu Leu Tyr Tyr Arg Xaa Pro
 1               5                  10                  15

<210> SEQ ID NO 81
<211> LENGTH: 16
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (15)..(15)
<223> OTHER INFORMATION: Xaa is D-Pro

<400> SEQUENCE: 81
```

Arg Arg Leu Leu Tyr Arg Arg Arg Tyr Leu Tyr Tyr Leu Arg Xaa Pro
1               5                   10                  15

<210> SEQ ID NO 82
<211> LENGTH: 16
<212> TYPE: PRT
<213> ORGANISM: Artificial Sequence
<220> FEATURE:
<223> OTHER INFORMATION: Description of Artificial Sequence:
              Cyclic peptide
<220> FEATURE:
<221> NAME/KEY: MISC_FEATURE
<222> LOCATION: (15)..(15)
<223> OTHER INFORMATION: Xaa is D-Pro

<400> SEQUENCE: 82

Arg Arg Leu Phe Leu Arg Arg Arg Phe Phe Leu Phe Phe Arg Xaa Pro
1               5                   10                  15

<210> SEQ ID NO 83
<211> LENGTH: 16
<212> TYPE: PRT
<213> ORGANISM: Artificial Sequence
<220> FEATURE:
<223> OTHER INFORMATION: Description of Artificial Sequence:
              Cyclic peptide
<220> FEATURE:
<221> NAME/KEY: MISC_FEATURE
<222> LOCATION: (15)..(15)
<223> OTHER INFORMATION: Xaa is D-Pro

<400> SEQUENCE: 83

Arg Arg Leu Tyr Leu Arg Arg Arg Tyr Tyr Leu Tyr Tyr Arg Xaa Pro
1               5                   10                  15

<210> SEQ ID NO 84
<211> LENGTH: 16
<212> TYPE: PRT
<213> ORGANISM: Artificial Sequence
<220> FEATURE:
<223> OTHER INFORMATION: Description of Artificial Sequence:
              Cyclic peptide
<220> FEATURE:
<221> NAME/KEY: MISC_FEATURE
<222> LOCATION: (15)..(15)
<223> OTHER INFORMATION: Xaa is D-Pro

<400> SEQUENCE: 84

Arg Arg Leu Tyr Leu Arg Arg Arg Tyr Leu Tyr Leu Tyr Arg Xaa Pro
1               5                   10                  15

<210> SEQ ID NO 85
<211> LENGTH: 18
<212> TYPE: PRT
<213> ORGANISM: Artificial Sequence
<220> FEATURE:
<223> OTHER INFORMATION: Description of Artificial Sequence:
              Cyclic peptide
<220> FEATURE:
<221> NAME/KEY: MISC_FEATURE
<222> LOCATION: (17)..(17)
<223> OTHER INFORMATION: Xaa is D-Pro

<400> SEQUENCE: 85

Lys Arg Leu Lys Tyr Val Arg Arg Trp Leu Val Lys Val Leu Arg
1               5                   10                  15

Xaa Pro

<210> SEQ ID NO 86

```
<211> LENGTH: 18
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (17)..(17)
<223> OTHER INFORMATION: Xaa is D-Pro

<400> SEQUENCE: 86

Lys Arg Leu Lys Tyr Val Arg Arg Gly Trp Leu Val Lys Val Leu Arg
1               5                   10                  15
Xaa Pro

<210> SEQ ID NO 87
<211> LENGTH: 18
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (17)..(17)
<223> OTHER INFORMATION: Xaa is D-Pro

<400> SEQUENCE: 87

Lys Arg Leu Lys Tyr Trp Arg Arg Trp Tyr Val Lys Val Leu Arg
1               5                   10                  15
Xaa Pro

<210> SEQ ID NO 88
<211> LENGTH: 18
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (17)..(17)
<223> OTHER INFORMATION: Xaa is D-Pro

<400> SEQUENCE: 88

Lys Arg Leu Tyr Tyr Trp Arg Arg Arg Trp Tyr Val Phe Val Leu Arg
1               5                   10                  15
Xaa Pro

<210> SEQ ID NO 89
<211> LENGTH: 18
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (17)..(17)
<223> OTHER INFORMATION: Xaa is D-Pro

<400> SEQUENCE: 89

Lys Arg Leu Lys Tyr Trp Arg Arg Gly Trp Tyr Val Lys Val Leu Arg
1               5                   10                  15
Xaa Pro
```

```
<210> SEQ ID NO 90
<211> LENGTH: 18
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (17)..(17)
<223> OTHER INFORMATION: Xaa is D-Pro

<400> SEQUENCE: 90

Lys Arg Leu Tyr Tyr Trp Arg Arg Gly Trp Tyr Val Phe Val Leu Arg
1               5                   10                  15

Xaa Pro

<210> SEQ ID NO 91
<211> LENGTH: 18
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (17)..(17)
<223> OTHER INFORMATION: Xaa is D-Pro

<400> SEQUENCE: 91

Lys Arg Leu Tyr Tyr Trp Arg Arg Arg Trp Lys Val Phe Val Leu Arg
1               5                   10                  15

Xaa Pro

<210> SEQ ID NO 92
<211> LENGTH: 18
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (17)..(17)
<223> OTHER INFORMATION: Xaa is D-Pro

<400> SEQUENCE: 92

Lys Arg Leu Lys Tyr Trp Arg Arg Gly Trp Lys Val Lys Val Leu Arg
1               5                   10                  15

Xaa Pro

<210> SEQ ID NO 93
<211> LENGTH: 18
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (17)..(17)
<223> OTHER INFORMATION: Xaa is D-Pro

<400> SEQUENCE: 93

Tyr Lys Leu Arg Leu Lys Tyr Arg Arg Trp Lys Tyr Arg Val Lys Phe
1               5                   10                  15

Xaa Pro
```

```
<210> SEQ ID NO 94
<211> LENGTH: 18
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (17)..(17)
<223> OTHER INFORMATION: Xaa is D-Pro

<400> SEQUENCE: 94

Tyr Lys Leu Gln Leu Lys Trp Arg Arg Phe Lys Tyr Gln Val Lys Phe
1               5                   10                  15

Xaa Pro

<210> SEQ ID NO 95
<211> LENGTH: 18
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (17)..(17)
<223> OTHER INFORMATION: Xaa is D-Pro

<400> SEQUENCE: 95

Tyr Lys Leu Gln Leu Gln Lys Lys Gly Trp Gln Tyr Gln Val Lys Phe
1               5                   10                  15

Xaa Pro

<210> SEQ ID NO 96
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 96

Leu Arg Leu Val Tyr Lys Gly Phe Leu Tyr Arg Val Xaa Pro
1               5                   10

<210> SEQ ID NO 97
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 97

Leu Arg Phe Val Tyr Lys Gly Phe Leu Tyr Arg Val Xaa Pro
1               5                   10

<210> SEQ ID NO 98
<211> LENGTH: 14
```

<212> TYPE: PRT
<213> ORGANISM: Artificial Sequence
<220> FEATURE:
<223> OTHER INFORMATION: Description of Artificial Sequence:
       Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 98

Leu Arg Thr Val Tyr Lys Gly Phe Leu Tyr Arg Val Xaa Pro
1               5                   10

<210> SEQ ID NO 99
<211> LENGTH: 14
<212> TYPE: PRT
<213> ORGANISM: Artificial Sequence
<220> FEATURE:
<223> OTHER INFORMATION: Description of Artificial Sequence:
       Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 99

Leu Arg Lys Val Arg Lys Gly Arg Leu Tyr Arg Val Xaa Pro
1               5                   10

<210> SEQ ID NO 100
<211> LENGTH: 14
<212> TYPE: PRT
<213> ORGANISM: Artificial Sequence
<220> FEATURE:
<223> OTHER INFORMATION: Description of Artificial Sequence:
       Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 100

Leu Arg Lys Trp Tyr Lys Gly Phe Trp Tyr Arg Val Xaa Pro
1               5                   10

<210> SEQ ID NO 101
<211> LENGTH: 14
<212> TYPE: PRT
<213> ORGANISM: Artificial Sequence
<220> FEATURE:
<223> OTHER INFORMATION: Description of Artificial Sequence:
       Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 101

Leu Arg Lys Val Tyr Arg Gly Phe Leu Tyr Arg Val Xaa Pro
1               5                   10

<210> SEQ ID NO 102
<211> LENGTH: 14
<212> TYPE: PRT
<213> ORGANISM: Artificial Sequence
<220> FEATURE:
<223> OTHER INFORMATION: Description of Artificial Sequence:
       Cyclic peptide
<220> FEATURE:
<221> NAME/KEY: MISC_FEATURE

```
<222> LOCATION: (13)..(13)
<223> OTHER INFORMATION: Xaa is D-Pro

<400> SEQUENCE: 102

Leu Lys Lys Val Tyr Arg Arg Phe Leu Lys Lys Val Xaa Pro
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 103

Leu Arg Leu Lys Tyr Arg Arg Phe Lys Tyr Arg Val Xaa Pro
1               5                   10

<210> SEQ ID NO 104
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 104

Leu Arg Leu Glu Tyr Arg Arg Phe Glu Tyr Arg Val Xaa Pro
1               5                   10

<210> SEQ ID NO 105
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 105

Leu Arg Leu Gln Tyr Thr Thr Phe Gln Tyr Arg Val Xaa Pro
1               5                   10

<210> SEQ ID NO 106
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 106

Leu Arg Leu Lys Lys Arg Arg Trp Lys Tyr Arg Val Xaa Pro
1               5                   10
```

<210> SEQ ID NO 107
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 107

Leu Arg Leu Lys Trp Arg Arg Lys Lys Tyr Arg Val Xaa Pro
1               5                   10

<210> SEQ ID NO 108
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 108

Leu Arg Trp Lys Tyr Arg Arg Phe Lys Tyr Arg Val Xaa Pro
1               5                   10

<210> SEQ ID NO 109
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 109

Lys Val Arg Phe Arg Arg Arg Lys Leu Lys Leu Arg Xaa Pro
1               5                   10

<210> SEQ ID NO 110
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 110

Leu Arg Leu Gln Tyr Arg Arg Trp Gln Tyr Arg Val Xaa Pro
1               5                   10

<210> SEQ ID NO 111
<211> LENGTH: 14
<212> TYPE: PRT
<213> ORGANISM: Artificial Sequence
<220> FEATURE:

```
<223> OTHER INFORMATION: Description of Artificial Sequence:
                       Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 111

Leu Arg Leu Gln Trp Arg Arg Phe Gln Tyr Arg Val Xaa Pro
1               5                   10

<210> SEQ ID NO 112
<211> LENGTH: 14
<212> TYPE: PRT
<213> ORGANISM: Artificial Sequence
<220> FEATURE:
<223> OTHER INFORMATION: Description of Artificial Sequence:
                       Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 112

Leu Arg Leu Gln Lys Arg Arg Trp Gln Tyr Arg Val Xaa Pro
1               5                   10

<210> SEQ ID NO 113
<211> LENGTH: 14
<212> TYPE: PRT
<213> ORGANISM: Artificial Sequence
<220> FEATURE:
<223> OTHER INFORMATION: Description of Artificial Sequence:
                       Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 113

Leu Arg Leu Gln Trp Arg Arg Lys Gln Tyr Arg Val Xaa Pro
1               5                   10

<210> SEQ ID NO 114
<211> LENGTH: 14
<212> TYPE: PRT
<213> ORGANISM: Artificial Sequence
<220> FEATURE:
<223> OTHER INFORMATION: Description of Artificial Sequence:
                       Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 114

Phe Arg Leu Gln Tyr Arg Arg Phe Gln Tyr Arg Val Xaa Pro
1               5                   10

<210> SEQ ID NO 115
<211> LENGTH: 14
<212> TYPE: PRT
<213> ORGANISM: Artificial Sequence
<220> FEATURE:
<223> OTHER INFORMATION: Description of Artificial Sequence:
                       Cyclic peptide
<220> FEATURE:
<221> NAME/KEY: MISC_FEATURE
<222> LOCATION: (13)..(13)
<223> OTHER INFORMATION: Xaa is D-Pro
```

-continued

```
<400> SEQUENCE: 115

Leu Arg Leu Gln Tyr Arg Arg Phe Gln Tyr Arg Phe Xaa Pro
1               5                   10

<210> SEQ ID NO 116
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 116

Phe Arg Leu Gln Tyr Arg Arg Phe Gln Tyr Arg Phe Xaa Pro
1               5                   10

<210> SEQ ID NO 117
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 117

Leu Arg Leu Gln Tyr Arg Arg Phe Gln Trp Arg Val Xaa Pro
1               5                   10

<210> SEQ ID NO 118
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 118

Leu Arg Trp Gln Tyr Arg Arg Phe Gln Tyr Arg Val Xaa Pro
1               5                   10

<210> SEQ ID NO 119
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 119

Gln Val Arg Phe Arg Arg Arg Lys Leu Gln Leu Arg Xaa Pro
1               5                   10

<210> SEQ ID NO 120
```

```
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 120

Phe Arg Leu Lys Lys Arg Arg Trp Lys Tyr Arg Val Xaa Pro
1               5                   10

<210> SEQ ID NO 121
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (1)..(1)
<223> OTHER INFORMATION: Xaa is Cha (L-cyclohexylalanine)
<220> FEATURE:
<221> NAME/KEY: MISC_FEATURE
<222> LOCATION: (13)..(13)
<223> OTHER INFORMATION: Xaa is D-Pro

<400> SEQUENCE: 121

Xaa Arg Leu Lys Lys Arg Arg Trp Lys Tyr Arg Val Xaa Pro
1               5                   10

<210> SEQ ID NO 122
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (1)..(1)
<223> OTHER INFORMATION: Xaa is hPhe (L-homo-phenylalanine)
<220> FEATURE:
<221> NAME/KEY: MISC_FEATURE
<222> LOCATION: (13)..(13)
<223> OTHER INFORMATION: Xaa is D-Pro

<400> SEQUENCE: 122

Xaa Arg Leu Lys Lys Arg Arg Trp Lys Tyr Arg Val Xaa Pro
1               5                   10

<210> SEQ ID NO 123
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (1)..(1)
<223> OTHER INFORMATION: Xaa is 2-Nal (L-2-naphthylalanine)
<220> FEATURE:
<221> NAME/KEY: MISC_FEATURE
<222> LOCATION: (13)..(13)
<223> OTHER INFORMATION: Xaa is D-Pro

<400> SEQUENCE: 123
```

```
Xaa Arg Leu Lys Lys Arg Arg Trp Lys Tyr Arg Val Xaa Pro
1               5                   10
```

<210> SEQ ID NO 124
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (1)..(1)
<223> OTHER INFORMATION: Xaa is 1-Nal (L-1-naphthylalanine)
<220> FEATURE:
<221> NAME/KEY: MISC_FEATURE
<222> LOCATION: (13)..(13)
<223> OTHER INFORMATION: Xaa is D-Pro

<400> SEQUENCE: 124

```
Xaa Arg Leu Lys Lys Arg Arg Trp Lys Tyr Arg Val Xaa Pro
1               5                   10
```

<210> SEQ ID NO 125
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (1)..(1)
<223> OTHER INFORMATION: Xaa is Nle (L-norleucine)
<220> FEATURE:
<221> NAME/KEY: MISC_FEATURE
<222> LOCATION: (13)..(13)
<223> OTHER INFORMATION: Xaa is D-Pro

<400> SEQUENCE: 125

```
Xaa Arg Leu Lys Lys Arg Arg Trp Lys Tyr Arg Val Xaa Pro
1               5                   10
```

<210> SEQ ID NO 126
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 126

```
Leu Arg Phe Lys Lys Arg Arg Trp Lys Tyr Arg Val Xaa Pro
1               5                   10
```

<210> SEQ ID NO 127
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (3)..(3)
<223> OTHER INFORMATION: Xaa is Cha (L-cyclohexylalanine)
<220> FEATURE:
<221> NAME/KEY: MISC_FEATURE

```
<222> LOCATION: (13)..(13)
<223> OTHER INFORMATION: Xaa is D-Pro

<400> SEQUENCE: 127

Leu Arg Xaa Lys Lys Arg Arg Trp Lys Tyr Arg Val Xaa Pro
1               5                   10

<210> SEQ ID NO 128
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (3)..(3)
<223> OTHER INFORMATION: Xaa is Y(Bzl) [L-O-benzyltyrosine]
<220> FEATURE:
<221> NAME/KEY: MISC_FEATURE
<222> LOCATION: (13)..(13)
<223> OTHER INFORMATION: Xaa is D-Pro

<400> SEQUENCE: 128

Leu Arg Xaa Lys Lys Arg Arg Trp Lys Tyr Arg Val Xaa Pro
1               5                   10

<210> SEQ ID NO 129
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 129

Leu Arg Trp Lys Lys Arg Arg Trp Lys Tyr Arg Val Xaa Pro
1               5                   10

<210> SEQ ID NO 130
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (3)..(3)
<223> OTHER INFORMATION: Xaa is hPhe (L-homo-phenylalanine)
<220> FEATURE:
<221> NAME/KEY: MISC_FEATURE
<222> LOCATION: (13)..(13)
<223> OTHER INFORMATION: Xaa is D-Pro

<400> SEQUENCE: 130

Leu Arg Xaa Lys Lys Arg Arg Trp Lys Tyr Arg Val Xaa Pro
1               5                   10

<210> SEQ ID NO 131
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
```

```
<221> NAME/KEY: MISC_FEATURE
<222> LOCATION: (3)..(3)
<223> OTHER INFORMATION: Xaa is 2-Nal (L-2-naphthylalanine)
<220> FEATURE:
<221> NAME/KEY: MISC_FEATURE
<222> LOCATION: (13)..(13)
<223> OTHER INFORMATION: Xaa is D-Pro

<400> SEQUENCE: 131

Leu Arg Xaa Lys Lys Arg Arg Trp Lys Tyr Arg Val Xaa Pro
1               5                   10

<210> SEQ ID NO 132
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (3)..(3)
<223> OTHER INFORMATION: Xaa is 1-Nal (L-1-naphthylalanine)
<220> FEATURE:
<221> NAME/KEY: MISC_FEATURE
<222> LOCATION: (13)..(13)
<223> OTHER INFORMATION: Xaa is D-Pro

<400> SEQUENCE: 132

Leu Arg Xaa Lys Lys Arg Arg Trp Lys Tyr Arg Val Xaa Pro
1               5                   10

<210> SEQ ID NO 133
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 133

Leu Arg Val Lys Lys Arg Arg Trp Lys Tyr Arg Val Xaa Pro
1               5                   10

<210> SEQ ID NO 134
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 134

Leu Arg Ile Lys Lys Arg Arg Trp Lys Tyr Arg Val Xaa Pro
1               5                   10

<210> SEQ ID NO 135
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
```

```
<220> FEATURE:
<221> NAME/KEY: MISC_FEATURE
<222> LOCATION: (3)..(3)
<223> OTHER INFORMATION: Xaa is Nle (L-norleucine)
<220> FEATURE:
<221> NAME/KEY: MISC_FEATURE
<222> LOCATION: (13)..(13)
<223> OTHER INFORMATION: Xaa is D-Pro

<400> SEQUENCE: 135

Leu Arg Xaa Lys Lys Arg Arg Trp Lys Tyr Arg Val Xaa Pro
1               5                   10

<210> SEQ ID NO 136
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 136

Leu Arg Leu Lys Lys Arg Arg Tyr Lys Tyr Arg Val Xaa Pro
1               5                   10

<210> SEQ ID NO 137
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (8)..(8)
<223> OTHER INFORMATION: Xaa is Y(Bzl) [L-O-benzyltyrosine]
<220> FEATURE:
<221> NAME/KEY: MISC_FEATURE
<222> LOCATION: (13)..(13)
<223> OTHER INFORMATION: Xaa is D-Pro

<400> SEQUENCE: 137

Leu Arg Leu Lys Lys Arg Arg Xaa Lys Tyr Arg Val Xaa Pro
1               5                   10

<210> SEQ ID NO 138
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (8)..(8)
<223> OTHER INFORMATION: Xaa is hPhe (L-homo-phenylalanine)
<220> FEATURE:
<221> NAME/KEY: MISC_FEATURE
<222> LOCATION: (13)..(13)
<223> OTHER INFORMATION: Xaa is D-Pro

<400> SEQUENCE: 138

Leu Arg Leu Lys Lys Arg Arg Xaa Lys Tyr Arg Val Xaa Pro
1               5                   10

<210> SEQ ID NO 139
<211> LENGTH: 14
```

```
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (8)..(8)
<223> OTHER INFORMATION: Xaa is 2-Nal (L-2-naphthylalanine)
<220> FEATURE:
<221> NAME/KEY: MISC_FEATURE
<222> LOCATION: (13)..(13)
<223> OTHER INFORMATION: Xaa is D-Pro

<400> SEQUENCE: 139

Leu Arg Leu Lys Lys Arg Arg Xaa Lys Tyr Arg Val Xaa Pro
1               5                   10

<210> SEQ ID NO 140
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (8)..(8)
<223> OTHER INFORMATION: Xaa is 1-Nal (L-1-naphthylalanine)
<220> FEATURE:
<221> NAME/KEY: MISC_FEATURE
<222> LOCATION: (13)..(13)
<223> OTHER INFORMATION: Xaa is D-Pro

<400> SEQUENCE: 140

Leu Arg Leu Lys Lys Arg Arg Xaa Lys Tyr Arg Val Xaa Pro
1               5                   10

<210> SEQ ID NO 141
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 141

Leu Arg Leu Lys Lys Arg Arg Val Lys Tyr Arg Cys Xaa Pro
1               5                   10

<210> SEQ ID NO 142
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 142

Leu Arg Leu Lys Lys Arg Arg Ile Lys Tyr Arg Val Xaa Pro
1               5                   10

<210> SEQ ID NO 143
```

<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 143

Leu Arg Leu Lys Lys Arg Arg Leu Lys Tyr Arg Val Xaa Pro
1               5                   10

<210> SEQ ID NO 144
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (8)..(8)
<223> OTHER INFORMATION: Xaa is Nle (L-norleucine)
<220> FEATURE:
<221> NAME/KEY: MISC_FEATURE
<222> LOCATION: (13)..(13)
<223> OTHER INFORMATION: Xaa is D-Pro

<400> SEQUENCE: 144

Leu Arg Leu Lys Lys Arg Arg Xaa Lys Tyr Arg Val Xaa Pro
1               5                   10

<210> SEQ ID NO 145
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 145

Leu Arg Leu Lys Lys Arg Arg His Lys Tyr Arg Val Xaa Pro
1               5                   10

<210> SEQ ID NO 146
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 146

Leu Arg Leu Lys Lys Arg Arg Trp Lys Phe Arg Val Xaa Pro
1               5                   10

<210> SEQ ID NO 147
<211> LENGTH: 14
<212> TYPE: PRT
<213> ORGANISM: Artificial Sequence

```
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (10)..(10)
<223> OTHER INFORMATION: Xaa is Y(Bzl) [L-O-benzyltyrosine]
<220> FEATURE:
<221> NAME/KEY: MISC_FEATURE
<222> LOCATION: (13)..(13)
<223> OTHER INFORMATION: Xaa is D-Pro

<400> SEQUENCE: 147

Leu Arg Leu Lys Lys Arg Arg Trp Lys Xaa Arg Val Xaa Pro
1               5                   10

<210> SEQ ID NO 148
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 148

Leu Arg Leu Lys Lys Arg Arg Trp Lys Trp Arg Val Xaa Pro
1               5                   10

<210> SEQ ID NO 149
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (10)..(10)
<223> OTHER INFORMATION: Xaa is hPhe (L-homo-phenylalanine)
<220> FEATURE:
<221> NAME/KEY: MISC_FEATURE
<222> LOCATION: (13)..(13)
<223> OTHER INFORMATION: Xaa is D-Pro

<400> SEQUENCE: 149

Leu Arg Leu Lys Lys Arg Arg Trp Lys Xaa Arg Val Xaa Pro
1               5                   10

<210> SEQ ID NO 150
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (10)..(10)
<223> OTHER INFORMATION: Xaa is 1-Nal (L-1-naphthylalanine)
<220> FEATURE:
<221> NAME/KEY: MISC_FEATURE
<222> LOCATION: (13)..(13)
<223> OTHER INFORMATION: Xaa is D-Pro

<400> SEQUENCE: 150

Leu Arg Leu Lys Lys Arg Arg Trp Lys Xaa Arg Val Xaa Pro
1               5                   10
```

```
<210> SEQ ID NO 151
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 151

Leu Arg Leu Lys Lys Arg Arg Trp Lys Val Arg Val Xaa Pro
 1               5                  10

<210> SEQ ID NO 152
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 152

Leu Arg Leu Lys Lys Arg Arg Trp Lys Ile Arg Val Xaa Pro
 1               5                  10

<210> SEQ ID NO 153
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 153

Leu Arg Leu Lys Lys Arg Arg Trp Lys Leu Arg Val Xaa Pro
 1               5                  10

<210> SEQ ID NO 154
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (10)..(10)
<223> OTHER INFORMATION: Xaa is Nle (L-norleucine)
<220> FEATURE:
<221> NAME/KEY: MISC_FEATURE
<222> LOCATION: (13)..(13)
<223> OTHER INFORMATION: Xaa is D-Pro

<400> SEQUENCE: 154

Leu Arg Leu Lys Lys Arg Arg Trp Lys Xaa Arg Val Xaa Pro
 1               5                  10

<210> SEQ ID NO 155
<211> LENGTH: 14
```

```
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 155

Leu Arg Leu Lys Lys Arg Arg Trp Lys Tyr Arg Phe Xaa Pro
1               5                   10

<210> SEQ ID NO 156
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (12)..(12)
<223> OTHER INFORMATION: Xaa is Cha (L-cyclohexylalanine)
<220> FEATURE:
<221> NAME/KEY: MISC_FEATURE
<222> LOCATION: (13)..(13)
<223> OTHER INFORMATION: Xaa is D-Pro

<400> SEQUENCE: 156

Leu Arg Leu Lys Lys Arg Arg Trp Lys Tyr Arg Xaa Xaa Pro
1               5                   10

<210> SEQ ID NO 157
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (12)..(12)
<223> OTHER INFORMATION: Xaa is Y (Bzl) [L-O-benzyltyrosine]
<220> FEATURE:
<221> NAME/KEY: MISC_FEATURE
<222> LOCATION: (13)..(13)
<223> OTHER INFORMATION: Xaa is D-Pro

<400> SEQUENCE: 157

Leu Arg Leu Lys Lys Arg Arg Trp Lys Tyr Arg Xaa Xaa Pro
1               5                   10

<210> SEQ ID NO 158
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 158

Leu Arg Leu Lys Lys Arg Arg Trp Lys Tyr Arg Trp Xaa Pro
1               5                   10

<210> SEQ ID NO 159
```

```
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (12)..(12)
<223> OTHER INFORMATION: Xaa is hPhe (L-homo-phenylalanine)
<220> FEATURE:
<221> NAME/KEY: MISC_FEATURE
<222> LOCATION: (13)..(13)
<223> OTHER INFORMATION: Xaa is D-Pro

<400> SEQUENCE: 159

Leu Arg Leu Lys Lys Arg Arg Trp Lys Tyr Arg Xaa Xaa Pro
1               5                   10

<210> SEQ ID NO 160
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (12)..(12)
<223> OTHER INFORMATION: Xaa is 2-Nal (L-2-naphthylalanine)
<220> FEATURE:
<221> NAME/KEY: MISC_FEATURE
<222> LOCATION: (13)..(13)
<223> OTHER INFORMATION: Xaa is D-Pro

<400> SEQUENCE: 160

Leu Arg Leu Lys Lys Arg Arg Trp Lys Tyr Arg Xaa Xaa Pro
1               5                   10

<210> SEQ ID NO 161
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (12)..(12)
<223> OTHER INFORMATION: Xaa is 1-Nal (L-1-naphthylalanine)
<220> FEATURE:
<221> NAME/KEY: MISC_FEATURE
<222> LOCATION: (13)..(13)
<223> OTHER INFORMATION: Xaa is D-Pro

<400> SEQUENCE: 161

Leu Arg Leu Lys Lys Arg Arg Trp Lys Tyr Arg Xaa Xaa Pro
1               5                   10

<210> SEQ ID NO 162
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 162
```

```
Leu Arg Leu Lys Lys Arg Arg Trp Lys Tyr Arg Ile Xaa Pro
1               5                   10
```

<210> SEQ ID NO 163
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (12)..(12)
<223> OTHER INFORMATION: Xaa is Nle (L-norleucine)
<220> FEATURE:
<221> NAME/KEY: MISC_FEATURE
<222> LOCATION: (13)..(13)
<223> OTHER INFORMATION: Xaa is D-Pro

<400> SEQUENCE: 163

```
Leu Arg Leu Lys Lys Arg Arg Trp Lys Tyr Arg Xaa Xaa Pro
1               5                   10
```

<210> SEQ ID NO 164
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 164

```
Leu Arg Leu Lys Lys Arg Arg Trp Lys Tyr Arg His Xaa Pro
1               5                   10
```

<210> SEQ ID NO 165
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 165

```
Leu Trp Leu Lys Lys Arg Arg Trp Lys Tyr Arg Val Xaa Pro
1               5                   10
```

<210> SEQ ID NO 166
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 166

```
Leu Leu Leu Lys Lys Arg Arg Trp Lys Tyr Arg Val Xaa Pro
1               5                   10
```

<210> SEQ ID NO 167
<211> LENGTH: 14
<212> TYPE: PRT
<213> ORGANISM: Artificial Sequence
<220> FEATURE:
<223> OTHER INFORMATION: Description of Artificial Sequence:
       Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 167

Leu Thr Leu Lys Lys Arg Arg Trp Lys Tyr Arg Val Xaa Pro
1               5                   10

<210> SEQ ID NO 168
<211> LENGTH: 14
<212> TYPE: PRT
<213> ORGANISM: Artificial Sequence
<220> FEATURE:
<223> OTHER INFORMATION: Description of Artificial Sequence:
       Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 168

Leu Gln Leu Lys Lys Arg Arg Trp Lys Tyr Arg Val Xaa Pro
1               5                   10

<210> SEQ ID NO 169
<211> LENGTH: 14
<212> TYPE: PRT
<213> ORGANISM: Artificial Sequence
<220> FEATURE:
<223> OTHER INFORMATION: Description of Artificial Sequence:
       Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 169

Leu Arg Leu Leu Lys Arg Arg Trp Lys Tyr Arg Val Xaa Pro
1               5                   10

<210> SEQ ID NO 170
<211> LENGTH: 14
<212> TYPE: PRT
<213> ORGANISM: Artificial Sequence
<220> FEATURE:
<223> OTHER INFORMATION: Description of Artificial Sequence:
       Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 170

Leu Arg Leu Arg Lys Arg Arg Trp Lys Tyr Arg Val Xaa Pro
1               5                   10

<210> SEQ ID NO 171
<211> LENGTH: 14
<212> TYPE: PRT
<213> ORGANISM: Artificial Sequence
<220> FEATURE:
<223> OTHER INFORMATION: Description of Artificial Sequence:

Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 171

Leu Arg Leu Thr Lys Arg Arg Trp Lys Tyr Arg Val Xaa Pro
1               5                   10

<210> SEQ ID NO 172
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 172

Leu Arg Leu Gln Lys Arg Arg Trp Lys Tyr Arg Val Xaa Pro
1               5                   10

<210> SEQ ID NO 173
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 173

Leu Arg Leu Lys Leu Arg Arg Trp Lys Tyr Arg Val Xaa Pro
1               5                   10

<210> SEQ ID NO 174
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 174

Leu Arg Leu Lys His Arg Arg Trp Lys Tyr Arg Val Xaa Pro
1               5                   10

<210> SEQ ID NO 175
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 175

Leu Arg Leu Lys Arg Arg Arg Trp Lys Tyr Arg Val Xaa Pro
1               5                   10

<210> SEQ ID NO 176
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 176

Leu Arg Leu Lys Thr Arg Arg Trp Lys Tyr Arg Val Xaa Pro
1               5                   10

<210> SEQ ID NO 177
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 177

Leu Arg Leu Lys Lys Leu Arg Trp Lys Tyr Arg Val Xaa Pro
1               5                   10

<210> SEQ ID NO 178
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 178

Leu Arg Leu Lys Lys His Arg Trp Lys Tyr Arg Val Xaa Pro
1               5                   10

<210> SEQ ID NO 179
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 179

Leu Arg Leu Lys Lys Lys Arg Trp Lys Tyr Arg Val Xaa Pro
1               5                   10

<210> SEQ ID NO 180
<211> LENGTH: 14

<212> TYPE: PRT
<213> ORGANISM: Artificial Sequence
<220> FEATURE:
<223> OTHER INFORMATION: Description of Artificial Sequence:
       Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 180

Leu Arg Leu Lys Lys Thr Arg Trp Lys Tyr Arg Val Xaa Pro
1               5                   10

<210> SEQ ID NO 181
<211> LENGTH: 14
<212> TYPE: PRT
<213> ORGANISM: Artificial Sequence
<220> FEATURE:
<223> OTHER INFORMATION: Description of Artificial Sequence:
       Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 181

Leu Arg Leu Lys Lys Gln Arg Trp Lys Tyr Arg Val Xaa Pro
1               5                   10

<210> SEQ ID NO 182
<211> LENGTH: 14
<212> TYPE: PRT
<213> ORGANISM: Artificial Sequence
<220> FEATURE:
<223> OTHER INFORMATION: Description of Artificial Sequence:
       Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 182

Leu Arg Leu Lys Lys Arg Trp Trp Lys Tyr Arg Val Xaa Pro
1               5                   10

<210> SEQ ID NO 183
<211> LENGTH: 14
<212> TYPE: PRT
<213> ORGANISM: Artificial Sequence
<220> FEATURE:
<223> OTHER INFORMATION: Description of Artificial Sequence:
       Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 183

Leu Arg Leu Lys Lys Arg His Trp Lys Tyr Arg Val Xaa Pro
1               5                   10

<210> SEQ ID NO 184
<211> LENGTH: 14
<212> TYPE: PRT
<213> ORGANISM: Artificial Sequence
<220> FEATURE:
<223> OTHER INFORMATION: Description of Artificial Sequence:
       Cyclic peptide
<220> FEATURE:
<221> NAME/KEY: MISC_FEATURE

```
<222> LOCATION: (13)..(13)
<223> OTHER INFORMATION: Xaa is D-Pro

<400> SEQUENCE: 184

Leu Arg Leu Lys Lys Arg Lys Trp Lys Tyr Arg Val Xaa Pro
1               5                   10

<210> SEQ ID NO 185
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (1)..(1)
<223> OTHER INFORMATION: Xaa is Bip [L-(4-phenyl)phenylalanine]
<220> FEATURE:
<221> NAME/KEY: MISC_FEATURE
<222> LOCATION: (13)..(13)
<223> OTHER INFORMATION: Xaa is D-Pro

<400> SEQUENCE: 185

Xaa Arg Leu Lys Lys Arg Arg Trp Lys Tyr Arg Val Xaa Pro
1               5                   10

<210> SEQ ID NO 186
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (1)..(1)
<223> OTHER INFORMATION: Xaa is 4Cl-Phe (L-4-chlorophenylalanine)
<220> FEATURE:
<221> NAME/KEY: MISC_FEATURE
<222> LOCATION: (13)..(13)
<223> OTHER INFORMATION: Xaa is D-Pro

<400> SEQUENCE: 186

Xaa Arg Leu Lys Lys Arg Arg Trp Lys Tyr Arg Val Xaa Pro
1               5                   10

<210> SEQ ID NO 187
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (1)..(1)
<223> OTHER INFORMATION: Xaa is AmPhe (L-aminophenylalanine)
<220> FEATURE:
<221> NAME/KEY: MISC_FEATURE
<222> LOCATION: (13)..(13)
<223> OTHER INFORMATION: Xaa is D-Pro

<400> SEQUENCE: 187

Xaa Arg Leu Lys Lys Arg Arg Trp Lys Tyr Arg Val Xaa Pro
1               5                   10

<210> SEQ ID NO 188
<211> LENGTH: 14
<212> TYPE: PRT
<213> ORGANISM: Artificial Sequence
```

```
<220> FEATURE:
<223> OTHER INFORMATION: Description of Artificial Sequence:
              Cyclic peptide
<220> FEATURE:
<221> NAME/KEY: MISC_FEATURE
<222> LOCATION: (1)..(1)
<223> OTHER INFORMATION: Xaa is S(Bzl) [L-O-benzylserine]
<220> FEATURE:
<221> NAME/KEY: MISC_FEATURE
<222> LOCATION: (13)..(13)
<223> OTHER INFORMATION: Xaa is D-Pro

<400> SEQUENCE: 188

Xaa Arg Leu Lys Lys Arg Arg Trp Lys Tyr Arg Val Xaa Pro
1               5                   10

<210> SEQ ID NO 189
<211> LENGTH: 14
<212> TYPE: PRT
<213> ORGANISM: Artificial Sequence
<220> FEATURE:
<223> OTHER INFORMATION: Description of Artificial Sequence:
              Cyclic peptide
<220> FEATURE:
<221> NAME/KEY: MISC_FEATURE
<222> LOCATION: (1)..(1)
<223> OTHER INFORMATION: Xaa is T(Bzl) [L-O-benzylthreonine)
<220> FEATURE:
<221> NAME/KEY: MISC_FEATURE
<222> LOCATION: (13)..(13)
<223> OTHER INFORMATION: Xaa is D-Pro

<400> SEQUENCE: 189

Xaa Arg Leu Lys Lys Arg Arg Trp Lys Tyr Arg Val Xaa Pro
1               5                   10

<210> SEQ ID NO 190
<211> LENGTH: 14
<212> TYPE: PRT
<213> ORGANISM: Artificial Sequence
<220> FEATURE:
<223> OTHER INFORMATION: Description of Artificial Sequence:
              Cyclic peptide
<220> FEATURE:
<221> NAME/KEY: MISC_FEATURE
<222> LOCATION: (1)..(1)
<223> OTHER INFORMATION: Xaa is Orn (L-ornithine)
<220> FEATURE:
<221> NAME/KEY: MISC_FEATURE
<222> LOCATION: (13)..(13)
<223> OTHER INFORMATION: Xaa is D-Pro

<400> SEQUENCE: 190

Xaa Arg Leu Lys Lys Arg Arg Trp Lys Tyr Arg Val Xaa Pro
1               5                   10

<210> SEQ ID NO 191
<211> LENGTH: 14
<212> TYPE: PRT
<213> ORGANISM: Artificial Sequence
<220> FEATURE:
<223> OTHER INFORMATION: Description of Artificial Sequence:
              Cyclic peptide
<220> FEATURE:
<221> NAME/KEY: MISC_FEATURE
<222> LOCATION: (3)..(3)
<223> OTHER INFORMATION: Xaa is Bip [L-(4-phenyl)phenylalanine]
<220> FEATURE:
<221> NAME/KEY: MISC_FEATURE
<222> LOCATION: (13)..(13)
<223> OTHER INFORMATION: Xaa is D-Pro

<400> SEQUENCE: 191
```

```
Leu Arg Xaa Lys Lys Arg Arg Trp Lys Tyr Arg Val Xaa Pro
1               5                   10
```

<210> SEQ ID NO 192
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (3)..(3)
<223> OTHER INFORMATION: Xaa is 4Cl-Phe (L-4-chlorophenylalanine)
<220> FEATURE:
<221> NAME/KEY: MISC_FEATURE
<222> LOCATION: (13)..(13)
<223> OTHER INFORMATION: Xaa is D-Pro

<400> SEQUENCE: 192

```
Leu Arg Xaa Lys Lys Arg Arg Trp Lys Tyr Arg Val Xaa Pro
1               5                   10
```

<210> SEQ ID NO 193
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (3)..(3)
<223> OTHER INFORMATION: Xaa is AmPhe (aminophenylalanine)
<220> FEATURE:
<221> NAME/KEY: MISC_FEATURE
<222> LOCATION: (13)..(13)
<223> OTHER INFORMATION: Xaa is D-Pro

<400> SEQUENCE: 193

```
Leu Arg Xaa Lys Lys Arg Arg Trp Lys Tyr Arg Val Xaa Pro
1               5                   10
```

<210> SEQ ID NO 194
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (3)..(3)
<223> OTHER INFORMATION: Xaa is S(Bzl) [L-O-benzyltyrosine]
<220> FEATURE:
<221> NAME/KEY: MISC_FEATURE
<222> LOCATION: (13)..(13)
<223> OTHER INFORMATION: Xaa is D-Pro

<400> SEQUENCE: 194

```
Leu Arg Xaa Lys Lys Arg Arg Trp Lys Tyr Arg Val Xaa Pro
1               5                   10
```

<210> SEQ ID NO 195
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:

```
<221> NAME/KEY: MISC_FEATURE
<222> LOCATION: (3)..(3)
<223> OTHER INFORMATION: Xaa is T(Bzl) [L-O-benzylthreonine]
<220> FEATURE:
<221> NAME/KEY: MISC_FEATURE
<222> LOCATION: (13)..(13)
<223> OTHER INFORMATION: Xaa is D-Pro

<400> SEQUENCE: 195

Leu Arg Xaa Lys Lys Arg Arg Trp Lys Tyr Arg Val Xaa Pro
1               5                   10

<210> SEQ ID NO 196
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (3)..(3)
<223> OTHER INFORMATION: Xaa is Orn (L-ornithine)
<220> FEATURE:
<221> NAME/KEY: MISC_FEATURE
<222> LOCATION: (13)..(13)
<223> OTHER INFORMATION: Xaa is D-Pro

<400> SEQUENCE: 196

Leu Arg Xaa Lys Lys Arg Trp Trp Lys Tyr Arg Val Xaa Pro
1               5                   10

<210> SEQ ID NO 197
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (8)..(8)
<223> OTHER INFORMATION: Xaa is Bip [L-(4-phenyl)phenylalanine]
<220> FEATURE:
<221> NAME/KEY: MISC_FEATURE
<222> LOCATION: (13)..(13)
<223> OTHER INFORMATION: Xaa is D-Pro

<400> SEQUENCE: 197

Leu Arg Leu Lys Lys Arg Arg Xaa Lys Tyr Arg Val Xaa Pro
1               5                   10

<210> SEQ ID NO 198
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (8)..(8)
<223> OTHER INFORMATION: Xaa is 4Cl-Phe (L-4-chlorophenylalanine)
<220> FEATURE:
<221> NAME/KEY: MISC_FEATURE
<222> LOCATION: (13)..(13)
<223> OTHER INFORMATION: Xaa is D-Pro

<400> SEQUENCE: 198

Leu Arg Leu Lys Lys Arg Arg Xaa Lys Tyr Arg Val Xaa Pro
1               5                   10
```

```
<210> SEQ ID NO 199
<211> LENGTH: 14
<212> TYPE: PRT
<213> ORGANISM: Artificial Sequence
<220> FEATURE:
<223> OTHER INFORMATION: Description of Artificial Sequence:
                       Cyclic peptide
<220> FEATURE:
<221> NAME/KEY: MISC_FEATURE
<222> LOCATION: (8)..(8)
<223> OTHER INFORMATION: Xaa is AmPhe (L-aminophenylalanine)
<220> FEATURE:
<221> NAME/KEY: MISC_FEATURE
<222> LOCATION: (13)..(13)
<223> OTHER INFORMATION: Xaa is D-Pro

<400> SEQUENCE: 199

Leu Arg Leu Leu Lys Arg Arg Xaa Lys Tyr Arg Val Xaa Pro
1               5                   10

<210> SEQ ID NO 200
<211> LENGTH: 14
<212> TYPE: PRT
<213> ORGANISM: Artificial Sequence
<220> FEATURE:
<223> OTHER INFORMATION: Description of Artificial Sequence:
                       Cyclic peptide
<220> FEATURE:
<221> NAME/KEY: MISC_FEATURE
<222> LOCATION: (8)..(8)
<223> OTHER INFORMATION: Xaa is S(Bzl) [L-O-benzylserine]
<220> FEATURE:
<221> NAME/KEY: MISC_FEATURE
<222> LOCATION: (13)..(13)
<223> OTHER INFORMATION: Xaa is D-Pro

<400> SEQUENCE: 200

Leu Arg Leu Lys Lys Arg Arg Xaa Lys Tyr Arg Val Xaa Pro
1               5                   10

<210> SEQ ID NO 201
<211> LENGTH: 14
<212> TYPE: PRT
<213> ORGANISM: Artificial Sequence
<220> FEATURE:
<223> OTHER INFORMATION: Description of Artificial Sequence:
                       Cyclic peptide
<220> FEATURE:
<221> NAME/KEY: MISC_FEATURE
<222> LOCATION: (8)..(8)
<223> OTHER INFORMATION: Xaa is T(Bzl) [L-O-benzylthreonine]
<220> FEATURE:
<221> NAME/KEY: MISC_FEATURE
<222> LOCATION: (13)..(13)
<223> OTHER INFORMATION: Xaa is D-Pro

<400> SEQUENCE: 201

Leu Arg Leu Lys Lys Arg Arg Xaa Lys Tyr Arg Val Xaa Pro
1               5                   10

<210> SEQ ID NO 202
<211> LENGTH: 14
<212> TYPE: PRT
<213> ORGANISM: Artificial Sequence
<220> FEATURE:
<223> OTHER INFORMATION: Description of Artificial Sequence:
                       Cyclic peptide
<220> FEATURE:
<221> NAME/KEY: MISC_FEATURE
<222> LOCATION: (8)..(8)
<223> OTHER INFORMATION: Xaa in position 8 is Orn (L-Ornithine)
<220> FEATURE:
```

```
<221> NAME/KEY: MISC_FEATURE
<222> LOCATION: (13)..(13)
<223> OTHER INFORMATION: Xaa is D-Pro

<400> SEQUENCE: 202

Leu Arg Leu Lys Lys Arg Arg Xaa Lys Tyr Arg Val Xaa Pro
1               5                   10

<210> SEQ ID NO 203
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (10)..(10)
<223> OTHER INFORMATION: Xaa is Bip [L-(4-phenyl)phenylalanine]
<220> FEATURE:
<221> NAME/KEY: MISC_FEATURE
<222> LOCATION: (13)..(13)
<223> OTHER INFORMATION: Xaa is D-Pro

<400> SEQUENCE: 203

Leu Arg Leu Lys Lys Arg Arg Trp Lys Xaa Arg Val Xaa Pro
1               5                   10

<210> SEQ ID NO 204
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (10)..(10)
<223> OTHER INFORMATION: Xaa is 4Cl-Phe (L-4-chlorophenylalanine)
<220> FEATURE:
<221> NAME/KEY: MISC_FEATURE
<222> LOCATION: (13)..(13)
<223> OTHER INFORMATION: Xaa is D-Pro

<400> SEQUENCE: 204

Leu Arg Leu Lys Lys Arg Arg Trp Lys Xaa Arg Val Xaa Pro
1               5                   10

<210> SEQ ID NO 205
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (10)..(10)
<223> OTHER INFORMATION: Xaa is S(Bzl) [L-O-benzylserine]
<220> FEATURE:
<221> NAME/KEY: MISC_FEATURE
<222> LOCATION: (13)..(13)
<223> OTHER INFORMATION: Xaa is D-Pro

<400> SEQUENCE: 205

Leu Arg Leu Lys Lys Arg Arg Trp Lys Xaa Arg Val Xaa Pro
1               5                   10

<210> SEQ ID NO 206
<211> LENGTH: 14
<212> TYPE: PRT
```

```
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (10)..(10)
<223> OTHER INFORMATION: Xaa is T(Bzl) [L-O-benzylthreonine]
<220> FEATURE:
<221> NAME/KEY: MISC_FEATURE
<222> LOCATION: (13)..(13)
<223> OTHER INFORMATION: Xaa is D-Pro

<400> SEQUENCE: 206

Leu Arg Leu Lys Lys Arg Arg Trp Lys Xaa Arg Val Xaa Pro
1               5                   10

<210> SEQ ID NO 207
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (10)..(10)
<223> OTHER INFORMATION: Xaa is Orn (L-Ornithine)
<220> FEATURE:
<221> NAME/KEY: MISC_FEATURE
<222> LOCATION: (13)..(13)
<223> OTHER INFORMATION: Xaa is D-Pro

<400> SEQUENCE: 207

Leu Arg Leu Lys Lys Arg Arg Trp Lys Xaa Arg Val Xaa Pro
1               5                   10

<210> SEQ ID NO 208
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (12)..(12)
<223> OTHER INFORMATION: Xaa is Bip [L-(4-phenyl)phenylalanine]
<220> FEATURE:
<221> NAME/KEY: MISC_FEATURE
<222> LOCATION: (13)..(13)
<223> OTHER INFORMATION: Xaa is D-Pro

<400> SEQUENCE: 208

Leu Arg Leu Lys Lys Arg Arg Trp Lys Tyr Arg Xaa Xaa Pro
1               5                   10

<210> SEQ ID NO 209
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (12)..(12)
<223> OTHER INFORMATION: Xaa is ccl-Phe (L-4-chlorophenylalanine)
<220> FEATURE:
<221> NAME/KEY: MISC_FEATURE
<222> LOCATION: (13)..(13)
<223> OTHER INFORMATION: Xaa is D-Pro
```

-continued

```
<400> SEQUENCE: 209

Leu Arg Leu Lys Lys Arg Arg Trp Lys Tyr Arg Xaa Xaa Pro
1               5                   10

<210> SEQ ID NO 210
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (12)..(12)
<223> OTHER INFORMATION: Xaa is AmPhe (L-aminophenylalanine)
<220> FEATURE:
<221> NAME/KEY: MISC_FEATURE
<222> LOCATION: (13)..(13)
<223> OTHER INFORMATION: Xaa is D-Pro

<400> SEQUENCE: 210

Leu Arg Leu Lys Lys Arg Arg Trp Lys Tyr Arg Xaa Xaa Pro
1               5                   10

<210> SEQ ID NO 211
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (12)..(12)
<223> OTHER INFORMATION: Xaa is T(Bzl) [L-O-benzylthreonine]
<220> FEATURE:
<221> NAME/KEY: MISC_FEATURE
<222> LOCATION: (13)..(13)
<223> OTHER INFORMATION: Xaa is D-Pro

<400> SEQUENCE: 211

Leu Arg Leu Lys Lys Arg Arg Trp Lys Tyr Arg Xaa Xaa Pro
1               5                   10

<210> SEQ ID NO 212
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (12)..(12)
<223> OTHER INFORMATION: Xaa is Orn (L-ornithine)
<220> FEATURE:
<221> NAME/KEY: MISC_FEATURE
<222> LOCATION: (13)..(13)
<223> OTHER INFORMATION: Xaa is D-Pro

<400> SEQUENCE: 212

Leu Arg Leu Lys Lys Arg Arg Trp Lys Tyr Arg Xaa Xaa Pro
1               5                   10

<210> SEQ ID NO 213
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
```

-continued

```
<220> FEATURE:
<221> NAME/KEY: MISC_FEATURE
<222> LOCATION: (2)..(2)
<223> OTHER INFORMATION: Xaa is Orn (L-ornithine)
<220> FEATURE:
<221> NAME/KEY: MISC_FEATURE
<222> LOCATION: (13)..(13)
<223> OTHER INFORMATION: Xaa is D-Pro

<400> SEQUENCE: 213

Leu Xaa Leu Lys Lys Arg Arg Trp Lys Tyr Arg Val Xaa Pro
1               5                   10

<210> SEQ ID NO 214
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (4)..(4)
<223> OTHER INFORMATION: Xaa is Orn (L-ornithine)
<220> FEATURE:
<221> NAME/KEY: MISC_FEATURE
<222> LOCATION: (13)..(13)
<223> OTHER INFORMATION: Xaa is D-Pro

<400> SEQUENCE: 214

Leu Arg Leu Xaa Lys Arg Arg Trp Lys Tyr Arg Val Xaa Pro
1               5                   10

<210> SEQ ID NO 215
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (5)..(5)
<223> OTHER INFORMATION: Xaa is Orn (L-ornithine)
<220> FEATURE:
<221> NAME/KEY: MISC_FEATURE
<222> LOCATION: (13)..(13)
<223> OTHER INFORMATION: Xaa is D-Pro

<400> SEQUENCE: 215

Leu Arg Leu Lys Xaa Arg Arg Trp Lys Tyr Arg Val Xaa Pro
1               5                   10

<210> SEQ ID NO 216
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (7)..(7)
<223> OTHER INFORMATION: Xaa is Orn (L-ornithine)
<220> FEATURE:
<221> NAME/KEY: MISC_FEATURE
<222> LOCATION: (13)..(13)
<223> OTHER INFORMATION: Xaa is D-Pro

<400> SEQUENCE: 216

Leu Arg Leu Lys Lys Arg Xaa Trp Lys Tyr Arg Val Xaa Pro
1               5                   10
```

```
<210> SEQ ID NO 217
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (9)..(9)
<223> OTHER INFORMATION: Xaa is Orn (L-ornithine)
<220> FEATURE:
<221> NAME/KEY: MISC_FEATURE
<222> LOCATION: (13)..(13)
<223> OTHER INFORMATION: Xaa is D-Pro

<400> SEQUENCE: 217

Leu Arg Leu Lys Lys Arg Arg Trp Xaa Tyr Arg Val Xaa Pro
1               5                   10

<210> SEQ ID NO 218
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (11)..(11)
<223> OTHER INFORMATION: Xaa is Orn (L-ornithine)
<220> FEATURE:
<221> NAME/KEY: MISC_FEATURE
<222> LOCATION: (13)..(13)
<223> OTHER INFORMATION: Xaa is D-Pro

<400> SEQUENCE: 218

Leu Arg Leu Lys Lys Arg Arg Trp Lys Tyr Xaa Val Xaa Pro
1               5                   10

<210> SEQ ID NO 219
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 219

Leu Arg Leu Lys Lys Arg Gln Trp Lys Tyr Arg Val Xaa Pro
1               5                   10

<210> SEQ ID NO 220
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 220

Leu Arg Leu Lys Lys Arg Arg Trp Tyr Tyr Arg Val Xaa Pro
```

```
1               5                   10
```

<210> SEQ ID NO 221
<211> LENGTH: 14
<212> TYPE: PRT
<213> ORGANISM: Artificial Sequence
<220> FEATURE:
<223> OTHER INFORMATION: Description of Artificial Sequence:
       Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 221

```
Leu Arg Leu Lys Lys Arg Arg Trp His Tyr Arg Val Xaa Pro
1               5                   10
```

<210> SEQ ID NO 222
<211> LENGTH: 14
<212> TYPE: PRT
<213> ORGANISM: Artificial Sequence
<220> FEATURE:
<223> OTHER INFORMATION: Description of Artificial Sequence:
       Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 222

```
Leu Arg Leu Lys Lys Arg Arg Trp Arg Tyr Arg Val Xaa Pro
1               5                   10
```

<210> SEQ ID NO 223
<211> LENGTH: 14
<212> TYPE: PRT
<213> ORGANISM: Artificial Sequence
<220> FEATURE:
<223> OTHER INFORMATION: Description of Artificial Sequence:
       Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 223

```
Leu Arg Leu Lys Lys Arg Arg Trp Thr Tyr Arg Val Xaa Pro
1               5                   10
```

<210> SEQ ID NO 224
<211> LENGTH: 14
<212> TYPE: PRT
<213> ORGANISM: Artificial Sequence
<220> FEATURE:
<223> OTHER INFORMATION: Description of Artificial Sequence:
       Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 224

```
Leu Arg Leu Lys Lys Arg Arg Trp Gln Tyr Arg Val Xaa Pro
1               5                   10
```

<210> SEQ ID NO 225
<211> LENGTH: 14
<212> TYPE: PRT
<213> ORGANISM: Artificial Sequence

```
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 225

Leu Arg Leu Lys Lys Arg Arg Trp Lys Tyr Tyr Val Xaa Pro
1               5                   10

<210> SEQ ID NO 226
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 226

Leu Arg Leu Lys Lys Arg Arg Trp Lys Tyr Trp Val Xaa Pro
1               5                   10

<210> SEQ ID NO 227
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (8)..(8)
<223> OTHER INFORMATION: Xaa is Bip [L-(4-phenyl)phenylalanine]
<220> FEATURE:
<221> NAME/KEY: MISC_FEATURE
<222> LOCATION: (10)..(10)
<223> OTHER INFORMATION: Xaa is Bip [L-(4-phenyl)phenylalanine]
<220> FEATURE:
<221> NAME/KEY: MISC_FEATURE
<222> LOCATION: (13)..(13)
<223> OTHER INFORMATION: Xaa is D-Pro

<400> SEQUENCE: 227

Leu Arg Leu Lys Lys Arg Arg Xaa Lys Xaa Arg Val Xaa Pro
1               5                   10

<210> SEQ ID NO 228
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (8)..(8)
<223> OTHER INFORMATION: Xaa is Bip [L-(4-phenyl)phenylalanine]
<220> FEATURE:
<221> NAME/KEY: MISC_FEATURE
<222> LOCATION: (13)..(13)
<223> OTHER INFORMATION: Xaa is D-Pro

<400> SEQUENCE: 228

Leu Arg Leu Arg Lys Arg Arg Xaa Lys Tyr Arg Val Xaa Pro
1               5                   10
```

```
<210> SEQ ID NO 229
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (8)..(8)
<223> OTHER INFORMATION: Xaa is Bip [L-(4-phenyl)phenylalanine]
<220> FEATURE:
<221> NAME/KEY: MISC_FEATURE
<222> LOCATION: (13)..(13)
<223> OTHER INFORMATION: Xaa is D-Pro

<400> SEQUENCE: 229

Leu Arg Leu Lys Lys Arg Arg Xaa Lys Tyr Arg Val Xaa Pro
1               5                   10

<210> SEQ ID NO 230
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (8)..(8)
<223> OTHER INFORMATION: Xaa is Bip [L-(4-phenyl)phenylalanine]
<220> FEATURE:
<221> NAME/KEY: MISC_FEATURE
<222> LOCATION: (13)..(13)
<223> OTHER INFORMATION: Xaa is D-Pro

<400> SEQUENCE: 230

Leu Trp Leu Lys Lys Arg Arg Xaa Lys Tyr Arg Val Xaa Pro
1               5                   10

<210> SEQ ID NO 231
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (8)..(8)
<223> OTHER INFORMATION: Xaa is Bip [L-(4-phenyl)phenylalanine]
<220> FEATURE:
<221> NAME/KEY: MISC_FEATURE
<222> LOCATION: (13)..(13)
<223> OTHER INFORMATION: Xaa is D-Pro

<400> SEQUENCE: 231

Leu Trp Leu Arg Lys Arg Arg Xaa Lys Tyr Arg Val Xaa Pro
1               5                   10

<210> SEQ ID NO 232
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (8)..(8)
<223> OTHER INFORMATION: Xaa is Bip [L-(4-phenyl)phenylalanine]
<220> FEATURE:
```

```
<221> NAME/KEY: MISC_FEATURE
<222> LOCATION: (13)..(13)
<223> OTHER INFORMATION: Xaa is D-Pro

<400> SEQUENCE: 232

Leu Trp Leu Lys Lys Arg Arg Xaa Arg Tyr Arg Val Xaa Pro
1               5                   10

<210> SEQ ID NO 233
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (8)..(8)
<223> OTHER INFORMATION: Xaa is Bip [L-(4-phenyl)phenylalanine]
<220> FEATURE:
<221> NAME/KEY: MISC_FEATURE
<222> LOCATION: (10)..(10)
<223> OTHER INFORMATION: Xaa is Bip [L-(4-phenyl)phenylalanine]
<220> FEATURE:
<221> NAME/KEY: MISC_FEATURE
<222> LOCATION: (13)..(13)
<223> OTHER INFORMATION: Xaa is D-Pro

<400> SEQUENCE: 233

Leu Trp Leu Arg Lys Arg Arg Xaa Lys Xaa Arg Val Xaa Pro
1               5                   10

<210> SEQ ID NO 234
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (8)..(8)
<223> OTHER INFORMATION: Xaa is Bip [L-(4-phenyl)phenylalanine]
<220> FEATURE:
<221> NAME/KEY: MISC_FEATURE
<222> LOCATION: (10)..(10)
<223> OTHER INFORMATION: Xaa is Bip [L-(4-phenyl)phenylalanine]
<220> FEATURE:
<221> NAME/KEY: MISC_FEATURE
<222> LOCATION: (13)..(13)
<223> OTHER INFORMATION: Xaa is D-Pro

<400> SEQUENCE: 234

Leu Trp Leu Lys Lys Arg Arg Xaa Arg Xaa Arg Val Xaa Pro
1               5                   10

<210> SEQ ID NO 235
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (8)..(8)
<223> OTHER INFORMATION: Xaa is Bip [L-(4-phenyl)phenylalanine]
<220> FEATURE:
<221> NAME/KEY: MISC_FEATURE
<222> LOCATION: (10)..(10)
<223> OTHER INFORMATION: Xaa is Bip [L-(4-phenyl)phenylalanine]
<220> FEATURE:
<221> NAME/KEY: MISC_FEATURE
```

```
<222> LOCATION: (12)..(12)
<223> OTHER INFORMATION: Xaa is Bip [L-(4-phenyl)phenylalanine]
<220> FEATURE:
<221> NAME/KEY: MISC_FEATURE
<222> LOCATION: (13)..(13)
<223> OTHER INFORMATION: Xaa is D-Pro

<400> SEQUENCE: 235

Leu Trp Leu Arg Lys Arg Arg Xaa Arg Xaa Arg Xaa Xaa Pro
1               5                   10

<210> SEQ ID NO 236
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (1)..(1)
<223> OTHER INFORMATION: Xaa is 4Cl-Phe (L-4-chlorophenylalanine)
<220> FEATURE:
<221> NAME/KEY: MISC_FEATURE
<222> LOCATION: (8)..(8)
<223> OTHER INFORMATION: Xaa is Bip [L-(4-phenyl)phenylalanine]
<220> FEATURE:
<221> NAME/KEY: MISC_FEATURE
<222> LOCATION: (13)..(13)
<223> OTHER INFORMATION: Xaa is D-Pro

<400> SEQUENCE: 236

Xaa Arg Leu Lys Lys Arg Arg Xaa Lys Tyr Arg Val Xaa Pro
1               5                   10

<210> SEQ ID NO 237
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (1)..(1)
<223> OTHER INFORMATION: Xaa is 4Cl-Phe (L-4-chlorophenylalanine)
<220> FEATURE:
<221> NAME/KEY: MISC_FEATURE
<222> LOCATION: (8)..(8)
<223> OTHER INFORMATION: Xaa is Bip [L-(4-phenyl)phenylalanine]
<220> FEATURE:
<221> NAME/KEY: MISC_FEATURE
<222> LOCATION: (10)..(10)
<223> OTHER INFORMATION: Xaa is Bip [L-(4-phenyl)phenylalanine]
<220> FEATURE:
<221> NAME/KEY: MISC_FEATURE
<222> LOCATION: (13)..(13)
<223> OTHER INFORMATION: Xaa is D-Pro

<400> SEQUENCE: 237

Xaa Arg Leu Lys Lys Arg Arg Xaa Lys Xaa Arg Val Xaa Pro
1               5                   10

<210> SEQ ID NO 238
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (1)..(1)
```

-continued

```
<223> OTHER INFORMATION: Xaa is 4Cl-Phe (L-4-chlorophenylalanine)
<220> FEATURE:
<221> NAME/KEY: MISC_FEATURE
<222> LOCATION: (8)..(8)
<223> OTHER INFORMATION: Xaa is Bip [L-(4-phenyl)phenylalanine]
<220> FEATURE:
<221> NAME/KEY: MISC_FEATURE
<222> LOCATION: (12)..(12)
<223> OTHER INFORMATION: Xaa is Bip [L-(4-phenyl)phenylalanine]
<220> FEATURE:
<221> NAME/KEY: MISC_FEATURE
<222> LOCATION: (13)..(13)
<223> OTHER INFORMATION: Xaa is D-Pro

<400> SEQUENCE: 238

Xaa Arg Leu Lys Lys Arg Arg Xaa Lys Tyr Arg Xaa Xaa Pro
1               5                   10

<210> SEQ ID NO 239
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (1)..(1)
<223> OTHER INFORMATION: Xaa is 4Cl-Phe (4-chlorophenylalanine)
<220> FEATURE:
<221> NAME/KEY: MISC_FEATURE
<222> LOCATION: (8)..(8)
<223> OTHER INFORMATION: Xaa is Bip [L-(4-phenyl)phenylalanine]
<220> FEATURE:
<221> NAME/KEY: MISC_FEATURE
<222> LOCATION: (10)..(10)
<223> OTHER INFORMATION: Xaa is Bip [L-(4-phenyl)phenylalanine]
<220> FEATURE:
<221> NAME/KEY: MISC_FEATURE
<222> LOCATION: (12)..(12)
<223> OTHER INFORMATION: Xaa is Bip [L-(4-phenyl)phenylalanine]
<220> FEATURE:
<221> NAME/KEY: MISC_FEATURE
<222> LOCATION: (13)..(13)
<223> OTHER INFORMATION: Xaa is D-Pro

<400> SEQUENCE: 239

Xaa Arg Leu Lys Lys Arg Arg Xaa Lys Xaa Arg Xaa Xaa Pro
1               5                   10

<210> SEQ ID NO 240
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (1)..(1)
<223> OTHER INFORMATION: Xaa is 4Cl-Phe (4-chlorophenylalanine)
<220> FEATURE:
<221> NAME/KEY: MISC_FEATURE
<222> LOCATION: (8)..(8)
<223> OTHER INFORMATION: Xaa is Bip [L-(4-phenyl)phenylalanine]
<220> FEATURE:
<221> NAME/KEY: MISC_FEATURE
<222> LOCATION: (13)..(13)
<223> OTHER INFORMATION: Xaa is D-Pro

<400> SEQUENCE: 240

Xaa Arg Leu Arg Lys Arg Arg Xaa Lys Tyr Arg Val Xaa Pro
1               5                   10
```

<210> SEQ ID NO 241
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (1)..(1)
<223> OTHER INFORMATION: Xaa is 4Cl-Phe (4-chlorophenylalanine)
<220> FEATURE:
<221> NAME/KEY: MISC_FEATURE
<222> LOCATION: (8)..(8)
<223> OTHER INFORMATION: Xaa is Bip [L-(4-phenyl)phenylalanine]
<220> FEATURE:
<221> NAME/KEY: MISC_FEATURE
<222> LOCATION: (13)..(13)
<223> OTHER INFORMATION: Xaa is D-Pro

<400> SEQUENCE: 241

Xaa Arg Leu Lys Lys Arg Arg Xaa Arg Tyr Arg Val Xaa Pro
1               5                   10

<210> SEQ ID NO 242
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (1)..(1)
<223> OTHER INFORMATION: Xaa is 4Cl-Phe (L-4-chlorophenylalanine)
<220> FEATURE:
<221> NAME/KEY: MISC_FEATURE
<222> LOCATION: (8)..(8)
<223> OTHER INFORMATION: Xaa is Bip [L-(4-phenyl)phenylalanine]
<220> FEATURE:
<221> NAME/KEY: MISC_FEATURE
<222> LOCATION: (13)..(13)
<223> OTHER INFORMATION: Xaa is D-Pro

<400> SEQUENCE: 242

Xaa Trp Leu Lys Lys Arg Arg Xaa Lys Tyr Arg Val Xaa Pro
1               5                   10

<210> SEQ ID NO 243
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (1)..(1)
<223> OTHER INFORMATION: Xaa is aCl-Phe (L-4-chlorophenylalanine)
<220> FEATURE:
<221> NAME/KEY: MISC_FEATURE
<222> LOCATION: (8)..(8)
<223> OTHER INFORMATION: Xaa is Bip [L-(4-phenyl)phenylalanine]
<220> FEATURE:
<221> NAME/KEY: MISC_FEATURE
<222> LOCATION: (13)..(13)
<223> OTHER INFORMATION: Xaa is D-Pro

<400> SEQUENCE: 243

Xaa Trp Leu Arg Lys Arg Arg Xaa Lys Tyr Arg Val Xaa Pro
1               5                   10

<210> SEQ ID NO 244
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (1)..(1)
<223> OTHER INFORMATION: Xaa is 4Cl-Phe (L-4-chlorophenylalanine)
<220> FEATURE:
<221> NAME/KEY: MISC_FEATURE
<222> LOCATION: (8)..(8)
<223> OTHER INFORMATION: Xaa is Bip [L-(4-phenyl)phenylalanine]
<220> FEATURE:
<221> NAME/KEY: MISC_FEATURE
<222> LOCATION: (13)..(13)
<223> OTHER INFORMATION: Xaa is D-Pro

<400> SEQUENCE: 244

Xaa Trp Leu Lys Lys Arg Arg Xaa Arg Tyr Arg Val Xaa Pro
 1               5                  10

<210> SEQ ID NO 245
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (1)..(1)
<223> OTHER INFORMATION: Xaa is 4Cl-Phe (L-4-chlorophenylalanine)
<220> FEATURE:
<221> NAME/KEY: MISC_FEATURE
<222> LOCATION: (8)..(8)
<223> OTHER INFORMATION: Xaa is Bip [L-(4-phenyl)phenylalanine]
<220> FEATURE:
<221> NAME/KEY: MISC_FEATURE
<222> LOCATION: (10)..(10)
<223> OTHER INFORMATION: Xaa is Bip [L-(4-phenyl)phenylalanine]
<220> FEATURE:
<221> NAME/KEY: MISC_FEATURE
<222> LOCATION: (13)..(13)
<223> OTHER INFORMATION: Xaa is D-Pro

<400> SEQUENCE: 245

Xaa Trp Leu Arg Lys Arg Arg Xaa Lys Xaa Arg Val Xaa Pro
 1               5                  10

<210> SEQ ID NO 246
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (1)..(1)
<223> OTHER INFORMATION: Xaa is 4Cl-Phe (L-4-chlorophenylalanine)
<220> FEATURE:
<221> NAME/KEY: MISC_FEATURE
<222> LOCATION: (8)..(8)
<223> OTHER INFORMATION: Xaa is Bip [L-(4-phenyl)phenylalanine]
<220> FEATURE:
<221> NAME/KEY: MISC_FEATURE
<222> LOCATION: (10)..(10)
<223> OTHER INFORMATION: Xaa is Bip [L-(4-phenyl)phenylalanine]
<220> FEATURE:
<221> NAME/KEY: MISC_FEATURE
<222> LOCATION: (13)..(13)
<223> OTHER INFORMATION: Xaa is D-Pro

```
<400> SEQUENCE: 246

Xaa Trp Leu Lys Lys Arg Arg Xaa Arg Xaa Arg Val Xaa Pro
1               5                   10

<210> SEQ ID NO 247
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 247

Leu Arg Leu Lys Lys Arg Arg Trp Lys Tyr Arg Val Xaa Gly
1               5                   10

<210> SEQ ID NO 248
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 248

Leu Arg Leu Lys Lys Arg Arg Trp Lys Tyr Arg Val Xaa Arg
1               5                   10

<210> SEQ ID NO 249
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 249

Leu Arg Leu Lys Lys Arg Arg Trp Lys Tyr Arg Val Xaa Tyr
1               5                   10

<210> SEQ ID NO 250
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 250

Leu Arg Leu Lys Lys Arg Arg Trp Lys Tyr Arg Val Xaa Phe
1               5                   10
```

```
<210> SEQ ID NO 251
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 251

Leu Arg Leu Lys Lys Arg Arg Trp Lys Tyr Arg Val Xaa Trp
1               5                   10

<210> SEQ ID NO 252
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 252

Leu Arg Leu Lys Lys Arg Arg Trp Lys Tyr Arg Val Xaa Leu
1               5                   10

<210> SEQ ID NO 253
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 253

Leu Arg Leu Lys Lys Arg Arg Trp Lys Tyr Arg Val Xaa Ile
1               5                   10

<210> SEQ ID NO 254
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro
<220> FEATURE:
<221> NAME/KEY: MISC_FEATURE
<222> LOCATION: (14)..(14)
<223> OTHER INFORMATION: Xaa is Cha (L-cyclohexylalanine)

<400> SEQUENCE: 254

Leu Arg Leu Lys Lys Arg Arg Trp Lys Tyr Arg Val Xaa Xaa
1               5                   10

<210> SEQ ID NO 255
<211> LENGTH: 14
<212> TYPE: PRT
```

```
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro
<220> FEATURE:
<221> NAME/KEY: MISC_FEATURE
<222> LOCATION: (14)..(14)
<223> OTHER INFORMATION: Xaa is 2-Nal (L-2-naphthylalanine)

<400> SEQUENCE: 255

Leu Arg Leu Lys Lys Arg Arg Trp Lys Tyr Arg Val Xaa Xaa
1               5                   10

<210> SEQ ID NO 256
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro
<220> FEATURE:
<221> NAME/KEY: MISC_FEATURE
<222> LOCATION: (14)..(14)
<223> OTHER INFORMATION: Xaa is 4-(n-hexylcarbonylamino)-Pro

<400> SEQUENCE: 256

Leu Arg Leu Lys Lys Arg Arg Trp Lys Tyr Arg Val Xaa Xaa
1               5                   10

<210> SEQ ID NO 257
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro
<220> FEATURE:
<221> NAME/KEY: MISC_FEATURE
<222> LOCATION: (14)..(14)
<223> OTHER INFORMATION: Xaa is 4-(n-heptylcarbonylamino)-Pro

<400> SEQUENCE: 257

Leu Arg Leu Lys Lys Arg Arg Trp Lys Tyr Arg Val Xaa Xaa
1               5                   10

<210> SEQ ID NO 258
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro
<220> FEATURE:
<221> NAME/KEY: MISC_FEATURE
<222> LOCATION: (14)..(14)
<223> OTHER INFORMATION: Xaa is 4-(4-phenylbenzylcarbonylamino)-Pro
```

<400> SEQUENCE: 258

Leu Arg Leu Lys Lys Arg Arg Trp Lys Tyr Arg Val Xaa Xaa
1               5                   10

<210> SEQ ID NO 259
<211> LENGTH: 14
<212> TYPE: PRT
<213> ORGANISM: Artificial Sequence
<220> FEATURE:
<223> OTHER INFORMATION: Description of Artificial Sequence:
            Cyclic peptide
<220> FEATURE:
<221> NAME/KEY: MISC_FEATURE
<222> LOCATION: (13)..(13)
<223> OTHER INFORMATION: Xaa is D-Pro
<220> FEATURE:
<221> NAME/KEY: MISC_FEATURE
<222> LOCATION: (14)..(14)
<223> OTHER INFORMATION: Xaa is 4-(diphenylmethylcarbonylamino)-Pro

<400> SEQUENCE: 259

Leu Arg Leu Lys Lys Arg Arg Trp Lys Tyr Arg Val Xaa Xaa
1               5                   10

<210> SEQ ID NO 260
<211> LENGTH: 14
<212> TYPE: PRT
<213> ORGANISM: Artificial Sequence
<220> FEATURE:
<223> OTHER INFORMATION: Description of Artificial Sequence:
            Cyclic peptide
<220> FEATURE:
<221> NAME/KEY: MISC_FEATURE
<222> LOCATION: (13)..(13)
<223> OTHER INFORMATION: Xaa is D-Pro
<220> FEATURE:
<221> NAME/KEY: MISC_FEATURE
<222> LOCATION: (14)..(14)
<223> OTHER INFORMATION: Xaa is 4-(3-aminopropylcarbonylamino)-Pro

<400> SEQUENCE: 260

Leu Arg Leu Lys Lys Arg Arg Trp Lys Tyr Arg Val Xaa Xaa
1               5                   10

<210> SEQ ID NO 261
<211> LENGTH: 14
<212> TYPE: PRT
<213> ORGANISM: Artificial Sequence
<220> FEATURE:
<223> OTHER INFORMATION: Description of Artificial Sequence:
            Cyclic peptide
<220> FEATURE:
<221> NAME/KEY: MISC_FEATURE
<222> LOCATION: (13)..(13)
<223> OTHER INFORMATION: Xaa is D-Pro
<220> FEATURE:
<221> NAME/KEY: MISC_FEATURE
<222> LOCATION: (14)..(14)
<223> OTHER INFORMATION: Xaa is 4-(5-aminopentylcarbonylamino)-Pro

<400> SEQUENCE: 261

Leu Arg Leu Lys Lys Arg Arg Trp Lys Tyr Arg Val Xaa Xaa
1               5                   10

<210> SEQ ID NO 262
<211> LENGTH: 14
<212> TYPE: PRT
<213> ORGANISM: Artificial Sequence
<220> FEATURE:
<223> OTHER INFORMATION: Description of Artificial Sequence:
            Cyclic peptide

```
<220> FEATURE:
<221> NAME/KEY: MISC_FEATURE
<222> LOCATION: (13)..(13)
<223> OTHER INFORMATION: Xaa is D-Pro
<220> FEATURE:
<221> NAME/KEY: MISC_FEATURE
<222> LOCATION: (14)..(14)
<223> OTHER INFORMATION: Xaa is 4-(methylcarbonylamino)-Pro

<400> SEQUENCE: 262

Leu Arg Leu Lys Lys Arg Arg Trp Lys Tyr Arg Val Xaa Xaa
1               5                   10

<210> SEQ ID NO 263
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro
<220> FEATURE:
<221> NAME/KEY: MISC_FEATURE
<222> LOCATION: (14)..(14)
<223> OTHER INFORMATION: Xaa is 4-(ethylcarbonylamino)-Pro

<400> SEQUENCE: 263

Leu Arg Leu Lys Lys Arg Arg Trp Lys Tyr Arg Val Xaa Xaa
1               5                   10

<210> SEQ ID NO 264
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro
<220> FEATURE:
<221> NAME/KEY: MISC_FEATURE
<222> LOCATION: (14)..(14)
<223> OTHER INFORMATION: Xaa is 4-(isopropylcarbonylamino)-Pro

<400> SEQUENCE: 264

Leu Arg Leu Lys Lys Arg Arg Trp Lys Tyr Arg Val Xaa Xaa
1               5                   10

<210> SEQ ID NO 265
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro
<220> FEATURE:
<221> NAME/KEY: MISC_FEATURE
<222> LOCATION: (14)..(14)
<223> OTHER INFORMATION: Xaa is 4-(isobutylcarbonylamino)-Pro

<400> SEQUENCE: 265

Leu Arg Leu Lys Lys Arg Arg Trp Lys Tyr Arg Val Xaa Xaa
1               5                   10
```

<210> SEQ ID NO 266
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro
<220> FEATURE:
<221> NAME/KEY: MISC_FEATURE
<222> LOCATION: (14)..(14)
<223> OTHER INFORMATION: Xaa is 4-(n-propylcarbonylamino)-Pro

<400> SEQUENCE: 266

Leu Arg Leu Leu Lys Arg Arg Trp Lys Tyr Arg Val Xaa Xaa
1               5                   10

<210> SEQ ID NO 267
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro
<220> FEATURE:
<221> NAME/KEY: MISC_FEATURE
<222> LOCATION: (14)..(14)
<223> OTHER INFORMATION: Xaa is 4-(cyclohexylcarbonylamino)-Pro

<400> SEQUENCE: 267

Leu Arg Leu Lys Lys Arg Arg Trp Lys Tyr Arg Val Xaa Xaa
1               5                   10

<210> SEQ ID NO 268
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro
<220> FEATURE:
<221> NAME/KEY: MISC_FEATURE
<222> LOCATION: (14)..(14)
<223> OTHER INFORMATION: Xaa is 4-(cyclohexylmethylcarbonylamino)-Pro

<400> SEQUENCE: 268

Leu Arg Leu Lys Lys Arg Arg Trp Lys Tyr Arg Val Xaa Xaa
1               5                   10

<210> SEQ ID NO 269
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

```
<220> FEATURE:
<221> NAME/KEY: MISC_FEATURE
<222> LOCATION: (14)..(14)
<223> OTHER INFORMATION: Xaa is 4-(n-butylcarbonylamino)-Pro

<400> SEQUENCE: 269

Leu Arg Leu Lys Lys Arg Arg Trp Lys Tyr Arg Val Xaa Xaa
1               5                   10

<210> SEQ ID NO 270
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro
<220> FEATURE:
<221> NAME/KEY: MISC_FEATURE
<222> LOCATION: (14)..(14)
<223> OTHER INFORMATION: Xaa is 4-(phenylcarbonylamino)-Pro

<400> SEQUENCE: 270

Leu Arg Leu Lys Lys Arg Arg Trp Lys Tyr Arg Val Xaa Xaa
1               5                   10

<210> SEQ ID NO 271
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro
<220> FEATURE:
<221> NAME/KEY: MISC_FEATURE
<222> LOCATION: (14)..(14)
<223> OTHER INFORMATION: Xaa is 4-(benzylcarbonylamino)-Pro

<400> SEQUENCE: 271

Leu Arg Leu Lys Lys Arg Arg Trp Lys Tyr Arg Val Xaa Xaa
1               5                   10

<210> SEQ ID NO 272
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro
<220> FEATURE:
<221> NAME/KEY: MISC_FEATURE
<222> LOCATION: (14)..(14)
<223> OTHER INFORMATION: Xaa is 4-(3-indolylmethyl)-Pro

<400> SEQUENCE: 272

Leu Arg Leu Lys Lys Arg Arg Trp Lys Tyr Arg Val Xaa Xaa
1               5                   10

<210> SEQ ID NO 273
<211> LENGTH: 14
```

```
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro
<220> FEATURE:
<221> NAME/KEY: MISC_FEATURE
<222> LOCATION: (14)..(14)
<223> OTHER INFORMATION: Xaa is 4-[2-(3-indolyl)ethyl]-Pro

<400> SEQUENCE: 273

Leu Arg Leu Lys Lys Arg Arg Trp Lys Tyr Arg Val Xaa Xaa
1               5                   10

<210> SEQ ID NO 274
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro
<220> FEATURE:
<221> NAME/KEY: MISC_FEATURE
<222> LOCATION: (14)..(14)
<223> OTHER INFORMATION: Xaa is 4-(4-phenylphenyl)-Pro

<400> SEQUENCE: 274

Leu Arg Leu Lys Lys Arg Arg Trp Lys Tyr Arg Val Xaa Xaa
1               5                   10

<210> SEQ ID NO 275
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro
<220> FEATURE:
<221> NAME/KEY: MISC_FEATURE
<222> LOCATION: (14)..(14)
<223> OTHER INFORMATION: Xaa is 4-(n-nonylcarbonylamino)-Pro

<400> SEQUENCE: 275

Leu Arg Leu Lys Lys Arg Arg Trp Lys Tyr Arg Val Xaa Xaa
1               5                   10

<210> SEQ ID NO 276
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 276

Leu Arg Leu Lys Lys Gly Arg Trp Lys Tyr Arg Val Xaa Pro
```

```
<210> SEQ ID NO 277
<211> LENGTH: 13
<212> TYPE: PRT
<213> ORGANISM: Artificial Sequence
<220> FEATURE:
<223> OTHER INFORMATION: Description of Artificial Sequence:
                       Template-fixed peptidomimetic incorporating
                       chain of 12 amino acid residues
<220> FEATURE:
<221> NAME/KEY: MISC_FEATURE
<222> LOCATION: (13)..(13)
<223> OTHER INFORMATION: Xaa is divalent radical of 5-aminomethyl-9,
                       9-dimethyl-3,6-dimethoxyxanthene-4-acetic acid

<400> SEQUENCE: 277

Leu Arg Leu Lys Lys Arg Arg Trp Lys Tyr Arg Val Xaa
1               5                   10

<210> SEQ ID NO 278
<211> LENGTH: 14
<212> TYPE: PRT
<213> ORGANISM: Artificial Sequence
<220> FEATURE:
<223> OTHER INFORMATION: Description of Artificial Sequence:
                       Cyclic peptide FEATURE:

<221> NAME/KEY: MISC_FEATURE
<222> LOCATION: (13)..(13)
<223> OTHER INFORMATION: Xaa is D-Pro

<400> SEQUENCE: 278

Leu Tyr Leu Lys Lys Arg Arg Trp Lys Tyr Tyr Val Xaa Pro
1               5                   10

<210> SEQ ID NO 279
<211> LENGTH: 14
<212> TYPE: PRT
<213> ORGANISM: Artificial Sequence
<220> FEATURE:
<223> OTHER INFORMATION: Description of Artificial Sequence:
                       Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 279

Leu Trp Leu Lys Lys Arg Arg Trp Lys Tyr Tyr Val Xaa Pro
1               5                   10

<210> SEQ ID NO 280
<211> LENGTH: 14
<212> TYPE: PRT
<213> ORGANISM: Artificial Sequence
<220> FEATURE:
<223> OTHER INFORMATION: Description of Artificial Sequence:
                       Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 280

Arg Trp Leu Lys Lys Arg Arg Trp Lys Tyr Trp Val Xaa Pro
1               5                   10

<210> SEQ ID NO 281
<211> LENGTH: 14
```

```
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 281

Arg Trp Leu Lys Lys Arg Arg Trp Lys Tyr Tyr Val Xaa Pro
1               5                   10

<210> SEQ ID NO 282
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 282

Leu Trp Leu Lys Lys Arg Arg Trp Lys Tyr Tyr Arg Xaa Pro
1               5                   10

<210> SEQ ID NO 283
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 283

Leu Trp Leu Lys Lys Arg Arg Trp Lys Tyr Tyr Arg Xaa Pro
1               5                   10

<210> SEQ ID NO 284
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 284

Arg Trp Leu Lys Lys Arg Arg Trp Lys Tyr Tyr Arg Xaa Pro
1               5                   10

<210> SEQ ID NO 285
<211> LENGTH: 14
<212> TYPE: PRT
<213> ORGANISM: Artificial Sequence
<220> FEATURE:
<223> OTHER INFORMATION: Description of Artificial Sequence:
      Cyclic peptide
<220> FEATURE:
<221> NAME/KEY: MISC_FEATURE
```

```
<222> LOCATION: (6)..(6)
<223> OTHER INFORMATION: Xaa is Y(Bzl) [L-O-benzylserine]
<220> FEATURE:
<221> NAME/KEY: MISC_FEATURE
<222> LOCATION: (13)..(13)
<223> OTHER INFORMATION: Xaa is D-Pro

<400> SEQUENCE: 285

Leu Arg Leu Lys Lys Xaa Arg Trp Lys Tyr Arg Val Xaa Pro
1               5                   10

<210> SEQ ID NO 286
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (6)..(6)
<223> OTHER INFORMATION: Xaa is D-Y(Bzl) [D-O-benzylserine]
<220> FEATURE:
<221> NAME/KEY: MISC_FEATURE
<222> LOCATION: (13)..(13)
<223> OTHER INFORMATION: Xaa is D-Pro

<400> SEQUENCE: 286

Leu Arg Leu Lys Lys Xaa Arg Trp Lys Tyr Arg Val Xaa Pro
1               5                   10

<210> SEQ ID NO 287
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (1)..(1)
<223> OTHER INFORMATION: Xaa is Bip [L-(4-phenyl)phenylalanine]
<220> FEATURE:
<221> NAME/KEY: MISC_FEATURE
<222> LOCATION: (13)..(13)
<223> OTHER INFORMATION: Xaa is D-Pro

<400> SEQUENCE: 287

Xaa Trp Leu Lys Lys Arg Arg Trp Lys Tyr Tyr Arg Xaa Pro
1               5                   10

<210> SEQ ID NO 288
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 288

Thr Trp Leu Lys Lys Arg Arg Trp Lys Tyr Tyr Arg Xaa Pro
1               5                   10

<210> SEQ ID NO 289
<211> LENGTH: 14
<212> TYPE: PRT
<213> ORGANISM: Artificial Sequence
```

```
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (2)..(2)
<223> OTHER INFORMATION: Xaa is Bip [L-(4-phenyl)phenylalanine]
<220> FEATURE:
<221> NAME/KEY: MISC_FEATURE
<222> LOCATION: (13)..(13)
<223> OTHER INFORMATION: Xaa is D-Pro

<400> SEQUENCE: 289

Arg Xaa Leu Lys Lys Arg Arg Trp Lys Tyr Tyr Arg Xaa Pro
1               5                   10

<210> SEQ ID NO 290
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 290

Arg Thr Leu Lys Lys Arg Arg Trp Lys Tyr Tyr Arg Xaa Pro
1               5                   10

<210> SEQ ID NO 291
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 291

Arg Trp Thr Lys Lys Arg Arg Trp Lys Tyr Tyr Arg Xaa Pro
1               5                   10

<210> SEQ ID NO 292
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 292

Arg Trp Leu Arg Lys Arg Arg Trp Lys Tyr Tyr Arg Xaa Pro
1               5                   10

<210> SEQ ID NO 293
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
```

```
<220> FEATURE:
<221> NAME/KEY: MISC_FEATURE
<222> LOCATION: (13)..(13)
<223> OTHER INFORMATION: Xaa is D-Pro

<400> SEQUENCE: 293

Arg Trp Leu Gln Lys Arg Arg Trp Lys Tyr Tyr Arg Xaa Pro
1               5                   10

<210> SEQ ID NO 294
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 294

Lys Trp Leu Lys Lys Arg Arg Trp Lys Tyr Tyr Arg Xaa Pro
1               5                   10

<210> SEQ ID NO 295
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 295

Tyr Trp Leu Lys Lys Arg Arg Trp Lys Tyr Tyr Arg Xaa Pro
1               5                   10

<210> SEQ ID NO 296
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 296

Trp Trp Leu Lys Lys Arg Arg Trp Lys Tyr Tyr Arg Xaa Pro
1               5                   10

<210> SEQ ID NO 297
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 297
```

```
Val Trp Leu Lys Lys Arg Arg Trp Lys Tyr Tyr Arg Xaa Pro
1               5                   10
```

<210> SEQ ID NO 298
<211> LENGTH: 14
<212> TYPE: PRT
<213> ORGANISM: Artificial Sequence
<220> FEATURE:
<223> OTHER INFORMATION: Description of Artificial Sequence:
                       Cyclic peptide
<220> FEATURE:
<221> NAME/KEY: MISC_FEATURE
<222> LOCATION: (13)..(13)
<223> OTHER INFORMATION: Xaa is D-Pro

<400> SEQUENCE: 298

```
Gln Trp Leu Lys Lys Arg Arg Trp Lys Tyr Tyr Arg Xaa Pro
1               5                   10
```

<210> SEQ ID NO 299
<211> LENGTH: 14
<212> TYPE: PRT
<213> ORGANISM: Artificial Sequence
<220> FEATURE:
<223> OTHER INFORMATION: Description of Artificial Sequence:
                       Cyclic peptide
<220> FEATURE:
<221> NAME/KEY: MISC_FEATURE
<222> LOCATION: (1)..(1)
<223> OTHER INFORMATION: Xaa is Cha (L-cyclohexylalanine)
<220> FEATURE:
<221> NAME/KEY: MISC_FEATURE
<222> LOCATION: (13)..(13)
<223> OTHER INFORMATION: Xaa is D-Pro

<400> SEQUENCE: 299

```
Xaa Trp Leu Lys Lys Arg Arg Trp Lys Tyr Tyr Arg Xaa Pro
1               5                   10
```

<210> SEQ ID NO 300
<211> LENGTH: 14
<212> TYPE: PRT
<213> ORGANISM: Artificial Sequence
<220> FEATURE:
<223> OTHER INFORMATION: Description of Artificial Sequence:
                       Cyclic peptide
<220> FEATURE:
<221> NAME/KEY: MISC_FEATURE
<222> LOCATION: (1)..(1)
<223> OTHER INFORMATION: Xaa is Y(Bzl) [L-O-benzylserine]
<220> FEATURE:
<221> NAME/KEY: MISC_FEATURE
<222> LOCATION: (13)..(13)
<223> OTHER INFORMATION: Xaa is D-Pro

<400> SEQUENCE: 300

```
Xaa Trp Leu Lys Lys Arg Arg Trp Lys Tyr Tyr Arg Xaa Pro
1               5                   10
```

<210> SEQ ID NO 301
<211> LENGTH: 14
<212> TYPE: PRT
<213> ORGANISM: Artificial Sequence
<220> FEATURE:
<223> OTHER INFORMATION: Description of Artificial Sequence:  Linear
                       side-chain protected peptide
<220> FEATURE:
<221> NAME/KEY: MISC_FEATURE
<222> LOCATION: (1)..(1)
<223> OTHER INFORMATION: Xaa is Arg(Pbf)

```
<220> FEATURE:
<221> NAME/KEY: MISC_FEATURE
<222> LOCATION: (2)..(2)
<223> OTHER INFORMATION: Xaa is Lys(Boc)
<220> FEATURE:
<221> NAME/KEY: MISC_FEATURE
<222> LOCATION: (3)..(3)
<223> OTHER INFORMATION: Xaa is Lys(Boc)
<220> FEATURE:
<221> NAME/KEY: MISC_FEATURE
<222> LOCATION: (4)..(4)
<223> OTHER INFORMATION: Xaa is Cys(Acm)
<220> FEATURE:
<221> NAME/KEY: MISC_FEATURE
<222> LOCATION: (5)..(5)
<223> OTHER INFORMATION: Xaa is Arg(Pbf)
<220> FEATURE:
<221> NAME/KEY: MISC_FEATURE
<222> LOCATION: (8)..(8)
<223> OTHER INFORMATION: Xaa is D-Pro
<220> FEATURE:
<221> NAME/KEY: MISC_FEATURE
<222> LOCATION: (11)..(11)
<223> OTHER INFORMATION: Xaa is Cys(Acm)
<220> FEATURE:
<221> NAME/KEY: MISC_FEATURE
<222> LOCATION: (12)..(12)
<223> OTHER INFORMATION: Xaa is Lys(Boc)
<220> FEATURE:
<221> NAME/KEY: MISC_FEATURE
<222> LOCATION: (13)..(13)
<223> OTHER INFORMATION: Xaa is Trp(Boc)
<220> FEATURE:
<221> NAME/KEY: MISC_FEATURE
<222> LOCATION: (14)..(14)
<223> OTHER INFORMATION: Xaa is Arg(Pbf)

<400> SEQUENCE: 301

Xaa Xaa Xaa Xaa Xaa Leu Pro Xaa Val Arg Xaa Xaa Xaa Xaa
1               5                   10

<210> SEQ ID NO 302
<211> LENGTH: 14
<212> TYPE: PRT
<213> ORGANISM: Artificial Sequence
<220> FEATURE:
<223> OTHER INFORMATION: Description of Artificial Sequence:
                        Cyclic peptide
<220> FEATURE:
<221> NAME/KEY: DISULFID
<222> LOCATION: (3)..(10)
<220> FEATURE:
<221> NAME/KEY: MISC_FEATURE
<222> LOCATION: (13)..(13)
<223> OTHER INFORMATION: Xaa is D-Pro

<400> SEQUENCE: 302

Leu Arg Cys Lys Lys Arg Arg Trp Lys Cys Arg Val Xaa Pro
1               5                   10

<210> SEQ ID NO 303
<211> LENGTH: 13
<212> TYPE: PRT
<213> ORGANISM: Artificial Sequence
<220> FEATURE:
<223> OTHER INFORMATION: Description of Artificial Sequence:  Linear
                        side-chain protected peptide
<220> FEATURE:
<221> NAME/KEY: MISC_FEATURE
<222> LOCATION: (1)..(1)
<223> OTHER INFORMATION: Xaa is Arg(Pbf)
```

```
<220> FEATURE:
<221> NAME/KEY: MISC_FEATURE
<222> LOCATION: (2)..(2)
<223> OTHER INFORMATION: Xaa is Trp(Boc)
<220> FEATURE:
<221> NAME/KEY: MISC_FEATURE
<222> LOCATION: (3)..(3)
<223> OTHER INFORMATION: Xaa is Lys(Boc)
<220> FEATURE:
<221> NAME/KEY: MISC_FEATURE
<222> LOCATION: (4)..(4)
<223> OTHER INFORMATION: Xaa is Tyr(tBu)
<220> FEATURE:
<221> NAME/KEY: MISC_FEATURE
<222> LOCATION: (5)..(5)
<223> OTHER INFORMATION: Xaa is Arg(Pbf)
<220> FEATURE:
<221> NAME/KEY: MISC_FEATURE
<222> LOCATION: (6)..(6)
<223> OTHER INFORMATION: Xaa is D-Pro
<220> FEATURE:
<221> NAME/KEY: MISC_FEATURE
<222> LOCATION: (7)..(7)
<223> OTHER INFORMATION: Xaa is 4-AllocNH-1-Fmoc_pro
<220> FEATURE:
<221> NAME/KEY: MISC_FEATURE
<222> LOCATION: (9)..(9)
<223> OTHER INFORMATION: Xaa is Arg(Pbf)
<220> FEATURE:
<221> NAME/KEY: MISC_FEATURE
<222> LOCATION: (11)..(11)
<223> OTHER INFORMATION: Xaa is Lys(Boc)
<220> FEATURE:
<221> NAME/KEY: MISC_FEATURE
<222> LOCATION: (12)..(12)
<223> OTHER INFORMATION: Xaa is Lys(Boc)
<220> FEATURE:
<221> NAME/KEY: MISC_FEATURE
<222> LOCATION: (13)..(13)
<223> OTHER INFORMATION: Xaa is Arg(PbF)

<400> SEQUENCE: 303

Xaa Xaa Xaa Xaa Xaa Xaa Xaa Leu Xaa Leu Xaa Xaa Xaa
1               5                   10

<210> SEQ ID NO 304
<211> LENGTH: 14
<212> TYPE: PRT
<213> ORGANISM: Artificial Sequence
<220> FEATURE:
<223> OTHER INFORMATION: Description of Artificial Sequence:  Dimeric
                        template-fixed peptidomimetics incorporating
                        two chains of 12 amino acid residues
<220> FEATURE:
<221> NAME/KEY: MISC_FEATURE
<222> LOCATION: (13)..(13)
<223> OTHER INFORMATION: Xaa is D-Pro
<220> FEATURE:
<221> NAME/KEY: MISC_FEATURE
<222> LOCATION: (14)..(14)
<223> OTHER INFORMATION: Xaa is 4-amino-Pro, linked via CO-trimethylene-
                        CO to another 4-amino-Pro as member of cyclic
                        Leu Arg Leu Lys Lys Arg Arg Trp Lys Tyr Arg Val
                        D-Pro 4-amino-Pro

<400> SEQUENCE: 304

Leu Arg Leu Lys Lys Arg Arg Trp Lys Tyr Arg Val Xaa Xaa
1               5                   10
```